US012799499B2

(12) United States Patent
Paciorek et al.

(10) Patent No.: US 12,799,499 B2
(45) Date of Patent: Nov. 17, 2026

(54) METHODS AND COMPOSITIONS FOR SHORT STATURE PLANTS THROUGH MANIPULATION OF GIBBERELLIN METABOLISM TO INCREASE HARVESTABLE YIELD

(71) Applicant: Monsanto Technology LLC, St. Louis, MO (US)

(72) Inventors: Tomasz Paciorek, Wildwood, MO (US); Thomas L. Slewinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 45 days.

(21) Appl. No.: 18/839,397

(22) PCT Filed: Feb. 22, 2023

(86) PCT No.: PCT/US2023/062985
§ 371 (c)(1),
(2) Date: Aug. 16, 2024

(87) PCT Pub. No.: WO2023/164456
PCT Pub. Date: Aug. 31, 2023

(65) Prior Publication Data
US 2025/0320518 A1 Oct. 16, 2025

Related U.S. Application Data

(60) Provisional application No. 63/312,703, filed on Feb. 22, 2022.

(51) Int. Cl.
*C12N 15/82* (2006.01)
*C12N 9/02* (2006.01)

(52) U.S. Cl.
CPC ....... *C12N 15/8297* (2013.01); *C12N 9/0071* (2013.01); *C12N 15/8205* (2013.01); *C12N 15/8261* (2013.01); *C12Y 114/11015* (2013.01); *C12N 2310/20* (2017.05)

(58) Field of Classification Search
CPC .............. C12N 15/8297; C12N 9/0071; C12N 15/8205
See application file for complete search history.

(56) References Cited

U.S. PATENT DOCUMENTS

| | | | |
|---|---|---|---|
| 4,368,592 | A | 1/1983 | Welch |
| 5,159,135 | A | 10/1992 | Umbeck |
| 5,188,958 | A | 2/1993 | Moloney et al. |
| 5,322,938 | A | 6/1994 | McPherson et al. |
| 5,352,605 | A | 10/1994 | Fraley et al. |
| 5,463,174 | A | 10/1995 | Moloney et al. |
| 5,510,474 | A | 4/1996 | Quail et al. |
| 5,538,880 | A | 7/1996 | Lundquist et al. |
| 5,550,318 | A | 8/1996 | Adams et al. |
| 5,591,616 | A | 1/1997 | Hiei et al. |
| 5,641,876 | A | 6/1997 | McElroy et al. |
| 5,750,871 | A | 5/1998 | Moloney et al. |
| 5,824,877 | A | 10/1998 | Hinchee et al. |
| 5,850,019 | A | 12/1998 | Maiti et al. |
| 5,939,539 | A | 8/1999 | Lange et al. |
| 6,153,812 | A | 11/2000 | Fry et al. |
| 6,160,208 | A | 12/2000 | Lundquist et al. |
| 6,198,021 | B1 | 3/2001 | Lange et al. |
| 6,372,211 | B1 | 4/2002 | Isaac et al. |
| 6,380,467 | B1 | 4/2002 | Duclos |
| 6,384,301 | B1 | 5/2002 | Martinell et al. |
| 6,399,861 | B1 | 6/2002 | Anderson et al. |
| 6,420,547 | B1 | 7/2002 | Maiti et al. |
| 6,429,357 | B1 | 8/2002 | McElroy et al. |
| 6,723,897 | B2 | 4/2004 | Brown et al. |
| 6,765,133 | B2 | 7/2004 | Koehring |
| 7,041,874 | B2 | 5/2006 | Johal et al. |
| 7,049,490 | B2 | 5/2006 | Tanaka et al. |
| 7,057,088 | B2 | 6/2006 | Tanaka et al. |
| 7,138,567 | B2 | 11/2006 | Okawa et al. |
| 7,154,028 | B2 | 12/2006 | Tanaka et al. |

(Continued)

FOREIGN PATENT DOCUMENTS

| | | |
|---|---|---|
| CN | 101440374 | 5/2009 |
| CN | 102149821 | 8/2011 |

(Continued)

OTHER PUBLICATIONS

U.S. Appl. No. 19/492,008, filed Aug. 19, 2024, Paciorek, Tomasz.*
Lv, J. et al., The length of guide RNA and target DNA heteroduplex effects on CRISPR/Cas9 mediated genome editing efficiency in porcine cells, J. Vet Sci., 20(3):e23. (Year: 2019).*
Hu, L et al. Gibberellin Oxidase Gene Family in L. chinense: Genome-Wide Identification and Gene Expression Analysis, Int. Jour. of Mol. Sci. 22, 7167, https://doi.org/10.3390/ijms22137167. (Year: 2021).*
International Search Report and Written Opinion for International Application No. PCT/US2023/062985 mailed Jul. 27, 2023.
Trellis. "When Should I Stop Irrigating?" (2018). Accessed from <https://www.mytrellis.com/blog/when-should-I-stop-irrigating>.
Lo, et al. "Ectopic expression of specific GA2 oxidase mutants promotes yield and stress tolerance in rice." Plant. Biotech. J. 15:850-864, (2017).

(Continued)

*Primary Examiner* — Bratislav Stankovic
*Assistant Examiner* — Emily K Johnson
(74) *Attorney, Agent, or Firm* — Denton US LLP; David Lanzotti

(57) ABSTRACT

The present disclosure provides compositions and methods for altering gibberellin (GA) content in corn or other cereal plants. Methods and compositions are also provided for altering the expression of genes related to gibberellin biosynthesis through suppression, mutagenesis and/or editing of specific subtypes of GA20 or GA3 oxidase genes. Modified plant cells and plants having a suppression element or mutation reducing the expression or activity of a GA oxidase gene are further provided comprising reduced gibberellin levels and improved characteristics, such as reduced plant height and increased lodging resistance, but without off-types.

13 Claims, 13 Drawing Sheets

Specification includes a Sequence Listing.

(56) References Cited

U.S. PATENT DOCUMENTS

| | | | |
|---|---|---|---|
| 7,597,055 | B2 | 10/2009 | Choulet |
| 8,835,353 | B2 | 9/2014 | Fugiel et al. |
| 8,843,283 | B2 | 9/2014 | Strelioff et al. |
| 9,012,722 | B2 | 4/2015 | Narva et al. |
| 9,040,774 | B2 | 5/2015 | Ivashuta et al. |
| 9,303,919 | B2 | 4/2016 | Hultgren |
| 9,309,512 | B2 | 4/2016 | Allen et al. |
| 9,845,479 | B2 | 12/2017 | Beghyn et al. |
| 10,123,473 | B2 | 11/2018 | Cavender-Bares et al. |
| 10,724,047 | B2 | 7/2020 | Allen et al. |
| 10,881,057 | B2 | 1/2021 | Cannon et al. |
| 11,627,736 | B2 | 4/2023 | Barten et al. |
| 11,632,921 | B2 | 4/2023 | Cannon et al. |
| 12,274,205 | B2 | 4/2025 | Barten et al. |
| 12,492,408 | B2 | 12/2025 | Cannon et al. |
| 12,527,250 | B2 | 1/2026 | Cannon et al. |
| 2002/0053095 | A1 | 5/2002 | Brown et al. |
| 2002/0162142 | A1 | 10/2002 | Johal et al. |
| 2003/0172409 | A1 | 9/2003 | Horn |
| 2003/0233679 | A1 | 12/2003 | Brown et al. |
| 2004/0053411 | A1 | 3/2004 | Cullen et al. |
| 2004/0121321 | A1 | 6/2004 | Brown et al. |
| 2004/0268441 | A1 | 12/2004 | Vance et al. |
| 2005/0037988 | A1 | 2/2005 | Zamore et al. |
| 2005/0064474 | A1 | 3/2005 | Urnov et al. |
| 2005/0144669 | A1 | 6/2005 | Reinhart et al. |
| 2005/0197253 | A1 | 9/2005 | Stoller et al. |
| 2005/0251883 | A1 | 11/2005 | Amasino et al. |
| 2006/0200878 | A1 | 9/2006 | Lutfiyya et al. |
| 2006/0253933 | A1 | 11/2006 | Brown et al. |
| 2007/0174931 | A1 | 7/2007 | Brown et al. |
| 2007/0294789 | A1 | 12/2007 | Ghiglione et al. |
| 2008/0034453 | A1 | 2/2008 | Cheikh et al. |
| 2009/0031441 | A1 | 1/2009 | Matsuoka et al. |
| 2009/0070898 | A1 | 3/2009 | Allen et al. |
| 2009/0117617 | A1 | 5/2009 | Holmes et al. |
| 2009/0313725 | A1 | 12/2009 | Yu et al. |
| 2010/0095406 | A1 | 4/2010 | Yu et al. |
| 2010/0107283 | A1 | 4/2010 | Dasgupta et al. |
| 2011/0004958 | A1 | 1/2011 | Aloni et al. |
| 2011/0035839 | A1 | 2/2011 | Lutfiyya et al. |
| 2011/0126310 | A1 | 5/2011 | Feng et al. |
| 2011/0145940 | A1 | 6/2011 | Voytas et al. |
| 2011/0167517 | A1 | 7/2011 | Danilevskaya et al. |
| 2011/0185456 | A1 | 7/2011 | Cheikh et al. |
| 2011/0296555 | A1 | 12/2011 | Ivashuta et al. |
| 2011/0301073 | A1 | 12/2011 | Gregory et al. |
| 2012/0142062 | A1 | 6/2012 | Doyon et al. |
| 2012/0174260 | A1 | 7/2012 | Narva et al. |
| 2012/0216318 | A1 | 8/2012 | La Rosa et al. |
| 2012/0297501 | A1 | 11/2012 | Beghyn et al. |
| 2013/0117869 | A1 | 5/2013 | Duchateau et al. |
| 2013/0121101 | A1 | 5/2013 | Ochampaugh et al. |
| 2013/0260012 | A1 | 10/2013 | Rommens et al. |
| 2013/0283461 | A1 | 10/2013 | Abad et al. |
| 2013/0345937 | A1 | 12/2013 | Strelioff et al. |
| 2014/0013464 | A1 | 1/2014 | Davie |
| 2014/0074360 | A1 | 3/2014 | Rosa et al. |
| 2014/0165228 | A1 | 6/2014 | Danilevskaya et al. |
| 2014/0344996 | A1 | 11/2014 | Inze et al. |
| 2014/0359836 | A1* | 12/2014 | Wu .................... C12N 15/8274 536/23.6 |
| 2015/0052634 | A1 | 2/2015 | Park et al. |
| 2015/0201619 | A1 | 7/2015 | Annigeri et al. |
| 2015/0247154 | A1 | 9/2015 | Ivashuta et al. |
| 2015/0307889 | A1 | 10/2015 | Petolino et al. |
| 2015/0376641 | A1 | 12/2015 | Etzioni et al. |
| 2016/0010109 | A1 | 1/2016 | Albertsen et al. |
| 2016/0017349 | A1 | 1/2016 | Ayele et al. |
| 2016/0046956 | A1 | 2/2016 | Yu et al. |
| 2016/0050865 | A1 | 2/2016 | Morse et al. |
| 2016/0050920 | A1 | 2/2016 | Ott et al. |
| 2016/0076046 | A1 | 3/2016 | Alexandrov et al. |
| 2016/0319375 | A1 | 11/2016 | Barten et al. |
| 2017/0079224 | A1 | 3/2017 | Jolliffe et al. |
| 2018/0051295 | A1* | 2/2018 | Allen ................. C12N 15/8261 |
| 2019/0014730 | A1 | 1/2019 | Dong et al. |
| 2019/0014731 | A1 | 1/2019 | Ovadya et al. |
| 2019/0241903 | A1 | 8/2019 | Ellis et al. |
| 2019/0246586 | A1 | 8/2019 | Cannon et al. |
| 2019/0246619 | A1 | 8/2019 | Barten et al. |
| 2021/0032649 | A1 | 2/2021 | Manjunath et al. |
| 2022/0159905 | A1 | 5/2022 | Barten et al. |
| 2022/0159919 | A1 | 5/2022 | Cannon et al. |
| 2022/0162632 | A1 | 5/2022 | Barten et al. |
| 2022/0364108 | A1 | 11/2022 | Allen et al. |
| 2023/0110884 | A1 | 4/2023 | Allen et al. |
| 2023/0292733 | A1 | 9/2023 | Barten et al. |
| 2023/0323381 | A1 | 10/2023 | Cannon et al. |
| 2025/0221340 | A1 | 7/2025 | Barten et al. |
| 2025/0277194 | A1 | 9/2025 | Allen et al. |
| 2026/0015625 | A1 | 1/2026 | Cannon et al. |
| 2026/0083046 | A1 | 3/2026 | Barten et al. |
| 2026/0144184 | A1 | 5/2026 | Cannon et al. |

FOREIGN PATENT DOCUMENTS

| | | | |
|---|---|---|---|
| CN | 102174519 | | 9/2011 |
| CN | 111778265 | | 10/2020 |
| CN | 112626113 | | 4/2021 |
| EP | 1398382 | B1 | 11/2005 |
| JP | 3829157 | B2 | 10/2006 |
| KR | 20150045611 | | 4/2015 |
| RU | 2013135491 | | 2/2015 |
| RU | 2013151447 | | 5/2015 |
| WO | 199428141 | | 12/1994 |
| WO | 199909174 | | 2/1999 |
| WO | 199966029 | A2 | 12/1999 |
| WO | 2000009722 | A2 | 2/2000 |
| WO | 2002055725 | A2 | 7/2002 |
| WO | 2003008540 | A2 | 1/2003 |
| WO | 2004092390 | | 10/2004 |
| WO | 2006032916 | A2 | 3/2006 |
| WO | 2007134234 | | 11/2007 |
| WO | 2008034648 | | 3/2008 |
| WO | 2010002984 | | 1/2010 |
| WO | 2011023537 | | 3/2011 |
| WO | 2013037959 | | 3/2013 |
| WO | 2013086499 | A2 | 6/2013 |
| WO | 2014055477 | A2 | 4/2014 |
| WO | 2014151749 | | 9/2014 |
| WO | 2015168124 | | 11/2015 |
| WO | 2016176286 | A1 | 11/2016 |
| WO | 2017011791 | A1 | 1/2017 |
| WO | 2018035354 | A1 | 2/2018 |
| WO | 2018119225 | A1 | 6/2018 |
| WO | 2018129302 | A1 | 7/2018 |
| WO | 2019161143 | A1 | 8/2019 |
| WO | 2019161145 | A2 | 8/2019 |
| WO | 2019161149 | A1 | 8/2019 |

OTHER PUBLICATIONS

International Search Report and Written Opinion mailed Apr. 22, 2020, in International Application No. PCT/US2019/064270, pp. 1-14.

"4 Series Sprayers," Published in May 2016, obtained from https://www.deere.com/en_CAF/docs/product/equipment/4_Series_Sprayers.pdf (2016).

Amanullah et al., "Phenology, Growth, and Grain Yield of Maize as Influenced by Foliar Applied Urea at Different Growth Stages," Journal of Plant Nutrition 33:1; 71-79 (2010).

"Corn Herbicide Application Timings," published by online by PennState Extension; obtained from https://extension.psu.edu/corn-herbicide- application-timings (2015).

Crommelinck et al., "Simulating an Autonomously Operating Low-Cost Static Terrestrial LiDAR for Multitemporal Maize Crop Height Measurements," Remote Sensing, 8(3):205, pp. 1-17 (2016).

D'Andrea et al., "Genotypic Variability in Morphological and Physiological Traits among Maize Inbred Lines-Nitrogen Responses," Crop Sci., 46:1266-1276 (2006).

(56) References Cited

OTHER PUBLICATIONS

GenBank Accession No. AY366085, "*Zea mays* cultivar B73 PGP1 (pgp1) gene, complete cds" (2003).
International Search Report and Written Opinion mailed Aug. 8, 2019, in International Application No. PCT/US2019/018129.
International Search Report and Written Opinion mailed May 10, 2019, in International Application No. PCT/US2019/018127.
Kempton, "Heritable Characters of Maize, III. Brachytic Culms," Jour. Hered., 11(1):111-115 (1920).
Lu, "Chapter 3 Research on Production Increase Technology in Late Harvesting of Maize in Optimum Period," Theory and Technology of High Yield of Maize (2015).
Mourtzinis et al., "Corn Grain and Stover Yield Prediction at RI Growth Stage," Agronomy Journal, 105 (4):1045-1050 (2013).
Multani et al., "Loss of an MDR Transporter in Compact Stalks of Maize br2 and Sorghum dw3 Mutants," Science, 302:81-84 (2003).
Pilu et al., "Isolation and characterization of a new mutant allele of brachytic 2 maize gene," Molecular Breeding, 20:83-91 (2007).
Qiao et al., "The influence of RNAi targeting of OsGA20ox2 gene on plant height in rice," Plant Molecular Biology Reporting 29.4:952-960 (2011).
Wang et al., "Analysis of hormone sensitivity of a dwarf mutant of maize," Journal of Northwest A&F University (Nat. Sci. Ed.) 45(8) (2017).
Weng et al., "Genome-Wide Association Study Identifies Candidate Genes That Affect Plant Height in Chinese Elite Maize (*Zea mays* L.) Inbred Lines," PLOS One 6(12) (2011).
Zaidi et al., "Phenotyping for Abiotic Stress Tolerance in Maize Heat Stress," CIMMYT, pp. 1-40 (2016).
Butzen, "Timing Corn Harvest," Crop Insights, (Sep. 2018).
Chen et al., "Identification and genetic mapping for rht-DM, a dominant dwarfing gene in mutant semi-dwarf maize using QTL-seq approach," Genes & Genomics 40, pp. 1091-1099 (Jun. 2018) (electronic publication).
Supplementary European Search Report dated Oct. 11, 2022 in EP 19 89 2688.
Thomison et al., "Corn Response to Harvest Date a Affected by Plant Population and Hybrid," Agron J. 103, pp. 1765-1772 (Sep. 2011) (electronic publication).
Altschul, "Basic local alignment search tool." Journal of Molecular Biology, 15:403-410 (1990).
Xia et al., "A book to understand high corn yield and disaster prevention and reduction technology", China Farmers Press, May 2016, p. 135.
Chinese Office Action regarding Chinese Patent Application No. 201980025083.0, dated Dec. 1, 2023, 19 pages.
Chenna, et al., "Multiple sequence alignment with the Clustal series of programs," Nucleic Acids Research, 31(13):3497-3500 (2003).
De Pater, et al., "The promoter of the rice gene GOS2 is active in various different monocot tissues and binds rice nuclear factor ASF-1," The Plant Journal, 2(6): 837-844 (1992).
Elmore, et al., "In-Field Drydown Rates and Harvest," Iowa State University Extension and Outreach, retrieved from <https://crops.extension.iastate.edu/cropnews/2010/09/field-drydown-rates-and-harvest> (Sep. 28, 2010).
Guo, et al., "RNA Silencing in Plants: Mechanism, Technologies and Applications in Horticulture Crops," Current Genomics, 17(6):476-489 (2016).
Hanway, "How a corn plant develops," Special Report No. 48, Iowa State University, CES, Ames, IA, (1966).
Inada, "Quality controls induced by aberrant translation," Nucleic Acids Research, 48(3): 1084-1096 (2020).
Israelsen, "Harvesting Corn Silage by Plant Moisture" article adapted from Crop and Soils Magazine, Utah State University Agricultural Extension Agents, (2009). Retrieved from <https://digitalcommons.usu.edu/cgi/viewcontent.cgi?article=1145&context=extension_curall>.
Karamyshev, et al., "Lost in Translation: Ribosome-Associated mRNA and Protein Quality Controls," Frontiers in Genetics, 9:431 (2018).
Larkin, et al., "Clustal W and Clustal X version 2.0," Bioinformatics, 23(21): 2947-48 (2007).
Last, et al., "pEmu: an improved promoter for gene expression in cereal cells," Theoretical and Applied Genetics, 81: 581-588 (1991).
Mcelroy, et al., "Construction of expression vectors based on the rice actin 1 (Actl) 5' region for use in monocot transformation," Molecular and General Genetics MGG, 231: 150-160 (1991).
Nickless, et al., "Control of gene expression through the nonsense-mediated RNA decay pathway," Cell & Bioscience, 7:26 (2017).
Ritchie, S.W. et al., "How a Corn Plant Develops," Special Report No. 48, Iowa State University, CES, Ames, IA, Reprinted 1986.
Spelhaug, "Predicting Your Corn Harvest Date," Peterson Farms Seed (2013).
Szadeczky-Kardoss, et al., "The nonstop decay and the RNA silencing systems operate cooperatively in plants," Nucleic Acids Research, 46(9): 4632-4648 (2018).
Thompson, et al., "Clustal W: Improving the sensitivity of progressive multiple sequence alignment through sequence weighting, position-specific gap penalties and weight matrix choice," Nucleic Acids Research, 22: 4673-4680 (1994).
Wilson, et al., "Molecular Mechanisms of RNA Interference," Annual Review of Biophysics, 42: 217-39 (2013).
Bage et al., Genetic characterization of novel and CRISPR-Cas9 gene edited maize brachytic 2 alleles, Plant Gene 21:100198, 2020.
Bolduc and Hake, The maize transcription factor KNOTTED1 directly regulates the gibberellin catabolismgene ga2ox1, Plant Cell 21:1647-1658, 2009.
R4038-sprayer by John Deere, available at https://kibbleeq.com/farmers/sprayers-&-applicators/self-propelled-sprayers/john-deere-sprayers/r4038-sprayer, accessed Apr. 29, 2024.
Sun et al., Identification and characterization of EI (Elongated Internode) gene in tomato (*Solanum lycopersicum*), Int. J. Mol. Sci. 20(2204):1-18, 2019.
Anonymous, Proceedings of the Caribbean Food Crops Society Fourth Annual Meeting, 1996.
Sehgal. "Inbred-Hybrid Method of Maize Improvement." Proceeding of the Caribbean Food Crops Society Fourth Annual Meeting, 1966.
John Deere Self Propelled Application Equipment (Brochure), accessed at https://johndeere.widen.net/s/xrvsnpcgcn/201806_dssa73528-sprayer_applicator-folder, 2018.
U.S. Appl. No. 19/425,440, filed Dec. 18, 2025, Cannon et al.
Hill and Furrow, "Pinch or Push Your Corn: Scouting for Lodging Potential", University of Illinois Urbana-Champaign, Illinois Extension, Sep. 12, 2016, 2 pages.
Cox, et al., "Row Spacing, Hybrid, and Plant Density Effects on Corn Silage Yield and Quality"; J. Prod. Agic, vol. 11, No. 1, 1998.
Pendleton, et al., "Plant Population and Row Spacing Studies with brachytic 2 Dwarf Corn"; Contribution from the Department of Agronomy, Illinois Agr. Exp. Sta., Urbana, III; pp. 433-435, 1961.
Begna, et al., "Effects of Population Density and Planting Pattern on the Yield and Yield Components of Leafy Reduced-Stature Maize in a Short-Season Area"; J. Agronomy & Crop Science 179, pp. 9-17; 1997.
Cox, et al., "Corn Silage and Grain Yield Responses to Plant Densities"; J. Prod. Agric, vol. 10, No. 3, pp. 405-410, 1997.
Abendroth & Elmore, presentation titled "Corn Growth and Development" available at https://www.ipm.iastate.edu/files/curriculum/03%20Corn%20Growth%20and%20Development_0.pdf, accessed Feb. 12, 2025.
Jayasundara et al., Energy and Greenhouse Gas Intensity of Corn (*Zea Mays* L.) Production in Ontario: a Regional Assessment, Can J. Soil Sci. 94:77-95, 2014.
Lindsey & Zoller, Useful Tables: Adjustments and Conversions on Corn and Soybean Parameters, article on the Ohio State University Extension website https://ohioline.osu.edu/factsheet/agf-502, 2018.
Nielsen, Short Corn at Tasseling, article for Purdue Agronomy available at https://www.agry.purdue.edu/ext/corn/news/articles.01/short_corn-0712.html, 2001.
GenBank AJ132435. "*Arabidopsis thaliana* mRNA for GA 2-oxidase, gene ga20x1" Dated 1999. Retrieved from: <https://www.ncbi.nlm.nih.gov/nuccore/AJ132435>.

(56) References Cited

OTHER PUBLICATIONS

Xing, et al. "A rare SNP mutation in Brachytic2 moderately reduces plant height and increases yield potential in maize." Journal of Experimental Botany, vol. 66, Issue 13, pp. 3791-3802, (2015).
Thomas, et al. "Size constraints for targeting post-transcriptional gene silencing and for RNA-directed methylation in Nicotiana benthamiana using a potato virus X vector." The Plant Journal, vol. 25(4), pp. 417-425, (2001).
Macrobert, et al. "Maize Hybrid Seed Production Manual." International Maize and Wheat Improvement Center. (2014).
Haegele, et al. "Row Arrangement, Phosphorus Fertility, and Hybrid Contributions to Managing Increased Plant Density of Maize." Agronomy, vol. 106(5), pp. 1838-1846, (2014).
Guo, et al. "Protein tolerance to random amino acid change." Proc. Natl. Acad. Sci. U.S.A., vol. 101 (25), pp. 9205-9210, (2004).
U.S. Appl. No. 19/337,629, filed Sep. 23, 2025, Cannon et al.
U.S. Appl. No. 19/367,230, filed Oct. 23, 2025, Barten et al.
Liu, et al., "Analysis of Complementarity Requirements for Plant MicroRNA Targeting Using a Nicotiana benthamiana Quantitative Transient Assay," The Plant Cell, 26(2):741-753 (2014).
Mitchum, et al., "Distinct and overlapping roles of two gibberellin 3-oxidases in *Arabidopsis* development," The Plant Journal, 45(5):804-818 (2006).
Molina, et al., "Transformation of a Dwarf Arabidopsis Mutant Illustrates Gibberellin Hormone Physiology and the Function of a Green Revolution Gene," Biochemistry and Molecular Biology Education, 37(3): 170-177 (2009).
Mutasa-Gottgens, et al., "Gibberellin as a factor in floral regulatory networks," Journal of Experimental Botany, 60 (7):1979-1989 (2009).
Offtype—Definition of Offtype by Merriam-Webster, pp. 1, retrieved Sep. 18, 2023 <https://www.merriam-webster.com/dictionary/offtype>.
Oikawa, et al., "A role of OsGA20Ox1, encoding an isoform of gibberellin 20-oxidase, for regulation of plant stature in rice," Plant Molecular Biology, 55:687-700 (2004).
Ookawa, et al., "Precise estimation of genomic regions controlling lodging resistance using a set of reciprocal chromosome segment substitution lines in rice," Scientific Reports, 6(30572) pp. 1-12 (2016).
Parizotto, et al., "In vivo investigation of the transcription, processing, endonucleolytic activity, and functional relevance of the spatial distribution of a plant miRNA," Genes & Development, 18:2237-2242 (2004).
Peiffer, et al., "The Genetic Architecture Of Maize Height," Genetics, 196(4):1337-1356 (2014).
Peng, et al., "'Green revolution' genes encode mutant gibberellin response modulators," Nature, 400:256-261 (1999).
Petti, et al., "Mapping of a Cellulose-Deficient Mutant Named dwarf1-1 in Sorghum bicolor to the Green Revolution Gene gibberellin20-oxidase Reveals a Positive Regulatory Association between Gibberellin and Cellulose Biosynthesis," Plant Physiology, 169(1):705-716 (2015).
Plackett, et al., "Analysis of the Developmental Roles of the *Arabidopsis* Gibberellin 20-Oxidases Demonstrates That GA20Ox1, -2, and -3 Are the Dominant Paralogs," The Plant Cell, 24(3):941-960 (2012).
Qiao, et al., "Alteration of rice growth and development via antisense expression of OsGA20ox2 gene," African Journal of Biotechnology, 12(5):3898-3904 (2013).
Qiao, et al., "Modification of plant height via RNAi suppression of OsGA20ox2 gene in rice," Euphytica, 158-35-45 (2007).
Reynolds, et al., "Rational siRNA design for RNA interference," Nature Biotechnology, 22(3):326-330 (2004).
Rhoades, et al., "Prediction of Plant MicroRNA Targets," Cell, 110(4):513-520 (2002).
Rieu, et al., "The gibberellin biosynthetic genes AtGA20ox1 and AtGA20ox2 act, partially redundantly, to promote growth and development throughout the *Arabidopsis* life cycle," The Plant Journal, 53 :488-504 (2008).
Ross, et al., "Gibberellin mutants," Physiologia Plantarum, 100(3):550-560 (1997).
Sarkar, et al., "Relationship between gibberellins, height, and stress tolerance in barley (*Hordeum vulgare* L.) seedlings," Plant Growth Regulation, 42: 125-135 (2004).
Sasaki, et al., "A mutant gibberellin-synthesis gene in rice," Nature, 416:701-702 (2002).
Russian Search Report dated Jun. 24, 2021, in Russian Patent Application 2019105536, and English translation of the same (pp. 1-4).
Singh, "The green revolution and the evolution of agricultural education and research in India," Genome, 42 (4):557-561 (1999).
Song, et al., "Association of the molecular regulation of ear leaf senescence/stress response and photosynthesis/metabolism with heterosis at the reproductive stage in maize," Scientific Reports, 6: 29843 (2016).
Song, et al., "Flowering time regulation: photoperiod- and temperature-sensing in leaves," Trends in Plant Science, 18(10):575-583 (2013).
Song, et al., "Genome-wide identification of gibberellins metabolic enzyme genes and expression profiling analysis during seed germination in maize," Gene, 482(1-2):34-42 (2011).
Spielmeyer, et al., "Semidwarf (sd-1), "green revolution" rice, contains a defective gibberellin 20-oxidase gene," PNAS, 99(13):9043-9048 (2002).
Sun, "Gibberellin Metabolism, Perception and Signaling Pathways in *Arabidopsis*," The *Arabidopsis* Book, 2008(6): pp. 1-28 (2008).
Sunkar, et al., "Novel and Stress-Regulated MicroRNAs and Other Small RNAs from *Arabidopsis*," Plant Cell, 16 (8):2001-2019 (2004).
Supplementary Partial European Search Report dated Jan. 14, 2020, in European Patent Application No. 17842139.2.
Svitashev, et al., "Targeted Mutagenesis, Precise Gene Editing, and Site-Specific Gene Insertion in Maize Using Cas9 and Guide RNA," Plant Physiology, 169(2):931-945 (2015).
Teng, et al., "ZmGA3ox2, a candidate gene for a major QTL, qPH3.1, for plant height in maize," The Plant Journal, 73 (3):405-416 (2013).
Tollenaar, et al., "Effect of Defoliation on Kernel Development in Maize," Canadian Journal of Plant Science, 58 (1):207-212 (1978).
Tong, et al., "Reply: Brassinosteroid Regulates Gibberellin Synthesis to Promote Cell Elongation in Rice: Critical Comments on Ross and Quittenden's Letter," The Plant Cell, vol. 28, pp. 833-835, (2016).
Traore, et al., "Bt and Non-Bt Maize Growth and Development as Affected by Temperature and Drought Stress," Agronomy Journal, 92(5): 1027-1035 (2000).
Unterholzner, et al., "Reply: Interaction Between Brassinosteroids and Gibberellins: Synthesis or Signaling? In *Arabidopsis* Both!," The Plant Cell, vol. 28, pp. 836-839, (2016).
Urakami, et al., "Immunomodulation of gibberellin biosynthesis using an anti-precursor gibberellin antibody confers gibberellin-deficient phenotypes," Planta, 228:863-873 (2008).
Voytas, "Plant Genome Engineering with Sequence-Specific Nucleases," Annual Review of Plant Biology, 64:327-50 (2013).
Wang, et al., "Gibberellin Biosynthetic Deficiency Is Responsible for Maize Dominant Dwarf11 (D11) Mutant Phenotype: Physiological and Transcriptomic Evidence," PLoS One, 8(6):e66466:1-8 (2013).
Wang, et al., "More than meets the eye? Factors that affect target selection by plant miRNAs and heterochromatic siRNAs," Current Opinion Plant Biology, 27:118-124 (2015).
Wu, et al., "Target specificity of the CRISPR-Cas9 system," Quantitative Biology, 2(2):59-70 (2014).
Xiao, et al., "Dissection of GA 20-oxidase members affecting tomato morphology by RNAi-mediated silencing," Plant Growth Regulation, 50:179-189 (2006).
Yamaguchi, et al., "Gibberellin Acts Positively Then Negatively to Control Onset of Flower Formation in *Arabidopsis*," Science, 344(6184):638-641 (2014).
Yamaguchi, "Gibberellin Metabolism and its Regulation," Annual Review of Plant Biology, 59:225-251 (2008).
Yanik, et al., "TALE-PvuII Fusion Proteins—Novel Tools for Gene Targeting," PLoS One, 8(12):e82539 pp. 1-13 (2013).

(56) References Cited

OTHER PUBLICATIONS

Yin, et al., “In-Season Prediction of Com Yield Using Plant Height under Major Production Systems,” Agronomy Journal, 103(3):923-929 (2011).
Yoshikawa, et al., “A pathway for the biogenesis of trans-acting siRNAs in *Arabidopsis*,” Genes & Development, 19:2164-2175 (2005).
Zeng, et al., “Both Natural and Designed Micro RNAs Can Inhibit the Expression of Cognate mRNAs When Expressed in Human Cells,” Molecular Cell, 9(6): 1327-1333 (2002).
Invitation to Pay Additional Fees for Application No. PCT/US23/62985, mailed May 23, 2023.
Klahre, et al. “High molecular weight RNAs and small interfering RNAs induce systemic posttranscriptional gene silencing in plants.” Proc. Natl. Acad. Sci. U.S.A., 99 (18) 11981-11986, (2002).
Chen, et al. “Development of dwarfish and yield-effective GM maize through passivation of bioactive gibberellin.” Transgenic Res, 28:589-599, (2019).
Köllner, et al. “Herbivore-Induced SABATH Methyltransferases of Maize that Methylate Anthranilic Acid Using S-Adenosyl-L-Methionine.” Plant Physiology, vol. 153, pp. 1795-1807, (2010).
Zhang, et al. “Maize brachtic2 (br2) suppresses the elongation of lower internodes for excessive auxin accumulation in the intercalary meristem region.” BMC Plant Biology, 19:589, (2019).
Search Report dated Jul. 21, 2022, in Chinese Application 2017800639820 including English translation of related Office Action.
Allen, et al., “Evolution of microRNA genes by inverted duplication of target gene sequences in *Arabidopsis thaliana*,” Nature Genetics, 36:1282-1290 (2004).
Allen, et al., “microRNA-directed phasing during Trans-acting siRNA Biogenesis in plants,” Cell, 121(2):207-221 (2005).
Altschul, et al., “Gapped BLAST and PSI-BLAST: a new generation of protein database search programs,” Nucleic Acids Research, 25 (17) : 3389-3402 (1997).
Ashikari, et al., “Loss-of-function of a Rice Gibberellin Biosynthetic Gene, GA20 oxidase (GA20ox-2), Led to the Rice ‘Green Revolution’,” Breeding Science, 52:143-150 (2002).
Axtell, et al., “A Two-Hit Trigger for siRNA Biogenesis in Plants,” Cell, 127:565-577 (2006).
Beurdeley, et al., “Compact designer TALENs for efficient genome engineering”, Nature Communications, 4: 1762 (2013).
Cai, et al., “Molecular Cloning, Characterization, and Expression Analysis of Genes Encoding Gibberellin 20-Oxidase in Dasypyrum villosum Dwarf Mutant,” Plant Molecular Biology Reporter, 30:1110-1116 (2012).
Carrera, et al.,“ Changes in GA 20-oxidase gene expression strongly affect stem length, tuber induction and tuber yield of potato plants,” The Plant Journal, 22(3):247-256 (2000).
Cermak, et al., “Efficient design and assembly of custom TALEN and other TAL effector-based constructs for DNA targeting,” Nucleic Acids Research, 39(12):e82 (2011).
Chen, et al., “Identification and Functional Analysis of Flowering Related microRNAs in Common Wild Rice (*Oryza rufipogon* Griff.),” PLoS ONE, 8:e82844 (2013).
Chen, et al., “New insight in the Gibberellin biosynthesis and signal transduction,” Plant Signaling & Behavior, 10(5): e1000140-1-e1000140-3:(2015).
Chen, et al., “The Maize DWARF1 Encodes a Gibberellin 3-Oxidase and Is Dual Localized to the Nucleus and Cytosol,” Plant Physiology, 166:2028-2039 (2014).
Ciampitti, et al., “A comprehensive study of plant density consequences on nitrogen uptake dynamics of maize plants from vegetative to reproductive stages,” Field Crops Research, 121(1):2-18 (2011).
Coles, et al., “Modification of gibberellin production and plant development in *Arabidopsis* by sense and antisense expression of gibberellin 20-oxidase genes,” The Plant Journal, 17 (5):547-556 (1999).
Davis, et al., “Gibberellin Biosynthesis in Maize. Metabolic Studies with GA15, GA24, GA25, GA7, and 2,3-Dehydro-GA91,” Plant Physiology, 121(3):1037-1045 (1999).
Doyle, et al., “TAL Effector-Nucleotide Targeter (TALE-NT) 2.0: tools for TAL effector design and target prediction,” Nucleic Acids Research, 40:W117-122 (2012).
Du, et al., “Cloning and characterization of an up-regulated GA 20-oxidase gene in hybrid maize,” Natural Science, 19 (2):161-166 (2009).
Eriksson, et al., “GA4 Is the Active Gibberellin in the Regulation of LEAFY Transcription and *Arabidopsis* Floral Initiation,” The Plant Cell, 18(9):2172-2181 (2006).
Extended European Search Report dated Mar. 9, 2020, in European Patent Application No. 17842139.2.
Fagoaga, et al., “Engineering of gibberellin levels in citrus by sense and antisense overexpression of a GA 20-oxidase gene modifies plant architecture,” Journal of Experimental Botany, 58(6):1407-1420 (2007).
Fambrini, et al., “The extreme dwarf phenotype of the GA-sensitive mutant of sunflower, dwarf2, is generated by a deletion in the ent-kaurenoic acid oxidase1 (HaKAO1) gene sequence,” Plant Molecular Biology, 75:431-450 (2011).
Franco-Zorrilla, et al., “Target mimicry provides a new mechanism for regulation of microRNA activity,” Nature Genetics, 39: 1033-1037 (2007).
Gabsalilow, et al., “Site- and strand-specific nicking of DNA by fusion proteins derived from MutH and I-Scel or TALE repeats,” Nucleic Acids Research, 41(7):e83 (2013).
Gaj, et al . . . “ZFN, TALEN, and CRISPR/Cas-based methods for genome engineering,” Trends Biotechnology, 31 (7):397-405 (2013).
GenBank Accession No. AY105651.1, “*Zea mays* PC0130567 mRNA sequence,” pp. 1-2, dated May 28, 2008.
GenBank Accession No. BT068785.2, “*Zea mays* full-length cDNA clone ZM_BFb0382B03 mRNA, complete cds,” pp. 1-2, dated Jun. 15, 2012.
GenBank Accession No. EU963664.1, “*Zea mays* clone 265382 gibberellin 20 oxidase 2 mRNA, complete cds,” pp. 1, dated Dec 10, 2008.
Griffiths-Jones, et al., “Rfam: an RNA family database,” Nucleic Acids Research, 31(1):439-441 (2003).
Gupta, et al., “Gibberellic acid in plant Still a mystery unresolved,” Plant Signaling & Behavior, 8(9):e25504 (2013).
Han, et al., “Gibberellin-associated cisgenes modify growth, stature and wood properties in Populus,” Plant Biotechnology Journal, 9(2):162-178 (2011).
Hedden, et al., “Gibberellin Biosynthesis: Enzymes, Genes and Their Regulation,” Annu. Rev. Plant Physiol. Plant Mol. Biol., 48:431-60 (1997).
Hedden, “The genes of the Green Revolution,” Trends in Genetics, 19(1):5-9 (2003).
Helliwell, et al “Constructs and Methods for Hairpin RNA-Mediated Gene Silencing in Plants,” Methods in Enzymology, 392:24-35 (2003).
Huang, et al., “A Gibberellin-Mediated DELLA-NAC Signaling Cascade Regulates Cellulose Synthesis in Rice,” The Plant Cell, 27(6):1681-1696 (2015).
International Search Report and Written Opinion mailed Dec. 28, 2017, in International Application No. PCT/US2017/047405.
Jia, et al., “GA-20 oxidase as a candidate for the semidwarf gene sdw1/denso in barley,” Functional & Integrative Genomics, 9:255-262 (2009).
Jia, et al., “Molecular characterization and functional analysis of barley semi-dwarf mutant Riso No. 9265,” BMC Genomics, 16(927):1-11 (2015).
Jones-Rhoades, et al., “Computational Identification of Plant MicroRNAs and Their Targets, Including a Stress-Induced miRNA,” Molecular Cell, 14(6):787-799 (2004).
Kamthan, et al., “Small RNAs in plants: recent development and application for crop improvement” Frontiers in Plant Science, 6:1-17 (2015).
Katoh, et al., “Specific residues at every third position of siRNA shape its efficient RNAi activity,” Nucleic Acids Research, 35(4):e27 (2007).

(56) References Cited

OTHER PUBLICATIONS

Khvorova, et al., "Functional siRNAs and miRNAs Exhibit Strand Bias," Cell, 115(2):209-216 (2003).
Kim, "MicroRNA Biogenesis: Coordinated Cropping and Dicing," Nature Reviews Molecular Cell Biology, 6:376-385 (2005).
King, et al., "Selective Deactivation of Gibberellins below the Shoot Apex is Critical to Flowering but Not to Stem Elongation of Lolium," Molecular Plant, 1(2):295-307 (2008).
Kobayashi, et al., "Gibberellin Metabolism in Maize (The Stepwise Conversion of Gibberellin A12-Aldehyde to Gibberellin A20)," Plant Physiology, 110(2):413-418 (1996).
Kusaba, et al., "Isolation and expression analysis of gibberellin 20-oxidase homologous gene in apple," Journal of Experimental Botany, 52(335):375-376 (2001).
Lange, et al., "Gibberellin Biosynthesis and the Regulation of Plant Development," Plant Biology, 8(3):281-290 (2006).
USPTO: Final Office Action regarding U.S. Appl. No. 17/530,873, mailed Jul. 31, 2025.
Elmore, et al. "How fast can corn dry down?" Iowa State University Extension and Outreach, Sep. 13, 2007, accessed from <https://crops.extension.iastate.edu/encyclopedia/how-fast-can-corn-dry-down>.
Silva, et al. "Adaptability and stability of corn hybrids grown from high grain yield." Acta Scientiarum, Agronomy, Maringa, V. 36, n.2, p. 175-181, (2014).
Gou et al., Tissue-specific expression of Populus C19 Ga 2-oxidases differentially regulate above- and below-ground 1 biomass growth through control of bioactive GA concentrations, New Phytologist, 2011.
Extended European Search Report regarding European App. No. 23760857.5, dated Apr. 17, 2026.

* cited by examiner

METHODS AND COMPOSITIONS FOR SHORT STATURE PLANTS THROUGH MANIPULATION OF GIBBERELLIN METABOLISM TO INCREASE HARVESTABLE YIELD

CROSS-REFERENCE TO RELATED APPLICATIONS

This application is a 371 National Stage application of International Application No. PCT/US2023/062985 filed Feb. 22, 2023 which claims the priority of U.S. Provisional Appl. Ser. No. 63/312,703, filed Feb. 22, 2022, the entire disclosure of which are incorporated herein by reference.

INCORPORATION OF SEQUENCE LISTING

The sequence listing file named "MONS550WO_ST26", which is 332 kilobytes in size (measured in MS-WINDOWS) and was created on Feb. 21, 2023, is submitted herewith and incorporated herein by reference in its entirety.

BACKGROUND

Field

The present disclosure relates to compositions and methods for improving traits, such as lodging resistance and increased yield, in monocot or cereal plants including corn.

Related Art

Gibberellins (gibberellic acids or GAs) are plant hormones that regulate a number of major plant growth and developmental processes. Manipulation of GA levels in semi-dwarf wheat, rice and *Sorghum* plant varieties led to increased yield and reduced lodging in these cereal crops during the 20th century, which was largely responsible for the Green Revolution. However, successful yield gains in other cereal crops, such as corn, have not been realized through manipulation of the GA pathway. Indeed, some mutations in the GA pathway genes have been associated with various off-types in corn that are incompatible with yield, which has led researchers away from finding semi-dwarf, high-yielding corn varieties via manipulation of the GA pathway.

There is a need in the art for the development of monocot or cereal crop plants, such as corn, having increased yield and/or resistance to lodging.

DETAILED DESCRIPTION

Definitions

Figure 1:
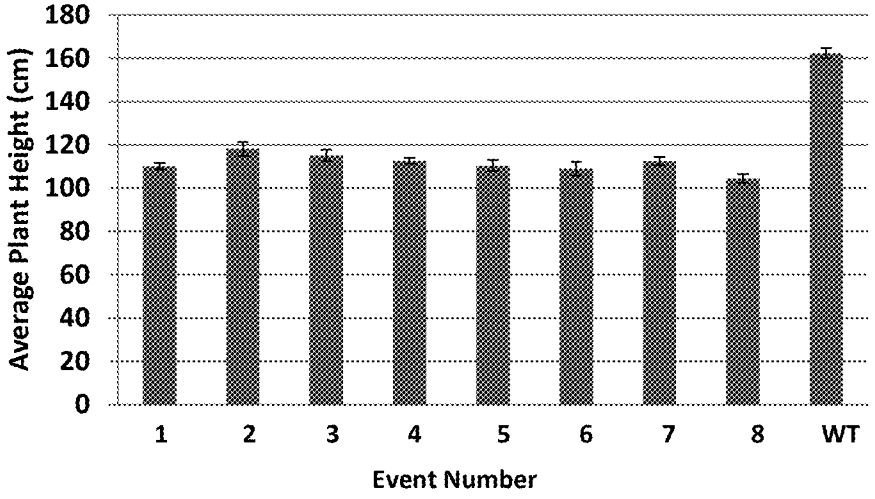
FIG. 1 shows reduced plant heights of corn inbred plants expressing a GA20 oxidase suppression construct across eight transformation events in comparison to inbred control plants.

To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

The term "cereal plant" as used herein refers a monocotyledonous (monocot) crop plant that is in the Poaceae or Gramineae family of grasses and is typically harvested for its seed, including, for example, wheat, corn, rice, millet, barley, *Sorghum*, oat and rye. As commonly understood, a "corn plant" or "maize plant" refers to any plant of species *Zea mays* and includes all plant varieties that can be bred with corn, including wild maize species.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity may be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pairwise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., "Multiple sequence alignment with the Clustal series of programs," *Nucleic Acids Research* 31:3497-3500 (2003); Thompson J D et al., "Clustal W: Improving the sensitivity of progressive multiple sequence alignment through sequence weighting, position-specific gap penalties and weight matrix choice," *Nucleic Acids Research* 22:4673-4680 (1994); and Larkin M A et al., "Clustal W and Clustal X version 2.0," *Bioinformatics* 23:2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

The term "plant-expressible promoter" refers to a promoter that can initiate, assist, affect, cause, and/or promote the transcription and expression of its associated transcribable DNA sequence, coding sequence or gene in a plant cell or tissue.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., may comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., may also refer to a polynucleotide or protein molecule or sequence that has been genetically engineered and/or constructed outside of a cell. For example, a recombinant DNA molecule may comprise any engineered or man-made plasmid, vector, etc., and may include a linear or circular DNA molecule. Such plasmids, vectors, etc., may contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more GA oxidase gene(s) relative to a wild-type or control plant, plant seed, plant part, plant cell, and/or plant genome, such as via (A) a transgenic event comprising a suppression construct or transcribable DNA sequence encoding a non-coding RNA that targets one or more GA3 and/or GA20 oxidase genes for suppression, or (B) a genome editing event or mutation affecting (e.g., reducing or eliminating) the expression level or activity of one or more endogenous GA3 and/or GA20 oxidase genes. Indeed, the term "modified" may further refer to a plant, plant seed, plant part, plant cell, and/or plant genome having one or more mutations affecting expression of one or more endogenous GA oxidase genes, such as one or more endogenous GA3 and/or GA20 oxidase genes, introduced through chemical mutagenesis, transposon insertion or excision, or any other known mutagenesis technique, or introduced through genome editing (i.e., a targeted genome editing technique). For clarity, therefore, a modified plant, plant seed, plant part, plant cell, and/or plant genome includes a mutated, edited and/or transgenic plant, plant seed, plant part, plant cell, and/or plant genome having a modified expression level, expression pattern, and/or coding sequence of one or more GA oxidase gene(s) relative to a wild-type or control plant, plant seed, plant part, plant cell, and/or plant genome. Modified plants or seeds may contain various molecular changes that affect expression of GA oxidase gene(s), such as GA3 and/or GA20 oxidase gene(s), including genetic and/or epigenetic modifications. Modified plants, plant parts, seeds, etc., may have been subjected to mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more GA oxidase genes. A modified seed provided herein may give rise to a modified plant provided herein. A modified plant, plant seed, plant part, plant cell, or plant genome provided herein may comprise a recombinant DNA construct or vector or genome edit as provided herein.

A “modified plant product” may be any product made from a modified plant, plant part, plant cell, or plant chromosome provided herein, or any portion or component thereof.

As used herein, the term “control plant” (or likewise a “control” plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgenic and/or genome editing event(s) affecting one or more GA oxidase genes. For example, a control plant may be an inbred line that is the same as the inbred line used to make the modified plant, or a control plant may be the product of the same hybrid cross of inbred parental lines as the modified plant, except for the absence in the control plant of any transgenic or genome editing event(s) affecting one or more GA oxidase genes. For purposes of comparison to a modified plant, plant seed, plant part, plant cell and/or plant genome, a “wild-type plant” (or likewise a “wild-type” plant seed, plant part, plant cell and/or plant genome) refers to a non-transgenic and non-genome edited control plant, plant seed, plant part, plant cell and/or plant genome. As used herein, a “control” plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, “locus” is a chromosomal or genomic locus or region where a polymorphic nucleic acid, trait determinant, gene, or marker is located. A “locus” can be shared by two homologous chromosomes to refer to their corresponding locus or region. As used herein, “allele” refers to an alternative nucleic acid sequence of a gene, or at a particular locus (e.g., a nucleic acid sequence of a gene or locus that is different than other alleles for the same gene or locus). Such an allele can be considered (i) wild-type, or (ii) mutant if one or more mutations or edits are present in the nucleic acid sequence of the mutant allele relative to the wild-type allele. As used herein, a “mutant gene” or “mutant allele” refers to a gene or allele having one or more mutations or edits in the nucleic acid sequence of the gene or allele relative to a wild-type gene or wild-type allele, wherein the mutant gene or mutant allele has a reduced and/or altered expression and/or a reduced and/or altered activity relative to a wild-type gene or wild-type allele. As used herein, a “wild-type gene” or “wild-type allele” refers to a gene or allele having a sequence or genotype that is most common in a particular plant species, or another sequence or genotype with natural variations, polymorphisms, or other silent mutations relative to the most common sequence or genotype that do not significantly impact the expression and activity of the gene or allele. Indeed, a “wild-type” gene or allele contains no variation, polymorphism, or any other type of mutation that substantially affects the normal function, activity, expression, or phenotypic consequence of the gene or allele. A mutant allele for a gene may be a loss-of-function allele and/or have a reduced or eliminated activity or expression level for the gene relative to the wild-type allele. A mutant allele may be a hypomorphic allele with a reduced activity and/or expression relative to the wild-type allele. A mutant allele may be a null allele with no activity and/or expression relative to the wild-type allele. A mutant allele of a gene or locus may have one or more mutations introduced into the gene or locus via any mutagenesis and/or targeted genome editing technique. For diploid organisms such as corn, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, a “target site” for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A “target site” for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A “target site” also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a “target region” or a “targeted region” refers to a polynucleotide sequence or region that is flanked by two or more target sites. Without being limiting, in some embodiments a target region may be subjected to a mutation, deletion, insertion or inversion. As used herein, “flanked” when used to describe a target region of a polynucleotide sequence or molecule, refers to two or more target sites of the polynucleotide sequence or molecule surrounding the target region, with one target site on each side of the target region. Apart from genome editing, the term “target site” may also be used in the context of gene suppression to refer to a portion of a mRNA molecule (e.g., a “recognition site”) that is complementary to at least a portion of a non-coding RNA molecule (e.g., a miRNA, siRNA, etc.) encoded by a suppression construct.

As used herein, a “donor molecule”, “donor template”, or “donor template molecule” (collectively a “donor template”), which may be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" may be used for site-directed integration of a transgene or suppression construct, or as a template to introduce a mutation, such as an insertion, deletion, etc., into a target site within the genome of a plant. A targeted genome editing technique provided herein may comprise the use of one or more, two or more, three or more, four or more, or five or more donor molecules or templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template.

An insertion sequence of a donor template may comprise one or more genes or sequences that each encode a transcribed non-coding RNA or mRNA sequence and/or a translated protein sequence. A transcribed sequence or gene of a donor template may encode a protein or a non-coding RNA molecule. An insertion sequence of a donor template may comprise a polynucleotide sequence that does not comprise a functional gene or an entire gene sequence (e.g., the donor template may simply comprise regulatory sequences, such as a promoter sequence, or only a portion of a gene or coding sequence), or may not contain any identifiable gene expression elements or any actively transcribed gene sequence. Further, the donor template may be linear or circular, and may be single-stranded or double-stranded. A donor template may be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively. An insertion sequence of a donor template provided herein may comprise a transcribable DNA sequence that may be transcribed into an RNA molecule, which may be non-coding and may or may not be operably linked to a promoter and/or other regulatory sequence.

According to some embodiments, a donor template may not comprise an insertion sequence, and instead comprise one or more homology sequences that include(s) one or more mutations, such as an insertion, deletion, substitution, etc., relative to the genomic sequence at a target site within the genome of a plant, such as at or near a GA3 oxidase or GA20 oxidase gene within the genome of a plant. Alternatively, a donor template may comprise an insertion sequence that does not comprise a coding or transcribable DNA sequence, wherein the insertion sequence is used to introduce one or more mutations into a target site within the genome of a plant, such as at or near a GA3 oxidase or GA20 oxidase gene within the genome of a plant.

A donor template provided herein may comprise at least one, at least two, at least three, at least four, at least five, at least six, at least seven, at least eight, at least nine, or at least ten genes or transcribable DNA sequences. Alternatively, a donor template may comprise no genes. Without being limiting, a gene or transcribable DNA sequence of a donor template may include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. According to other embodiments, an insertion sequence of a donor template may comprise a transcribable DNA sequence that encodes a non-coding RNA molecule, which may target a GA oxidase gene, such as a GA3 oxidase or GA20 oxidase gene, for suppression. A donor template may comprise a promoter, such as a tissue-specific or tissue-preferred promoter, a constitutive promoter, or an inducible promoter. A donor template may comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter may be operably linked to a gene or transcribable DNA sequence encoding a non-coding RNA, a guide RNA, an mRNA and/or protein.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue (s) may comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

As used herein, the term "homozygous" refers to a genotype comprising two identical alleles at a given locus in a diploid genome, or a genotype comprising two non-identical mutant alleles at a given locus in a diploid genome. The latter genotype comprising two non-identical mutant alleles is also referred to as being heteroallelic or transheterozygous, or as a heteroallelic combination. As used herein, "heterozygous" describes a genotype comprising a mutant allele and a wild-type allele at a given locus in a diploid genome.

DESCRIPTION

Most grain producing grasses, such as wheat, rice and *Sorghum*, produce both male and female structures within each floret of the panicle (i.e., they have a single reproductive structure). However, corn or maize is unique among the grain-producing grasses in that it forms separate male (tassel) and female (ear) inflorescences. Corn produces completely sexually dimorphic reproductive structures by selective abortion of male organs (anthers) in florets of the ear, and female organs (ovules) in the florets of the tassel within early stages of development. Precisely regulated gibberellin synthesis and signaling is critical to regulation of this selective abortion process, with the female reproductive ear being most sensitive to disruptions in the GA pathway. Indeed, the "anther ear" phenotype is the most common reproductive phenotype in GA corn mutants.

In contrast to corn, mutations in the gibberellin synthesis or signaling pathways that led to the "Green Revolution" in wheat, rice and *Sorghum* had little impact on their reproductive structures because these crop species do not undergo the selective abortion process of the grain bearing panicle during development, and thus are not sensitive to disruptions in GA levels. The same mutations have not been utilized in corn because disruption of the GA synthesis and signaling pathway has repeatedly led to dramatic distortion and masculinization of the ear ("anther ear") and sterility (disrupted anther and microspore development) in the tassel, in addition to extreme dwarfing in some cases. See, e.g., Chen, Y. et al., "The Maize DWARF1 Encodes a Gibberellin 3-Oxidase and Is Dual Localized to the Nucleus and Cytosol," *Plant Physiology* 166:2028-2039 (2014). These GA mutant phenotypes (off-types) in corn led to significant reductions in kernel production and a reduction in yield. Furthermore, production of anthers within the ear increases the likelihood of fungal or insect infections, which reduces the quality of the grain that is produced on those mutant ears. Forward breeding to develop semi-dwarf lines of corn has not been successful, and the reproductive off-types (as well as the extreme dwarfing) of GA mutants have been challenging to overcome. Thus, the same mutations in the GA pathway that led to the Green Revolution in other grasses have not yet been successful in corn.

Despite these prior difficulties in achieving higher grain yields in corn through manipulation of the GA pathway, the present inventors have discovered a way to manipulate GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants may also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Suppression and/or reduced or lowered expression and/or activity of GA20 or GA3 oxidase gene(s) may be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, may be sufficient to produce a short-stature plant with increased lodging resistance, but without significant off-types in reproductive tissues. Expression of a GA20 or GA3 oxidase suppression element in a tissue-specific or tissue-preferred manner may be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) may be targeted for suppression using a vascular promoter, such as a rice tungro bacilliform virus (RTBV) promoter, that drives expression in vascular tissues of plants. As supported in the Examples below, the expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn or cereal plant that produce active GAs may reduce plant height and increase lodging resistance, and off-types may be avoided in those plants if active GA levels are not also significantly impacted or lowered in reproductive tissues, such as the developing female organ or ear of the plant. If active GA levels could be reduced in the stalk, stem, or internode(s) of corn or cereal plants, perhaps without significantly affecting GA levels in reproductive tissues (e.g., the female or male reproductive organs or inflorescences), then corn or cereal plants having reduced plant height and increased lodging resistance could be created without off-types in the reproductive tissues of the plant.

Thus, recombinant DNA constructs and transgenic plants are provided herein comprising a GA20 or GA3 oxidase suppression element or sequence operably linked to a plant expressible promoter, which may be a tissue-specific or tissue-preferred promoter. Such a tissue-specific or tissue-preferred promoter may drive expression of its associated GA oxidase suppression element or sequence in one or more active GA-producing tissue(s) of the plant to suppress or reduce the level of active GAs produced in those tissue(s). Such a tissue-specific or tissue-preferred promoter may drive expression of its associated GA oxidase suppression construct or transgene during one or more vegetative stage(s) of development. Such a tissue-specific or tissue-preferred promoter may also have little or no expression in one or more cell(s) or tissue(s) of the developing female organ or ear of the plant to avoid the possibility of off-types in those reproductive tissues. According to some embodiments, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66.

Active or bioactive gibberellic acids (i.e., “active gibberellins” or “active GAs”) are known in the art for a given plant species, as distinguished from inactive GAs. For example, active GAs in corn and higher plants include the following: GA1, GA3, GA4, and GA7. Thus, an “active GA-producing tissue” is a plant tissue that produces one or more active GAs.

In addition to suppressing GA20 oxidase genes in active GA-producing tissues of the plant with a vascular tissue promoter, suppression of the same GA20 oxidase genes with various constitutive promoters could also cause the short, semi-dwarf stature phenotypes in corn, but without any visible off-types in the ear. Given that mutations in the GA pathway have previously been shown to cause off-types in reproductive tissues, it was surprising that constitutive suppression of GA20 oxidase did not cause similar reproductive phenotypes in the ear. Thus, suppression of one or more GA20 oxidase genes could be carried out using a constitutive promoter to create a short stature, lodging-resistant corn or cereal plant without any significant or observable reproductive off-types in the plant. Other surprising observations were made when the same GA20 oxidase suppression construct was expressed in the stem, leaf or reproductive tissues. As described further below, targeted suppression of the same GA20 oxidase genes in the stem or ear tissues of corn plants did not cause the short stature, semi-dwarf phenotype. Moreover, directed expression of the GA20 oxidase suppression construct directly in reproductive tissues of the developing ear of corn plants with a female reproductive tissue (ear) promoter did not cause any significant or observable off-types in the ear. However, expression of the same GA20 oxidase suppression construct in leaf tissues was sufficient to cause a moderate short stature phenotype without significant or observable reproductive off-types in the plant.

Without being limited by theory, short stature, semi-dwarf phenotypes in corn and other cereal plants may result from a sufficient level of expression of a suppression construct targeting certain GA oxidase gene(s) in active GA-producing tissue(s) of the plant. At least for targeted suppression of certain GA20 oxidase genes in corn, restricting the pattern of expression to avoid reproductive ear tissues may not be necessary to avoid reproductive off-types in the developing ear. However, expression of the GA20 or GA3 oxidase suppression construct at low levels, and/or in a limited number of plant tissues, may be insufficient to cause a significant short stature, semi-dwarf phenotype. Given that the observed semi-dwarf phenotype with targeted GA20 oxidase suppression is the result of shortening the stem internodes of the plant, it was surprising that suppression of GA20 oxidase genes in at least some stem tissues was not sufficient to cause shortening of the internodes and reduced plant height. Without being bound by theory, suppression of certain GA oxidase gene(s) in tissue(s) and/or cell(s) of the plant where active GAs are produced, and not necessarily in stem or internode tissue(s), may be sufficient to produce semi-dwarf plants, even though the short stature trait is due to shortening of the stem internodes. Given that GAs can migrate through the vasculature of the plant, it is proposed that manipulating GA oxidase genes in plant tissue(s) where active GAs are produced may result in a short stature, semi-dwarf plant, even though this may be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues was found to cause a moderate semi-dwarf phenotype in corn plants. Given that expression of a GA20 oxidase suppression construct with several different “stem” promoters did not produce the semi-dwarf phenotype in corn, it is noteworthy that expression of the same GA20 oxidase suppression construct with a RTBV vascular promoter was effective at consistently producing the semi-dwarf phenotype with a high degree of penetrance across events and germplasms. This semi-dwarf phenotype was also observed with expression of the same GA20 oxidase suppression construct using other vascular promoters.

According to embodiments of the present disclosure, modified cereal or corn plants are provided that have at least one beneficial agronomic trait and at least one female reproductive organ or ear that is substantially or completely free of off-types. The beneficial agronomic trait may include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. Off-types may include male (tassel or anther) sterility, reduced kernel or seed number, and/or the presence of one or more masculinized or male (or male-like) reproductive structures in the female organ or ear (e.g., anther ear) of the plant. A modified cereal or corn plant is provided herein that lacks significant off-types in the reproductive tissues of the plant. Such a modified cereal or corn plant may have a female reproductive organ or ear that appears normal relative to a control or wild-type plant. Indeed, modified cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears. As used herein, a female organ or ear of a plant, such as corn, is “substantially free” of male reproductive structures if male reproductive structures are absent or nearly absent in the female organ or ear of the plant based on visual inspection of the female organ or ear at later reproductive stages. A female organ or ear of a plant, such as corn, is “completely free” of mature male reproductive structures if male reproductive structures are absent or not observed or observable in the female organ or ear of the plant, such as a corn plant, by visual inspection of the female organ or ear at later reproductive stages. A female organ or ear of a plant, such as corn, without significant off-types and substantially free of male reproductive structures in the ear may have a number of kernels or seeds per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the number of kernels or seeds per female organ or ear of a wild-type or control plant. Likewise, a female organ or ear of a plant, such as corn, without significant off-types and substantially free of male reproductive structures in the ear may have an average kernel or seed weight per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the average kernel or seed weight per female organ or ear of a wild-type or control plant. A female organ or ear of a plant, such as corn, that is completely free of mature male reproductive structures may have a number of kernels or seeds per female organ or ear of the plant that is about the same as a wild-type or control plant. In other words, the reproductive development of the female organ or ear of the plant may be normal or substantially normal. However, the number of seeds or kernels per female organ or ear may depend on other factors that affect resource utilization and development of the plant. Indeed, the number of kernels or seeds per female organ or ear of the plant, and/or the kernel or seed weight per female organ or ear of the plant, may be about the same or greater than a wild-type or control plant.

The plant hormone gibberellin plays an important role in a number of plant developmental processes including germination, cell elongation, flowering, embryogenesis and seed development. Certain biosynthetic enzymes (e.g., GA20 oxidase and GA3 oxidase) and catabolic enzymes (e.g., GA2 oxidase) in the GA pathway are critical to affecting active GA levels in plant tissues. Thus, in addition to suppression of certain GA20 oxidase genes, it is further proposed that suppression of a GA3 oxidase gene in a constitutive or tissue-specific or tissue-preferred manner may also produce corn plants having a short stature phenotype and increased lodging resistance, with possible increased yield, but without off-types in the ear. Thus, according to some embodiments, constructs and transgenes are provided comprising a GA3 oxidase suppression element or sequence operably linked to a constitutive or tissue-specific or tissue-preferred promoter, such as a vascular or leaf promoter. According to some embodiments, the tissue-specific or tissue-preferred promoter is a vascular promoter, such as the RTBV promoter. However, other types of tissue-specific or tissue preferred promoters may potentially be used for GA3 oxidase suppression in active GA-producing tissues of a corn or cereal plant to produce a semi-dwarf phenotype without significant off-types.

Any method known in the art for suppression of a target gene may be used to suppress GA oxidase gene(s) according to embodiments of the present invention including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules may be used that target the coding and/or non-coding genomic sequences or regions within or near a GA oxidase gene to cause silencing of the gene. Accordingly, any of these methods may be used for the targeted suppression of an endogenous GA20 oxidase(s) or GA3 oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

The term "suppression" as used herein, refers to a lowering, reduction or elimination of the expression level of a mRNA and/or protein encoded by a target gene in a plant, plant cell or plant tissue at one or more stage(s) of plant development, as compared to the expression level of such target mRNA and/or protein in a wild-type or control plant, cell or tissue at the same stage(s) of plant development. According to some embodiments, a modified or transgenic plant is provided having a GA20 oxidase gene expression level that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified or transgenic plant is provided having a GA3 oxidase gene expression level that is reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant. According to some embodiments, a modified or transgenic plant is provided having a GA20 oxidase gene expression level that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to some embodiments, a modified or transgenic plant is provided having a GA3 oxidase gene expression level that is reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant. According to these embodiments, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In some embodiments, suppression of an endogenous GA20 oxidase gene or a GA3 oxidase gene is tissue-specific (e.g., only in leaf and/or vascular tissue). Suppression of a GA20 oxidase gene or a GA3 oxidase gene may be constitutive and/or vascular or leaf tissue specific or preferred. In other embodiments, suppression of a GA20 oxidase gene or a GA3 oxidase gene is constitutive and not tissue-specific. According to some embodiments, expression of an endogenous GA20 oxidase gene and/or a GA3 oxidase gene is reduced in one or more tissue types (e.g., in leaf and/or vascular tissue(s)), such as one or more active GA producing tissues, of a modified or transgenic plant as compared to the same tissue(s) of a control plant.

According to embodiments of the present disclosure, a recombinant DNA molecule, construct or vector is provided comprising a suppression element targeting GA20 oxidase or GA3 oxidase gene(s) that is operably linked to a plant-expressible constitutive or tissue-specific or tissue-preferred promoter. The suppression element may comprise a transcribable DNA sequence of at least 19 nucleotides in length, such as from about 19 nucleotides in length to about 27 nucleotides in length, or 19, 20, 21, 22, 23, 24, 25, 26, or 27 nucleotides in length, wherein the transcribable DNA sequence corresponds to at least a portion of the target GA oxidase gene to be suppressed, and/or to a DNA sequence complementary thereto. The suppression element may be 19-30, 19-50, 19-100, 19-200, 19-300, 19-500, 19-1000, 19-1500, 19-2000, 19-3000, 19-4000, or 19-5000 nucleotides in length. The suppression element may be at least 19, at least 20, at least 21, at least 22, or at least 23 nucleotides or more in length (e.g., at least 25, at least 30, at least 50, at least 100, at least 200, at least 300, at least 500, at least 1000, at least 1500, at least 2000, at least 3000, at least 4000, or at least 5000 nucleotides in length). Depending on the length and sequence of a suppression element, one or more sequence mismatches or non-complementary bases, such as 1, 2, 3, 4, 5, 6, 7, 8 or more mismatches, may be tolerated without a loss of suppression if the non-coding RNA molecule encoded by the suppression element is still able to sufficiently hybridize and bind to the target mRNA molecule of the GA20 oxidase or GA3 oxidase gene(s). Indeed, even shorter RNAi suppression elements ranging from about 19 nucleotides to about 27 nucleotides in length may have one or more mismatches or non-complementary bases, yet still be effective at suppressing a target GA oxidase gene. Accordingly, a sense or anti-sense suppression element sequence may be at least 80%, at least 85%, at least 90%, at least 95%, at least 96%, at least 97%, at least 98%, at least 99%, at least 99.5% or 100% identical or complementary to a corresponding sequence of at least a segment or portion of the targeted GA oxidase gene, or its complementary sequence, respectively.

A suppression element or transcribable DNA sequence of the present disclosure for targeted suppression of GA oxidase gene(s) may include one or more of the following: (a) a DNA sequence that includes at least one anti-sense DNA sequence that is anti-sense or complementary to at least one segment or portion of the targeted GA oxidase gene; (b) a DNA sequence that includes multiple copies of at least one anti-sense DNA sequence that is anti-sense or complementary to at least one segment or portion of the targeted GA oxidase gene; (c) a DNA sequence that includes at least one sense DNA sequence that comprises at least one segment or portion of the targeted GA oxidase gene; (d) a DNA sequence that includes multiple copies of at least one sense DNA sequence that each comprise at least one segment or portion of the targeted GA oxidase gene; (e) a DNA sequence that includes an inverted repeat of a segment or portion of a targeted GA oxidase gene and/or transcribes into RNA for suppressing the targeted GA oxidase gene by forming double-stranded RNA, wherein the transcribed RNA includes at least one anti-sense DNA sequence that is anti-sense or complementary to at least one segment or portion of the targeted GA oxidase gene and at least one sense DNA sequence that comprises at least one segment or portion of the targeted GA oxidase gene; (f) a DNA sequence that is transcribed into RNA for suppressing the targeted GA oxidase gene by forming a single double-stranded RNA and includes multiple serial anti-sense DNA sequences that are each anti-sense or complementary to at least one segment or portion of the targeted GA oxidase gene and multiple serial sense DNA sequences that each comprise at least one segment or portion of the targeted GA oxidase gene; (g) a DNA sequence that is transcribed into RNA for suppressing the targeted GA oxidase gene by forming multiple double strands of RNA and includes multiple anti-sense DNA sequences that are each anti-sense or complementary to at least one segment or portion of the targeted GA oxidase gene and multiple sense DNA sequences that each comprise at least one segment or portion of the targeted GA oxidase gene, wherein the multiple anti-sense DNA segments and multiple sense DNA segments are arranged in a series of inverted repeats; (h) a DNA sequence that includes nucleotides derived from a miRNA, preferably a plant miRNA; (i) a DNA sequence that includes a miRNA precursor that encodes an artificial miRNA complementary to at least one segment or portion of the targeted GA oxidase gene; (j) a DNA sequence that includes nucleotides of a siRNA; (k) a DNA sequence that is transcribed into an RNA aptamer capable of binding to a ligand; and (1) a DNA sequence that is transcribed into an RNA aptamer capable of binding to a ligand and DNA that transcribes into a regulatory RNA capable of regulating expression of the targeted GA oxidase gene, wherein the regulation of the targeted GA oxidase gene is dependent on the conformation of the regulatory RNA, and the conformation of the regulatory RNA is allosterically affected by the binding state of the RNA aptamer by the ligand. Any of these gene suppression elements, whether transcribed into a single stranded or double-stranded RNA, may be designed to suppress more than one GA oxidase target gene, depending on the number and sequence of the suppression element(s).

Multiple sense and/or anti-sense suppression elements for more than one GA oxidase target may be arranged serially in tandem or arranged in tandem segments or repeats, such as tandem inverted repeats, which may also be interrupted by one or more spacer sequence(s), and the sequence of each suppression element may target one or more GA oxidase gene(s). Furthermore, the sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length may have one or more mismatches or non-complementary bases, yet still be effective at suppressing the target GA oxidase gene. Accordingly, a sense or anti-sense suppression element sequence may be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For anti-sense suppression, the transcribable DNA sequence or suppression element comprises a sequence that is anti-sense or complementary to at least a portion or segment of the targeted GA oxidase gene. The suppression element may comprise multiple anti-sense sequences that are complementary to one or more portions or segments of the targeted GA oxidase gene(s), or multiple copies of an anti-sense sequence that is complementary to a targeted GA oxidase gene. The anti-sense suppression element sequence may be at least 80%, at least 85%, at least 90%, at least 95%, at least 96%, at least 97%, at least 98%, at least 99%, at least 99.5% or 100% identical to a DNA sequence that is complementary to at least a segment or portion of the targeted GA oxidase gene. In other words, the anti-sense suppression element sequence may be at least 80%, at least 85%, at least 90%, at least 95%, at least 96%, at least 97%, at least 98%, at least 99%, at least 99.5% or 100% complementary to the targeted GA oxidase gene or mRNA.

For suppression of GA oxidase gene(s) using an inverted repeat or a transcribed dsRNA, a transcribable DNA sequence or suppression element may comprise a sense sequence that comprises a segment or portion of a targeted GA oxidase gene and an anti-sense sequence that is complementary to a segment or portion of the targeted GA oxidase gene, wherein the sense and anti-sense DNA sequences are arranged in tandem. The sense and/or anti-sense sequences, respectively, may each be less than 100% identical or complementary to a segment or portion of the targeted GA oxidase gene as described above. The sense and anti-sense sequences may be separated by a spacer sequence, such that the RNA molecule transcribed from the suppression element forms a stem, loop or stem-loop structure between the sense and anti-sense sequences. The suppression element may instead comprise multiple sense and anti-sense sequences that are arranged in tandem, which may also be separated by one or more spacer sequences. Such suppression elements comprising multiple sense and anti-sense sequences may be arranged as a series of sense sequences followed by a series of anti-sense sequences, or as a series of tandemly arranged sense and anti-sense sequences. Alternatively, one or more sense DNA sequences may be expressed separately from the one or more anti-sense sequences (i.e., one or more sense DNA sequences may be expressed from a first transcribable DNA sequence, and one or more anti-sense DNA sequences may be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element may comprise a DNA sequence derived from a miRNA sequence native to a virus or eukaryote, such as an animal or plant, or modified or derived from such a native miRNA sequence. Such native or native-derived miRNA sequences may form a fold back structure and serve as a scaffold for the precursor miRNA (pre-miRNA), and may correspond to the stem region of a native miRNA precursor sequence, such as from a native (or native-derived) primary-miRNA (pri-miRNA) or pre-miRNA sequence. However, in addition to these native or native-derived miRNA scaffold or preprocessed sequences, engineered or synthetic miRNAs of the present embodiments further comprise a sequence corresponding to a segment or portion of the targeted GA oxidase gene(s). Thus, in addition to the pre-processed or scaffold miRNA sequences, the suppression element may further comprise a sense and/or anti-sense sequence that corresponds to a segment or portion of a targeted GA oxidase gene, and/or a sequence that is complementary thereto, although one or more sequence mismatches may be tolerated.

Engineered miRNAs are useful for targeted gene suppression with increased specificity. See, e.g., Parizotto et al., Genes Dev. 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. The mature miRNA hybridizes to target mRNA transcripts and guides the binding of a complex of proteins to the target transcripts, which may function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., Cell 121:207-221 (2005), Vaucheret Science STKE, 2005: pe43 (2005), and Yoshikawa et al. Genes Dev., 19:2164-2175 (2005), the contents and disclosures of which are incorporated herein by reference.

Plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) Nature Genetics, 39:1033-1037; and Axtell et al. (2006) Cell, 127:565-577.

Many microRNA genes (MIR genes) have been identified and made publicly available in a database ("miRBase", available online at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) Mol. Cell, 9:1327-1333. According to many embodiments, the target may be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402); cDNA and/or genomic DNA sequences may be used to identify target transcript orthologues and any potential matches to unrelated genes, thereby avoiding unintentional silencing or suppression of non-target sequences; (b) Analyzing the target gene for undesirable sequences (e.g., matches to sequences from non-target species), and score each potential target sequence for GC content, Reynolds score (see Reynolds et al. (2004) Nature Biotechnol., 22:326-330), and functional asymmetry characterized by a negative difference in free energy ("ΔΔG") (see Khvorova et al. (2003) Cell, 115:209-216). Preferably, target sequences (e.g., 19-mers) may be selected that have all or most of the following characteristics: (1) a Reynolds score >4, (2) a GC content between about 40% to about 60%, (3) a negative ΔAG, (4) a terminal adenosine, (5) lack of a consecutive run of 4 or more of the same nucleotide; (6) a location near the 3' terminus of the target gene; (7) minimal differences from the miRNA precursor transcript. In one aspect, a non-coding RNA molecule used herein to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element may be important in influencing RNAi efficacy; for example, an algorithm, "siExplorer" is publicly available at rna.chem.t.u-tokyo.ac.jp/siexplorer.htm (see Katoh and Suzuki (2007) Nucleic Acids Res., 10.1093/nar/gk11120); (c) Determining a reverse complement of the selected target sequence (e.g., 19-mer) to use in making a modified mature miRNA. Relative to a 19-mer sequence, an additional nucleotide at position 20 may be matched to the selected target or recognition sequence, and the nucleotide at position 21 may be chosen to either be unpaired to prevent spreading of silencing on the target transcript or paired to the target sequence to promote spreading of silencing on the target transcript; and (d) Transforming the artificial miRNA into a plant.

According to embodiments of the present disclosure, a recombinant DNA molecule, construct or vector is provided comprising a transcribable DNA sequence or suppression element encoding a miRNA or precursor miRNA molecule for targeted suppression of a GA oxidase gene(s). Such a transcribable DNA sequence and suppression element may comprise a sequence of at least 19 nucleotides in length that corresponds to one or more GA oxidase gene(s) and/or a sequence complementary to one or more GA oxidase gene (s), although one or more sequence mismatches or non-base-paired nucleotides may be tolerated.

GA oxidase gene(s) may also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element may encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector is thus provided comprising a transcribable DNA sequence and suppression element encoding a siRNA molecule for targeted suppression of a GA oxidase gene(s). Such a transcribable DNA sequence and suppression element may be at least 19 nucleotides in length and have a sequence corresponding to one or more GA oxidase gene(s), and/or a sequence complementary to one or more GA oxidase gene(s).

GA oxidase gene(s) may also be suppressed using one or more trans-acting small interfering RNAs (ta-siRNAs). In the ta-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) Cell, 121:207-221). The size or length of ta-siRNAs ranges from about 20 to about 22 nucleotides or base pairs, but are mostly commonly 21 base pairs. Thus, a transcribable DNA sequence or suppression element of the present invention may encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element may be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to embodiments of the present invention, a recombinant DNA molecule, vector or construct is provided comprising a transcribable DNA sequence encoding a non-coding RNA molecule that binds or hybridizes to a target mRNA in a plant cell, wherein the target mRNA molecule encodes a GA20 or GA3 oxidase gene, and wherein the transcribable DNA sequence is operably linked to a constitutive or tissue-specific or tissue-preferred promoter. In addition to targeting a mature mRNA sequence, a non-coding RNA molecule may instead target an intronic sequence of a GA oxidase gene or mRNA transcript, or a GA oxidase mRNA sequence overlapping coding and non-coding sequences. According to other embodiments, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter. For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

According to embodiments of the present disclosure, suitable tissue-specific or tissue preferred promoters for expression of a GA20 oxidase or GA3 oxidase suppression element may include those promoters that drive or cause expression of its associated suppression element or sequence at least in the vascular and/or leaf tissue(s) of a corn or cereal plant, or possibly other tissues in the case of GA3 oxidase. Expression of the GA oxidase suppression element or construct with a tissue-specific or tissue-preferred promoter may also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear may proceed normally in the transgenic plant without off-types in the ear and a loss in yield potential.

Any vascular promoters known in the art may potentially be used as the tissue-specific or tissue-preferred promoter. Examples of vascular promoters include the RTBV promoter (see, e.g., SEQ ID NO: 65), a known sucrose synthase gene promoter, such as a corn sucrose synthase-1 (Sus1 or Sh1) promoter (see, e.g., SEQ ID NO: 67), a corn Sh1 gene paralog promoter, a barley sucrose synthase promoter (Ss1) promoter, a rice sucrose synthase-1 (RSs1) promoter (see, e.g., SEQ ID NO: 68), or a rice sucrose synthase-2 (RSs2) promoter (see, e.g., SEQ ID NO: 69), a known sucrose transporter gene promoter, such as a rice sucrose transporter promoter (SUT1) (see, e.g., SEQ ID NO: 70), or various known viral promoters, such as a *Commelina* yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter (SEQ ID NO: 71), and any functional sequence portion or truncation of any of the foregoing promoters with a similar pattern of expression, such as a truncated RTBV promoter (see, e.g., SEQ ID NO: 66).

Any leaf promoters known in the art may potentially be used as the tissue-specific or tissue-preferred promoter. Examples of leaf promoters include a corn pyruvate phosphate dikinase or PPDK promoter (see, e.g., SEQ ID NO: 72), a corn fructose 1,6 bisphosphate aldolase or FDA promoter (see, e.g., SEQ ID NO: 73), and a rice Nadh-Gogat promoter (see, e.g., SEQ ID NO: 74), and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

Any other vascular and/or leaf promoters known in the art may also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. For example, a vascular promoter may comprise a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 65, 66, 67, 68, 69, 70, and 71, any functional sequence portion or truncation thereof, and/or any sequence complementary to any of the foregoing sequences; a leaf promoter may comprise, for example, a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 72, 73, and 74, any functional sequence portion or truncation thereof, and/or any sequence complementary to any of the foregoing sequences; and a constitutive promoter may comprise a DNA sequence that is at least at least 70%, at least 80%, at least 85%, at least 90%, at least 95%, at least 96%, at least 97%, at least 98%, at least 99%, at least 99.5% or 100% identical to one or more of SEQ ID NOs: 75, 76, 77, 78, 79, 80, 81, 82, and 83, any functional sequence portion or truncation thereof, and/or any sequence complementary to any of the foregoing sequences. Examples of vascular and/or leaf promoters may further include other known, engineered and/or later-identified promoter sequences shown to have a pattern of expression in vascular and/or leaf tissue(s) of a cereal or corn plant. Furthermore, any known or later-identified constitutive promoter may also be used for expression of a GA20 oxidase or GA3 oxidase suppression element. Common examples of constitutive promoters are provided below.

As understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetic or artificial and/or engineered, varied or derived from a known or naturally occurring promoter sequence. A promoter may be a chimeric promoter comprising a combination of two or more heterologous sequences. A promoter of the present invention may thus include variants of promoter sequences that are similar in composition, but not identical to, other promoter sequence(s) known or provided herein. A promoter may be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or nearly all tissues of the plant are referred to as "constitutive" promoters. However, the expression level with a "constitutive promoter" is not necessarily uniform across different tissue types and cells. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential or predominant expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A tissue-specific or tissue-preferred promoter may also be defined in terms of the specific or preferred tissue(s) in which it drives expression of its associated transcribable DNA sequence or suppression element. For example, a promoter that causes specific expression in vascular tissues may be referred to as a "vascular-specific promoter", whereas a promoter that causes preferential or predominant expression in vascular tissues may be referred to as a "vascular-preferred promoter". Likewise, a promoter that causes specific expression in leaf tissues may be referred to as a "leaf-specific promoter", whereas a promoter that causes preferential or predominant expression in leaf tissues may be referred to as a "leaf-preferred promoter". An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed, as defined above.

Several of the GA oxidases in cereal plants consist of a family of related GA oxidase genes. For example, corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are three known or potential GA3 oxidases in corn, GA3 oxidase_1, GA3 oxidase_2, and GA3 oxidase_3. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |
| GA3 oxidase_3 | SEQ ID NO: 171 | SEQ ID NO: 172 | SEQ ID NO: 173 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR (nucleotides 1-3000); nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

The genomic DNA sequence of GA3 oxidase_1 is provided in SEQ ID NO: 36 and 168, the genomic DNA sequence of GA3 oxidase_2 is provided in SEQ ID NO: 37 and 169, and the genomic DNA sequence of GA3 oxidase_3 is provided in SEQ ID NO: 170. While SEQ ID NOS: 36 and 37 provide 5'-UTR, exon, intron and 3'-UTR sequences for the GA3 oxidase_1 and GA3 oxidase_2 genes, respectively, SEQ ID NOs: 168 and 169 further provide upstream and downstream genomic sequences and additional 5' and 3' UTR sequences for the GA3 oxidase_1 and GA3 oxidase_2 genes, respectively. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. Alternatively for the GA3 oxidase_1 gene, SEQ ID NO: 168 provides 3000 nucleotides upstream of the GA3 oxidase_1 5'-UTR (nucleotides 1-3000); nucleotides 3001-3161 of SEQ ID NO: 168 correspond to the 5'-UTR; nucleotides 3162-3646 of SEQ ID NO: 168 correspond to the first exon; nucleotides 3647-4011 of SEQ ID NO: 168 correspond to the first intron; nucleotides 4012-4170 of SEQ ID NO: 168 correspond to the second exon; nucleotides 4171-4290 of SEQ ID NO: 168 correspond to the second intron; nucleotides 4291-4795 of SEQ ID NO: 168 correspond to the third exon; and nucleotides 4796-5406 of SEQ ID NO: 168 correspond to the 3'-UTR. SEQ ID NO: 168 also provides 3000 nucleotides downstream of the end of the 3'-UTR (nucleotides 5407-8406). For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR. Alternatively for the GA3 oxidase_2 gene, SEQ ID NO: 169 provides 3000 nucleotides upstream of the GA3 oxidase_2 5'-UTR (nucleotides 1-3000); nucleotides 3001-3056 of SEQ ID NO: 169 correspond to the 5'-UTR; nucleotides 3057-3550 of SEQ ID NO:

169 correspond to the first exon; nucleotides 3551-3710 of SEQ ID NO: 169 correspond to the first intron; nucleotides 3711-3869 of SEQ ID NO: 169 correspond to the second exon; nucleotides 3870-3991 of SEQ ID NO: 169 correspond to the second intron; nucleotides 3992-4463 of SEQ ID NO: 169 correspond to the third exon; and nucleotides 4464-4581 of SEQ ID NO: 169 correspond to the 3'-UTR. SEQ ID NO: 169 also provides 3000 nucleotides downstream of the end of the 3'-UTR (nucleotides 4582-7581). For the GA3 oxidase_3 gene, SEQ ID NO: 170 provides 3000 nucleotides upstream of the GA3 oxidase_3 5'-UTR (nucleotides 1-3000); nucleotides 3001-3130 of SEQ ID NO: 170 correspond to the 5'-UTR; nucleotides 3131-3483 of SEQ ID NO: 170 correspond to the first exon; nucleotides 3484-3582 of SEQ ID NO: 170 correspond to the first intron; nucleotides 3583-3907 of SEQ ID NO: 170 correspond to the second exon; nucleotides 3908-3998 of SEQ ID NO: 170 correspond to the second intron; nucleotides 3999-4274 of SEQ ID NO: 170 correspond to the third exon; and nucleotides 4275-4332 of SEQ ID NO: 170 correspond to the 3'-UTR. SEQ ID NO: 170 also provides 3000 nucleotides downstream of the end of the 3'-UTR (nucleotides 4333-7332).

In addition to phenotypic observations with targeting the GA20 oxidase_3 and/or GA20 oxidase_5 gene(s), or the GA3 oxidase_1 and/or GA3 oxidase_2 gene(s), for suppression, a semi-dwarf phenotype is also observed with suppression of the GA20 oxidase_4 gene. The genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

According to embodiments of the present disclosure, a recombinant DNA molecule, vector or construct is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule (i) expressed from an endogenous GA oxidase gene and/or (ii) encoding an endogenous GA oxidase protein in the plant, wherein the transcribable DNA sequence is operably linked to a plant-expressible promoter, and wherein the plant is a cereal or corn plant.

According to some embodiments, a non-coding RNA molecule targets GA20 oxidase gene(s), such as GA20 oxidase_3 and/or GA20 oxidase_5 gene(s), for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 7, 8, 13 and 14. According to some embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to one or both of SEQ ID NOs: 9 and 15. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% similar to one or both of SEQ ID NOs: 9 and 15. In addition to targeting a mature mRNA sequence (including either or both of the untranslated or exonic sequences), a non-coding RNA molecule may further target the intronic sequences of a GA20 oxidase gene or transcript.

According to some embodiments, a non-coding RNA molecule targets GA3 oxidase gene(s) for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 171 and 172. According to other embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to one or both of SEQ ID NOs: 30, 33 and 173. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% similar to one or both of SEQ ID NOs: 30, 33 and 173. In addition to targeting a mature mRNA sequence (including either or both of the untranslated or exonic sequences), a non-coding RNA molecule may further target the intronic sequences of a GA3 oxidase gene or transcript.

According to some embodiments, a non-coding RNA molecule targets GA20 oxidase_4 gene for suppression and comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or both of SEQ ID NOs: 10 and 11. According to other embodiments, a non-coding RNA molecule is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to one or both of SEQ ID NO: 12. According to further embodiments, a non-coding RNA molecule may comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% similar to SEQ ID NOs: 12. In addition to targeting a mature mRNA sequence (including either or both of the untranslated or exonic sequences), a non-coding RNA molecule may further target the intronic sequences of a GA20 oxidase gene or transcript.

According to many embodiments, the non-coding RNA molecule encoded by the transcribable DNA sequence of the recombinant DNA molecule, vector or construct may be a precursor miRNA or siRNA that is processed or cleaved in a plant cell to form a mature miRNA or siRNA that targets a GA20 oxidase or GA3 oxidase gene.

According to embodiments of the present invention, GA levels may be reduced in the stalk or stem of a cereal or corn plant by targeting only a limited subset of genes within a GA oxidase family for suppression. Without being bound by theory, it is proposed that targeting of a limited number of genes within a GA oxidase family for suppression may produce the short stature phenotype and resistance to lodging in transgenic plants, but without off-types in the reproductive or ear tissues of the plant due to differential expression among GA oxidase genes, sufficient compensation for the suppressed GA oxidase gene(s) by other GA oxidase gene(s) in those reproductive tissues, and/or incomplete suppression of the targeted GA oxidase gene(s). Thus, not only may off-types be avoided by limiting expression or suppression of GA oxidase gene(s) with a tissue-specific or tissue preferred promoter, it is proposed that a limited subset of GA oxidase genes (e.g., a limited number of GA20 oxidase genes) may be targeted for suppression, such that the other GA oxidase genes within the same gene family (e.g., other GA20 oxidase genes) may compensate for loss of expression of the suppressed GA oxidase gene(s) in those tissues. Incomplete suppression of the targeted GA oxidase gene(s) may also allow for a sufficient level of expression of the targeted GA oxidase gene(s) in one or more tissues to avoid off-types or undesirable traits in the plant that would negatively affect crop yield, such as reproductive off-types or excessive shortening of plant height. Unlike complete loss-of-function mutations in a gene, suppression may allow for partial activity of the targeted gene to persist. Since the different GA20 oxidase genes have different patterns of expression in plants, targeting of a limited subset of GA20 oxidase genes for suppression may allow for modification of certain traits while avoiding off-types previously associated with GA mutants in cereal plants. In other words, the growth, developmental and reproductive traits or off-types previously associated with GA mutants in corn and other cereal crops may be decoupled by targeting only a limited number or subset (i.e., one or more, but not all) of the GA20 or GA3 oxidase genes and/or by incomplete suppression of a targeted GA oxidase gene. By transgenically targeting a subset of one or more endogenous GA3 or GA20 oxidase genes for suppression within a plant, a more pervasive pattern of expression (e.g., with a constitutive promoter) may be used to produce semi-dwarf plants without significant reproductive off-types and/or other undesirable traits in the plant, even with expression of the transgenic construct in reproductive tissue(s). Indeed, suppression elements and constructs are provided herein that selectively target the GA20 oxidase_3 and/or GA20 oxidase_5 genes (identified in Table 1 above) for suppression, which may be operably linked to a vascular, leaf and/or constitutive promoter.

With a suppression construct that only targets a limited subset of GA20 oxidase genes, such as the GA20 oxidase_3, GA20 oxidase_4, and/or GA20 oxidase_5 gene(s), or which targets the GA3 oxidase_1, GA3 oxidase_2, and/or GA3 oxidase_3 gene(s), restricting the pattern of expression of the suppression element may be less crucial for obtaining normal reproductive development of the cereal or corn plant and avoidance of off-types in the female organ or ear due to compensation, etc., from the other GA20 and/or GA3 oxidase genes. Therefore, expression of a suppression construct and element, selectively or preferentially targeting, for instance, the GA20 oxidase_3 and/or GA20 oxidase_5 gene (s), the GA20 oxidase_4 gene, and/or the GA3 oxidase_1, GA3 oxidase_2, and/or GA3 oxidase_3 gene(s) in corn, or similar genes and homologs in other cereal plants, may be driven by a variety of different plant-expressible promoter types including constitutive and tissue-specific or tissue-preferred promoters, such as a vascular or leaf promoter, which may include, for example, the RTBV promoter introduced above (e.g., a promoter comprising the RTBV (SEQ ID NO: 65) or truncated RTBV (SEQ ID NO: 66) sequence), and any other promoters that drive expression in tissues encompassing much or all of the vascular and/or leaf tissue(s) of a plant. Any known or later-identified constitutive promoter with a sufficiently high level of expression may also be used for expression of a suppression construct targeting a subset of GA20 and/or GA3 oxidase genes in corn, particularly the GA20 oxidase_3 and/or GA20 oxidase_5 gene(s), the GA20 oxidase_4 gene, and/or the GA3 oxidase_1, GA3 oxidase_2, and/or GA3 oxidase_3 gene(s), or similar genes and homologs in other cereal plants.

Examples of constitutive promoters that may be used in monocot plants, such as cereal or corn plants, include, for example, various actin gene promoters, such as a rice Actin 1 promoter (see, e.g., U.S. Pat. No. 5,641,876; see also SEQ ID NO: 75 or SEQ ID NO: 76) and a rice Actin 2 promoter (see, e.g., U.S. Pat. No. 6,429,357; see also, e.g., SEQ ID NO: 77 or SEQ ID NO: 78), a CaMV 35S or 19S promoter (see, e.g., U.S. Pat. No. 5,352,605; see also, e.g., SEQ ID NO: 79 for CaMV 35S), a maize ubiquitin promoter (see, e.g., U.S. Pat. No. 5,510,474), a *Coix lacryma-jobi* polyubiquitin promoter (see, e.g., SEQ ID NO: 80), a rice or maize Gos2 promoter (see, e.g., Pater et al., The Plant Journal, 2 (6): 837-44 1992; see also, e.g., SEQ ID NO: 81 for the rice Gos2 promoter), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547; see also, e.g., SEQ ID NO: 82), a PCLSV promoter (see, e.g., U.S. Pat. No. 5,850,019; see also, e.g., SEQ ID NO: 83), an Emu promoter (see, e.g., Last et al., Theor. Appl. Genet. 81:581 (1991); and Mcelroy et al., Mol. Gen. Genet. 231:150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that may be used in monocot or cereal plants, and any functional sequence portion or truncation of any of the foregoing promoters.

A sufficient level of expression of a transcribable DNA sequence encoding a non-coding RNA molecule targeting a GA oxidase gene for suppression may be necessary to produce a short stature, semi-dwarf phenotype that resists lodging, since lower levels of expression may be insufficient to lower active GA levels in the plant to a sufficient extent to cause a significant phenotype. Thus, tissue-specific and tissue-preferred promoters that drive, etc., a moderate or strong level of expression of their associated transcribable DNA sequence in active GA-producing tissue(s) of a plant may be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): VE, V1, V2, V3, V4, V5, V6, V7, V8, V9, V10, V11, V12, V13, V14, Vn, Vr, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to many embodiments, the plant-expressible promoter may preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1, GA3 oxidase_2, and/or GA3 oxidase_3 gene(s) in corn, or similar genes and homologs in other cereal plants, may be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a significant short stature or anti-lodging phenotypes due to the spatial-temporal pattern of expression of the promoter during plant development, and/or the amount or strength of expression of the promoter being too low or weak. Furthermore, some suppression constructs may only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

According to present embodiments, a recombinant DNA molecule, vector or construct for suppression of one or more endogenous GA20 or GA3 oxidase gene(s) in a plant is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule expressed from an endogenous GA oxidase gene and encoding an endogenous GA oxidase protein in the plant, wherein the transcribable DNA sequence is operably linked to a plant-expressible promoter, and wherein the plant is a cereal or corn plant. As stated above, in addition to targeting a mature mRNA sequence, a non-coding RNA molecule may further target the intronic sequence(s) of a GA oxidase gene or transcript. According to many embodiments, a non-coding RNA molecule may target a GA20 oxidase_3 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or SEQ ID NO: 8. According to some embodiments, a non-coding RNA molecule targeting a GA20 oxidase_3 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 7 or SEQ ID NO: 8. According to some embodiments, a non-coding RNA molecule may target a GA20 oxidase gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 9.

As mentioned above, a non-coding RNA molecule may target an intron sequence of a GA oxidase gene instead of, or in addition to, an exonic, 5' UTR or 3' UTR of the GA oxidase gene. Thus, a non-coding RNA molecule targeting the GA20 oxidase_3 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34. It is important to note that the sequences provided herein for the GA20 oxidase_3 gene may vary across the diversity of corn plants, lines and germplasms due to polymorphisms and/or the presence of different alleles of the gene. Furthermore, a GA20 oxidase_3 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_3 gene for suppression may be more broadly defined as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34.

According to embodiments of the present disclosure, a recombinant DNA molecule, vector or construct for suppression of an endogenous GA20 oxidase_5 gene in a plant is provided comprising a transcribable DNA sequence encoding a non-coding RNA molecule, wherein the non-coding RNA molecule targeting the GA20 oxidase_5 gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14. According to some embodiments, a non-coding RNA molecule targeting the GA20 oxidase_5 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 13 or SEQ ID NO: 14. According to some embodiments, a non-coding RNA molecule may target a GA20 oxidase gene for suppression comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 15.

As mentioned above, a non-coding RNA molecule may target an intron sequence of a GA oxidase gene instead of, or in addition to, an exonic or untranslated region of the mature mRNA of the GA oxidase gene. Thus, a non-coding RNA molecule targeting the GA20 oxidase_5 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35. The sequences provided herein for GA20 oxidase_5 may vary across the diversity of corn plants, lines and germplasms due to polymorphisms and/or the presence of different alleles of the gene. Furthermore, a GA20 oxidase_5 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_3 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35.

According to further embodiments, a recombinant DNA molecule, vector or construct for joint suppression of endogenous GA20 oxidase_3 and GA20 oxidase_5 genes in a plant is provided comprising a transcribable DNA sequence encoding a non-coding RNA molecule, wherein the non-coding RNA molecule targeting the GA20 oxidase_3 and GA20 oxidase_5 genes for suppression comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 and/or SEQ ID NO: 8, and (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 and/or SEQ ID NO: 14. According to some of these embodiments, the non-coding RNA molecule jointly targeting the GA20 oxidase_3 and GA20 oxidase_5 genes for suppression may be complementary to at least 19 consecutive nucleotides, but no more than 27 consecutive nucleotides, such as complementary to 19, 20, 21, 22, 23, 24, 25, 26, or 27 consecutive nucleotides, of (i) SEQ ID NO: 7 (and/or SEQ ID NO: 8) and (ii) SEQ ID NO: 13 (and/or SEQ ID NO: 14). According to many embodiments, the non-coding RNA molecule jointly targeting the GA20 oxidase_3 and GA20 oxidase_5 genes for suppression comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9, and (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15. As mentioned above, the non-coding RNA molecule may target an intron sequence of a GA oxidase gene. Thus, the non-coding RNA molecule may target an intron sequence(s) of one or both of the GA20 oxidase_3 and/or GA20 oxidase_5 gene(s) as identified above.

According to particular embodiments, the non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular embodiment, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene may include one mismatch at the first position of SEQ ID NO: 39 (i.e., the “C” at the first position of SEQ ID NO: 39 is replaced with a “G”; i.e., GTCCATCATGCGGTGCAACTA). However, the non-coding RNA molecule or miRNA sequence in SEQ ID NO: 40 may still bind and hybridize to the mRNA encoded by the endogenous GA20 oxidase_5 gene despite this slight mismatch.

According to embodiments of the present disclosure, a recombinant DNA molecule, vector or construct for suppression of one or more endogenous GA3 oxidase gene(s) in a plant is provided comprising a transcribable DNA sequence encoding a non-coding RNA molecule, wherein the non-coding RNA molecule comprises a sequence that is at least 80%, at least 85%, at least 90%, at least 95%, at least 96%, at least 97%, at least 98%, at least 99%, at least 99.5%, or 100% complementary to at least a segment or portion of a mRNA molecule expressed from an endogenous GA3 oxidase gene and encoding an endogenous GA3 oxidase protein in the plant, wherein the transcribable DNA sequence is operably linked to a plant-expressible promoter, and wherein the plant is a cereal or corn plant. In addition to targeting a mature mRNA sequence, a non-coding RNA molecule may further target the intronic sequences of a GA3 oxidase gene or transcript.

According to some embodiments, a non-coding RNA molecule may target a GA3 oxidase_1 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28 or SEQ ID NO: 29. According to some embodiments, a non-coding RNA molecule targeting a GA3 oxidase gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 28 or SEQ ID NO: 29. According to some embodiments, a non-coding RNA molecule targeting a GA3 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 30. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein that is at least 80%, at least 85%, at least 90%, at least 95%, at least 96%, at least 97%, at least 98%, at least 99%, at least 99.5%, or 100% similar to SEQ ID NO: 30.

As mentioned above, a non-coding RNA molecule may target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36 and/or 168, of nucleotides 515-879 or 1039-1158 of SEQ ID NO: 36, and/or of nucleotides 3647-4011 or 4171-4290 of SEQ ID NO: 168. The sequences provided herein for GA3 oxidase_1 may vary across the diversity of corn plants, lines and germplasms due to polymorphisms and/or the presence of different alleles of the gene. Furthermore, a GA3 oxidase_1 gene may be expressed as alternatively spliced isoforms that may give rise to different mRNA, cDNA and coding sequences that can affect the design of a suppression construct and non-coding RNA molecule. Thus, a non-coding RNA molecule targeting a GA3 oxidase_1 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36 and/or 168.

According to some embodiments, a non-coding RNA molecule may target a GA3 oxidase_2 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 31 or SEQ ID NO: 32. According to some embodiments, a non-coding RNA molecule targeting the GA3 oxidase gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 31 or SEQ ID NO: 32. According to some embodiments, a non-coding RNA molecule targeting the GA3 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 33. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein that is at least 80%, at least 85%, at least 90%, at least 95%, at least 96%, at least 97%, at least 98%, at least 99%, at least 99.5%, or 100% similar to SEQ ID NO: 33.

As mentioned above, a non-coding RNA molecule may target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37 and/or 169, of nucleotides 533-692 or 852-982 of SEQ ID NO: 37, and/or of nucleotides 3551-3710 or 3870-3991 of SEQ ID NO: 169. The sequences provided herein for GA3 oxidase_2 may vary across the diversity of corn plants, lines and germplasms due to polymorphisms and/or the presence of different alleles of the gene. Furthermore, a GA3 oxidase_2 gene may be expressed as alternatively spliced isoforms that may give rise to different mRNA, cDNA and coding sequences that can affect the design of a suppression construct and non-coding RNA molecule. Thus, a non-coding RNA molecule targeting a GA3 oxidase_2 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37 and/or 169.

According to some embodiments, a non-coding RNA molecule may target a GA3 oxidase_3 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 171 or SEQ ID NO: 172. According to some embodiments, a non-coding RNA molecule targeting the GA3 oxidase gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 171 or SEQ ID NO: 172. According to some embodiments, a non-coding RNA molecule targeting the GA3 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 173. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein that is at least 80%, at least 85%, at least 90%, at least 95%, at least 96%, at least 97%, at least 98%, at least 99%, at least 99.5%, or 100% similar to SEQ ID NO: 173.

As mentioned above, a non-coding RNA molecule may target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 170 and/or of nucleotides 3484-3582 or 3908-3998 of SEQ ID NO: 170. The sequences provided herein for GA3 oxidase_3 may vary across the diversity of corn plants, lines and germplasms due to polymorphisms and/or the presence of different alleles of the gene. Furthermore, a GA3 oxidase_3 gene may be expressed as alternatively spliced isoforms that may give rise to different mRNA, cDNA and coding sequences that can affect the design of a suppression construct and non-coding RNA molecule. Thus, a non-coding RNA molecule targeting a GA3 oxidase_3 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 170.

According to particular embodiments, a non-coding RNA molecule encoded by a transcribable DNA sequence for targeting a GA3 oxidase gene comprises (i) a sequence that is at least 95%, at least 96%, at least 97%, at least 98%, at least 99%, at least 99.5%, or 100% complementary to SEQ ID NO: 57 or 59, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 58 or 60. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA3 oxidase gene mRNA, such as a sequence that is nearly complementary to SEQ ID NO: 57 or 59 but with one or more complementary mismatches relative to SEQ ID NO: 57 or 59. According to a particular embodiment, the non-coding RNA molecule encoded by the transcribable DNA sequence comprises a sequence that is 100% identical to SEQ ID NO: 58 or 60, which is 100% complementary to a target sequence within the cDNA and coding sequences of a GA3 oxidase_1 or GA3 oxidase_2 gene in corn (i.e., SEQ ID NOs: 28, 29, 31 and/or 32), and/or to a corresponding sequence of a mRNA encoded by an endogenous GA3 oxidase_1 or GA3 oxidase_2 gene.

According to some embodiments, a non-coding RNA molecule may target a GA20 oxidase_4 gene for suppression and comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or SEQ ID NO: 11. According to some embodiments, a non-coding RNA molecule targeting a GA20 oxidase_4 gene for suppression may be complementary to at least 19 consecutive nucleotides, but no more than 27 consecutive nucleotides, such as complementary to 19, 20, 21, 22, 23, 24, 25, 26, or 27 consecutive nucleotides, of SEQ ID NO: 10 or SEQ ID NO: 11. According to some embodiments, a non-coding RNA molecule targeting the GA20 oxidase gene for suppression comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 12. According to further embodiments, a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein that is at least 80%, at least 85%, at least 90%, at least 95%, at least 96%, at least 97%, at least 98%, at least 99%, at least 99.5%, or 100% similar to SEQ ID NO: 12.

As mentioned above, a non-coding RNA molecule may target an intron sequence of a GA20 oxidase gene instead of, or in addition to, an exonic, 5' UTR or 3' UTR of the GA20 oxidase gene. Thus, a non-coding RNA molecule targeting a GA20 oxidase_4 gene for suppression may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38. The sequences provided herein for GA20 oxidase_4 may vary across the diversity of corn plants, lines and germplasms due to polymorphisms and/or the presence of different alleles of the gene. Furthermore, a GA20 oxidase_4 gene may be expressed as alternatively spliced isoforms that may give rise to different mRNA, cDNA and coding sequences that can affect the design of a suppression construct and non-coding RNA molecule. Thus, a non-coding RNA molecule targeting a GA20 oxidase_4 gene for suppression may be defined more broadly as comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38.

According to particular embodiments, a non-coding RNA molecule encoded by a transcribable DNA sequence for targeting a GA20 oxidase_4 gene comprises (i) a sequence that is at least 95%, at least 96%, at least 97%, at least 98%, at least 99%, at least 99.5%, or 100% complementary to SEQ ID NO: 61, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 62. According to some embodiments, the non-coding RNA molecule encoded by a transcribable DNA sequence may comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 61 but with one or more complementary mismatches relative to SEQ ID NO: 61. According to a particular embodiment, the non-coding RNA molecule encoded by the transcribable DNA sequence comprises a sequence that is 100% identical to SEQ ID NO: 62, which is 100% complementary to a target sequence within the cDNA and coding sequences of a GA20 oxidase_4 gene in corn (i.e., SEQ ID NO: 10 or 11), and/or to a corresponding sequence of a mRNA encoded by an endogenous GA20 oxidase_4 gene.

According to embodiments of the present disclosure, a recombinant DNA construct is provided comprising a transcribable DNA sequence encoding a non-coding RNA molecule targeting an endogenous GA20 oxidase_3 and/or the GA20 oxidase_5 gene(s) for suppression, wherein the transcribable DNA sequence is operably linked to a constitutive, tissue-specific or tissue-preferred promoter, and wherein the transcribable DNA sequence causes the expression level of an endogenous GA20 oxidase_3 and/or the GA20 oxidase_5 gene(s) to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 9, and/or (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 15.

According to embodiments of the present disclosure, a recombinant DNA construct is provided comprising a transcribable DNA sequence encoding a non-coding RNA molecule targeting an endogenous GA3 oxidase_1, GA3 oxidase_2, and/or the GA3 oxidase_3 gene(s) for suppression, wherein the transcribable DNA sequence is operably linked to a constitutive, tissue-specific or tissue-preferred promoter, and wherein the transcribable DNA sequence causes the expression level of an endogenous GA3 oxidase_1, GA3 oxidase_2, and/or the GA3 oxidase_3 gene(s) to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 30, (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 33, and/or (iii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein in the plant that is at least 80%, at least 85%, at least 90%, at least 95%, at least 96%, at least 97%, at least 98%, at least 99%, at least 99.5%, or 100% identical to SEQ ID NO: 173.

According to embodiments of the present disclosure, a recombinant DNA construct is provided comprising a transcribable DNA sequence encoding a non-coding RNA molecule targeting an endogenous GA20 oxidase_4 gene for suppression, wherein the transcribable DNA sequence is operably linked to a constitutive, tissue-specific or tissue-preferred promoter, and wherein the transcribable DNA sequence causes the expression level of an endogenous GA20 oxidase_4 gene to become reduced or lowered in one or more tissue(s) of a plant transformed with the transcribable DNA sequence. Such a non-coding RNA molecule encoded by the transcribable DNA sequence may comprise a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein in the plant that is at least 80%, at least 85%, at least 90%, at least 95%, at least 96%, at least 97%, at least 98%, at least 99%, at least 99.5%, or 100% identical to SEQ ID NO: 12.

According to many embodiments, a modified or transgenic plant is provided that is transformed with a recombinant DNA construct comprising a transcribable DNA sequence encoding a non-coding RNA molecule targeting an endogenous GA20 oxidase_3 and/or GA20 oxidase_5 gene(s) for suppression, and/or has an endogenous GA20 oxidase_3 and/or GA20 oxidase_5 gene(s) edited through targeted genome editing techniques, as provided herein, wherein the transcribable DNA sequence is operably linked to a constitutive promoter or a tissue-specific or tissue-preferred promoter, such as a vascular promoter or a leaf promoter, and wherein the expression level of the endogenous GA20 oxidase_3 and/or GA20 oxidase_5 gene(s) is eliminated, reduced or lowered in one or more plant tissue (s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA20 oxidase_3 and/or GA20 oxidase_5 gene(s) for suppression, and/or has an endogenous GA20 oxidase_3 and/or GA20 oxidase_5 gene(s) edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and/or wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA3 oxidase_1, GA3 oxidase_2, and/or GA3 oxidase_3 gene(s) for suppression, and/or has an endogenous GA3 oxidase_1, GA3 oxidase_2, or GA3 oxidase_3 gene edited through targeted genome editing techniques, as provided herein, wherein the transcribable DNA sequence is operably linked to a constitutive promoter or a tissue-specific or tissue-preferred promoter, such as a vascular promoter or a leaf promoter, and/or wherein the expression level of the endogenous GA3 oxidase_1, GA3 oxidase_2, and/or GA3 oxidase_3 gene(s) is eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA3 oxidase_1, GA3 oxidase_2, and/or GA3 oxidase_3 gene(s) for suppression, and/or has an endogenous GA3 oxidase_1, GA3 oxidase_2, and/or GA3 oxidase_3 gene edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and/or wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA20 oxidase_4 gene for suppression, and/or has an endogenous GA20 oxidase_4 gene edited through targeted genome editing techniques, as provided herein, wherein the transcribable DNA sequence is operably linked to a constitutive promoter or a tissue-specific or tissue-preferred promoter, such as a vascular promoter or a leaf promoter, and/or wherein the expression level of the endogenous GA20 oxidase_4 gene(s) is eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant. According to many embodiments, a modified or transgenic plant is provided that is transformed with a recombinant DNA construct comprising a transcribable DNA sequence encoding a non-coding RNA molecule targeting an endogenous GA20 oxidase_4 gene(s) for suppression, and/or has an endogenous GA20 oxidase_4 gene edited through targeted genome editing techniques to reduce or eliminate its level of expression and/or activity, wherein the transcribable DNA sequence is operably linked to a constitutive promoter or a tissue-specific or tissue-preferred promoter, such as a vascular promoter or a leaf promoter, and/or wherein the level of one or more active GAs, such as GA1, GA3, GA4, and/or GA7, is reduced or lowered in one or more plant tissue(s), such as one or more stem, internode, vascular and/or leaf tissue(s) or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many embodiments, a modified or transgenic plant is provided that is transformed with a recombinant DNA construct comprising a transcribable DNA sequence encoding a non-coding RNA molecule targeting an endogenous GA20 oxidase_3, GA20 oxidase_4, and/or GA20 oxidase_5 gene(s) for suppression, is transformed with a recombinant DNA construct comprising a transcribable DNA sequence encoding a non-coding RNA molecule targeting an endogenous GA3 oxidase_1, GA3 oxidase_2, and/or the GA3 oxidase_3 gene(s) for suppression, has an endogenous GA20 oxidase_3, GA20 oxidase_4, or the GA20 oxidase_5 gene edited through targeted genome editing techniques, and/or has an endogenous GA3 oxidase_1, GA3 oxidase_2, or the GA3 oxidase_3 gene edited through targeted genome editing techniques, to reduce or eliminate its level of expression and/or activity, as provided herein, wherein the transcribable DNA sequence is operably linked to a constitutive promoter or a tissue-specific or tissue-preferred promoter, such as a vascular promoter or a leaf promoter, and/or wherein the modified or transgenic plant has one or more of the following traits: a semi-dwarf or reduced plant height or stature, decreased stem internode length, increased lodging resistance, and/or increased stem or stalk diameter. Such a modified or transgenic plant may not have any significant reproductive off-types. A modified or transgenic plant may have one or more of the following additional traits: reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and anthocyanin area in leaves under normal and/or nitrogen or water limiting stress conditions, increased ear weight, increased kernel number, increased kernel weight, increased yield, and/or increased harvest index. According to many of these embodiments, the level of expression and/or activity of an endogenous GA20 oxidase_3, GA20 oxidase_4, and/or GA20 oxidase_5 gene(s), or an endogenous GA3 oxidase_1, GA3 oxidase_2, and/or GA3 oxidase_3 gene(s), may be eliminated, reduced or lowered in one or more plant tissue(s), such as one or more vascular and/or leaf tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant, and/or the level of one or more active GAs, such as GA1, GA3, GA4, and/or GA7, is reduced or lowered in one or more plant tissue(s), such as one or more stem, internode, vascular and/or leaf tissue(s), or one or more stem and/or internode tissue(s), of the modified or transgenic plant by at least 5%, at least 10%, at least 20%, at least 25%, at least 30%, at least 40%, at least 50%, at least 60%, at least 70%, at least 75%, at least 80%, at least 90%, or 100% as compared to a wild type or control plant.

According to many of the embodiments described in the above paragraphs, the non-coding RNA molecule encoded by the transcribable DNA sequence of the recombinant DNA molecule, vector or construct may be a precursor miRNA or siRNA that may be subsequently processed or cleaved in a plant cell to form a mature miRNA or siRNA.

A recombinant DNA molecule, construct or vector of the present disclosure may comprise a transcribable DNA sequence encoding a non-coding RNA molecule that targets an endogenous GA oxidase gene for suppression, wherein the transcribable DNA sequence is operatively linked to a plant-expressible promoter, such as a constitutive or vascular and/or leaf promoter. For purposes of the present disclosure, a non-coding RNA molecule encoded by a transcribable DNA sequence that targets an endogenous GA oxidase gene for suppression may include a mature non-coding RNA molecule that targets an endogenous GA oxidase gene for suppression, and/or a precursor RNA molecule that may become processed in a plant cell into a mature non-coding RNA molecule, such as a miRNA or siRNA, that targets an endogenous GA oxidase gene for suppression. In addition to its associated promoter, a transcribable DNA sequence encoding a non-coding RNA molecule for suppression of an endogenous GA oxidase gene may also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) may be optional and/or used to enhance or optimize expression of the transgene or transcribable DNA sequence. As provided herein, an "enhancer" may be distinguished from a "promoter" in that an enhancer typically lacks a transcription start site, TATA box, or equivalent sequence and is thus insufficient alone to drive transcription. As used herein, a "leader" may be defined generally as the DNA sequence of the 5'-UTR of a gene (or transgene) between the transcription start site (TSS) and 5' end of the transcribable DNA sequence or protein coding sequence start site of the transgene.

According to further embodiments, methods are provided for transforming a plant cell, tissue or explant with a recombinant DNA molecule or construct comprising a transcribable DNA sequence or transgene operably linked to a plant-expressible promoter to produce a transgenic plant. The transcribable DNA sequence may encode a non-coding RNA molecule that targets a GA oxidase gene(s) for suppression, or a RNA precursor that is processed into a mature RNA molecule, such as a miRNA or siRNA, that targets one or more GA oxidase gene(s) for suppression. Numerous methods for transforming chromosomes or plastids in a plant cell with a recombinant DNA molecule or construct are known in the art, which may be used according to method embodiments of the present invention to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation, and microprojectile or particle bombardment-mediated transformation. A variety of methods are known in the art for transforming explants with a transformation vector via bacterially mediated transformation or microprojectile or particle bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art.

Methods of transforming plant cells and explants are well known by persons of ordinary skill in the art. Methods for transforming plant cells by microprojectile bombardment with particles coated with recombinant DNA are provided, for example, in U.S. Pat. Nos. 5,550,318; 5,538,880 6,160,208; 6,399,861; and 6,153,812, and *Agrobacterium*-mediated transformation is described, for example, in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any suitable method of plant transformation known or later developed in the art can be used to transform a plant cell or explant with any of the nucleic acid molecules, constructs or vectors provided herein.

Transgenic plants produced by transformation methods may be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods may be used to create transgenic cereal or corn plants having a shorter, semi-dwarf stature, reduced internode length, increased stalk/stem diameter, and/or improved lodging resistance. Such transgenic cereal or corn plants may further have other traits that may be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Transgenic plants expressing a GA oxidase transgene or non-coding RNA molecule that targets an endogenous GA oxidase gene for suppression, or modified plants having one or more mutations in a GA oxidase gene, may have an earlier canopy closure (e.g., approximately one day earlier, or 12-48 hours, 12-36 hours, 18-36 hours, or about 24 hours earlier canopy closure) than a wild type or control plant. Although transgenic plants expressing a GA oxidase transgene or non-coding RNA molecule that targets an endogenous GA oxidase gene for suppression and modified plants having one or more mutations in a GA oxidase gene may have a lower ear height than a wild type or control plant, the height of the ear may generally be at least 18 inches above the ground. Transgenic plants expressing a non-coding RNA molecule that targets an endogenous GA oxidase gene for suppression or modified plants having one or more mutations in a GA oxidase gene may have greater biomass and/or leaf area during one or more late vegetative stages (e.g., V8-V12) than a wild type or control plant. Transgenic plants expressing a GA oxidase transgene or non-coding RNA molecule that targets an endogenous GA oxidase gene for suppression or modified plants having one or more mutations in a GA oxidase gene may have deeper roots during later vegetative stages when grown in the field, than a wild type or control plant, which may be due to an increased root front velocity. These transgenic or modified plants may reach a depth 90 cm below ground sooner (e.g., 10-25 days sooner, 15-25 days sooner, or about 20 days sooner) than a wild type or control plant, which may occur by the vegetative to reproductive transition of the plant (e.g., by V16/R1 at about 50 days after planting as opposed at about 70 days after planting for control plants).

Recipient cell(s) or explant or cellular targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, a callus cell, a chloroplast, a stomatal cell, a trichome cell, a root hair cell, a storage root cell, or a vascular tissue cell, a seed, embryo, meristem, cotyledon, hypocotyl, endosperm, root, shoot, stem, node, callus, cell suspension, protoplast, flower, leaf, pollen, anther, ovary, ovule, pericarp, bud, and/or vascular tissue, or any transformable portion of any of the foregoing. For plant transformation, any target cell(s), tissue(s), explant(s), etc., that may be used to receive a recombinant DNA transformation vector or molecule of the present disclosure may be collectively be referred to as an "explant" for transformation. Preferably, a transformable or transformed explant cell or tissue may be further developed or regenerated into a plant. Any cell or explant from which a fertile plant can be grown or regenerated is contemplated as a useful recipient cell or explant for practice of this disclosure (i.e., as a target explant for transformation). Callus can be initiated or created from various tissue sources, including, but not limited to, embryos or parts of embryos, non-embryonic seed tissues, seedling apical meristems, microspores, and the like. Any cells that are capable of proliferating as callus may serve as recipient cells for transformation. Transformation methods and materials for making transgenic plants (e.g., various media and recipient target cells or explants and methods of transformation and subsequent regeneration of into transgenic plants) are known in the art.

Transformation of a target plant material or explant may be practiced in tissue culture on nutrient media, for example a mixture of nutrients that allow cells to grow in vitro or cell culture. Transformed explants, cells or tissues may be subjected to additional culturing steps, such as callus induction, selection, regeneration, etc., as known in the art. Transformation may also be carried out without creation or use of a callus tissue. Transformed cells, tissues or explants containing a recombinant DNA sequence insertion or event may be grown, developed or regenerated into transgenic plants in culture, plugs, or soil according to methods known in the art. Transgenic plants may be further crossed to themselves or other plants to produce transgenic seeds and progeny. A transgenic plant may also be prepared by crossing a first plant comprising the recombinant DNA sequence or transformation event with a second plant lacking the insertion. For example, a recombinant DNA construct or sequence may be introduced into a first plant line that is amenable to transformation, which may then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

A transgenic, mutant or edited plant, plant part, cell, or explant provided herein may be of an elite variety or an elite line. An elite variety or an elite line refers to a variety that has resulted from breeding and selection for superior agronomic performance. A transgenic, mutant or edited plant, cell, or explant provided herein may be a hybrid plant, cell, or explant. As used herein, a "hybrid" is created by crossing two plants from different varieties, lines, inbreds, or species, such that the progeny comprises genetic material from each parent. Skilled artisans recognize that higher order hybrids can be generated as well. For example, a first hybrid can be made by crossing Variety A with Variety B to create a A×B hybrid, and a second hybrid can be made by crossing Variety C with Variety D to create an C×D hybrid. The first and second hybrids can be further crossed to create the higher order hybrid (A×B)×(C×D) comprising genetic information from all four parent varieties.

According to embodiments of the present disclosure, a modified plant is provided comprising a GA oxidase suppression element that targets two or more GA oxidase genes for suppression, or a combination of two or more GA oxidase suppression element(s) and/or gene edit(s) or mutation(s). A recombinant DNA construct or vector may comprise a single cassette or suppression element comprising a transcribable DNA sequence designed or chosen to encode a non-coding RNA molecule that is complementary to mRNA recognition or target sequences of two or more GA oxidase genes including at least a first GA oxidase gene and a second GA oxidase gene—i.e., the mRNAs of the targeted GA oxidase genes share an identical or nearly identical (or similar) sequence such that a single suppression element and encoded non-coding RNA molecule can target each of the targeted GA oxidase genes for suppression. For example, an expression cassette and suppression construct is provided herein comprising a transcribable DNA sequence that encodes a single non-coding RNA molecule that targets both the GA20 oxidase_3 and GA20 oxidase_5 genes for suppression.

According to other embodiments, a recombinant DNA construct or vector may comprise two or more suppression elements or sequences that may be stacked together in a construct or vector either in tandem in a single expression cassette or separately in two or more expression cassettes. A recombinant DNA construct or vector may comprise a single expression cassette or suppression element comprising a transcribable DNA sequence that encodes a non-coding RNA molecule comprising two or more targeting sequences arranged in tandem, including at least a first targeting sequence and a second targeting sequence, wherein the first targeting sequence is complementary to a mRNA recognition or target site of a first GA oxidase gene, and the second targeting sequence is complementary to a mRNA recognition or target site of a second GA oxidase gene, and wherein the transcribable DNA sequence is operably linked to a plant-expressible promoter. The plant-expressible promoter may be a constitutive promoter, or a tissue-specific or tissue-preferred promoter, as provided herein. The non-coding RNA molecule may be expressed as a pre-miRNA that becomes processed into two or more mature miRNAs including at least a first mature miRNA and a second miRNA, wherein the first miRNA comprises a targeting sequence that is complementary to the mRNA recognition or target site of the first GA oxidase gene, and the second miRNA comprises a targeting sequence that is complementary to the mRNA recognition or target site of the second GA oxidase gene.

According to other embodiments, a recombinant DNA construct or vector may comprise two or more expression cassettes including a first expression cassette and a second expression cassette, wherein the first expression cassette comprises a first transcribable DNA sequence operably linked to a first plant-expressible promoter, and the second expression cassette comprises a second transcribable DNA sequence operably linked to a second plant-expressible promoter, wherein the first transcribable DNA sequence encodes a first non-coding RNA molecule comprising a targeting sequence that is complementary to a mRNA recognition or target site of a first GA oxidase gene, and the second transcribable DNA sequence encodes a second non-coding RNA molecule comprising a targeting sequence that is complementary to a mRNA recognition or target site of a second GA oxidase gene. The first and second plant-expressible promoters may each be a constitutive promoter, or a tissue-specific or tissue-preferred promoter, as provided herein, and the first and second plant-expressible promoters may be the same or different promoters.

According to other embodiments, two or more suppression elements or constructs targeting GA oxidase gene(s) and/or GA oxidase gene edit(s) or mutation(s) may be combined in a modified plant by crossing two or more plants together in one or more generations to produce a modified plant having a desired combination of suppression element (s) and/or gene edit(s) or mutation(s). According to these embodiments, a first modified plant comprising a suppression element or construct targeting a GA oxidase gene(s) (or a GA oxidase gene edit or mutation) may be crossed to a second modified plant comprising a suppression element or construct targeting a GA oxidase gene(s) (or a GA oxidase gene edit or mutation), such that a modified progeny plant may be made comprising a first suppression element or construct and a second suppression element or construct, a suppression element or construct and a GA oxidase gene edit or mutation, or a first GA oxidase gene edit or mutation and a second GA oxidase gene edit or mutation. Alternatively, a modified plant comprising two or more suppression elements or constructs targeting GA oxidase gene(s) and/or GA oxidase gene edit(s) or mutation(s) may be made by (i) co-transforming a first suppression element or construct and a second suppression element or construct (each targeting a GA oxidase gene for suppression), (ii) transforming a modified plant with a second suppression element or construct, wherein the modified plant already comprises a first suppression element or construct, (iii) transforming a modified plant with a suppression element or construct, wherein the modified plant already comprises an edited or mutated GA oxidase gene, (iv) transforming a modified plant with a construct(s) for making one or more edits or mutations in GA oxidase gene(s), wherein the modified plant already comprises a suppression element or construct, or (v) transforming with construct(s) for making two or more edits or mutations in GA oxidase gene(s).

According to embodiments of the present disclosure, modified plants are provided comprising two or more constructs targeting GA oxidase gene(s) for suppression including a first recombinant DNA construct and a second recombinant DNA construct, wherein the first recombinant DNA construct comprises a first transcribable DNA sequence encoding a first non-coding RNA molecule that is complementary to a mRNA recognition or target sequence of a first GA oxidase gene, and the second recombinant DNA construct comprises a second transcribable DNA sequence encoding a second non-coding RNA molecule that is complementary to a mRNA recognition or target sequence of a second GA oxidase gene. The first and second recombinant DNA constructs may be stacked in a single vector and transformed into a plant as a single event, or present in separate vectors or constructs that may be transformed as separate events. According to these embodiments, the first GA oxidase gene may be a GA20 oxidase_3, GA20 oxidase_5, GA20 oxidase_4, GA3 oxidase_1, GA3 oxidase_2, or GA3 oxidase_3 gene, the first non-coding RNA molecule is complementary to a recognition or target sequence of an mRNA expressed from such GA oxidase gene, and the second GA oxidase gene may be a GA20 oxidase_3, GA20 oxidase_5, GA20 oxidase_4, GA3 oxidase_1, GA3 oxidase_2, or GA3 oxidase_3 gene. According to some embodiments, the first and second GA oxidase genes may be the same or different GA oxidase gene(s). Alternatively, the second GA oxidase gene may be another GA oxidase gene, such as a GA20 oxidase_1, GA20 oxidase_2, GA20 oxidase_6, GA20 oxidase_7, GA20 oxidase_8, or GA20 oxidase_9 gene, and the second non-coding RNA molecule is complementary to a recognition or target sequence of an mRNA expressed from such GA oxidase gene.

According to embodiments of the present disclosure, modified plants are provided comprising a recombinant DNA construct targeting GA oxidase genes for suppression comprising a transcribable DNA sequence encoding a non-coding RNA molecule that comprises two or more targeting sequences arranged in tandem including at least a first targeting sequence that is complementary to a mRNA recognition or target sequence of a first GA oxidase gene and a second targeting sequence that is complementary to a mRNA recognition or target sequence of a second GA oxidase gene. The non-coding RNA molecule may be expressed as a pre-miRNA that becomes processed into two or more mature miRNAs including at least a first mature miRNA and a second miRNA, wherein the first miRNA comprises the first targeting sequence that is complementary to the mRNA recognition or target site of the first GA oxidase gene, and the second miRNA comprises the second targeting sequence that is complementary to the mRNA recognition or target site of the second GA oxidase gene. According to these embodiments, the first GA oxidase gene may be a GA20 oxidase_3, GA20 oxidase_5, GA20 oxidase_4, GA3 oxidase_1, GA3 oxidase_2, or GA3 oxidase_3 gene, the first non-coding RNA molecule is complementary to a recognition or target sequence of an mRNA expressed from such GA oxidase gene, and the second GA oxidase gene may be a GA20 oxidase_3, GA20 oxidase_5, GA20 oxidase_4, GA3 oxidase_1, GA3 oxidase_2, or GA3 oxidase_3 gene. According to some embodiments, the first and second GA oxidase genes may be the same or different GA oxidase gene(s). Alternatively, the second GA oxidase gene may be another GA oxidase gene, such as a GA20 oxidase_1, GA20 oxidase_2, GA20 oxidase_6, GA20 oxidase_7, GA20 oxidase_8, or GA20 oxidase_9 gene, and the second non-coding RNA molecule is complementary to a recognition or target sequence of an mRNA expressed from such GA oxidase gene.

In the above stacking scenarios, and regardless of whether the targeting sequences are stacked in tandem in a single transcribable DNA sequence (or expression cassette) or in separate transcribable DNA sequences (or expression cassettes), the second GA oxidase gene may be a GA oxidase gene other than a GA20 oxidase_3, GA20 oxidase_5, GA20 oxidase_4, GA3 oxidase_1, GA3 oxidase_2, or GA3 oxidase_3 gene, such as a GA20 oxidase_1, GA20 oxidase_2, GA20 oxidase_6, GA20 oxidase_7, GA20 oxidase_8, or GA20 oxidase_9 gene. According to these embodiments, the second targeting sequence of a non-coding RNA molecule may be at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NOs: 1, 2, 4, 5, 16, 17, 19, 20, 22, 23, 25, and/or 26. According to some embodiments, the second targeting sequence of a non-coding RNA molecule may be complementary to at least 19 consecutive nucleotides, but no more than 27 consecutive nucleotides, such as complementary to 19, 20, 21, 22, 23, 24, 25, 26, or 27 consecutive nucleotides, of any one or more of SEQ ID NOs: 1, 2, 4, 5, 16, 17, 19, 20, 22, 23, 25, and/or 26. According to some embodiments, the second targeting sequence of a non-coding RNA molecule may be at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in the plant that is at least 80%, at least 85%, at least 90%, at least 95%, at least 96%, at least 97%, at least 98%, at least 99%, at least 99.5%, or 100% identical to any one or more of SEQ ID NOs: 3, 6, 18, 21, 24, and/or 27. According to further embodiments, the second targeting sequence of a non-coding RNA molecule may comprise a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein that is at least 80%, at least 85%, at least 90%, at least 95%, at least 96%, at least 97%, at least 98%, at least 99%, at least 99.5%, or 100% similar to any one or more of SEQ ID NO: 3, 6, 18, 21, 24, and/or 27.

A recombinant DNA molecule or construct of the present disclosure may comprise or be included within a DNA transformation vector for use in transformation of a target plant cell, tissue or explant. Such a transformation vector may generally comprise sequences or elements necessary or beneficial for effective transformation in addition to at least one transgene, expression cassette and/or transcribable DNA sequence encoding a GA oxidase gene or a non-coding RNA molecule targeting an endogenous GA oxidase gene for suppression. For *Agrobacterium*-mediated, *Rhizobia*-mediated or other bacteria-mediated transformation, the transformation vector may comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette encoding a non-coding RNA molecule targeting an endogenous GA oxidase gene for suppression may be located between the left and right borders of the T-DNA, perhaps along with an additional transgene(s) or expression cassette(s), such as a plant selectable marker transgene and/or other gene(s) of agronomic interest that may confer a trait or phenotype of agronomic interest to a plant. According to alternative embodiments, the transcribable DNA sequence, transgene or expression cassette encoding a non-coding RNA molecule targeting an endogenous GA oxidase gene for suppression and the plant selectable marker transgene (or other gene of agronomic interest) may be present in separate T-DNA segments on the same or different recombinant DNA molecule(s), such as for co-transformation. According to some embodiments, a transcribable DNA sequence(s), transgene(s) or expression cassette(s) of a recombinant DNA molecule or construct or a DNA transformation vector for genome editing may encode one or more guide RNA(s) and/or a site-specific nuclease. A transformation vector or construct may further comprise prokaryotic maintenance elements, which may be located in the vector outside of the T-DNA region(s).

A plant selectable marker transgene in a transformation vector or construct of the present disclosure may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known. In some embodiments, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation may also be carried out in the absence of selection during one or more steps or stages of culturing, developing or regenerating transformed explants, tissues, plants and/or plant parts.

According to present embodiments, methods for transforming a plant cell, tissue or explant with a recombinant DNA molecule or construct may further include site-directed or targeted integration. According to these methods, a portion of a recombinant DNA donor template molecule (i.e., an insertion sequence) may be inserted or integrated at a desired site or locus within the plant genome. The insertion sequence of the donor template may comprise a transgene or construct, such as a transgene or transcribable DNA sequence encoding a non-coding RNA molecule that targets an endogenous GA oxidase gene for suppression. The donor template may also have one or two homology arms flanking the insertion sequence to promote the targeted insertion event through homologous recombination and/or homology-directed repair. Each homology arm may be at least 70%, at least 75%, at least 80%, at least 85%, at least 90%, at least 95%, at least 96%, at least 97%, at least 99% or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence within the genome of a monocot or cereal plant. Thus, a recombinant DNA molecule of the present disclosure may comprise a donor template for site-directed or targeted integration of a transgene or construct, such as a transgene or transcribable DNA sequence encoding a non-coding RNA molecule that targets an endogenous GA oxidase gene for suppression, into the genome of a plant.

Any site or locus within the genome of a plant may potentially be chosen for site-directed integration of a transgene, construct or transcribable DNA sequence provided herein. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9 or Cpf1). Any method known in the art for site-directed integration may be used. In the presence of a donor template molecule with an insertion sequence, the DSB or nick may then be repaired by homologous recombination between homology arm(s) of the donor template and the plant genome, or by non-homologous end joining (NHEJ), resulting in site-directed integration of the insertion sequence into the plant genome to create the targeted insertion event at the site of the DSB or nick. Thus, site-specific insertion or integration of a transgene, construct or sequence may be achieved.

The introduction of a DSB or nick may also be used to introduce targeted mutations in the genome of a plant. According to this approach, mutations, such as deletions, insertions, inversions and/or substitutions, may be introduced at a target site via imperfect repair of the DSB or nick to produce a knock-out or knock-down of a GA oxidase gene. Such mutations may be generated by imperfect repair of the targeted locus even without the use of a donor template molecule. A "knock-out" of a GA oxidase gene may be achieved by inducing a DSB or nick at or near the endogenous locus of the GA oxidase gene that results in non-expression of the GA oxidase protein or expression of a non-functional protein, whereas a "knock-down" of a GA oxidase gene may be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein. For example, the site of the DSB or nick within the endogenous locus may be in the upstream or 5' region of the GA oxidase gene (e.g., a promoter and/or enhancer sequence) to affect or reduce its level of expression. Similarly, such targeted knock-out or knock-down mutations of a GA oxidase gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene may be achieved by deleting or inverting at least a portion of the gene or by introducing a frame shift or premature stop codon into the coding sequence of the gene. A deletion of a portion of a GA oxidase gene may also be introduced by generating DSBs or nicks at two target sites and causing a deletion of the intervening target region flanked by the target sites.

A site-specific nuclease provided herein may be selected from the group consisting of a zinc-finger nuclease (ZFN), a meganuclease, an RNA-guided endonuclease, a TALE-endonuclease (TALEN), a recombinase, a transposase, or any combination thereof. See, e.g., Khandagale, K. et al., "Genome editing for targeted improvement in plants," *Plant Biotechnol Rep* 10:327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 enzyme.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1. In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a GA oxidase gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol.* 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto). For genome editing at or near the GA20 oxidase_5 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto). As used herein, the term "consecutive" in reference to a polynucleotide or protein sequence means without deletions or gaps in the sequence.

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_3 or GA20 oxidase_5 gene to mutate one or more promoter and/or regulatory sequences of the gene and affect or reduce its level of expression. For knockdown (and possibly knockout) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3096 of SEQ ID NO: 34, the nucleotide sequence range 3666-3775 of SEQ ID NO: 34, the nucleotide sequence range 4098-5314 of SEQ ID NO: 34, the nucleotide sequence range 5585-5800 of SEQ ID NO: 34, or the nucleotide sequence range 5801-8800 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3096, 3666-3775, 4098-5314, 5585-5800, 5801-8800, or 5585-8800 of SEQ ID NO: 34, or a sequence complementary thereto).

For knockdown (and possibly knockout) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3000 of SEQ ID NO: 35, the nucleotide sequence range 1-3000 of SEQ ID NO: 35, the nucleotide sequence range 3792-3906 of SEQ ID NO: 35, the nucleotide sequence range 4476-5197 of SEQ ID NO: 35, or the nucleotide sequence range 5860-8859 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3792-3906, 4476-5197, or 5860-8859 of SEQ ID NO: 35, or a sequence complementary thereto).

For knockout (and possibly knockdown) mutations through genome editing, an RNA-guided endonuclease may be targeted to a coding and/or intron sequence of a GA20 oxidase_3 or GA20 oxidase_5 gene to potentially eliminate expression and/or activity of a functional GA oxidase protein from the gene. However, a knockout of a GA oxidase gene expression may also be achieved in some cases by targeting the upstream and/or 5'UTR sequence(s) of the gene, or other sequences at or near the genomic locus of the gene. Thus, a knockout of a GA oxidase gene expression may be achieved by targeting a genomic sequence at or near the site or locus of a targeted GA20 oxidase_3 or GA20 oxidase_5 gene, an upstream or downstream sequence, such as a promoter and/or enhancer sequence, or an intron, 5'UTR, and/or 3'UTR sequence, of a GA20 oxidase_3 or GA20 oxidase_5 gene, as described above for knockdown of a GA20 oxidase_3 or GA20 oxidase_5 gene.

For knockout (and possibly knockdown) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3097-5584 of SEQ ID NO: 34, the nucleotide sequence range 3097-3665 of SEQ ID NO: 34, the nucleotide sequence range 3776-4097 of SEQ ID NO: 34, or the nucleotide sequence range 5315-5584 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 3097-5584, 3097-3665, 3097-3775, 3665-4097, 3776-4097, 3776-5314, 4098-5584, or 5315-5584 of SEQ ID NO: 34, or a sequence complementary thereto).

For knockout (and possibly knockdown) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3001-5473 of SEQ ID NO: 35, the nucleotide sequence range 3001-3791 of SEQ ID NO: 35, the nucleotide sequence range 3907-4475 of SEQ ID NO: 35, or the nucleotide sequence range 5198-5473 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 3001-5473, 3001-3791, 3001-3906, 3792-4475, 3907-4475, 3907-5197, 4476-5473, or 5198-5473 of SEQ ID NO: 35, or a sequence complementary thereto).

According to some embodiments, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA20 oxidase_4 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For knockout (and possibly knockdown) mutations through genome editing, an RNA-guided endonuclease may be targeted to a coding and/or intron sequence of a GA20 oxidase_4 gene to potentially eliminate expression and/or activity of a functional GA20 oxidase_4 protein from the gene. For the GA20 oxidase_4 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1544-2852 of SEQ ID NO: 38, the nucleotide sequence range 1544-1995 of SEQ ID NO: 38, the nucleotide sequence range 2084-2411 of SEQ ID NO: 38, or the nucleotide sequence range 2517-2852 of SEQ ID NO: 38, or a sequence complementary thereto (e.g., 10, 11, 12, 13, 14, 15, 16, 17, 18, 19, 20, 21, 22, 23, 24, 25 or more consecutive nucleotides within the nucleotide sequence range 1544-2852, 1544-1995, 1544-2083, 1996-2411, 2084-2411, 2084-2516, 2412-2852, or 2517-2852 of SEQ ID NO: 38, or a sequence complementary thereto).

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_4 gene to mutate one or more promoter and/or regulatory sequences of the gene and affect or reduce its level of expression. For knockdown of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-1416 of SEQ ID NO: 38, the nucleotide sequence range 1417-1543 of SEQ ID NO: 38, the nucleotide sequence range 1996-2083 of SEQ ID NO: 38, the nucleotide sequence range 2412-2516 of SEQ ID NO: 38, the nucleotide sequence range 2853-3066 of SEQ ID NO: 38, or the nucleotide sequence range 3067-4465 of SEQ ID NO: 38, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-1416, 1417-1543, 1-1543, 1996-2083, 2412-2516, 2853-3066, 3067-4465 or 2853-4465 of SEQ ID NO: 38, or a sequence complementary thereto).

For genome editing at or near the GA3 oxidase_1 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 168 or a sequence complementary thereto (e.g., 12, 13, 14, 15, 16, 17, 18, 19, 20, 21, 22, 23, 24, 25 or more consecutive nucleotides of SEQ ID NO: 168 or a sequence complementary thereto. For genome editing at or near the GA3 oxidase_2 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 169 or a sequence complementary thereto (e.g., 12, 13, 14, 15, 16, 17, 18, 19, 20, 21, 22, 23, 24, 25 or more consecutive nucleotides of SEQ ID NO: 169 or a sequence complementary thereto. For genome editing at or near the GA3 oxidase_3 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 170 or a sequence complementary thereto (e.g., 12, 13, 14, 15, 16, 17, 18, 19, 20, 21, 22, 23, 24, 25 or more consecutive nucleotides of SEQ ID NO: 170 or a sequence complementary thereto.

For knockout (and possibly knockdown) mutations through genome editing, an RNA-guided endonuclease may be targeted to a coding and/or intron sequence of a GA3 oxidase_1 gene to potentially eliminate expression and/or activity of a functional GA3 oxidase_1 protein from the gene. For the GA3 oxidase_1 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3162-4795 of SEQ ID NO: 168, the nucleotide sequence range 3162-3646 of SEQ ID NO: 168, the nucleotide sequence range 4012-4170 of SEQ ID NO: 168, or the nucleotide sequence range 4291-4795 of SEQ ID NO: 168, or a sequence complementary thereto (e.g., 10, 11, 12, 13, 14, 15, 16, 17, 18, 19, 20, 21, 22, 23, 24, 25 or more consecutive nucleotides within the nucleotide sequence range 3162-3646, 3162-4011, 3647-4170, 4012-4170, 4012-4290, 4171-4795, 4291-4795, or 3162-4795 of SEQ ID NO: 168, or a sequence complementary thereto).

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA3 oxidase_1 gene to mutate one or more promoter and/or regulatory sequences of the gene and affect or reduce its level of expression. For knockdown of the GA3 oxidase_1 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3161 of SEQ ID NO: 168, the nucleotide sequence range 3001-3161 of SEQ ID NO: 168, the nucleotide sequence range 3647-4011 of SEQ ID NO: 168, the nucleotide sequence range 4171-4290 of SEQ ID NO: 168, the nucleotide sequence range 4796-5406 of SEQ ID NO: 168, or the nucleotide sequence range 4796-8406 of SEQ ID NO: 168, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3001-3161, 1-3161, 3647-4011, 4171-4290, 4796-5406, 5407-8406 or 4796-8406 of SEQ ID NO: 168, or a sequence complementary thereto).

For knockout (and possibly knockdown) mutations through genome editing, an RNA-guided endonuclease may be targeted to a coding and/or intron sequence of a GA3 oxidase_2 gene to potentially eliminate expression and/or activity of a functional GA3 oxidase_2 protein from the gene. For the GA3 oxidase_2 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3057-4463 of SEQ ID NO: 169, the nucleotide sequence range 3057-3550 of SEQ ID NO: 169, the nucleotide sequence range 3711-3869 of SEQ ID NO: 169, or the nucleotide sequence range 3992-4463 of SEQ ID NO: 169, or a sequence complementary thereto (e.g., 10, 11, 12, 13, 14, 15, 16, 17, 18, 19, 20, 21, 22, 23, 24, 25 or more consecutive nucleotides within the nucleotide sequence range 3057-4463, 3057-3550, 3057-3710, 3551-3869, 3711-3869, 3711-3991, 3870-4463, or 3992-4463 of SEQ ID NO: 169, or a sequence complementary thereto).

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA3 oxidase_2 gene to mutate one or more promoter and/or regulatory sequences of the gene and affect or reduce its level of expression. For knockdown of the GA3 oxidase_2 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3056 of SEQ ID NO: 169, the nucleotide sequence range 3001-3056 of SEQ ID NO: 169, the nucleotide sequence range 3551-3710 of SEQ ID NO: 169, the nucleotide sequence range 3870-3991 of SEQ ID NO: 169, the nucleotide sequence range 4464-4581 of SEQ ID NO: 169, or the nucleotide sequence range 4464-7581 of SEQ ID NO: 169, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3001-3056, 1-3056, 3551-3710, 3870-3991, 4464-4581, 4464-7581 or 4582-7581 of SEQ ID NO: 169, or a sequence complementary thereto).

For knockout (and possibly knockdown) mutations through genome editing, an RNA-guided endonuclease may be targeted to a coding and/or intron sequence of a GA3 oxidase_3 gene to potentially eliminate expression and/or activity of a functional GA3 oxidase_3 protein from the gene. For the GA3 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3131-4274 of SEQ ID NO: 170, the nucleotide sequence range 3131-3483 of SEQ ID NO: 170, the nucleotide sequence range 3583-3907 of SEQ ID NO: 170, or the nucleotide sequence range 3999-4274 of SEQ ID NO: 170, or a sequence complementary thereto (e.g., 10, 11, 12, 13, 14, 15, 16, 17, 18, 19, 20, 21, 22, 23, 24, 25 or more consecutive nucleotides within the nucleotide sequence range 3131-4274, 3131-3483, 3131-3582, 3484-3907, 3583-3907, 3583-3998, 3908-4274, or 3999-4274 of SEQ ID NO: 170, or a sequence complementary thereto).

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA3 oxidase_3 gene to mutate one or more promoter and/or regulatory sequences of the gene and affect or reduce its level of expression. For knockdown of the GA3 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3130 of SEQ ID NO: 170, the nucleotide sequence range 3001-3130 of SEQ ID NO: 170, the nucleotide sequence range 3484-3582 of SEQ ID NO: 170, the nucleotide sequence range 3908-3998 of SEQ ID NO: 170, the nucleotide sequence range 4275-4332 of SEQ ID NO: 170, or the nucleotide sequence range 4275-7332 of SEQ ID NO: 170, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3001-3130, 1-3130, 3484-3582, 3908-3998, 4275-4332, 4275-7332 or 4333-7332 of SEQ ID NO: 170, or a sequence complementary thereto).

In addition to the guide sequence, a guide RNA may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

According to some embodiments, recombinant DNA constructs and vectors are provided comprising a polynucleotide sequence encoding a site-specific nuclease, such as a zinc-finger nuclease (ZFN), a meganuclease, an RNA-guided endonuclease, a TALE-endonuclease (TALEN), a recombinase, or a transposase, wherein the coding sequence is operably linked to a plant expressible promoter. For RNA-guided endonucleases, recombinant DNA constructs and vectors are further provided comprising a polynucleotide sequence encoding a guide RNA, wherein the guide RNA comprises a guide sequence of sufficient length having a percent identity or complementarity to a target site within the genome of a plant, such as at or near a targeted GA oxidase gene. According to some embodiments, a polynucleotide sequence of a recombinant DNA construct and vector that encodes a site-specific nuclease or a guide RNA may be operably linked to a plant expressible promoter, such as an inducible promoter, a constitutive promoter, a tissue-specific promoter, etc.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. Such recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous GA oxidase gene of a corn or cereal plant, such as the GA20 oxidase_3 gene or the GA20 oxidase_5 gene in corn, to create a DSB or nick at such genomic locus to knockout or knockdown expression of the GA oxidase gene via repair of the DSB or nick. For example, an engineered site-specific nuclease, such as a recombinase, zinc finger nuclease (ZFN), meganuclease, or TALEN, may be designed to target and bind to (i) a target site within the genome of a plant corresponding to a sequence within SEQ ID NO: 34, or its complementary sequence, to create a DSB or nick at the genomic locus for the GA20 oxidase_3 gene, (ii) a target site within the genome of a plant corresponding to a sequence within SEQ ID NO: 35, or its complementary sequence, to create a DSB or nick at the genomic locus for the GA20 oxidase_5 gene, (iii) a target site within the genome of a plant corresponding to a sequence within SEQ ID NO: 38, or its complementary sequence, to create a DSB or nick at the genomic locus for the GA20 oxidase_4 gene, (iv) a target site within the genome of a plant corresponding to a sequence within SEQ ID NO: 36 and/or 168, or its complementary sequence, to create a DSB or nick at the genomic locus for the GA3 oxidase_1 gene, (v) a target site within the genome of a plant corresponding to a sequence within SEQ ID NO: 37 and/or 169, or its complementary sequence, to create a DSB or nick at the genomic locus for the GA3 oxidase_2 gene, or (vi) a target site within the genome of a plant corresponding to a sequence within SEQ ID NO: 170, or its complementary sequence, to create a DSB or nick at the genomic locus for the GA3 oxidase_3 gene, which may then lead to the creation of a mutation or insertion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp recombinase, and a Tnp1 recombinase. In an aspect, a Cre recombinase or a Gin recombinase provided herein may be tethered to a zinc-finger DNA binding domain. The Flp-FRT site-directed recombination system may come from the 2μ plasmid from the baker's yeast *Saccharomyces cerevisiae*. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions-1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs may be introduced as ZEN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLOS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4:1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39: e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase. As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution or insertion, whereas "edits" or "genomic edits" refers to two or more targeted mutation(s), deletion(s), inversion(s), substitution(s) and/or insertion(s), with each "edit" being introduced via a targeted genome editing technique.

Given that suppression of GA20 oxidase_3, GA20 oxidase_4, GA20 oxidase_5, and/or GA3 oxidase_1 genes in corn produces plants having a shorter plant height and internode length in addition to other beneficial traits, it is proposed that expression of one or more of GA20 oxidase and/or GA3 oxidase genes may be reduced or eliminated through genome editing one or more of these gene(s) to provide similar beneficial traits to corn plants. Given further that constitutive expression of suppression constructs targeting these GA20 oxidase or GA3 oxidase genes produces corn plants having the beneficial short height traits without off-types in the ear, and that expression directly in reproductive ear tissues also does not give rise to reproductive off-types, it is proposed that one or more of these gene loci may be edited to knock-down or knock-out their expression to produce similar effects in corn plants. Targeted gene editing approaches could be used to modify the sequence of the promoter and/or regulatory region(s) of one or more of the GA20 oxidase_3, GA20 oxidase_4, GA20 oxidase_5, GA3 oxidase_1, GA3 oxidase_2, and/or GA3 oxidase_3 genes to knock-down or knock-out expression of these gene(s), such as through targeted deletions, insertions, mutations, or other sequence changes. Indeed, the promoter and/or regulatory region(s) or sequence(s), or the 5'-UTR, 3'UTR, and/or intron sequence(s), of one or more of the GA20 oxidase_3, GA20 oxidase_4, GA20 oxidase_5, GA3 oxidase_1, GA3 oxidase_2, and/or GA3 oxidase_3 genes may be largely deleted or mutated. Alternatively, all or a portion of the coding (exon), 5-UTR, 3'UTR, and/or intron sequence(s) of one or more of the GA20 oxidase_3, GA20 oxidase_4, GA20 oxidase_5, GA3 oxidase_1, GA3 oxidase_2, and/or GA3 oxidase_3 genes may be edited, deleted, mutated, or otherwise modified to knock-down or knock-out expression or activity of these gene(s). Such targeted modifications to the GA20 oxidase_3, GA20 oxidase_4, GA20 oxidase_5, GA3 oxidase_1, GA3 oxidase_2, and/or GA3 oxidase_3 gene loci may be achieved using any suitable genome editing technology known in the art, such as via repair of a double strand break (DSB) or nick introduced by a site-specific nuclease, such as, for example, a zinc-finger nuclease, an engineered or native meganuclease, a TALE-endonuclease, or an RNA-guided endonuclease (e.g., Cas9 or Cpf1). Such repair of the DSB or nick may introduce spontaneous or stochastic deletions, additions, mutations, etc., at the targeted site where the DSB or nick was introduced, or repair of the site may involve the use of a donor template molecule to direct or cause a preferred or specific deletion, addition, mutation, etc., at the targeted site.

As provided herein, a plant transformed with a recombinant DNA molecule or transformation vector comprising a transgene encoding a transcribable DNA sequence encoding a non-coding RNA molecule that targets an endogenous GA oxidase gene for suppression may include a variety of monocot or cereal plants, such as maize/corn and other monocot or cereal plants that have separate male and female flowers (similarly to corn) and may thus be susceptible to off-types in female reproductive organs, structures or tissues with mutations to the GA pathway.

The present compositions and methods may be further applicable to other cereal plants that would benefit from a reduced plant height and/or increased resistance to lodging. Such plants may be transformed with recombinant DNA molecules or constructs to suppress one or more endogenous GA20 and/or GA3 oxidase genes in the plant according to the methods and approaches provided herein to produce a cereal plant that may be shorter and/or resistant to lodging. Indeed, a cereal plant ectopically expressing a transcribable DNA sequence encoding a non-coding RNA molecule that targets an endogenous GA oxidase gene for suppression may have a variety of beneficial traits, such as shorter stature or plant height, shorter internode length, increased stalk/stem diameter, improved lodging resistance, in addition to other improved yield-related and/or drought tolerant traits as provided herein, relative to a wild-type or control plant not having the transgene or transcribable DNA sequence. As described further below, cereal crop plants that have already been modified to have increased yield and resist lodging through mutations in the GA pathway, such as wheat, rice, millet, barley and *Sorghum*, may instead be transformed with a recombinant DNA molecule or construct as provided herein. Unlike many of the GA pathway mutations in these crops which may be recessive, transgenic constructs expressing a suppression element targeting an endogenous biosynthetic GA oxidase gene in those crops may be dominant even when hemizygous or present in the plant as a single copy. Thus, plants that may be transformed with a recombinant DNA molecule or construct expressing a suppression construct may potentially include a variety of monocot or cereal crops. Having a dominant transgenic locus that causes a semi-dwarf, lodging resistant phenotype may be advantageous and preferred over a recessive mutant allele for the same phenotype due to benefits in breeding and trait integration.

According to embodiments of the present disclosure, it is further proposed that GA oxidase genes in other cereal plants having the greatest sequence identity/similarity to the GA20 oxidase_3, GA20 oxidase_4, GA20 oxidase_5, GA3 oxidase_1, and/or GA3 oxidase_2 genes in corn that are shown herein to produce a short stature, semi-dwarf phenotype and other beneficial traits when suppressed with a recombinant DNA suppression construct, may also be targets for suppression to produce transgenic cereal plants having similar semi-dwarf and/or lodging resistance phenotypes. Table 3 provides a list of GA oxidase genes from other cereal plants (*Sorghum*—*Sorghum bicolor*; rice—*Oryza sativa*; foxtail millet—*Setaria italica*; wheat—*Triticum aestivum*; and barley—*Hordeum vulgare*) having a high degree of sequence identity with one of the GA oxidase genes in corn that when suppressed produces a short stature, semi-dwarf phenotype.

TABLE 3

Homologs of corn GA oxidase genes from other cereal crop plants.

| Gene Name | Cereal Species | Corn Homolog | cDNA (SEQ ID NO) | CDS (SEQ ID NO) | Protein (SEQ ID NO) | Genomic (SEQ ID NO) |
|---|---|---|---|---|---|---|
| GA20 oxidase 2 | *Sorghum bicolor* | GA20 Ox_3/ GA20 Ox_5 | 84 | 85 | 86 | 87 |

TABLE 3-continued

Homologs of corn GA oxidase genes from other cereal crop plants.

| Gene Name | Cereal Species | Corn Homolog | cDNA (SEQ ID NO) | CDS (SEQ ID NO) | Protein (SEQ ID NO) | Genomic (SEQ ID NO) |
|---|---|---|---|---|---|---|
| GA20 oxidase 2-like | *Setaria italica* | GA20 Ox_3/ GA20 Ox_5 | 88 | 89 | 90 | 91 |
| GA20 oxidase 2 | *Oryza Sativa* | GA20 Ox_3/ GA20 Ox_5 | 92 | 93 | 94 | 95 |
| GA20 oxidase-D2 | *Triticum aestivum* | GA20 Ox_3/ GA20 Ox_5 | — | 96 | 97 | 98 |
| Fe2OG dioxygenase | *Hordeum vulgare* | GA20 Ox_3/ GA20 Ox_5 | 99 | 100 | 101 | — |
| Probable 2-ODD | *Sorghum bicolor* | GA20 Ox_4 | 102 | 103 | 104 | 105 |
| flavonol synthase/flavanone 3-hydroxylase-like | *Setaria Itá*lica | GA20 Ox_4 | 106 | 107 | 108 | 109 |
| naringenin, 2-oxoglutarate 3-dioxygenase | *Oryza Sativa* | GA20 Ox_4 | 110 | 111 | 112 | 113 |
| Fe2OG dioxygenase | *Triticum aestivum* | GA20 Ox_4 | 114 | 115 | 116 | 117 |
| Fe2OG dioxygenase | *Hordeum vulgare* | GA20 Ox_4 | — | — | 118 | — |
| GA3-beta-dioxygenase 2-2 | *Sorghum bicolor* | GA3 Ox_1/ GA3 Ox_2 | 119 | 120 | 121 | 122 |
| GA3-beta-dioxygenase 2-2-like | *Setaria Itá*lica | GA3 Ox_1/ GA3 Ox_2 | 123 | 124 | 125 | 126 |
| GA3-beta-dioxygenase 2-3 | *Oryza Sativa* | GA3 Ox_1/ GA3 Ox_2 | 127 | 128 | 129 | 130 |
| GA3-beta-hydroxylase | *Hordeum vulgare* | GA3 Ox_1/ GA3 Ox_2 | 131 | 132 | 133 | — |
| GA3ox-D2 protein | *Triticum aestivum* | GA3 Ox_1/ GA3 Ox_2 | 134 | 135 | 136 | 137 |

According to another aspect of the present disclosure, a recombinant DNA molecule, vector or construct is provided for suppression of an endogenous GA oxidase (or GA oxidase-like) gene in a cereal plant, the recombinant DNA molecule, vector or construct comprising a transcribable DNA sequence encoding a non-coding RNA molecule, wherein the non-coding RNA molecule comprises a sequence that is (i) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 119, 120, 122, 123, 124, 126, 127, 128, 130, 131, 132, 134, 135, and/or 137, and/or (ii) at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 80%, at least 85%, at least 90%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule may target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 80%, at least 85%, at least 90%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule may target an exon, intron and/or UTR sequence of a GA oxidase (or GA oxidase-like) gene.

Further provided are methods for introducing or transforming into a cereal plant, plant part, or plant cell any of the foregoing constructs, vectors, or constructs, according to any of the methods described herein, which may be constructed in any suitable manner described herein including different stacking or joint targeting arrangements, as well as modified cereal plants, plant parts, plant tissues, and plant cells made thereby and/or comprising any such recombinant DNA molecule, vector or construct. Since a non-coding RNA molecule expressed from the above constructs would be designed to target an endogenous GA oxidase gene, the cereal plant transformed with such recombinant DNA molecules, vectors or constructs should preferably correspond to the species of origin for the target sequence, or closely related species, strains, germplasms, lines, etc. For example, a suppression construct complementary to SEQ ID NO: 84 should be used to transform a *Sorghum* plant, such as a *Sorghum bicolor* plant, or perhaps related *Sorghum* species, strains, etc., that would be expected to have a closely related or similar GA oxidase (or GA oxidase-like) gene sequence.

The genomic sequences for each of the above identified genes from cereal plants are further provided in Table 3, which may be used to target those genes for genome editing according to any known technique. Any site-specific nuclease and method may be used as described herein to generate a DSB or nick at or near the genomic locus for the gene, which may be repaired imperfectly or via template-mediated recombination to create mutations, etc., at, near or within the gene. Suitable nucleases may be selected from the group consisting of a zinc-finger nuclease (ZFN), a meganuclease, an RNA-guided endonuclease, a TALE-endonuclease (TALEN), a recombinase, a transposase, or any combination thereof. For an RNA-guided endonuclease, a recombinant DNA construct or vector is provided comprising a guide RNA may be used to direct the nuclease to the target site. Accordingly, a guide RNA for editing a GA oxidase (or GA-oxidase-like) gene in a cereal crop may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 119, 120, 122, 123, 124, 126, 127, 128, 130, 131, 132, 134, 135, and/or 137. For site-specific nucleases that are not RNA-guided, such as a zinc-finger nuclease (ZFN), a meganuclease, a TALE-endonuclease (TALEN), a recombinase, and/or a transposase, the genomic target specificity for editing is determined by its protein structure, particularly its DNA binding domain. Such site-specific nucleases may be chosen, designed or engineered to bind and cut a desired target site at or near any of the above GA oxidase (or GA oxidase-like) genes within the genome of a cereal plant. Similar to transformation with a suppression construct, a cereal plant transformed with a particular guide RNA, or a recombinant DNA molecule, vector or construct encoding a guide RNA, should preferably be the species in which the targeted genomic sequence exists, or a closely related species, strain, germplasm, line, etc., such that the guide RNA is able to recognize and bind to the desired target cut site.

Further provided are methods for introducing or transforming into a cereal plant, plant part, or plant cell any guide RNA described above, or any construct, vector, or construct encoding such a guide RNA, perhaps in addition to an RNA-guided nuclease, according to any of the methods described herein, as well as modified cereal plants, plant parts, plant tissues, and plant cells made thereby and/or comprising any such recombinant DNA molecule, vector or construct and/or an edited GA oxidase (or GA oxidase-like) gene. Modified cereal plants having an edited GA oxidase (or GA oxidase-like) gene, and/or a suppression element targeting a GA oxidase (or GA oxidase-like) gene, may have one or more beneficial traits provided herein, such as a shorter plant height, shorter internode length, increased stalk/stem diameter, improved lodging resistance, and/or drought tolerance, relative to a wild-type or control plant not having any such edit or suppression element. In addition to genome editing, mutations in a GA oxidase (or GA oxidase-like) gene may be introduced through other mutagenesis techniques as described herein According to another aspect of the present disclosure, a transgenic plant(s), plant cell(s), seed(s), and plant part(s) are provided comprising a transformation event or insertion into the genome of at least one plant cell thereof, wherein the transformation event or insertion comprises a recombinant DNA sequence, construct or expression cassette comprising a transcribable DNA sequence encoding a non-coding RNA molecule that targets an endogenous GA oxidase gene for suppression, wherein the transcribable DNA sequence is operably linked to a plant-expressible promoter, such as a constitutive, vascular and/or leaf promoter. Such a transgenic plant may be produced by any suitable transformation method as provided above, to produce a transgenic $R_0$ plant, which may then be selfed or crossed to other plants to generate $R_1$ seed and subsequent progeny generations and seed through additional crosses, etc. Embodiments of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA oxidase gene for suppression.

Transgenic plants, plant cells, seeds, and plant parts of the present disclosure may be homozygous or hemizygous for a transgenic event or insertion of a transcribable DNA sequence for suppression of a GA oxidase gene into the genome of at least one plant cell thereof, or a targeted genome editing event, and plants, plant cells, seeds, and plant parts of the present embodiments may contain any number of copies of such transgenic event(s), insertion(s) and/or edit(s). The dosage or amount of expression of a transgene or transcribable DNA sequence may be altered by its zygosity and/or number of copies, which may affect the degree or extent of phenotypic changes in the transgenic plant, etc. As introduced above, transgenic plants provided herein may include a variety of monocot or cereal plants, and even crop plants, such as wheat, rice and *Sorghum*, already having increased yield and/or lodging resistance due to prior breeding efforts and mutations of the GA pathway in these plants. Advantages of using a transgene or transcribable DNA sequence to express a suppression element targeting a biosynthetic GA oxidase gene include not only the ability to limit expression in a tissue-specific or tissue-preferred manner, but also the potential dominance (e.g., dominant negative effects) of a single or hemizygous copy of the transcribable DNA sequence to cause the beneficial short-stature, semi-dwarf traits or phenotypes in crop plants. Thus, recombinant DNA molecules or constructs of the present disclosure may be used to create beneficial traits in a variety of monocot or cereal plants without off-types using only a single copy of the transgenic event, insertion or construct. Unlike previously described mutations or alleles in the GA pathway that are recessive and require plants to be homozygous for the mutant allele, plants transformed with the GA-modifying transgenes and suppression constructs of the present disclosure may improve traits, yield and crop breeding efforts by facilitating the production of hybrid cereal plants since they only require a single or hemizygous copy of the transgene or suppression construct.

According to some embodiments, a transgenic or modified cereal or corn plant comprising a GA oxidase transgene or transcribable DNA sequence for suppression of an endogenous GA oxidase gene, or a genome edited GA oxidase gene, may be further characterized as having one or more beneficial traits, such as a shorter stature or semi-dwarf plant height, reduced internode length, increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, relative to a wild type or control plant. Such a transgenic cereal or corn plant may further have increased stress tolerance, such as increased drought tolerance, nitrogen utilization, and/or tolerance to high density planting.

For purposes of the present disclosure, a "plant" includes an explant, plant part, seedling, plantlet or whole plant at any stage of regeneration or development. As used herein, a "transgenic plant" refers to a plant whose genome has been altered by the integration or insertion of a recombinant DNA molecule, construct or sequence. A transgenic plant includes an $R_0$ plant developed or regenerated from an originally transformed plant cell(s) as well as progeny transgenic plants in later generations or crosses from the $R_0$ transgenic plant. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure may be viable, nonviable, regenerable, and/or non-regenerable. A "propagule" may include any plant part that can grow into an entire plant.

According to present embodiments, a plant cell transformed with a construct or molecule comprising a transcribable DNA sequence for suppression of an endogenous GA oxidase gene, or with a construct used for genome editing of a GA oxidase gene, may include any plant cell that is competent for transformation as understood in the art based on the method of transformation, such as a meristem cell, an embryonic cell, a callus cell, etc. As used herein, a "transgenic plant cell" simply refers to any plant cell that is transformed with a stably-integrated recombinant DNA molecule, construct or sequence. A transgenic plant cell may include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

Embodiments of the present disclosure further include methods for making or producing transgenic or modified plants, such as by transformation, genome editing, crossing, etc., wherein the method comprises introducing a recombinant DNA molecule, construct or sequence comprising a GA oxidase transgene or a transcribable DNA sequence for suppression of an endogenous GA oxidase gene into a plant cell, or editing the genomic locus of an endogenous GA oxidase gene, and then regenerating or developing the transgenic or modified plant from the transformed or edited plant cell, which may be performed under selection pressure favoring a transgenic event. Such methods may comprise transforming a plant cell with a recombinant DNA molecule, construct or sequence comprising the transcribable DNA sequence for suppression of an endogenous GA oxidase gene, and selecting for a plant having one or more altered phenotypes or traits, such as one or more of the following traits at one or more stages of development: shorter or semi-dwarf stature or plant height, shorter internode length in one or more internode(s), increased stalk/stem diameter, improved lodging resistance, reduced green snap, deeper roots, increased leaf area, earlier canopy closure, increased foliar water content and/or higher stomatal conductance under water limiting conditions, reduced anthocyanin content and/or area in leaves under normal or nitrogen or water limiting stress conditions, improved yield-related traits including a larger female reproductive organ or ear, an increase in ear weight, harvest index, yield, seed or kernel number, and/or seed or kernel weight, increased stress tolerance, such as increased drought tolerance, increased nitrogen utilization, and/or increased tolerance to high density planting, as compared to a wild type or control plant.

According to another aspect of the present disclosure, methods are provided for planting a modified or transgenic plant(s) provided herein at a normal/standard or high density in field. According to some embodiments, the yield of a crop plant per acre (or per land area) may be increased by planting a modified or transgenic plant(s) of the present disclosure at a higher density in the field. As described herein, modified or transgenic plants expressing a transcribable DNA sequence that encodes a non-coding RNA molecule targeting an endogenous GA oxidase gene for suppression, or having a genome-edited GA oxidase gene, may have reduced plant height, shorter internode(s), increased stalk/stem diameter, and/or increased lodging resistance. It is proposed that modified or transgenic plants may tolerate high density planting conditions since an increase in stem diameter may resist lodging and the shorter plant height may allow for increased light penetrance to the lower leaves under high density planting conditions. Thus, modified or transgenic plants provided herein may be planted at a higher density to increase the yield per acre (or land area) in the field. For row crops, higher density may be achieved by planting a greater number of seeds/plants per row length and/or by decreasing the spacing between rows.

According to some embodiments, a modified or transgenic crop plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an average stem or stalk diameter of at least 18 mm, at least 18.5 mm, at least 19 mm, at least 19.5 mm, at least 20 mm, at least 20.5 mm, at least 21 mm, at least 21.5 mm, or at least 22 mm. Stated a different way, a modified corn plant(s) is/are provided that comprise a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or an average stem or stalk diameter that is greater than 18 mm, greater than 18.5 mm, greater than 19 mm, greater than 19.5 mm, greater than 20 mm, greater than 20.5 mm, greater than 21 mm, greater than 21.5 mm, or greater than 22 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or stem diameter of a modified corn plant may depend on the environment and genetic background. Thus, the change in plant height and/or stem diameter of a modified corn plant may instead be described in terms of a minimum difference or percent change relative to a control plant. A modified corn plant may further comprise at least one ear that is substantially free of male reproductive tissues or structures or other off-types.

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant may be substantially free of off-types, such as male reproductive tissues or structures in one or more ears of the modified corn plant.

According to embodiments of the present disclosure, modified corn plants are provided that have (i) a plant height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) a stem or stalk diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or a stem or stalk diameter that is less than (or not more than) 10%, 15%, 20%, 25%, 30%, 35%, 40%, 45%, 50%, 55%, 60%, 65%, 70%, 75%, 80%, 85%, 90%, 95%, or 100% greater than the stem or stalk diameter of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) a stem or stalk diameter that is that is at least 5%, at least 10%, or at least 15% greater, but not more than 30%, 35%, or 40% greater, than a wild type or control plant. For clarity, the phrases "at least 20% shorter" and "greater than or equal to 20% shorter" would exclude, for example, 10% shorter. Likewise for clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or a stem or stalk diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, between 50% and 75%, between 8% and 20%, or between 8% and 15% greater than the stem or stalk diameter of the wild-type or control plant.

According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the ear weight of a wild-type or control plant.

According to embodiments of the present disclosure, modified corn or cereal plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn or cereal plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified cereal or corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified cereal or corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of cereal or corn plants having increased lodging resistance and a reduced lodging frequency. Populations of modified cereal or corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a significantly increased stem diameter (e.g., 18 mm or more), relative to a wild-type or control plant. According to these embodiments, the decrease or reduction in plant height and increase in stem diameter may be within any of the height, diameter or percentage ranges recited herein. Such modified corn plants having a reduced plant height and increased stem diameter relative to a wild-type or control plant may be transformed with a transcribable DNA sequence encoding a non-coding RNA molecule that targets at least one GA20 oxidase gene and/or at least one GA3 oxidase gene for suppression and/or may comprise one or more mutations or edits in one or more GA20 oxidase and/or GA3 oxidase gene(s). Modified corn plants having a significantly reduced plant height and/or a significantly increased stem diameter relative to a wild-type or control plant may further have at least one ear that is substantially free of male reproductive tissues or structures and/or other off-types. Modified corn plants having a significantly reduced plant height and/or an increased stem diameter relative to a wild-type or control plant may have reduced activity of one or more GA20 oxidase and/or GA3 oxidase gene(s) in one or more tissue(s) of the plant, such as one or more vascular and/or leaf tissue(s) of the plant, relative to the same tissue(s) of the wild-type or control plant. According to many embodiments, modified corn plants may comprise at least one polynucleotide or transcribable DNA sequence encoding a non-coding RNA molecule operably linked to a promoter, which may be a constitutive, tissue-specific or tissue-preferred promoter, wherein the non-coding RNA molecule targets at least one GA20 oxidase and/or GA3 oxidase gene(s) for suppression as provided herein. The non-coding RNA molecule may be a miRNA, siRNA, or miRNA or siRNA precursor molecule. According to some embodiments, modified corn plants may be homozygous or heterozygous for one or more mutations or edits in one or more GA20 oxidase and/or GA3 oxidase gene(s). According to some embodiments, modified corn plants having a significantly reduced plant height and/or an increased stem diameter relative to a wild-type or control plant may further have an increased harvest index and/or increased lodging resistance relative to the wild-type or control plant.

Modified corn or cereal plants having a significantly reduced plant height and/or a significantly increased stem diameter relative to a wild-type or control plant may comprise a mutation (e.g., an insertion, deletion, substitution, etc.) in a GA oxidase gene introduced through a gene editing technology or other mutagenesis technique, wherein expression of the GA oxidase gene is reduced or eliminated in one or more tissues of the modified plant. Such modified corn plants having a reduced plant height and/or an increased stem diameter relative to a wild-type or control plant may further have an increased harvest index and/or increased lodging resistance relative to the wild-type or control plant. Such modified corn plants may be substantially free of off-types, such as male reproductive tissues or structures and/or other off-types in at least one ear of the modified plants. Plant mutagenesis techniques (excluding genome editing) may include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells may be subjected to mutagenesis. Treated plants may be reproduced to collect seeds or produce a progeny plant, and treated plant parts, plant tissues or plant cells may be developed or regenerated into plants or other plant tissues. Mutations generated with chemical or physical mutagenesis techniques may include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA oxidase gene may be used to identify whether a mutated plant has a mutation in the GA oxidase gene. Plants having mutations in the GA oxidase gene may then be tested for an altered trait, such as reduced plant height. Alternatively, mutagenized plants may be tested for an altered trait, such as reduced plant height, and then PCR amplification and sequencing of a nucleic acid sequence of a GA oxidase gene may be used to determine whether a plant having the altered trait also has a mutation in the GA oxidase gene. See, e.g., Colbert et al., 2001, *Plant Physiol* 126:480-484; and McCallum et al., 2000, Nature Biotechnology 18:455-457. TILLING can be used to identify mutations that alter the expression a gene or the activity of proteins encoded by a gene, which may be used to introduce and select for a targeted mutation in a GA oxidase gene of a corn or cereal plant.

Corn or cereal plants that have been subjected to a mutagenesis or genome editing treatment may be screened and selected based on an observable phenotype (e.g., any phenotype described herein, such as shorter plant height, increased stem/stalk diameter, etc.), or using a selection agent with a selectable marker (e.g., herbicide, etc.), a screenable marker, or a molecular technique (e.g., lower GA levels, lower GA oxidase transcript or protein levels, presence of transgene or transcribable sequence, etc.). Such screening and/or selecting techniques may be used to identify and select plants having a mutation in a GA oxidase gene that leads to a desirable plant phenotype.

According to embodiments of the present disclosure, a population of modified corn or cereal plants are provided, wherein the population of modified corn or cereal plants have an average plant height that is significantly less, and/or an average stem or stalk diameter that is significantly more, than a population of wild-type or control plants. The population of modified corn or cereal plants may share ancestry with a single modified corn or cereal plant and/or have a single transgenic GA oxidase suppression construct insertion, event or edit in common. Modified corn plants within a population of modified corn plants may generally comprise at least one ear that is substantially free of male reproductive tissues or structures and/or other off-types. A population of modified corn or cereal plants may have increased lodging resistance on average or per number of plants or field area than a population of wild-type or control plants. The population of modified corn or cereal plants may have a lodging frequency that is at least 5%, at least 10%, at least 20%, at least 30%, at least 40%, at least 50%, at least 60%, at least 70% at least 80%, at least 90%, or 100% less (or lower) than a population of control corn or cereal plants. A population of modified corn plants may have a harvest index of at least 0.57 or greater.

According to embodiments of the present invention, modified corn or cereal plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn or cereal plants are provided having a significantly reduced plant height and/or a significantly increased stem diameter relative to wild-type or control plants, wherein the modified corn or cereal plants further have significantly reduced or decreased level(s) of active gibberellins or active GAs (e.g., one or more of GA1, GA3, GA4, and/or GA7) in one or more stem, internode, leaf and/or vascular tissue(s), relative to the same tissue(s) of the wild-type or control plants. For example, the level of one or more active GAs in the stem, internode, leaf and/or vascular tissue(s) of a modified corn or cereal plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn or cereal plant may comprise an active gibberellin (GA) level(s) (e.g., one or more of GA1, GA3, GA4, and/or GA7) in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn or cereal plant having a reduced active gibberellin (GA) level(s) in one or more stem, internode, leaf and/or vascular tissue(s) may further be substantially free of off-types, such as male reproductive tissues or structures and/or other off-types in at least one ear of a modified corn plant.

According to embodiments of the present disclosure, modified corn or cereal plants are provided having a significantly reduced or eliminated expression level and/or activity of one or more GA3 oxidase and/or GA20 oxidase gene transcript(s) and/or protein(s) in one or more tissue(s), such as one or more stem, internode, leaf and/or vascular tissue(s), of the modified plants, as compared to the same tissue(s) of wild-type or control plants. According to many embodiments, a modified corn or cereal plant is provided comprising a significantly reduced plant height and/or a significantly increased stem diameter relative to wild-type or control plants, wherein the modified corn or cereal plant has a significantly reduced or eliminated expression level and/or activity of one or more GA20 oxidase and/or GA3 oxidase gene transcript(s) and/or protein(s) in one or more tissues, such as one or more stem, internode, leaf and/or vascular tissue(s), of the modified plant, as compared to the same tissue(s) of a wild-type or control corn plant. For example, a modified corn or cereal plant has a significantly reduced or eliminated expression level and/or activity of a GA20 oxidase_3 and/or GA20 oxidase_5 gene transcript(s) and/or protein(s), and/or a significantly reduced or eliminated expression level of a GA3 oxidase_1, GA3 oxidase_2, and/or GA3 oxidase_3 gene transcript(s) and/or protein(s), in one or more stem, internode, leaf and/or vascular tissue(s) of the modified plant, as compared to the same tissue(s) of a wild-type or control plant. For example, the level and/or activity of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn or cereal plant.

According to some embodiments, a modified corn or cereal plant may comprise level(s) and/or activity(-ies) of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or lower than in the same tissue(s) of a wild-type or control corn or cereal plant. A modified corn or cereal plant having a reduced or eliminated expression level and/or activity of at least one GA20 oxidase and/or GA3 oxidase gene(s) in one or more tissue(s), may also be substantially free of off-types, such as male reproductive tissues or structures and/or other off-types in at least one ear of the modified corn plant.

According to some embodiments, methods are provided comprising reducing or eliminating the expression of at least one GA20 oxidase gene and/or at least one GA3 oxidase gene in a crop plant, such as in one or more stem, internode, vascular and/or leaf tissue of the crop plant, wherein the expression of the at least one GA20 oxidase gene and/or at least one GA3 oxidase gene(s) is/are not significantly altered or changed in at least one reproductive tissue of the plant, and/or wherein the level(s) of one or more active GAs is/are not significantly altered or changed in at least one reproductive tissue of the plant, as compared to a wild-type or control plant. According to many embodiments, the expression level(s) of at least one GA20 oxidase or GA3 oxidase gene is reduced or eliminated in at least one tissue of a modified plant with a recombinant DNA construct comprising a transcribable DNA sequence encoding a suppression element for the GA20 oxidase or GA3 oxidase gene, such as at least one mature miRNA or miRNA precursor that is processed into a mature miRNA, wherein the miRNA is able to reduce or suppress the expression level of the at least one GA20 oxidase or GA3 oxidase gene, and wherein the transcribable DNA sequence is operably linked to a constitutive, tissue-specific or tissue-preferred promoter.

Methods and techniques are provided for screening for, and/or identifying, cells or plants, etc., for the presence of targeted edits, mutations or transgenes, and selecting cells or plants comprising targeted edits, mutations or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified, edited or transgenic plants or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

EXAMPLES

Example 1. Reduced Plant Height in Inbred Corn Lines Across Transformation Events for the GA20 Oxidase Suppression Element An inbred corn plant line was transformed via *Agrobacterium* mediated transformation with a transformation vector having an expression construct comprising a transcribable DNA sequence with a sequence (SEQ ID NO: 39) encoding a targeting sequence (SEQ ID NO: 40) of a miRNA under the control of a rice tungro bacilliform virus (RTBV) promoter (SEQ ID NO: 65) that is known to cause expression in vascular tissues of plants. The miRNA encoded by the construct comprises a RNA sequence that targets the GA20 oxidase_3 and GA20 oxidase_5 genes in corn plants for suppression. Several transformation events were generated with this construct, and these transformants were tested in the greenhouse to determine if they had reduced plant height relative to non-transgenic wild type control plants. As can be seen in FIG. 1, a significant reduction in plant height was consistently observed in transgenic plants expressing the suppression construct across several transformation events (see Events 1-8) relative to wild type (WT) control plants. Plant height for each of the transformation events was calculated as an average among approximately 10 plants for each event and compared to the average height for control plants. Standard errors were calculated for each event and the control plants, which are represented as error bars in FIG. 1. Furthermore, ear development in each of these transformants appeared normal.

As can be seen from the results of this experiment, average plant height in plants expressing the miRNA targeting the GA20 oxidase_3 and GA20 oxidase_5 genes for suppression had consistently reduced plant heights of up to 35% relative to control plants across multiple events. This data supports the conclusion that the effects seen with this suppression construct are not due to insertion of the construct at any one locus within the plant genome.

This data further indicates that expression of this GA20 oxidase suppression construct using the RTBV vascular promoter is effective at causing these plant height phenotypes. In addition, early data in R0 corn plants constitutively expressing the same GA20 oxidase suppression construct under the control of different constitutive promoters also produce short stature plants (see Example 15 below). Thus, expression of the targeted GA20 oxidase suppression construct may be effective at reducing plant height and providing the other beneficial anti-lodging and yield-related traits described herein given that different expression patterns including vascular and constitutive expression provide similar plant height phenotypes without apparent off-types in the ear.

Figure 2A:
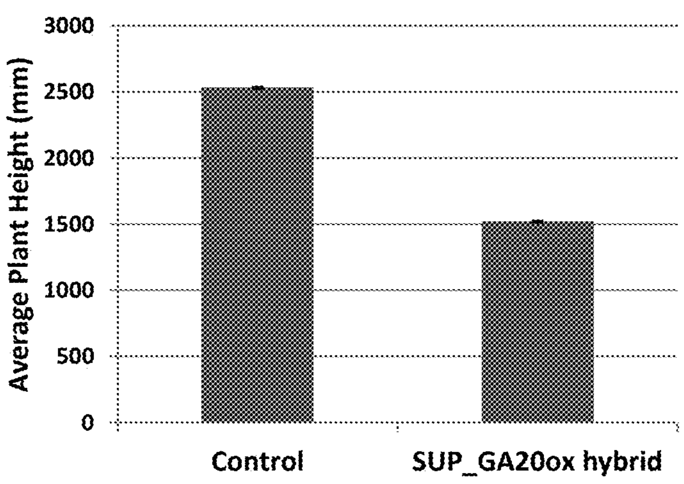
FIG. 2A shows a reduced plant height on average of hybrid corn plants expressing a GA20 oxidase suppression construct in comparison to hybrid control plants.
Figure 2B:
FIG. 2B shows an image of a wild type hybrid control plant (left) next to a hybrid corn plant expressing a GA20 oxidase suppression construct (right) having a reduced plant height.

Example 2. Reduced Plant Height in Hybrid Corn Plants Expressing the GA20 Oxidase Suppression Element Hybrid corn plants carrying the GA20 oxidase suppression construct described in Example 1 also showed reduced plant height relative to wild type control plants when grown under field conditions. Average plant height of transgenic hybrid corn plants expressing the GA20 oxidase suppression element in 10 microplots was calculated and compared to average plant height of (non-transgenic) wild type control hybrid corn plants in 32 microplots. Each microplot for the transgenic and non-transgenic control included approximately 6 plants, although the actual number of plants per plot may vary depending on the number of plants that germinate and develop into plants having ears. As can be seen in FIG. 2A, a significant reduction in average plant height was observed in transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 2A. An image of a hybrid control plant (left) next to a transgenic hybrid plant expressing the GA20 oxidase suppression element (right) is further shown in FIG. 2B.

In this experiment, average plant height of field grown hybrid corn plants expressing the miRNA targeting the GA20 oxidase_3 and GA20 oxidase_5 genes was reduced by about 40% relative to wild type hybrid control plants. This data shows that the plant height phenotype is present in hybrid corn plants in addition to inbred lines. However, overall biomass in this experiment appeared neutral in the semi-dwarf corn plants compared to controls.

Figure 3A:
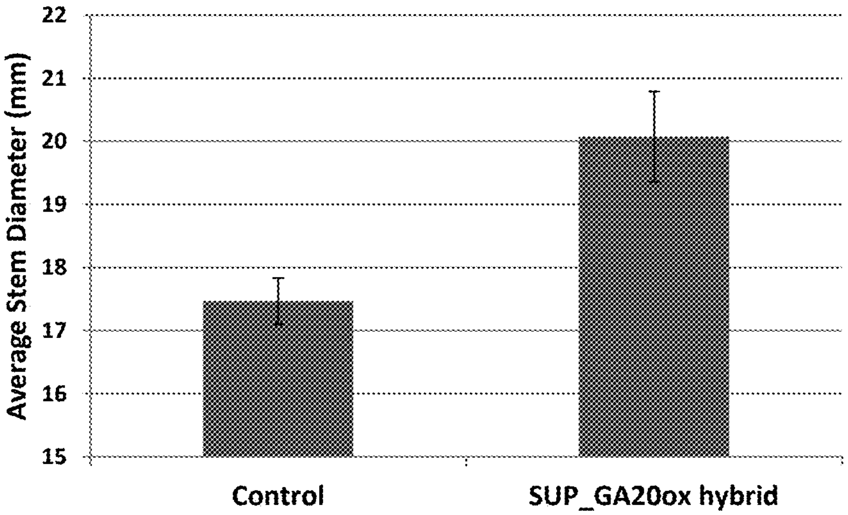
FIG. 3A shows an increased stem diameter on average of hybrid corn plants expressing a GA20 oxidase suppression construct in comparison to hybrid control plants.
Figure 3B:
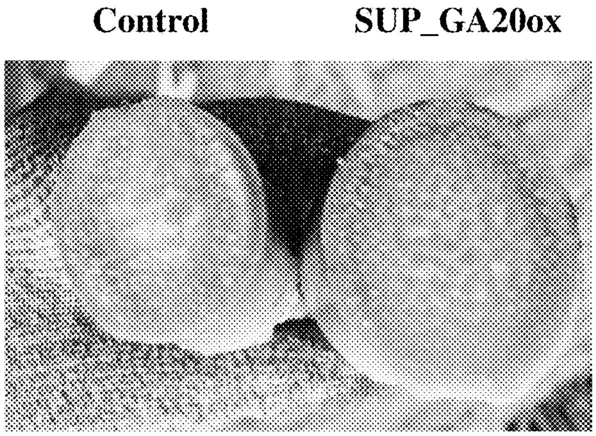
FIG. 3B shows an image of a cross-section of the stalk of a wild type hybrid control plant (left) next to a cross-section of the stalk of a hybrid corn plant expressing a GA20 oxidase suppression construct (right) having an increased stem diameter.

Example 3. Increased Stem Diameter in Hybrid Corn Plants Expressing the GA20 Oxidase Suppression Element Hybrid corn plants carrying the GA20 oxidase suppression construct described in Example 1 also showed increased stem diameter relative to wild type control plants when grown under field conditions. Stem diameter was measured on the second internode below the primary ear. Average stem diameter of transgenic hybrid corn plants expressing the GA20 oxidase suppression element in 8 microplots was calculated and compared to the average stem diameter of (non-transgenic) wild type control hybrid corn plants in 8 microplots. Each microplot included approximately 6 plants. As can be seen in FIG. 3A, a significant increase in average stem diameter was observed in transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 3A. An image of the cross-section of a stalk from a hybrid control plant (Control; left) is shown next to the cross-section of a stalk from a transgenic hybrid plant expressing the GA20 oxidase suppression element (SUP_GA20ox; right) is further shown in FIG. 3B.

In this experiment, average stem diameter of field grown hybrid corn plants expressing the miRNA targeting the GA20 oxidase_3 and GA20 oxidase_5 genes was increased about 13% relative to wild type hybrid control plants. This data shows that hybrid corn plants expressing the GA20 oxidase miRNA may have thicker stalks in addition to the reduced plant height phenotype.

Figure 4:
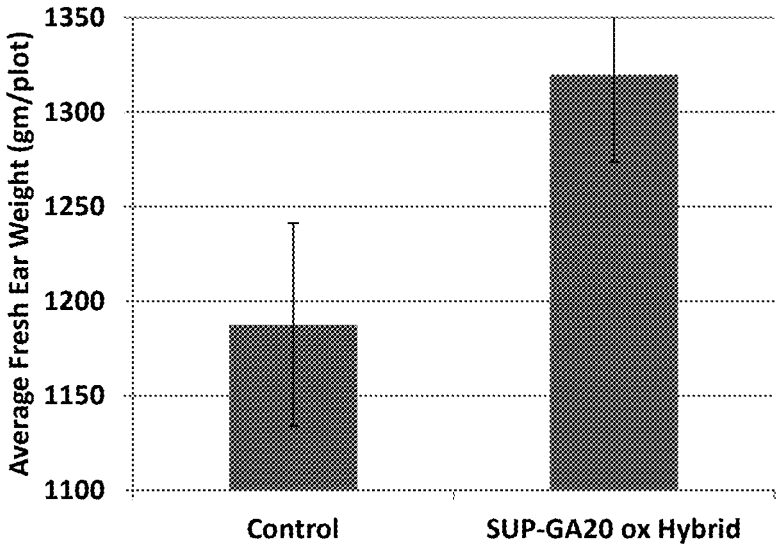
FIG. 4 shows an increased fresh ear weight on average of hybrid corn plants expressing a GA20 oxidase suppression construct in comparison to hybrid control plants.
Figure 5:
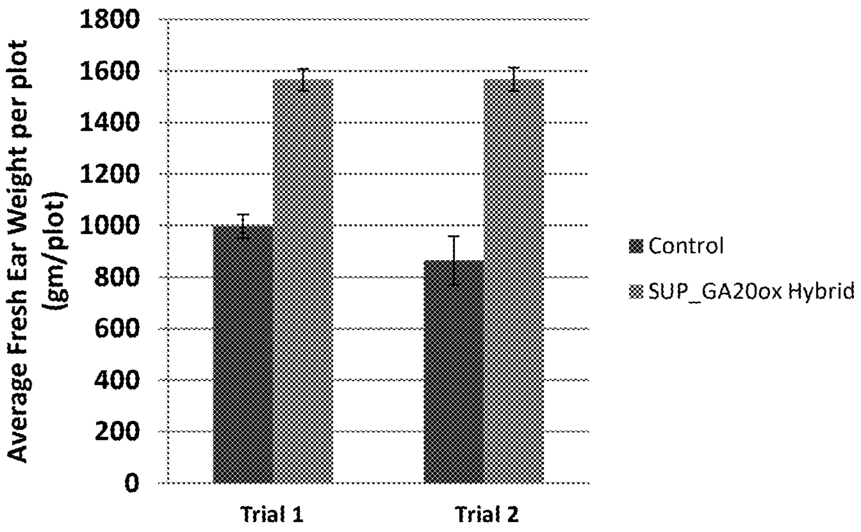
FIG. 5 shows the increased fresh ear weight on average of hybrid corn plants expressing a GA20 oxidase suppression construct in two field trials in comparison to wild type hybrid control plants in response to a wind event that caused greater lodging in the hybrid control plants.

Example 4. Hybrid Corn Plants Expressing the GA20 Oxidase Suppression Element had an Increase in Fresh Ear Weight Hybrid corn plants carrying the GA20 oxidase suppression construct described in Example 1 also showed an increase in fresh ear weight relative to wild type control plants when grown under field conditions. Average fresh ear weight per plot of transgenic hybrid corn plants expressing the GA20 oxidase suppression element in 24 microplots was calculated and compared to the average fresh ear weight of (non-transgenic) hybrid corn control plants in 8 microplots. Again, each microplot included about 6 plants. As can be seen in FIG. 4, an increase in average fresh ear weight per plot was observed in transgenic hybrid plants expressing the suppression construct (SUP-GA20ox hybrid), relative to wild type hybrid corn plants (Control), and ear and kernel development appeared normal. Standard deviations for this experiment were calculated for the transgenic hybrid and control plants, which are represented as error bars in FIG. 4. As shown in FIG. 5, similar results were obtained at another field testing site that also experienced wind damage.

In this experiment, average fresh ear weight of field grown hybrid corn plants expressing the miRNA targeting the GA20 oxidase_3 and GA20 oxidase_5 genes was increased relative to wild type hybrid control plants, indicating that these transgenic plants may further have improved yield-related traits. However, these results are based on observational data without a large-scale statistical comparison to controls, and yield performance should be tested under broad acre conditions.

Example 5. Hybrid Corn Plants Expressing the GA20 Oxidase Suppression Element Displayed Increased Resistance to Lodging At a field testing location, wind damage to pre-flowering hybrid corn plants demonstrated an increased lodging resistance with plants expressing the GA20 oxidase suppression construct described in Example 1, relative to wild type hybrid control plants. While the wild type (non-transgenic) hybrid control plants were visually lodged in response to this high wind event, transgenic hybrid corn plants expressing the GA20 oxidase suppression element in a neighboring field location resisted lodging damage. To evaluate the effects of lodging resistance by hybrid corn plants expressing the GA20 oxidase suppression construct, average fresh ear weights per plot of transgenic GA20 oxidase-suppressing hybrid corn plants across two field trial locations experiencing the lodging damage, were compared to average fresh ear weights of wild type hybrid control plants. Data collected from these two trials indicated that the hybrid control plants had average fresh ear weights that were reduced by about 57% and 81%, respectively in the two trials, relative to hybrid plants expressing the GA20 oxidase suppression construct.

The visual observation that transgenic GA20 oxidase-suppressing hybrid corn plants had increased lodging resistance than non-transgenic control plants, along with the increase in average fresh ear weight in these trials with the transgenic GA20 oxidase-suppressing plants, indicate that increased lodging resistance may translate into an increase in average fresh ear weight. Thus, increased lodging resistance in GA20 oxidase-suppressing plants may further increase the yield potential/stability of these transgenic corn plants by resisting the effects of lodging during severe weather events.

Figure 6:
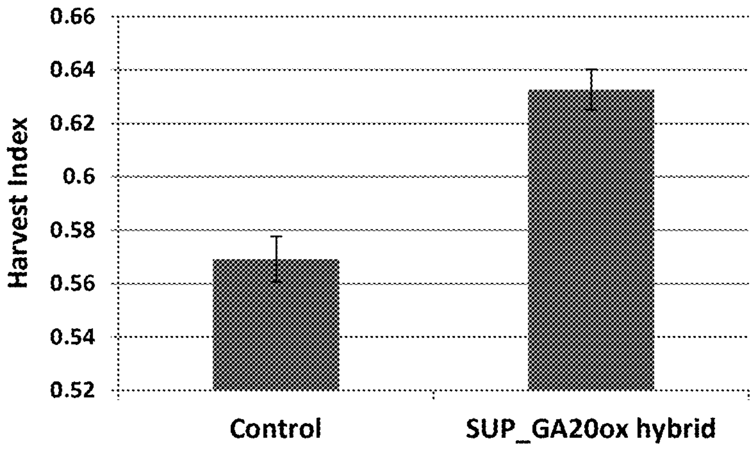
FIG. 6 shows an increased harvest index of hybrid corn plants expressing a GA20 oxidase suppression construct in comparison to hybrid control plants.

Example 6. Hybrid Corn Plants Expressing the GA20 Oxidase Suppression Element had an Increase in Harvest Index Hybrid corn plants carrying the GA20 oxidase suppression construct described in Example 1 further showed an increase in harvest index relative to wild type control plants when grown under field conditions. The harvest index of transgenic hybrid corn plants expressing the GA20 oxidase suppression element was determined from plants grown in 8 microplots and compared to non-transgenic hybrid corn control plants. Each microplot included approximately 6 plants. As can be seen in FIG. 6, a significant increase in harvest index was observed in the transgenic hybrid plants expressing the suppression construct (SUP-GA20ox hybrid), relative to wild type hybrid corn plants (Control). Standard errors were calculated for the transgenic hybrid and control plants, which are represented as error bars in FIG. 6.

In this experiment, the harvest index of field grown hybrid corn plants expressing the miRNA targeting the GA20 oxidase_3 and GA20 oxidase_5 genes was increased about 11% relative to wild type hybrid control plants. This increase in harvest index was further associated with a reduction in stover weight as compared to wild type control plants, but no difference in total dry biomass weight was observed in the transgenic plants.

Figure 7:
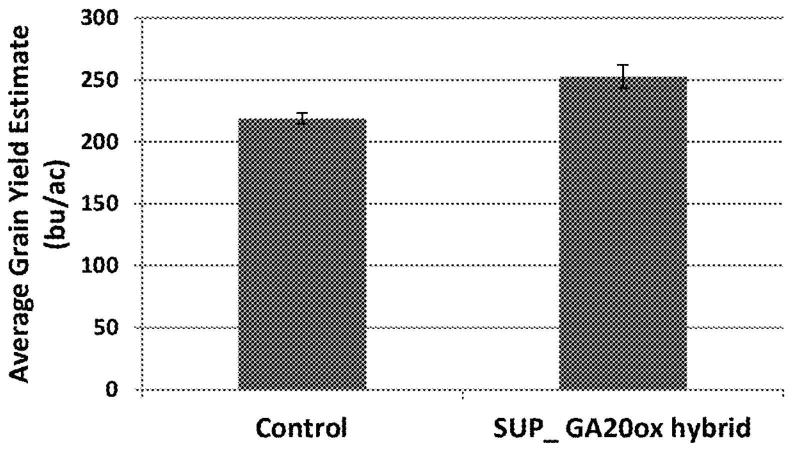
FIG. 7 shows an increase in the average grain yield estimate of hybrid corn plants expressing a GA20 oxidase suppression construct in comparison to hybrid control plants.

Example 7. Hybrid Corn Plants Expressing the GA20 Oxidase Suppression Element had an Increase in Average Grain Yield Estimate The average grain yield estimate for hybrid corn plants expressing the GA20 oxidase suppression element (identified in Example 1) was calculated from 16 microplots in the field (with approximately 6 plants per plot). The calculated average grain yield estimate for these transgenic hybrid corn plants suppressing GA20 oxidase was increased by about 15% over corn hybrid control plants (FIG. 7). Grain yield estimate is a metric that provides a general estimation of expected yield based on the ear trait metrics. Grain yield estimate is derived from hand harvested ears on small plots, and units are kg/ha (instead of bu/ac). Grain yield estimate (kg/ha) is calculated by the formula (Kernel number per unit area (kernels/$m^2$)×Single Kernel Weight (mg)×15.5%/100).

Figure 8:
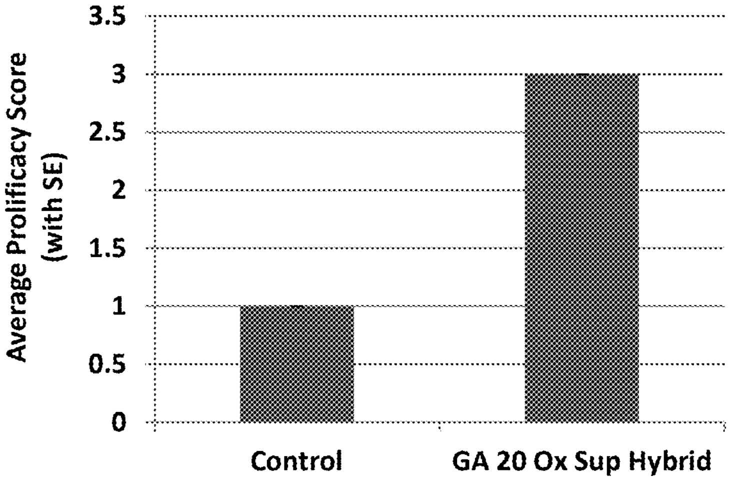
FIG. 8 shows an increased prolificacy score on average of hybrid corn plants expressing a GA20 oxidase suppression construct in comparison to hybrid control plants.

Example 8. Hybrid Corn Plants Expressing the GA20 Oxidase Suppression Element had an Increase in Average Prolificacy Score Hybrid corn plants expressing the GA20 oxidase suppression element (identified in Example 1) was also shown in a microplot experiment to have increased prolificacy and secondary ears as compared to non-transgenic hybrid control plants. The prolificacy score was determined from 10 microplots of the transgenic hybrid corn plants in the field (with approximately 6 plants per plot). As shown in FIG. 8, the average prolificacy score of transgenic hybrid corn plants suppressing the GA 20 oxidase was 3, whereas the average prolificacy score of control plants was 1. To determine the prolificacy score, plants were assayed for the development of secondary ears at the R1 stage of development. Plants were rated on the following scale: 1=Little or no secondary ear formation; 2=Silks are prominent on the secondary ear; 3=Developed secondary ear emerged from the ear leaf sheath; and 4=Good secondary ear development similar to the primary ear. End-of-season harvest further indicated at least some secondary ears were productive with normally developed kernels.

Example 9. Broad-Acre Yield and Trait Trials in the Field with Hybrid Corn Plants Transformed with the GA20 Oxidase Suppression Construct The GA20 oxidase suppression construct described in Example 1 was transformed into a female commercial corn inbred line, and a number of transformation events were created. The transformed plants were grown and self-crossed to bulk up sufficient seeds, and then crossed to various male commercial corn inbred lines to produce hybrid corn plants. Each distinct male inbred line used to produce the male-female hybrid is called a tester. The hybrid corn plants with different testers were then grown on broad acres in the field according to standard agronomic practice (SAP). The planting density for SAP was 34,000 plants per acres with 30" row spacing.

For yield trials, four different transformation events expressing the GA20 oxidase suppression construct were crossed to 2 different commercial tester lines. The hybrid corn plants were then tested in 16 geographic locations across 6 US Midwest states. Yield of transgenic hybrid corn plants across these locations was calculated and compared to the yield of non-transgenic hybrid corn control plants. Table 4 provides the yield difference in bushels/acre between the transgenic hybrid corn plants for each event as compared to a non-transgenic control. A negative number indicates a yield decrease. Yield differences with a statistical p-value of less than 0.2 are indicated in Table 4 with bold and italic font. This notation is also used to indicate statistical significance for the remaining tables in these Examples, unless otherwise noted. As shown in Table 4 under the SAP heading, a significant increase in yield was observed in transgenic hybrid corn plants expressing the suppression construct (transgenic plants) under SAP conditions, relative to wild type hybrid corn plants (Control). The significant increase in yield was observed across 4 transgenic events, and 2 tester lines.

A comparable broad-acre yield trial was conducted under high density (HD) planting conditions with 42,000 plants per acre and 30" row spacing, and compared to standard agronomic practice (SAP) density. The differences in yield under HD conditions are provided in Table 4 under the HD heading. Mixed results were obtained under these high density conditions with yield varying across events and testers. However, an increase in yield was observed for two events with one of the two testers, and the possibility remains for higher yield across a greater number of germplasms under different high density conditions.

TABLE 4

Broad-acre yield difference between transgenic plants and control, under SAP and HD

| | SAP | | | HD | | |
|---|---|---|---|---|---|---|
| | Tester-1 | Tester-2 | Across Testers | Tester-1 | Tester-2 | Across Testers |
| Across Events | 3.7 | 3.9 | 4 | 3.5 | −10.7 | −3.9 |

TABLE 4-continued

Broad-acre yield difference between transgenic plants and control, under SAP and HD

| | SAP | | | HD | | |
|---|---|---|---|---|---|---|
| | Tester-1 | Tester-2 | Across Testers | Tester-1 | Tester-2 | Across Testers |
| Event-1 | 7.5 | 2.7 | 5.1 | 7.5 | −4.3 | 1.3 |
| Event-2 | 3.2 | 7.0 | 5.6 | −5.1 | −14.9 | −10.3 |
| Event-3 | 2.3 | 1.8 | 2 | 7.6 | −9 | −0.7 |
| Event-4 | 1.7 | 4.6 | 3.4 | 3.1 | −14.2 | −6.1 |

Trait trials were also conducted in the field to measure a number of developmental and reproductive traits. These trials were conducted under normal density (SAP) as described above and ultra high density (UHD) planting conditions of 54,000 plants per acre with 20" row spacing. The trials were conducted in hybrid corn plants with 7 transformation events and 3 testers, and the data for each tester was pooled over the 7 events.

Table 5 summarizes the trait trial results in hybrid corn plants. The measurement is either a percent difference, or a difference of days or number of leaves, between the transgenic plants and the control. Where appropriate, the development stage, such as R3, etc., at which the measurement was taken, is indicated in parenthesis under the column "Trait Name". Pollen shedding is measured in terms of the number of days from germination to 50% of plants shedding pollen. Silking emergence is measured in terms of the number of days from germination to 50% of plants silking. Pollen-silk interval is a measure of the number of days from 50% of plants shedding pollen to silking. Stalk strength is a measure of the amount of force at which the stalk segment breaks laterally, using a stalk breaker instrument. Leaf area index (LAI) is a dimensionless quantity that characterizes the extent of the plant canopy, defined as the one-sided green leaf area per unit ground surface area within a broadleaf canopy space.

TABLE 5

Trait differences between transgenic and control plants under SAP and UHD.

| | | 30" SAP | | | 20" UHD | | |
|---|---|---|---|---|---|---|---|
| Measurement | Trait Name | Tester-1 | Tester-2 | Tester-3 | Tester-1 | Tester-2 | Tester-3 |
| % Delta | Plant height (R3) | −46 | −47.7 | −45.2 | −38.3 | −42.3 | −41.6 |
| | Plant height below 6 ft | YES | YES | YES | YES | YES | YES |
| | Ear height (R3) | −35.3 | −39.8 | −38.8 | −48.3 | −51.4 | −48.4 |
| | Ear height above 18 inches | YES | YES | YES | YES | YES | YES |
| % Delta | Internode length (ear minus 2) (R3) | −34.2 | −34.7 | −34 | −44.9 | −36.4 | −42.3 |
| | Internode length (ear minus 4) (R3) | −54.2 | −49.4 | −54.9 | −60.1 | −55.7 | −59.4 |
| | Stalk Diameter (2 nodes below ear) (R3) | 4.4 | 5.8 | 4.5 | 37.7 | 43.1 | 35.5 |
| | Stalk Diameter (4 nodes below ear) (R3) | 3.9 | −1.6 | 1 | 16.3 | 15.6 | 16.5 |
| | Stalk strength 2nd node below ear (R5) | 10.2 | 0.1 | 0.7 | 50.1 | 115 | N/A |
| | Stalk strength 4th node below ear (R5) | −13.6 | −22.3 | −11.5 | 13.3 | 78.4 | N/A |

TABLE 5-continued

Trait differences between transgenic and control plants under SAP and UHD.

| Measurement | Trait Name | 30" SAP Tester-1 | 30" SAP Tester-2 | 30" SAP Tester-3 | 20" UHD Tester-1 | 20" UHD Tester-2 | 20" UHD Tester-3 |
|---|---|---|---|---|---|---|---|
| Days | Pollen-silk interval | −0.88 | −1 | −0.5 | 0 | −0.33 | −0.07 |
| | Pollen shedding | 1.5 | 0.75 | 0.13 | −0.21 | 0.31 | −0.91 |
| | Silking emergence | 0.63 | −0.25 | −0.38 | −0.26 | −0.06 | −1.03 |
| Number | Green leaf # (R4) | −1.4 | −1.4 | −1.7 | −1.7 | −1.4 | −1.4 |
| | Green leaf # (R5) | −1.8 | −1.7 | −1.6 | −2.1 | −1 | −1.7 |
| | Green leaf # (7 days after R5) | −0.5 | −0.4 | −0.3 | −1.1 | −0.3 | −0.6 |
| | Green leaf # (14 days after R5) | −0.2 | −0.4 | −0.2 | −0.7 | −0.3 | −0.3 |
| % Delta | Leaf area index (V6) | 30.8 | 33.9 | 51.5 | −33.2 | −14.8 | −16.6 |
| | Leaf area index (V8) | 20.1 | −1.4 | 15.4 | 37.5 | 29.7 | 32.5 |
| | Leaf area index (V10) | 10.7 | 2 | 8.5 | 25.9 | 27.9 | −7.7 |
| | Leaf area index (V12) | 2.3 | −5.4 | 3.6 | 20.2 | 19 | 15.7 |

As shown in Table 5, a significant decrease in plant height, ear height, and internode length was observed in transgenic plants relative to the control. The transgenic plants consistently exhibited plant heights below 6 feet, and ear heights above 18 inches, allowing harvesting by combine without modification to the machinery. In this experiment, increased stalk diameter was observed particularly under higher density planting conditions.

Table 6 summarizes the ear trait trial results for hybrid corn. The trials were conducted in hybrid corn plants with 7 transformation events and 3 testers, and the data for each tester was pooled over the 7 events. The measurements are the percent delta difference between the transgenic plants and the control. Where appropriate, the development stage, such as R3, etc., at which the measurement was taken, is indicated in parenthesis under the column "Trait Name". Ear area is a measure of the plot average size of an ear in terms of area from a 2-dimensional view taken by imaging the ear, including kernels and void. Ear diameter is a measures the plot average of the ear diameter measured as the maximal "wide" axis of the ear over its widest section. Ear length is a measure of the plot average of the length of ear measured from the tip of the ear in a straight line to the base of the ear node. Ear tip void_pct is a measure of the plot average of the area percentage of void at the top 30% area of the ear, from a 2-dimensional view taken by imaging the ear, including kernels and void. Ear void measures the plot average of the area percentage of void on an ear, from a 2-dimensional view, is measured by imaging the ear, including kernels and void. Grain yield estimate is defined in Example 7. Kernels per unit area is measured as the plot average of the number of kernels per unit area of the field. Ears were collected from a set row length, typically one meter, and shelled and combined to count the kernels, and the count was then converted to the total kernels per unit area of the field. Single kernel weight measures the plot average of weight per kernel. It is calculated as the ratio of (sample kernel weight adjusted to 15.5% moisture)/(sample kernel number). Kernels per ear is a measure of the plot average of the number of kernels per ear. It is calculated as (total kernel weight/(Single Kernel Weight*total ear count), where total kernel weight and total ear count are measured from ear samples over an area between 0.19 to 10 square meters.

TABLE 6

Ear trait differences between transgenic and control plants, under SAP and UHD.

| Trait Name | 30" SAP Tester-1 | 30" SAP Tester-2 | 30" SAP Tester-3 | 20" UHD Tester-1 | 20" UHD Tester-2 | 20" UHD Tester-3 |
|---|---|---|---|---|---|---|
| Ear area (R6) ($cm^2$) | 5.5 | 11.6 | 4.8 | 14.9 | 16.9 | 8.8 |
| Ear diameter (R6) (mm) | −2.2 | −0.7 | −2.5 | −1.7 | 1.3 | −1.8 |
| Ear length (R6) (cm) | 7.3 | 12.5 | 7.4 | 15.4 | 14.3 | 11.1 |
| Ear tip void_pct (R6) (%) | −9.1 | −1.1 | 7.7 | −5.8 | 24 | 11.1 |
| Ear void (R6) (%) | −3.3 | 1.9 | 9.5 | −6.7 | 10 | 16.4 |
| Grain yield estimate (R6) (kg/hectare) | 2.8 | −4.6 | −5.0 | 0.2 | 19.2 | 0.9 |
| Kernels per unit area (R6) ($kernels/m^2$) | −0.7 | −9.8 | −6.7 | 11.6 | 34.4 | 9 |
| Kernels per ear (R6) (count) | −3.2 | 0.5 | −3.5 | 19.1 | 35.2 | 6.5 |
| Single kernel weight (R6) (mg) | 1.8 | 5.1 | 1.1 | −10.5 | −12.3 | −7.5 |

As shown in Table 6, there was a significant increase in ear area and ear length observed in these experiments for the transgenic plants as compared to the control. There was also a noticeable decrease in the ear diameter. In this experiment, the grain yield estimate was mostly neutral between transgenic plants and the control.

Additional data was collected in the field at standard density across 8 events crossed to one tester showing a reduction in plant height, ear height, and internode length, and an increase in stem diameter and harvest index, as compared to a control (data not shown). Plant heights were measured from the ground to the uppermost ligulated leaf at R3 stage. Ear heights were measured from the ground to the ear node at R3 stage. Stalk diameters were measured at the middle of the stalk internode 2 nodes below the ear, unless otherwise indicated. These data demonstrated high penetrance of plant height and stalk traits across events, although an increase in prolificacy (or the number of secondary ears) was not significant or pronounced in these studies.

Figure 9:
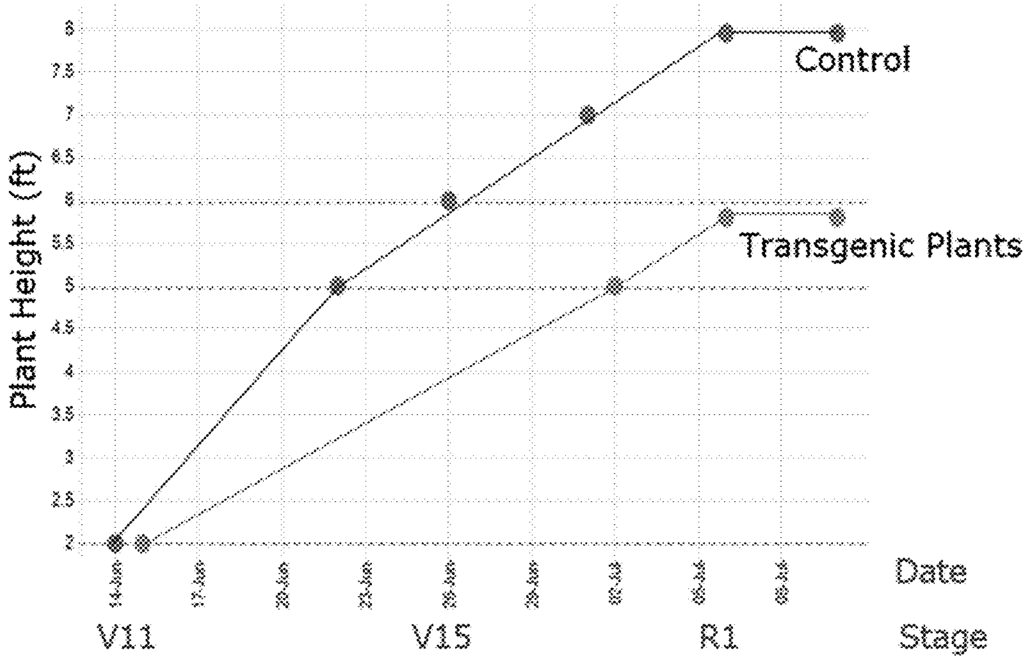
FIG. 9 shows the change in plant height over time during developmental stages V11 to beyond R1 between transgenic corn plants and control.

In a separate experiment, plant height growth was measured from V11 to R1 stage and beyond. FIG. 9 shows the differences in plant height between transgenic plants and the control over this time frame. Drawn on the figure are dotted lines for 5-foot and 6-foot heights for reference.

Example 10. Transgenic Plants Exhibited Enhanced Traits Under Nitrogen and Water Stress Conditions in Controlled Environment Conditions This example illustrates the enhanced water and nitrogen stress response of transgenic corn plants having the GA20 oxidase suppression construct described in Example 1 versus the control, in an automated greenhouse (AGH) or the field as indicated. The apparatus and the methods for automated phenotypic assaying of plants in AGH are disclosed, for example, in U.S. Patent Publication No. 2011/0135161, which is incorporated herein by reference in its entirety.

In the AGH setting, corn plants were tested under five different conditions including non-stress, mild and moderate nitrogen deficit, and mild and moderate water deficit stress conditions. The corn plants were grown under the stress-specific conditions shown in Table 7.

TABLE 7

Description of the five AGH growth conditions.

| Condition | Volumetric Water Content (VWC) | Nitrogen Concentration |
|---|---|---|
| No stress | 50% | 8 mM |
| Water Stress: mild | 40% | 8 mM |
| Water Stress: moderate | 35% | 8 mM |
| Nitrogen Stress: mild | 50% | 6 mM |
| Nitrogen Stress: moderate | 50% | 4 mM |

Water deficit is defined as a specific Volumetric Water Content (VWC) that is lower than the VWC of a non-stressed plant. For example, a non-stressed plant might be maintained at 50% VWC, and the VWC for a water-deficit assay might be defined between 35% to 40% VWC. Data were collected using visible light and hyperspectral imaging as well as direct measurement of pot weight and amount of water and nutrient applied to individual plants on a daily basis. Nitrogen deficit is defined (in part) as a specific mM concentration of nitrogen that is lower than the nitrogen concentration of a non-stressed plant. For example, a non-stressed plant might be maintained at 8 mM nitrogen, while the nitrogen concentration applied in a nitrogen-deficit assay might be maintained at a concentration between 4 to 6 mM.

Up to ten parameters were measured for each screen. The visible light color imaging based measurements are: plant height, biomass, and canopy area. Plant Height (PlntH) refers to the distance from the top of the pot to the highest point of the plant derived from a side image (mm). Biomass (Bmass) is defined as the estimated shoot fresh weight (g) of the plant obtained from images acquired from multiple angles of view. Canopy Area (Cnop) is defined as leaf area as seen in a top-down image ($mm^2$). Anthocyanin score and area, chlorophyll score and concentration, and water content score were measured with hyperspectral imaging. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Chlorophyll Concentration (ClrpC) are both measurements of chlorophyll in the leaf canopy obtained from a top-down hyperspectral image, where Chlorophyll Score measures in relative units, and Chlorophyll Concentration is measured in parts per million (ppm) units. Foliar Water Content (FlrWtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment. These physiological trials were set up so that tested transgenic plants were compared to the control. Transgenic plants of two transformation events were measured in comparison with the control. All data are in percent delta difference of the transgenic plant with respect to the control. Data point with statistical p-value<0.1 were shown in bold italic font. Other data points have p-value>0.1.

Table 8 summarizes the AGH trait trial results as measured at 21 days from planting in the vegetative stage, whereas Table 9 summarizes the AGH trait trial results as measured at 55 days from planting in the reproductive stage, in transgenic plants having one of two events of the GA20 oxidase suppression construct described in Example 1 relative to control plants.

TABLE 8

Transgenic versus control plants in the greenhouse under normal and stress conditions, 21 days from planting.

| | Event-1 | | | | | Event-2 | | | | |
|---|---|---|---|---|---|---|---|---|---|---|
| | No | Nitrogen stress | | Water stress | | No | Nitrogen stress | | Water stress | |
| Trait Name | stress | Mild | Moderate | Mild | Moderate | stress | Mild | Moderate | Mild | Moderate |
| Plant height | −17.6 | −20.1 | −19 | −21.2 | −20.8 | −16.1 | −19.9 | −21.6 | −22.4 | −21.3 |
| Biomass | −0.06 | −8.9 | 5.61 | −7.48 | 8.47 | −0.32 | −8.11 | −1.77 | −6.45 | −1.48 |
| Canopy area | 0.79 | −7.6 | 11.4 | 1.45 | 16.9 | 0.36 | −4.84 | 5.62 | 4.38 | 2.75 |
| Foliar water content | 18.6 | 23 | 16.3 | 55 | 10.1 | 8.9 | 30.9 | 15.5 | 55.9 | 21.4 |
| Anthocyanin area | −38.9 | −28.9 | −35.4 | −41 | −55.5 | −42.3 | −39.7 | −35.4 | −46 | −26 |
| Anthocyanin score | −10.21 | −14.5 | −2.9 | 129.5 | 2.4 | 78.1 | 4.5 | 3.3 | 119.6 | −2.5 |
| Chlorophyll concentration | 1.2 | 0.68 | 0.04 | −5.84 | 3.27 | −8.56 | −2.03 | −3.46 | −4.14 | 2.05 |

TABLE 9

Transgenic versus control plants in the greenhouse under normal and stress conditions, 55 days from planting.

| | Event-1 | | | | | Event-2 | | | | |
|---|---|---|---|---|---|---|---|---|---|---|
| | No | Nitrogen stress | | Water stress | | No | Nitrogen stress | | Water stress | |
| Trait Name | stress | Mild | Moderate | Mild | Moderate | stress | Mild | Moderate | Mild | Moderate |
| Plant height | −31.9 | N/A | N/A | −40.7 | −25.4 | −33.3 | N/A | N/A | −41.3 | −29.6 |
| Biomass | −26.1 | N/A | N/A | −25.2 | −5.5 | −26.1 | N/A | N/A | −26.8 | −13.7 |
| Ear weight | 60.7 | 28.7 | 36 | 10.7 | 203.3 | 75.7 | 40.4 | 33.5 | 23.2 | 109.9 |
| Stover weight | −12.9 | −12.1 | −15.8 | −13.7 | 0 | −12.1 | −11.9 | −22.9 | −11.4 | −6.8 |
| Harvest index | 74.6 | 42.5 | 60.4 | 25.9 | 192 | 90.7 | 54.1 | 65 | 35.3 | 120.5 |
| Water applied | −8 | N/A | N/A | −16.8 | 3.4 | −11.3 | N/A | N/A | −16.3 | −2.3 |
| WUE | −19.2 | N/A | N/A | −10.1 | −8.5 | −16.5 | N/A | N/A | −12.5 | −11.3 |

As shown in Table 8, in comparison with the control, transgenic plants exhibited some enhanced traits related to stress resistance and maintained other positive traits under stress conditions. The plant height decreased significantly across all treatments and was not affected by stress condition. Biomass and canopy area were neutral in no-stress condition but increased in more severe stress conditions. The foliar water content increased significantly in no-stress and stress conditions, indicating that the transgenic plants retained more water in leaf tissues. The anthocyanin area decreased significantly in no-stress and stress conditions, indicating there was no nitrogen deficiency in the transgenic plants.

As shown in Table 9, in comparison with the control, transgenic plants exhibited significant decrease in the trait areas of Water Applied, WUE, biomass and stover weight, indicating that the transgenic plants had improved water use efficiency, with plants of lower biomass requiring less water. Harvest index increased significantly under non-stress and stress conditions.

Figure 10:
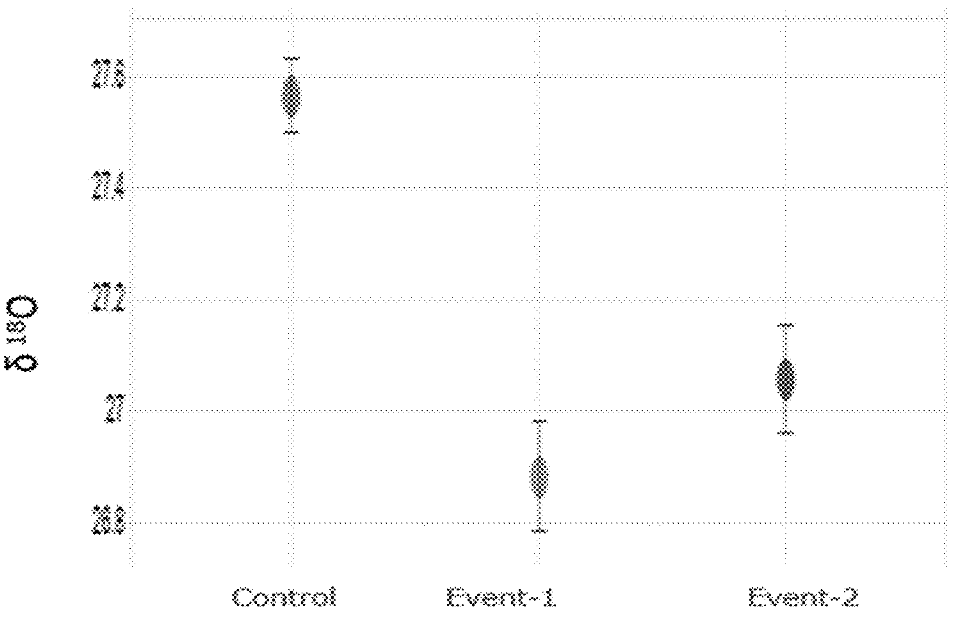
FIG. 10 shows a graph comparing measurements of stable oxygen isotope ratios ($\delta^{18}O$) as an indication of stomatal conductance and water levels in leaf tissue at R5 stage between transgenic corn plants and control.

Example 11. Transgenic Plants Exhibited Increased Drought Tolerance, Stomatal Conductance, and Root Front Velocity at Reproductive Stages at Both Standard and High Density in the Field Direct observations were made of decreased leaf rolling in transgenic corn plants having the GA20 oxidase suppression construct from Example 1 under drought conditions in the field compared to control plants. Corn leaf rolling occurs when leaf water potential drops below a threshold of approximately −1.1 MPa. Stomatal conductance also decreases under water stress. Stable oxygen isotope ratios ($\delta^{18}O$) were used as an index of the stomatal conductance, which is inversely proportional to stomatal conductance. A significant decrease of $\delta^{18}O$, and thus a significant increase in the stomatal conductance, in transgenic plants over the control was observed from ear leaf samples collected at R5 stage (see FIG. 10). Data was taken from transgenic plants across two transformation events and averaged across 10 testers with 2 reps per tester. Increased 8180 in the leaf of control plants indicates that stomatal conductance was lower for the control. In conjunction with the reduced leaf rolling observed in the field, the significant increase of stomatal conductance in leaves of transgenic plants from yield trials at 15 out of 16 field locations indicates improved leaf water status during late vegetative growth for the transgenic plants.

Figure 11:
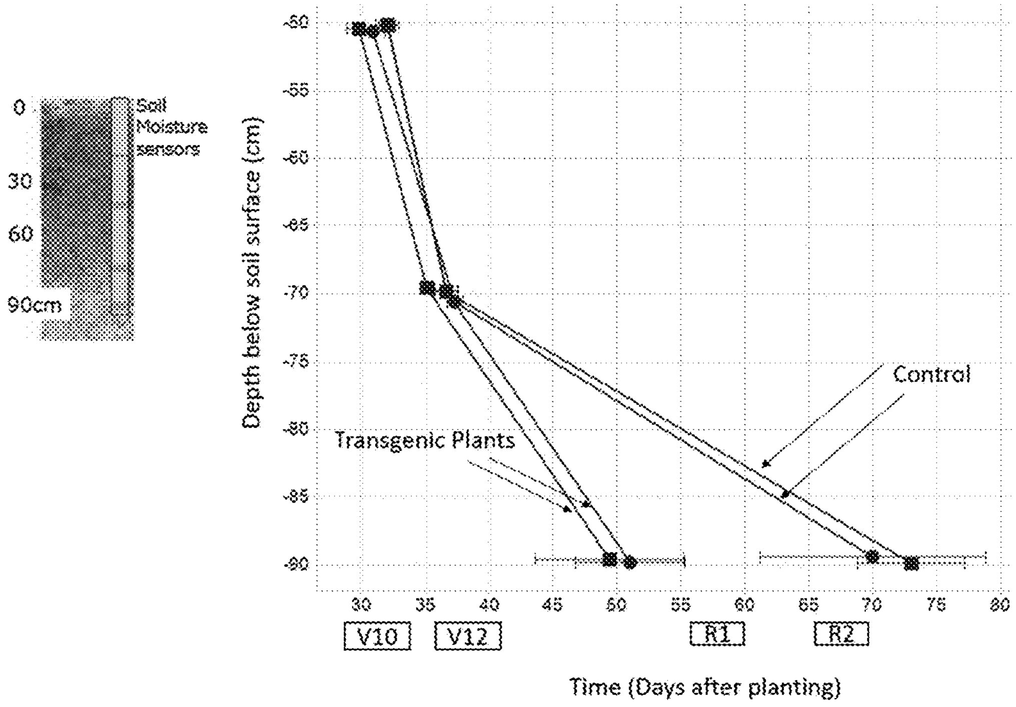
FIG. 11 shows a graph comparing root front velocity during developmental stages V10 to beyond R2 between transgenic and control plants at both SAP and HD conditions using sensors at different soil depths that detect changes in water levels indicating the presence of roots at that depth.

Effective water uptake by the roots is an important factor in plant growth. To measure the developmental progress of rooting depth, Sentek® SOLO soil moisture capacitance probes were installed at V4 stage within the row between plants at one field location. Soil moisture was measured on an hourly basis with capacitance sensors at depths of 10, 20, 30, 50, 70, 90, 120, and 150 cm from the ground level. The depth of the rooting front was inferred by the presence of diurnal patterns in soil moisture depletion recorded by the sensors. Root activity was already present at 10, 20, and 30 cm depth at the time of installation at V4 stage. We detected the first occurrence of soil moisture depletion at 50, 70, and 90 cm depths. The soil at 120 and 150 cam depth was saturated throughout the growing season. While root growth may have reached these depths, we were not able to detect root activity at these depths for this experiment due to the inability to detect soil moisture depletion in a saturated zone. FIG. 11 shows the time (days after planting) for the frontal root of the plant to reach various depths on the Y axis. Lines with circles are for plants at 30-inch row spacing and 34,000 plants per acre planting density, and lines with squares are for plants at 20-inch row spacing, and 55,000 plants per acre planting density. Growth stages are shown on the X axis.

As shown in FIG. 11, root growth was similar in this experiment between transgenic and control plants up to V12, with roots reaching 50 and 70 cm depth at about 30 and 36 days after planting, respectively. However, the transgenic plant roots reached 90 cm depth at or before R1 (i.e., at about day 50 after planting), or about 20 days earlier than control plant roots. The transgenic plants exhibited increased rooting front velocity after V11/V12 stage, which may lead to increased drought avoidance during the critical period of plant development around flowering. This increase in rooting front velocity may allow the transgenic plants to take advantage of deeper reserves of soil water during the critical period around R1 stage, possibly allowing drought effects on flowering and pollination to be avoided, reduced or minimized. Improved pollination under drought conditions may likely improve kernel set and yield potential.

To complement the above field experiment with moisture sensors, root front velocity for transgenic corn plants having the GA20 oxidase suppression construct from Example 1 (n=10) was measured in a root box experiment and compared to wild-type control plants (n=9). Plexiglass root boxes (5 feet tall and six-by-eight inches in cross section; ½ inch wall thickness) were filled with a mix of #10 field soil/vermiculite/perlite (1:1:1 ratio) and used for root visualization for each plant. Maximum rooting depth in each box was measured at regular intervals after planting (approximately every two days). In this experiment, median root front depth of transgenic plants was consistently greater or deeper than WT control plants starting at about 21 days after planting (i.e., at about V4 stage) and continuing until at least 34 days after planting when measurements were stopped (data not shown). This observation in controlled environment root boxes is consistent with the increased root depth observed with moisture sensors in the field and shows that deeper roots may occur at earlier developmental stages, although differences in root depth were not detected in the field experiment until after V11/V12 stage.

Although the root traits measured in the controlled environment experiments described in Example 14 below generally did not show a significant difference in root depth (or only a minimal difference), the vermiculite experiment in Example 14 was performed at V3 stage before the difference in root depth was observed in the root box experiment in this Example 11 (i.e., starting around V4 stage), and although the aeroponic apparatus experiment in Example 14 was performed at V5 stage, the aeroponic system does not have any plant-soil interaction (unlike the vermiculite experiments) that might affect normal (or more natural) root growth and development.

Figure 12A:
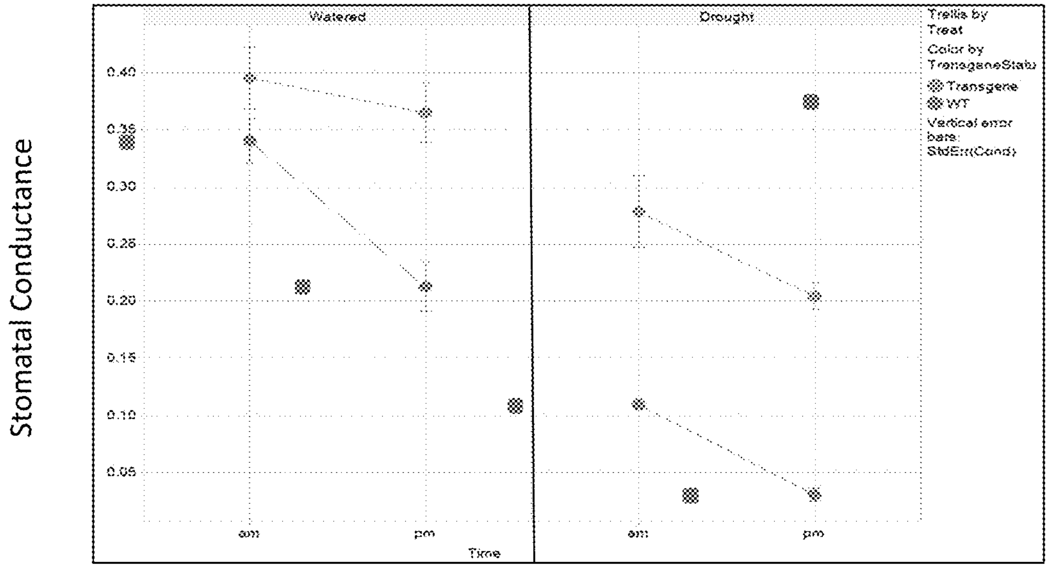
FIG. 12A shows differences in stomatal conductance during the morning and afternoon between transgenic corn plants and control under normal and drought conditions in the greenhouse.
Figure 12B:
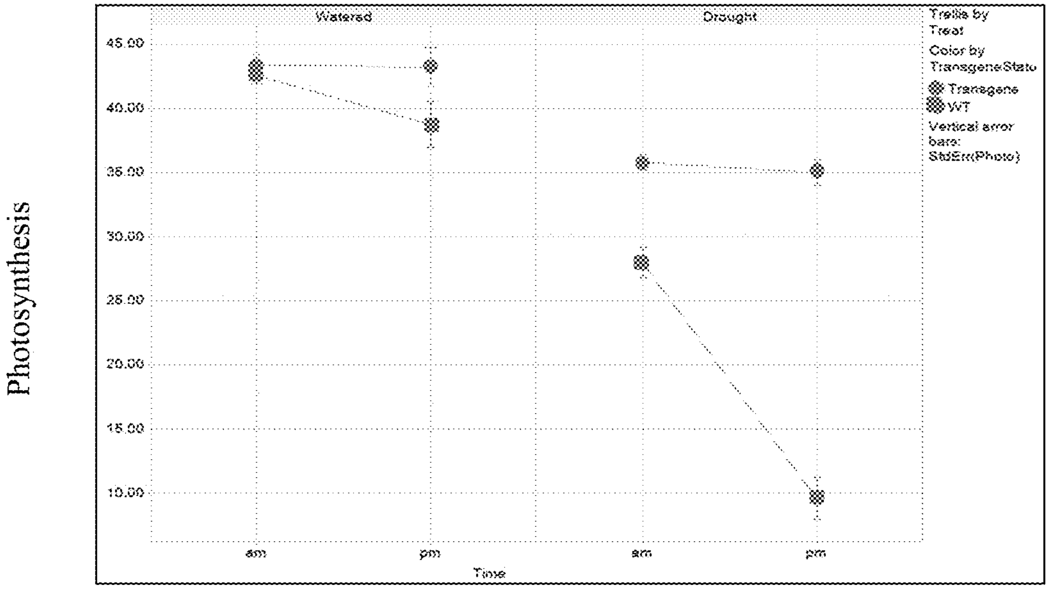
FIG. 12B shows differences in photosynthesis during the morning and afternoon between transgenic corn plants and control under normal and drought conditions in the greenhouse.

Example 12. Transgenic Plants have Higher Stomatal Conductance in Normal and Drought Conditions and Maintain Higher Photosynthesis Capacity Under Drought Stress Stomatal conductance and photosynthesis levels in leaves under normal and drought conditions was also measured in the greenhouse. For this experiment, transgenic plants with the GA20 oxidase suppression construct from Example 1 and wild-type control plants were subjected to a well watered (1500 ml water per day) or limited water/chronic drought (1000 ml water per day) treatment. Twenty (20) reps of the wild-type control plants and ten (10) reps per event (two events total) for the GA20 oxidase suppression construct were subjected to the well watered treatment, and one-hundred and forty (140) reps of the wild-type control plants and seventy (70) reps per event (two events total) for the GA20 oxidase suppression construct were subjected to the limited water/chronic drought treatment. Border plants of appropriate height (hybrids for WT plants and inbreds for transgenic plants) were placed around the perimeter of the experimental plants in the greenhouse to normalize the effects of shading. Diurnal stomatal conductance and photosynthesis measurements were taken in the morning and afternoon with a LI-COR® device at V12 stage per manufacturer's instructions. As shown in FIG. 12A, stomatal conductance was found to be consistently higher for the transgenic plants under both well-watered and drought conditions at both daily time points. Transgenic plants were also observed to have less leaf rolling under the drought condition. As further shown in FIG. 12B, a higher photosynthesis rate was also observed in response to drought conditions that did not significantly respond to increased sunlight in the afternoon, unlike control plants that showed a drop in the rate of photosynthesis in the afternoon particularly under drought conditions.

These results (in combination with the separate field observations above) demonstrate that the transgenic plants with the GA20 oxidase suppression construct not only had higher gas exchange and photosynthesis in the leaf, but maintained a higher gas exchange and photosynthesis in the leaf in response to water limiting/chronic drought conditions. It was further observed that transgenic plants had a lower leaf temperature than control plants (data not shown). Thus, it is predicted that transgenic plants expressing a GA20 oxidase suppression construct may have greater drought tolerance and an ability to maintain photosynthesis under water limiting conditions as compared to controls. Without being bound by theory, it is further proposed that the deeper roots observed for transgenic plants with the GA20 oxidase suppression construct (particularly during late vegetative and early reproductive stages) may contribute to the drought tolerance of these transgenic plant.

Example 13. Transgenic Plants Exhibited Reproductive Traits Comparable to Those of the Control in Greenhouse Conditions Transgenic corn plants having the GA20 oxidase suppression construct described in Example 1 and control plants were grown in pots in the greenhouse to reproductive R1 stage, and reproductive traits were measured in V8 and R1 stages. Data were taken for transgenic plants of two transformation events (Table 10). The data are provided either in terms of a difference in the number of days, or as a percent difference, for the transgenic plants as compared to a wild-type control, and significant changes are in bold. Trait names are defined in Examples 9 and 10 above. Specific observations of the traits and trait classes of flowering, immature ear, mature ear and tassel are summarized in the table. Overall, reproductive development in transgenic plants was nearly equivalent to control plants with only a few slight or minor changes.

TABLE 10

Greenhouse reproductive traits of transgenic plants vs control.

| Class | Trait | Event-1 | Event-2 | Observations |
|---|---|---|---|---|
| Development (R1) | Plant Height | −17.60% | −14% | Shorter plant |
| | Leaf Tip Number | 2% | 1.10% | Slight increase in leaf numbers (0.3) |
| Flowering (R1) | Days to 50% Silking and 50% Pollen Shed | −0.4 day | −0.5 day | Slightly delayed pollen shedding time with normal silking time; lower ASI |
| | Days to 50% Pollen Shedding | 1.10% | 1.10% | |
| | Days to 50% Visible Silk | 0.40% | −0.10% | |
| Immature Ear (V8) | Immature Ear Diameter at base | −28.50% | −22.60% | Slower initiation of ear development |
| | Immature Ear Internode Length | −6.10% | −4.20% | |
| | Immature Ear Length | −42% | −31% | |
| | Immature Kernels/Row Longitudinally | −38.70% | −29.70% | |
| Mature Ear (R1) | Kernels/Row Longitudinally | −1% | −0.40% | Properly developed mature ear |
| | Kernel Row Number | 2.20% | 0% | |
| | Total floret number | 1.10% | −0.50% | |
| | Shank internode number | −3.60% | 0.10% | |
| Tassel (R1) | Number of Tassel Branches | −5.40% | −3.80% | Properly developed tassel but with shorter first interlode |
| | Primary Lateral Tassel Branch Number | −10.40% | −9.10% | |
| | Secondary Lateral Tassel Branch Number | −17.60% | −13.70% | |
| | Rachilla Floret Density | −8.50% | −0.40% | |
| | First Tassel Internode Length | −34.10% | −32.70% | |

Example 14. Root Traits of Transgenic and Control Plants in Greenhouse Conditions Transgenic plants having the GA20 oxidase suppression construct described in Example 1 and control plants were grown in the greenhouse in vermiculite medium to V3 stage or in an aeroponic apparatus to V5 stage. Plants were extracted and roots washed for direct or optical imaging measurements of the root traits. Transgenic plants of 4 transformation events were tested in comparison to a control. Measurement results are summarized in Table 11 and 12 for plants from vermiculite medium growth, or in the aeroponic growth apparatus, respectively. Root Branch Point Number measures the number of root branch tip points of a plant through imaging of the plant root. The root system image was skeletonized for the root length measurement. Up to 40 images were taken at various angles around the root vertical axis and the measurement was averaged over the images. Root Total Length measures the cumulative length of roots of a plant, as if the roots were all lined up in a row, through imaging of the root system of the plant. The root system image was skeletonized for the root length measurement. Up to 40 images were taken at various angles around the root vertical axis and measurement was averaged over the images. Data in Tables 11 and 12 are the percent delta difference of the transgenic plants in comparison to the control with significant changes presented in bold.

TABLE 11

Greenhouse root traits of transgenic plants vs control at V3, in vermiculite medium

| | Event-1 | Event-2 | Event-3 | Event-4 |
|---|---|---|---|---|
| Average Root Diameter | −12.2 | −9.3 | −13.8 | −5.9 |
| Root Branch Point Number | 12.6 | 5.8 | 11.7 | −0.4 |
| Root Dry Weight | 1 | −5.6 | −7.1 | −5 |
| Root Surface Area | 2.2 | −6.2 | −6 | 0 |
| Root Total Length | 10 | −1.9 | 3 | 1.4 |
| Plant Height | −15.7 | −14.4 | −12.3 | −17.3 |
| Shoot Dry Weight | −3.6 | −2 | −4.5 | −7.7 |
| Shoot to Root Ratio | −1.5 | 3.4 | 1.8 | −3.4 |

TABLE 12

Greenhouse root traits of transgenic plants vs control at V5, in aeroponic apparatus.

| | Event-1 | Event-2 | Event-3 | Event-4 |
|---|---|---|---|---|
| Root Branch Point Number | −6.18 | 5.01 | 5.63 | 6.38 |
| Root Total Length | −1.47 | 5.43 | 2.46 | 6.92 |
| Average Root Width | −1.12 | −5.05 | −5.23 | −3.56 |
| Root Volume | −1.1 | −4.21 | −8.47 | −1.09 |
| Root Dry Weight | 5.21 | −7.51 | −2.61 | 4.52 |
| Root Surface Area | −1.51 | 0.93 | −2.71 | 3.06 |
| Plant Height | −13.84 | −16.29 | −14.02 | −12.83 |
| Shoot Dry Weight | −9.04 | −16.58 | −11.58 | −7.06 |
| Total Dry Weight | −4.41 | −14.19 | −8.54 | −3.24 |
| Shoot/Root Ratio | −17.16 | −13.13 | −10.17 | −13.52 |

As shown in Tables 11 and 12, the transgenic plants exhibited significant decrease in plant heights at V3 and V5 stages, but only minor variations in the overall root architecture were observed in these experiments between transgenic and control plants.

Example 15. Phenotypic Observations of Transgenic Plants with Alternate Promoters In Examples 1 through 14, transgenic plants contained a GA20 oxidase suppression element operably linked to an RTBV promoter. Corn plants were also transformed with the same suppression element operably linked to various other promoters, to test how different patterns of expression of the GA20 oxidase suppression element might affect plant height and other phenotypes.

Transgenic plants (R0 plants) regenerated from explants transformed with constructs operably linked to various promoters were observed at R5 growth stage in the greenhouse, and the ears were observed after being peeled back for dry down. The various promoters tested are identified in Table 13. Observations were made for plants of multiple transformation events for each construct containing a different promoter in comparison to control plants of the same breeding line without the GA20 oxidase suppression construct. The results of these observations are summarized in Table 13 across transformation events for each construct.

TABLE 13

Summary of R0 observations of transgenic plants with a miRNA suppression construct for GA20 oxidase under the control of different promoters.

| Promoter Name | Expression pattern | R0 plants observations |
|---|---|---|
| RTBV promoter | vascular enhanced | short; no off type |
| CAMV e35S promoter | constitutive | some short (variable); no off type |
| Coix lacryma-jobi polyubiquitin promoter | constitutive | some short (variable); no off type |
| rice actin promoter | constitutive | some short (variable); no off type |
| rice Gos2 promoter | constitutive | some short (variable); no off type |
| Enhancer + RTBV promoter | constitutive | short; no off type |
| C1 | constitutive | Short |
| corn PPDK promoter | leaf enhanced, high | mid-short; no off type |
| corn FDA promoter | leaf enhanced, medium | some short (variable); no off type |
| rice Nadh-Gogat promoter | leaf enhanced, low | mid-short; no off type |
| rice Cyp2 promoter | vascular enhanced | some short (variable); no off type |
| V1 | vascular enhanced | short; no off type |
| V2 | vascular enhanced | normal height; no off type |
| V3 | vascular enhanced | normal height; no off-type |
| MMV.FLT promoter | stem enhanced, high | normal height; no off-type |
| S1 | stem enhanced, medium | normal height; no off-type |
| S2 | stem enhanced, medium | normal height; no off-type |
| S3 | stem enhanced, medium | normal height; no off-type |
| SETit.Ifr promoter | root enhanced, high vascular enhanced | mid-short; no off-type |
| Rice Rcc3 promoter | root enhanced, low | normal height; no off-type |
| Rice Expb promoter | ear enhanced, high | normal height; no off-type |
| Maize H2a promoter | ear enhanced, low | normal height; no off-type |

As shown in Table 13, in comparison with controls, R0 transgenic plants with the GA20 oxidase suppression construct did not exhibit any significant off-types by observation for all of the promoters tested. Even expression directly in reproductive ear tissues did not cause any observable off-types. Plant heights were clearly decreased not only for the RTBV promoter construct (in the previous Examples), but also for transgenic plants having the same GA20 oxidase suppression construct operably linked to various constitutive promoters, leaf promoters at different expression levels, some vascular promoters, and a root promoter with a high expression level. An engineered promoter with constitutive expression (C1) linked to the GA20 oxidase suppression construct was tested and also found to cause a short stature phenotype. Similarly, at least one engineered promoter with vascular expression (V1) linked to the GA20 oxidase suppression construct was found to cause a short stature phenotype, in addition to the vascular rice Cyp2 promoter, although plants with two other engineered vascular promoters (V2, V3), and three engineered stem promoters (S1, S2, S3), did not have a reduced plant height. However, changing the transcriptional terminator sequence for the GA20 oxidase suppression construct under the control of the RTBV promoter did not alter the short stature phenotype (not shown in Table 11). As used herein, the term "mid-short" refers to a moderate reduction in plant height (relative to the reduction in plant height observed with the RTBV promoter), and an observation of "some short" means that there was some variation in the amount of reduction in plant height.

These results show that expression of the GA20 oxidase suppression element with constitutive promoters consistently produced a short stature phenotype, although there was some variability in the plant height phenotypes observed with these constitutive promoters. Likewise, a combination of the RTBV promoter with an enhancer element to convert the pattern of expression from vascular to constitutive still produced a short stature phenotype (indicating the sufficiency of the RTBV promoter). A few of the vascular promoters including the RTBV promoter produced a short stature phenotype, but a couple other engineered vascular promoters did not produce the short stature phenotype, which may be attributed to a lower expression level with these promoters. None of the stem promoters produced a short stature phenotype, indicating that expression of the GA20 suppression construct in the stem was not sufficient to produce this phenotype. Surprisingly, expression of the GA20 suppression construct in the leaf consistently produced short stature phenotypes with different levels of expression, although the results were somewhat variable. This data indicates that the production of active GAs in leaf tissue contributes to plant growth and ultimately plant height, even though such vertical growth occurs in the stem or stalk of the plant. Expression of the GA20 oxidase suppression construct with various root promoters generally did not produce a short stature phenotype, although one root promoter did produce a moderate phenotype, which may be due to additional expression in above-ground plant tissues.

R0 plants were then self-crossed and the resulting seeds were grown in the nursery to generate homozygous inbred progeny plants (R1 plants). Observations of R1 progeny transgenic plants with some of the promoter constructs (at least 4 transformation events per construct) were made at the R1 developmental stage, in comparison to control plants of the same breeding line without the GA20 oxidase suppression construct. Like the R0 plants, R1 progeny plants expressing the GA20 oxidase suppression construct with each of the RTBV, CAMV e35S, and *Coix lacryma-jobi* polyubiquitin promoters were also found to have a short stature, semi-dwarf phenotype without any significant off-types observed.

Example 16. Phenotypic Observations of Transgenic Corn Plants with Constructs Targeting Different GA Oxidase Genes The Examples above demonstrate that a miRNA-expressing construct targeting the GA20 oxidase_3 and GA20 oxidase_5 genes for suppression, and operably linked to a plant-expressible vascular, constitutive and/or leaf promoter, may be used to generate a short stature, semi-dwarf corn plant. To test how targeting different GA20 or GA3 oxidase genes, or different portions of the GA20 oxidase_3 and/or GA20 oxidase_5 genes, for suppression might affect plant height, several constructs were generated and transformed into corn plants. Constructs were also made with the same targeting sequence as in the above Examples, but with a different miRNA backbone sequence (two from corn miRNAs, one from a soybean miRNA, and one from a cotton miRNA—the construct in the above Examples used a rice miRNA backbone sequence). Table 14 provides a list of these additional suppression constructs, along with observations of transgenic R0 plants comprising these constructs in the greenhouse (in comparison to wild-type control plants). Constructs targeting (i) GA20 oxidase_1/GA20 oxidase_2, (ii) GA20 oxidase_3/GA20 oxidase_9, (iii) GA20 oxidase_7/GA20 oxidase_8, and (iv) GA20 oxidase_3/GA20 oxidase_5 (with different miRNA backbones), each encoded a miRNA with a single targeting sequence complementary to both gene targets, whereas the stacks of (i) the individual GA20 oxidase_3 and GA20 oxidase_5 targeting sequences, (ii) the individual GA20 oxidase_4 and GA20 oxidase_6 targeting sequences, and (iii) the individual GA20 oxidase_4 and GA20 oxidase_7/8 targeting sequences, were each expressed as a single pre-miRNA with the two targeting sequences arranged in tandem that become cleaved and separated into two mature miRNAs. Table 14 provides the miRNA targeting sequence and the cDNA sequence complementary to the miRNA targeting sequence. For the GA20 oxidase_1/GA20 oxidase_2 construct, the asterisk (*) indicates that the alignment length between the targeting sequence of the miRNA and the mRNA target or recognition site was shorter (17 vs. 20 nucleotides) for GA20 oxidase_1 than for GA20 oxidase_2. Similarly for the GA20 oxidase_3/GA20 oxidase_9 construct, the asterisk (*) indicates that the alignment length between the targeting sequence of the miRNA and the mRNA target or recognition site was shorter (17 vs. 20 nucleotides) for GA20 oxidase_9 than for GA20 oxidase_3. For each of the constructs listed in Table 14, no significant off-types were observed, apart from the observations provided in the table.

TABLE 14

Summary of R0 observations of transgenic plants with miRNA suppression constructs targeting different GA oxidase genes.

| Targeted Gene(s) (Construct/Promoter) | mRNA Targeted Area | cDNA Target Sequence (SEQ ID NO) | miRNA Targeting Sequence (SEQ ID NO) | Observations |
|---|---|---|---|---|
| GA20 oxidase_1 and GA20 oxidase_2 (RTBV promoter) | 1: exon*<br>2: exon | 47 | 48 | All events tall (WT) |

TABLE 14-continued

Summary of R0 observations of transgenic plants with miRNA suppression constructs targeting different GA oxidase genes.

| Targeted Gene(s) (Construct/Promoter) | mRNA Targeted Area | cDNA Target Sequence (SEQ ID NO) | miRNA Targeting Sequence (SEQ ID NO) | Observations |
|---|---|---|---|---|
| GA20 oxidase_3 and GA20 oxidase_9 (RTBV promoter) | 3: exon 9: exon* | 49 | 50 | All events tall (WT) |
| GA20 oxidase_7 and GA20 oxidase_8 (RTBV promoter) | exon | 51 | 52 | All events - tall (WT) |
| GA20 oxidase_3 (Individual; RTBV and 35S promoter) | UTR | 53 | 54 | Events slightly shorter (~6 inches vs. WT) |
| GA20 oxidase_5 (Individual; RTBV and 35S promoter) | UTR | 55 | 56 | All events - tall (WT) |
| GA20 oxidase_3 and GA20 oxidase_5 (Individuals; Tandem stack) | 3: UTR 5: UTR | 53 55 | 54 56 | All events - shorter |
| GA20 oxidase_3 and GA20 oxidase_5 (Different miRNA backbones) (RTBV promoter) | 3/5: exons | 39 | 40 | All events/constructs - shorter |
| GA3 oxidase_1 (RTBV promoter) | UTR | 57 | 58 | All events - tall (WT) (only 3 events observed) |
| GA3 oxidase_1 (CAMV e35S promoter) | UTR | 57 | 58 | Some events - shorter |
| GA3 oxidase_2 (RTBV promoter) | exon | 59 | 60 | All events - shorter (darker green leaves) |
| GA3 oxidase_2 (CAMV e35S promoter) | exon | 59 | 60 | Some events - shorter |
| GA20 oxidase_4 and GA20 oxidase_6 (Individuals; Tandem stack) | 4: exon 6: exon | 61 63 | 62 64 | Some events - moderately shorter (~20%) |
| GA20 oxidase_4 and GA20 oxidase_7/8 (Individuals; Tandem stack) | 4: exon 7/8: exon | 61 51 | 62 52 | Some events - moderately shorter (~20%) |

The observations summarized in Table 14 demonstrate that targeting of several other GA20 oxidase genes did not produce a short stature, semi-dwarf phenotype. None of the constructs targeting (i) the related GA20 oxidase_1 and GA20 oxidase_2 genes, (ii) the related GA20 oxidase_3 and GA20 oxidase_9 genes, (iii) the related GA20 oxidase_7 and GA20 oxidase_8 genes, or (iv) the GA20 oxidase_9 gene alone produced an observable short stature, semi-dwarf phenotype in R0 plants. In contrast, those constructs encoding a single miRNA jointly targeting the GA20 oxidase_3 and GA20 oxidase_5 genes in transgenic R0 and R1 plants did produce a short stature, semi-dwarf phenotype, even if a different transcriptional termination sequence or different miRNA backbones are used (total of 5 miRNA backbone sequences tested). In addition, targeting different sequences of the GA20 oxidase_3 and GA20 oxidase_5 genes still produced semi-dwarf plants. Interestingly, suppression constructs that were designed to target either of the GA20 oxidase_3 and GA20 oxidase_5 genes individually did not produce a short stature, semi-dwarf phenotype, unlike constructs jointly targeting the GA20 oxidase_3 and GA20 oxidase_5 genes, although the construct individually targeting the GA20 oxidase_3 gene did produce a slight reduction in plant height. However, transgenic plants having a tandem vector stack of the suppression constructs individually targeting the GA20 oxidase_3 and GA20 oxidase_5 genes did produce a short stature, semi-dwarf phenotype similar to constructs encoding a single miRNA jointly targeting the GA20 oxidase_3 and GA20 oxidase_5 genes. These data demonstrate that a short stature, semi-dwarf phenotype is observed with constructs targeting both of the GA20 oxidase_3 and GA20 oxidase_5 genes, but the full semi-dwarf phenotype is not observed with targeting of the GA20 oxidase_3 and GA20 oxidase_5 genes individually for suppression (only a slight reduction in height with targeting GA20 oxidase_3, and no plant height phenotype observed with targeting GA20 oxidase_5). Moreover, no plant height phenotype was observed with targeting the GA20 oxidase_1, GA20 oxidase_2, GA20 oxidase_6, GA20 oxidase_7, GA20 oxidase_8, and/or GA20 oxidase_9 gene(s) as described.

Apart from the GA20 oxidase_3 and GA20 oxidase_5 genes, a moderate reduction in plant height was observed in R0 transgenic plants with a suppression construct comprising two targeting sequences in tandem complementary to jointly target (i) the GA20 oxidase_4 and GA20 oxidase_6 genes, or (ii) the GA20 oxidase_4, GA20 oxidase_7 and GA20 oxidase_8 genes-one of the two targeting sequences targets both the GA20 oxidase_7 and GA20 oxidase_8 genes. Given that a separate construct that targets the GA20 oxidase_7 and GA20 oxidase_8 genes did not produce a plant height phenotype, and the suppression construct targeting the GA20 oxidase_4 and GA20 oxidase_6 genes produced a plant height phenotype that was similar to the suppression construct targeting the GA20 oxidase_4, GA20 oxidase_7 and GA20 oxidase_8 genes, it is believed that targeting of the GA20 oxidase_4 gene is largely (if not fully) responsible for the plant height phenotype observed in these transgenic plants. Furthermore, transgenic corn plants with constructs targeting the GA3 oxidase_1 or GA3 oxidase_2 genes also displayed a reduction in plant height, although there was some variability in this phenotype depending on the constitutive promoter. Thus, in addition the GA20 oxidase_3 and GA20 oxidase_5 genes, the GA20 oxidase_4, GA3 oxidase_1, and GA3 oxidase_2 genes may also be targeted for suppression to produce short stature, semi-dwarf plants.

Example 17. Phenotypic Observations of Corn Plants Having an Edited GA20 Oxidase_3 or GA20 Oxidase_5 Gene In addition to the above suppression constructs, several genome-edited mutations were created in the endogenous GA20 oxidase_3 and GA20 oxidase_5 genes in corn plants to test for the phenotypic effect of knocking out each of these genes. A series of ten single-chain guide RNA (sgRNAs) encoding targeting constructs were created for each of the GA20 oxidase_3 and GA20 oxidase_5 genes that target different positions along the genomic sequence for each gene. An additional series of ten sgRNAs were created that each target both of the GA20 oxidase_3 and GA20 oxidase_5 genes, at similar or different positions along the genomic sequence for each gene. Targeted genome edits were made by delivering the sgRNA along with expression of a Cas9 protein to corn explants to cause a DSB or nick to occur at or near the genomic target site for the gRNA, which may then be imperfectly repaired to introduce a mutation at or near the target site. The presence of a mutation was subsequently confirmed by RFLP analysis and/or sequencing of plants. Table 15 below provides a list of the guide RNA (gRNA) constructs that were tested, which may be used for genome editing of one or both of the GA20 oxidase_3 and GA20 oxidase_5 gene(s) with a RNA-guided endonuclease. These guide RNA constructs are generally designed to target the coding sequences of the GA20 oxidase_3 and GA20 oxidase_5 genes, but some of the joint targeting constructs may instead target a UTR sequence of one of the two genes. These gRNAs may be used with a suitable endonuclease to produce a double stranded break (DSB) or nick in the genome at or near the genomic target site of the respective gRNA, which may be imperfectly repaired to produce a mutation (e.g., an insertion, deletion, substitution, etc.). Transgenic plants that were homozygous for an edited GA20 oxidase_3 gene or homozygous for an edited GA20 oxidase_5 gene were generated from a few of the constructs (see bold text). Events were also generated from constructs targeting both genes for editing. For the constructs jointly targeting the GA20 oxidase_3 and GA20 oxidase_5 genes, the coding sequence (CDS) coordinates are provided in reference to one of the two genes as indicated in parenthesis. Table 15 further shows which constructs produced gene editing events, whether those events were homozygous or heterozygous in the R0 plants, and the ± numbers in parenthesis indicate the likely sequence change with the mutation (e.g., +1 means an insertion of 1 nucleotide, etc., and larger or more complicated Indels are labeled "del." or insert."). For stacked targeting of GA20 oxidase_3 and GA20 oxidase_5, the identity of the mutated gene is also provided in parenthesis. Consistent with the results for the suppression constructs, transgenic plants homozygous for an edited GA20 oxidase_3 or GA20 oxidase_5 gene did not have a short stature, semi-dwarf phenotype and had a normal plant height relative to control plants (See constructs GA20 oxidase_3-D and GA20 oxidase_3-G, and constructs GA20 oxidase_5-B and GA20 oxidase_5-G in Table 15), indicating that knockout of only one of these genes is not sufficient to produce the semi-dwarf phenotype.

TABLE 15

Guide RNAs (gRNAs) targeting GA20 oxidase_3 and GA oxidase_5 genes for editing.

| gRNA Gene Target | gRNA Targeting Sequence (SEQ ID NO) | Gene CDS coordinates | Events Generated |
|---|---|---|---|
| GA20 oxidase_3-A | 138 | 552-572 | — |
| GA20 oxidase_3-B | 139 | 879-899 | — |
| GA20 oxidase_3-C | 140 | 147-167 | — |
| GA20 oxidase_3-D | 141 | 526-546 | 1. homozygous (−1)<br>2. heterozygous (−1)<br>3. bi-allelic (−2, +1) |
| GA20 oxidase_3-E | 142 | 446-466 | — |
| GA20 oxidase_3-F | 143 | 2227-2247 | — |
| GA20 oxidase_3-G | 144 | 548-568 | 1. homozygous (+1)<br>2. heterozygous (−1)<br>3. bi-allelic (+1, −1) |
| GA20 oxidase_3-H | 145 | 547-567 | — |
| GA20 oxidase_3-I | 146 | 43-63 | — |
| GA20 oxidase_3-J | 147 | 548-567 | — |
| GA20 oxidase_5-A | 148 | 356-376 (+) | 1. heterozygous (−1) |
| GA20 oxidase_5-B | 149 | 99-119 | 1. homozygous (−1)<br>2. heterozygous (+1)<br>3. heterozygous (+1, −7)<br>4. heterozygous (−3, −1) |
| GA20 oxidase_5-C | 150 | 369-389 | — |
| GA20 oxidase_5-D | 151 | 48-68 | — |
| GA20 oxidase_5-E | 152 | 356-376 (−) | — |
| GA20 oxidase_5-F | 153 | 748-768 | 1. heterozygous (−1, +1) |

TABLE 15-continued

Guide RNAs (gRNAs) targeting GA20 oxidase_3 and GA oxidase_5 genes for editing.

| gRNA Gene Target | gRNA Targeting Sequence (SEQ ID NO) | Gene CDS coordinates | Events Generated |
|---|---|---|---|
| GA20 oxidase_5-G | 154 | 770-790 | 1. homozygous (−1)<br>2. homozygous (−1) |
| GA20 oxidase_5-H | 155 | 10-30 | — |
| GA20 oxidase_5-I | 156 | 262-282 | — |
| GA20 oxidase_5-J | 157 | 768-788 | — |
| GA20 oxidase_3/5-A | 158 | 290 . . . 310 (GA20 Ox_3) | — |
| GA20 oxidase_3/5-B | 159 | 289 . . . 309 (GA20 Ox_3) | — |
| GA20 oxidase_3/5-C | 160 | 270 . . . 290 (GA20 Ox_5) | — |
| GA20 oxidase_3/5-D | 161 | 49 . . . 69 (GA20 Ox_3) | — |
| GA20 oxidase_3/5-E | 162 | 265 . . . 285 (GA20 Ox_5) | 1. heterozygous (Ox5, +1) |
| GA20 oxidase_3/5-F | 163 | 419 . . . 439 (GA20 Ox_3) | 1. hetero (Ox3, +1, −1) hetero (Ox5, +1, del.)<br>2. hetero (Ox3, +1, del.) hetero (Ox5, +1, insert.) |
| GA20 oxidase_3/5-G | 164 | 110 . . . 130 (GA20 Ox_3) | — |
| GA20 oxidase_3/5-H | 165 | 634 . . . 654 (GA20 Ox_5) | |
| GA20 oxidase_3/5-I | 166 | 98 . . . 118 (GA20 Ox_5) | — |
| GA20 oxidase_3/5-J | 167 | 517 . . . 537 (GA20 Ox_5) | — |

Example 18. Suppression Construct Targeting GA20 Oxidase_3 and GA20 Oxidase_5 Genes Reduces GA20 Oxidase Transcript and Active GA Levels in the Plant To determine how GA20 oxidase transcript levels were affected in transgenic plants with the suppression construct targeting the GA20 oxidase_3 and GA20 oxidase_5 genes, whole tissues from various parts of transgenic plants grown in the greenhouse were taken at different vegetative stages (V3, V8, and V14), and mRNA transcript levels for each of the GA20 oxidase genes were analyzed using a TaqMan® assay. For these experiments, total RNA was extracted using a Direct-Zol RNA extraction kit from Zymo Research™ and treated with Turbo™ DNase to reduce genomic DNA contamination. RNA was then reverse transcribed to generate double-stranded cDNA. Reverse transcription quantitative PCR was performed with gene specific primers and FAM labeled TaqMan® probes on the Bio-Rad® CFX96 Real Time System. Quality control metrics were calculated using tissue specific standards to determine qPCR efficiency and total RNA that had not undergone reverse transcription to account for residual genomic DNA contamination. The difference between cycle threshold values for genes of interest versus normalizer genes determined the relative quantity of each gene transcript in each tissue. This relative quantity was calculated using either one (18S) or the geometric mean of two (18S and ELF1A) normalizer genes.

In this experiment, the level of the GA20 oxidase_3 transcript was reduced in most of the vegetative tissues at these stages, including leaf and stem tissue at V3, internode tissue at V8, and leaf and internode tissue at V14, although the level of GA20 oxidase_3 transcript in V3 root and V8 leaf appeared unchanged (data not shown). Furthermore, the level of GA20 oxidase_5 transcript for this experiment was generally unchanged in the vegetative tissues tested (data not shown), although the level of expression of the GA20 oxidase_5 transcript was relatively low in these tissues. Neither GA20 oxidase_3 nor GA20 oxidase_5 were significantly reduced in root tissue samples of transgenic plants. Each of the other GA20 oxidase genes (i.e., the 1, 2, 4 and 6-9 subtypes) were generally unchanged or increased in some tissues of the transgenic plants.

A similar experiment was conducted with reproductive tissues from transgenic plants expressing the same suppression construct. Whole tissues from various parts of transgenic plants grown in the greenhouse were taken at different reproductive stages (R1 and R3), and mRNA transcript levels for each of the GA20 oxidase genes were analyzed using a TaqMan® assay. In this experiment, the levels of GA20 oxidase_3 and GA20 oxidase_5 transcripts were mostly unchanged in R1 leaf, ear, tassel and internode and R3 leaf and internode, relative to controls (data not shown). Results for the other GA20 oxidase genes were mostly mixed or neutral (data not shown).

These data show that the level of GA20 oxidase_3 transcripts in transgenic corn plants during vegetative stages was generally reduced in this experiment, but appears mostly unchanged relative to control plant tissues during later reproductive stages. Although a clear reduction in the level of GA20 oxidase_5 gene transcripts was not generally observed in these transgenic plant tissues, the expression level of this gene was relatively low. Thus, changes in its expression level may have been difficult to detect with this method. In addition, the suppression construct appears to be specific to the targeted GA20 oxidase genes since no consistent reduction in expression level was observed in this experiment for any of the other GA20 oxidase genes.

Figure 13A:
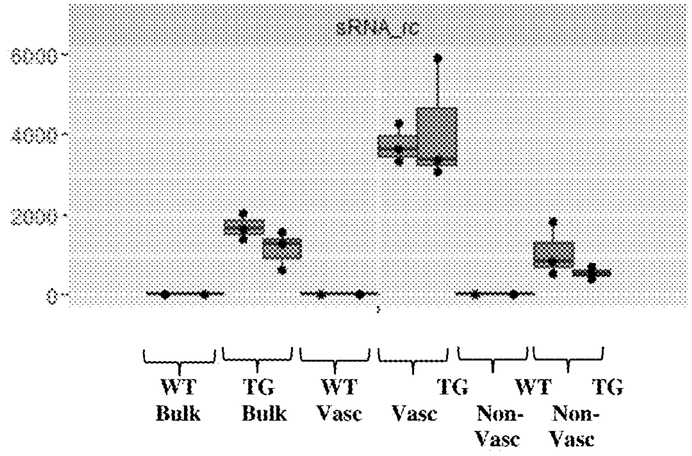
FIG. 13A shows differences in miRNA expression levels in bulk stem tissue, or separated vascular and non-vascular stem tissues, of transgenic corn plants versus control.

In a separate experiment, GA20 oxidase expression levels were determined in stem tissues of transgenic plants expressing the suppression construct from the prior Examples (targeting the GA20 oxidase_3 and GA20 oxidase_5 genes for suppression under the control of the RTBV promoter), in comparison to a wild-type control. Tissue samples were taken from V3-V6 stems/stalks and parts of those stems were further dissected to separate vascular and non-vascular tissues to determine differential expression levels among these tissues. Transcript expression levels were determined using a RNA sequencing (RNA-Seq) approach for quantitative comparison between transgenic and wild-type plant tissues. The data presented in FIG. 13A are generated from transgenic plants having one of two events and wild type control plants having one of two germplasms, with each bar in FIG. 13A representing one of the two transgenic events or germplasms, respectively. For these experiments, individual vascular bundles were separated from the remaining stem/stalk tissue of the samples and subjected to separate analysis. As shown in FIG. 13A, the miRNA expressed by the suppression construct was detected in bulk plant stem tissue ("bulk"; i.e., without separation of vascular and non-vascular tissues), as well as in separated vascular ("Vasc") and non-vascular ("Non-Vasc") tissues from the bulk stem/stalk sample. However, the expression level of the miRNA was much higher in vascular tissue than in non-vascular tissue indicating the vascular expression pattern of the RTBV promoter.

The bulk stem/stalk samples and the separated vascular and non-vascular samples were also analyzed in a similar RNA-Seq experiment to measure and compare the levels of GA20 oxidase_3 and GA20 oxidase_5 gene transcripts in transgenic versus wild-type control plants (along with other GA20 oxidase genes), although only one wild-type sample is shown for each tissue type. For these experiments, stalk tissue from control or transgenic plants (two events) were sectioned to separate vascular bundles and non-vascular tissues as described above. Total sRNA and mRNA were sequenced for each sample, and data was analyzed and compared using principle component analysis.

Figure 13B:
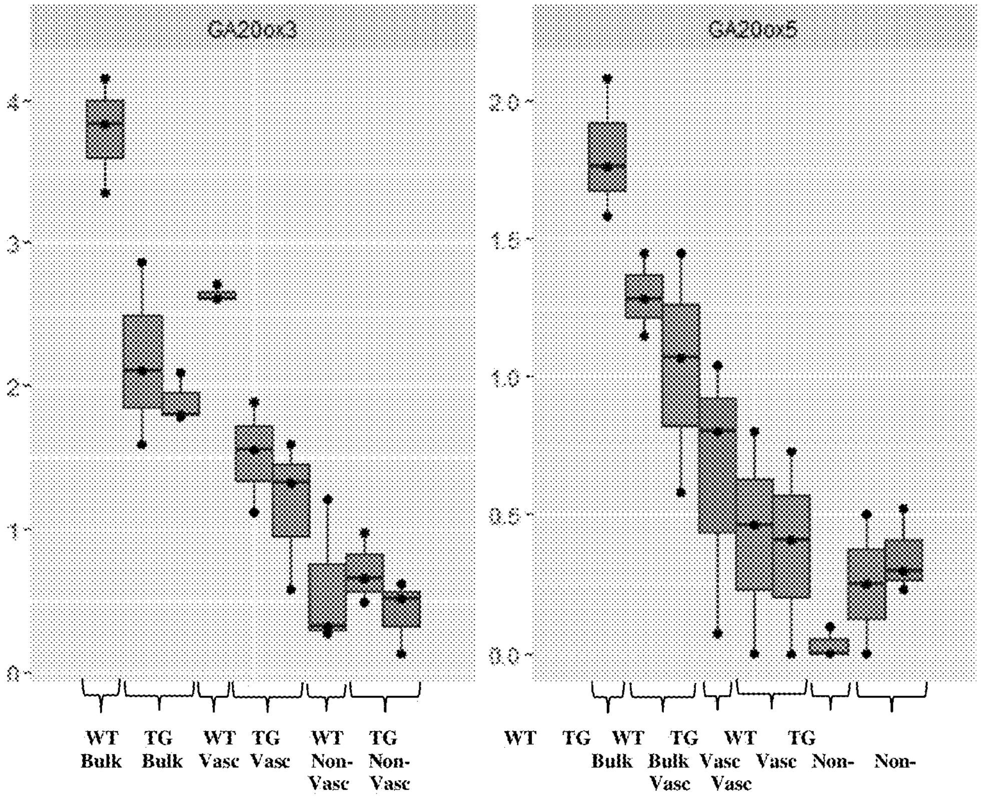
FIG. 13B shows differences in GA20 oxidase_3 and GA20 oxidase_5 mRNA transcript expression levels in bulk stem tissue, or separated vascular and non-vascular stem tissues, of transgenic corn plants versus control.

As shown in FIG. 13B, transcript levels of the GA20 oxidase_3 gene were significantly reduced in bulk stem tissue (Bulk) and separated stem vascular tissues (Vasc) of transgenic plants (TG) relative to wild-type controls (WT), but appeared unchanged in separated non-vascular (Non-Vasc) tissue. However, transcript levels of the GA20 oxidase_5 gene were significantly reduced in bulk stem tissue (Bulk), but relatively unchanged in separated vascular (Vasc) and non-vascular (Non-Vasc) tissues of transgenic plants, although there was a downward trend line for the GA20 oxidase_5 transcript in vascular (Vasc) tissue samples from transgenic plants. The level of expression of the GA20 oxidase_5 gene was low, particularly in non-vascular tissues. All other GA20 oxidase genes did not show a significant reduction in their transcript levels in the transgenic plant tissues analyzed, although a couple GA20 oxidase genes did show a slight upward trend in their level of expression. This data further demonstrates that the expression levels of the GA20 oxidase_3 and GA20 oxidase_5 genes are decreased to varying extents in one or more tissues of transgenic plants having the suppression construct relative to controls. Indeed, the higher expression of the miRNA and greater suppression of the endogenous GA20 oxidase_3 gene in vascular tissues is consistent with the vascular pattern of expression of the RTBV promoter, and perhaps the higher levels of GA20 oxidase_3 gene expression in vascular versus non-vascular tissues of wild-type plants. A similar pattern is also observed for the GA20 oxidase_5 gene, although not as pronounced as the GA20 oxidase_3 gene between vascular and non-vascular tissues.

The short stature, semi-dwarf phenotype observed with GA20 oxidase suppression in transgenic plants is likely mediated by a reduction in the level of active GAs present in the stem or internode tissues and/or in plant tissues that produce active GAs. To determine the levels of active GAs (particularly G1, G3 and G4) relative to other inactive forms of the hormone, GA levels were measured in different tissue samples taken from transgenic and wild-type control plants at different stages of development. For these experiments, fresh frozen samples for each tissue were milled and dispensed into 96 well glass tubes along with internal standards. Samples were extracted using methanol: water: acetic acid (80:19:1 v/v/v) solvent two times for 4 hours at 4 °C. Solvent was evaporated from the extract to near dryness using multi-channel SPE with nitrogen. Samples were further purified using a SPE cartridge. After purification, samples were run using standard LC-MS/MS method with Shimadzu® Nexera® UPLC and SCIEX® triple quad 5500 mass spec instrumentation. Chromatographs were analyzed and quantified using internal standards.

Two sets of experiments were performed with samples taken from various tissues of vegetative stage plants. As shown in Table 16 for one experiment in the greenhouse, reduced levels of active GAs (GA1, GA3, and GA4) were observed in various tissues of transgenic plants at different vegetative stages. The data in Table 16 is displayed as the number of transgenic plants having a significant change in the amount of each GA hormone for a given tissue ("U"=up or increased; "D"=down or decreased; "N"=neutral or no change; and "T"=total number of plants). The GAs that showed at least a partial reduction in tissue samples are presented in bold. Active GA1 was reduced in leaf and internode tissues at V8 stage and internode tissue at V14 stage, and active GA4 was reduced in V3 stem and V8 and V14 internode. However, active GA3 was not observably reduced in this experiment. Other inactive forms of GAs were altered in various tissues of transgenic plants as shown in Table 16. In general, GAs that are downstream of GA20 oxidase genes in the gibberellic acid pathway (e.g., GA9, GA20, and GA34) tended to be reduced, whereas GAs that are upstream of GA20 oxidase genes tended to be higher (e.g., GA12 and GA53), which may be due to the lower activity of GA oxidase genes causing the precursor GAs upstream to accumulate. This data is consistent with suppression of GA20 oxidase activity in these tissues and lower levels of active GA hormones in the stem and leaf of transgenic plants.

In a separate experiment, similar measurements of GA hormones were taken from various plant tissues during vegetative stages of development. As shown in in Table 17 for an experiment using tissues taken from plants in the greenhouse and field, reduced levels of one or more active GAs (GA1, GA3, and GA4) were observed in the leaf and internode of transgenic plants at V3 and V8 stages. The leaf samples at V8 stage for this experiment were taken from plants in the field, unlike the other samples taken from plants in the greenhouse. The data in Table 17 is displayed in a similar manner as described for Table 16. Other inactive forms of GAs were altered in various tissues of transgenic plants as shown in Table 17. Similar to the observations above, GAs that are downstream of GA20 oxidase genes in the gibberellic acid pathway (e.g., GA9, GA20, and GA34) tended to be reduced, whereas GAs that are upstream of GA20 oxidase genes tended to be higher (e.g., GA12 and GA53). This data is again consistent with suppression of GA20 oxidase activity in these tissues and lower levels of active GA hormones in the stem and leaf of transgenic plants.

TABLE 16

Change in GA hormone levels in tissues of transgenic corn plants expressing a GA20 oxidase suppression construct in the greenhouse.

| | Stage: | | | | | | | |
|---|---|---|---|---|---|---|---|---|
| | V3 | | | V8 | | V14 | | |
| Tissue: | Leaf | Stem | Root | Leaf | Internode | Leaf | Internode | Tassel |
| GA1 | 2N/2T | 2N/2T | 2N/2T | 2D/2T | 1D/1N/2T | 2N/2T | 2D/2T | 2N/2T |
| GA3 | 2N/2T | 2N/2T | 2N/2T | 2N/2T | 2N/2T | 2N/2T | 2N/2T | 2N/2T |
| GA4 | 2N/2T | 2D/2T | 2N/2T | 2N/2T | 2D/2T | 2U/2T | 2D/2T | 2N/2T |
| GA8 | 1U/1N/2T | 2N/2T | 1U/1N/2T | 2N/2T | 2D/2T | 1D/1N/2T | 1D/1N/2T | 1U/1N/2T |
| GA9 | 2N/2T | 2D/2T | 2N/2T | 2N/2T | 2D/2T | 2U/2T | 2D/2T | 1D/1N/2T |
| GA12 | 1D/1N/2T | 2U/2T | 2N/2T | 2U/2T | 2N/2T | 1U/1N/2T | 2N/2T | 2N/2T |
| GA20 | 2D/2T | 2N/2T | 2N/2T | 2D/2T | 2D/2T | 2D/2T | 1D/1N/2T | 2N/2T |
| GA34 | 2N/2T | 2D/2T | 2N/2T | 2N/2T | 2D/2T | 2N/2T | 2D/2T | 2N/2T |
| GA53 | 2U/2T | 2U/2T | 2N/2T | 2U/2T | 2N/2T | 2U/2T | 1U/1N/2T | 1U/1N/2T |

TABLE 17

Change in GA hormone levels in tissues of transgenic corn plants expressing a GA20 oxidase suppression construct in the greenhouse (GH) or field.

| | Stage: | | | |
|---|---|---|---|---|
| | V3 | | V8 | |
| Tissue: | Leaf (GH) | Root (GH) | Internode (GH) | Leaf (Field) |
| GA1 | 3D/1N/4T | 2D/1U/1N/4T | 3D/1N/4T | 7D/1N/8T |
| GA3 | 3D/1N/4T | 4N/4T | 3D/1N/4T | 7D/1N/8T |
| GA4 | 4N/4T | 4N/4T | 4D/4T | 8D/8T |
| GA8 | 4N/4T | 4N/4T | 4N/4T | 4N/4T |
| GA9 | 4D/4T | 4N/4T | 4D/4T | 5U/3N/8T |
| GA12 | ND | ND | ND | 7U/1N/8T |
| GA20 | 4D/4T | 1D/3N/4T | 4D/4T | 8D/8T |
| GA34 | 1U/3N/4T | 4D/4T | 4D/4T | 4U/4N/8T |
| GA53 | 4U/4T | 2U/2N/4T | 1D/3N/4T | 8U/8T |

Suppression of the GA20 oxidase_3 and GA20 oxidase_5 genes in transgenic corn plants reduces the levels of targeted GA oxidase transcripts in various tissues including the stem, internode, vascular tissues and leaves, and suppression of these GA20 oxidase genes is further associated with reduced levels of active GAs in tissues of the transgenic plant including the stem and internode, which is the site of action for affecting plant growth during vegetative stages and ultimately plant height by later vegetative and reproductive stages. Similar to observations that GA20 oxidase transcript levels are mostly unchanged or mixed in reproductive stage tissues, the levels of GA hormones including active GAs are also mostly unchanged or mixed in reproductive stage tissues (data not shown).

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

The invention claimed is:

1. A recombinant DNA construct comprising a transcribable DNA sequence encoding a non-coding guide RNA molecule, wherein the non-coding guide RNA comprises a guide sequence that is at least 97%, at least 99%, or 100% identical or complementary to at least 18, at least 19, at least 20, at least 21, at least 22, at least 23, at least 24, or at least 25 consecutive nucleotides of a target DNA sequence within a genomic locus of an endogenous GA3 oxidase gene of a corn or cereal plant, wherein the GA3 oxidase gene encodes a protein that comprises an amino acid sequence that is at least 95% identical to the amino acid sequence of SEQ ID NO:173.

2. The recombinant DNA construct of claim 1, wherein the target DNA sequence comprises the nucleotide sequence of SEQ ID NO:170.

3. A composition comprising the recombinant DNA construct of claim 1, further comprising an RNA-guided endonuclease.

4. The composition of claim 3, wherein the RNA-guided endonuclease in the presence of the guide RNA molecule causes a double strand break or nick at the target DNA sequence in a genome of the corn or cereal plant.

5. A composition comprising the recombinant DNA construct of claim 1, further comprising a recombinant DNA donor template comprising at least one homology sequence or homology arm, wherein the at least one homology sequence or homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of the target DNA sequence.

6. The recombinant DNA construct of claim 1, wherein:

a) the transcribable DNA sequence is operably linked to a plant-expressible promoter;

b) the guide RNA molecule is a CRISPR RNA (crRNA) or a single-chain guide RNA (sgRNA);

c) the guide RNA comprises a sequence complementary to a protospacer adjacent motif (PAM) sequence present in the genome of the corn or cereal plant immediately adjacent to the target DNA sequence at the genomic locus of the endogenous GA3 oxidase gene; and/or d) the endogenous GA3 oxidase gene encodes a protein that comprises an amino acid sequence that is at least 96% identical to SEQ ID NO:173.

7. A DNA molecule or vector comprising the recombinant DNA construct of claim 1.

8. A bacterial or host cell comprising the recombinant DNA construct of claim 1.

9. A corn or cereal plant, plant part or plant cell comprising the recombinant DNA construct of claim 1.

10. A composition comprising a first DNA molecule or vector and a second DNA molecule or vector, wherein the first DNA molecule or vector comprises the recombinant DNA construct of claim 1, and the second DNA molecule or vector comprises:

a) a second recombinant DNA construct encoding an RNA-guided endonuclease; and/or b) a recombinant DNA donor template comprising at least one homology sequence or homology arm, wherein the at least one homology sequence or homology arm is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of the target DNA sequence.

11. The recombinant DNA construct of claim 1, wherein the target DNA sequence comprises a coding sequence comprising the nucleotide sequence of SEQ ID NO:172.

12. The recombinant DNA construct of claim 1, wherein the target DNA sequence comprises the exonic nucleotide sequences of SEQ ID NO:171.

13. The recombinant DNA construct of claim 1, wherein the GA3 oxidase gene encodes a protein that comprises the amino acid sequence of SEQ ID NO:173.

* * * * *

SEQUENCE LISTING

```
Sequence total quantity: 173
SEQ ID NO: 1            moltype = DNA  length = 1741
FEATURE                 Location/Qualifiers
source                  1..1741
                        mol_type = other DNA
                        organism = Zea mays
SEQUENCE: 1
gacggtagtt ttcatctaaa gtttattctt cgtcacatgg gatggccgtt tgcttgtttg  60
ttgcttccgg gaggcggtgg tgaattgaag cagatcgaca agcatggctg cccactggtc  120
tcgatcgatc ggcctgccat gccatgccat gccactagag tccgtcctga ctggccgccc  180
gttcccccgt ataaaaaggc aggcaggcag gcagagcggg gacgagcaag caagcagttg  240
cagttgcagc ggcctcctcc tctgcttcct ccctcctcct cctcaccatg gtgctggctg  300
cgcacgatcc ccctcccctt gtgttcgacg ctgcccgcct gagcggcctc tccgacatcc  360
cgcagcagtt catctggccg gcggacgaga gccccaccc ggactccgcc gaggagctgg  420
ccgtgccgct catcgacctc tccggggacg ccgccgaggt ggtccggcag gtccggcgcg  480
cctgcgacct gcacggcttc ttccaggtgg tggggcacgg catcgacgcg gcgctgacgg  540
cggaggccca ccgctgcatg gacgccttct tcacgctgcc gctcccggac aagcagcgcg  600
cgcagcgccg ccagggggac agctgcggct acgccagcag cttcacgggc cggttcgcgt  660
ccaagctgcc ctggaaggag acgctgtcgt tccgctacac cgacgacgac gacggcgaca  720
agtccaagga cgtcgtggcg tcctacttcg tggacaagct gggcgagggg taccggcacc  780
acggggaggt gtacgggcgc tactgctctg agatgagccg tctgtcgctg gagctcatgg  840
aggtgctagg cgagagcctg ggcgtgggcc ggcgccactt ccggcgcttc ttccagggga  900
acgactccat catgcgcctc aactactacc cgccgtgcca gcggccctac gacacgctgg  960
gcacggggcc gcattgcgac cccacgtcgc tcaccatcct gcaccaggac gacgtgggcg  1020
gactccaggt gttcgacgcc gccacgctcg cgtggcgctc catcaggccc cgcccgggcg  1080
ccttcgtcgt caacatcggc gacaccttca tggcgctctc caacgggcgc tacaggagct  1140
gcctccaccg cgccgtcgtc aacagccggg tggcacgccg ctcgctcgcc ttcttcctgt  1200
gcccggagat ggacaaggtg gtcaggccgc ccaaggagct ggtggacgac gccaacccga  1260
gggcgtaccc ggacttcacg tggaggacgc tgctggactt caccatgagg cactacaggt  1320
```

```
cggacatgag gacgctcgag gccttctcca actggctcag caccagtagc aatggcggac  1380
agcacctgct ggagaagaag taggcatgct atttgggtat ggaagatggt ggatgtaagc  1440
aaacaaagcc aaattaagca gagtaggtta attaaggttg gctgatgatc catttaggga  1500
aggagctgat ctccctgact ccctcctcca attttctcaa ccaaatttat atagtataat  1560
aataataata aaatagcaag taatagttgt atcgtattat tattaattaa tttattagct  1620
ggtaggcaag tagtattaaa taccatttgt agtacgatgg gcgtatttct attttggcgt  1680
tttgctctgt gttttttgac gtttcctttg gatttggggg gacctcagat cagctcggcc  1740
t                                                                  1741

SEQ ID NO: 2           moltype = DNA  length = 1116
FEATURE                Location/Qualifiers
source                 1..1116
                       mol_type = other DNA
                       organism = Zea mays
SEQUENCE: 2
atggtgctgg ctgcgcacga tccccctccc cttgtgttcg acgctgcccg cctgagcggc  60
ctctccgaca tcccgcagca gttcatctgg ccggcggacg agagccccac cccggactcc  120
gccgaggagc tggccgtgcc gctcatcgac ctctccgggg acgccgccga ggtggtccgg  180
caggtccggc gcgcctgcga cctgcacggc ttcttccagg tggtggggca cggcatcgac  240
gcggcgctga cggcggaggc ccaccgctgc atggacgcct tcttcacgct gccgctcccg  300
gacaagcagc gcgcgcagcg ccgccagggg gacagctgcg gctacgccag cagcttcacg  360
ggccggttcg cgtccaagct gccctggaag gagacgctgt cgttccgcta caccgacgac  420
gacgacggcg acaagtccaa ggacgtcgtg gcgtcctact tcgtggacaa gctgggcgag  480
gggtaccggc accacgggga ggtgtacggg cgctactgct ctgagatgag ccgtctgtcg  540
ctggagctca tggaggtgct aggcgagagc ctgggcgtgg gccggcgcca cttccggcgc  600
ttcttccagg ggaacgactc catcatgcgc ctcaactact acccgccgtg ccagcggccc  660
tacgacacgc tgggcacggg gccgcattgc gaccccacgt cgctcaccat cctgcaccag  720
gacgacgtgg gcggactcca ggtgttcgac gccgccacgc tcgcgtggcg ctccatcagg  780
ccccgcccgg gcgccttcgt cgtcaacatc ggcgacacct tcatggcgct ctccaacggg  840
cgctacagga gctgcctcca ccgcgccgtc gtcaacagcc gggtggcacg ccgctcgctc  900
gccttcttcc tgtgcccgga gatggacaag gtggtcaggc cgcccaagga gctggtggac  960
gacgccaacc cgagggcgta cccggacttc acgtggagga cgctgctgga cttcaccatg  1020
aggcactaca ggtcggacat gaggacgctc gaggccttct ccaactggct cagcaccagt  1080
agcaatggcg gacagcacct gctggagaag aagtag                            1116

SEQ ID NO: 3           moltype = AA  length = 371
FEATURE                Location/Qualifiers
source                 1..371
                       mol_type = protein
                       organism = Zea mays
SEQUENCE: 3
MVLAAHDPPP LVFDAARLSG LSDIPQQFIW PADESPTPDS AEELAVPLID LSGDAAEVVR  60
QVRRACDLHG FFQVVGHGID AALTAEAHRC MDAFFTLPLP DKQRAQRRQG DSCGYASSFT  120
GRFASKLPWK ETLSFRYTDD DDGDKSKDVV ASYFVDKLGE GYRHHGEVYG RYCSEMSRLS  180
LELMEVLGES LGVGRRHFRR FFQGNDSIMR LNYYPPCQRP YDTLGTGPHC DPTSLTILHQ  240
DDVGGLQVFD AATLAWRSIR PRPGAFVVNI GDTFMALSNG RYRSCLHRAV VNSRVARRSL  300
AFFLCPEMDK VVRPPKELVD DANPRAYPDF TWRTLLDFTM RHYRSDMRTL EAFSNWLSTS  360
SNGGQHLLEK K                                                       371

SEQ ID NO: 4           moltype = DNA  length = 1517
FEATURE                Location/Qualifiers
source                 1..1517
                       mol_type = other DNA
                       organism = Zea mays
SEQUENCE: 4
caggaataaa ataagcctcc gcccggcttc gttgcatcca cgcacgcagc aagcgatcgg  60
atttcgccag catggcggcg gcggccgtgg tgttcgacgc cgaggcgctg agccgggagg  120
agcacatccc ggcgcagttc gtgtggccca ccgaggagcg ggcgccggcg ggcggcgtgg  180
aggaggtcgc catccccgtg gtcgacctcg gcgagttcct ccgccgcggg gtgctcccgc  240
gcggcgtggc ggaggcgtgc gagcgccacg gcgtcttcca ggtggtgaac cacggcgtgg  300
gcgccgcgct gctcgccgag gcctaccgct gttgcgacgc cttttacgcg ctcccgctcg  360
cggacaagca gcgcgcgcag cgccggcacg gggagaacca cggctacgcc agcagcttca  420
cgggccgctt ccactgctgc ctgccgtgga aggagacgct gtccttcaac tgccccgccg  480
gtgccgggac tgcgcgcgcc gtcgtcggct acttcgtcga cgtcctcggc gaggactacc  540
gccacatggg ggaggtgtac caggagtact gcgacgcgat gacgcgtctg gcgctggacg  600
tgacggaggt gctggcggca gcgctggggc tggaccgcgg cgcactgcgc ggcttcttcg  660
agggcggcga ctccgtcatg cggctgaacc actacccggc gtgccggcag ccgcacctga  720
cgctggggac gggcccgcac cgggacccga cgtcgctgac gctgctgcac caggacgacg  780
tgggcgggct gcaggtgcgc gccggcggcg ggccgtggcg cgcggtgcgg ccccgcgcgg  840
acgcgttcgt ggtcaacatt ggcgacacct tcgccgcgct caccgacggg cgtcacacca  900
gctgcctgca ccgcgccgtg gtgaccggcg gcggctcccg ccggtcgctc gccttcttcc  960
tcaacccgcc gctggaccgc gtcgtccgcc cgccgggcgc gctcctccag gagaacaagc  1020
aggcgggccg cccgcgcgcg ttcccggact tcacgtggcg cgagttcctc gagttcacgc  1080
agaagcacta ccggtcggac gcgggcacca tggacgcctt cgtgtcgtgg atcgcgggag  1140
gccgccgcca ccatggcgga caggaggagg gcaactgaga tcgatgcatc tctagctgta  1200
ggcagcagcg cagcagctac caagaataat ggccggcgac ggagatgcag ctacgacgca  1260
caaataaatt gagtgtttgt ggtacaataa ggacgaggac gatcaatggc gacctgtaac  1320
cggtgcagtt ttagttaatc tttcatggcg atatggcatt aaccaatcgt tggtgtaaaa  1380
tgcgtgcatg ctttgcatgc caatgttggc catgtgatgg cacagcgtga gtgtagctca  1440
```

-continued

```
cccaccgtga caacgtgcta atttcgtgtg gtcctagata ccaaggtcgt ctaatgaact  1500
tgatggattg atgattt                                                 1517

SEQ ID NO: 5            moltype = DNA  length = 1107
FEATURE                 Location/Qualifiers
source                  1..1107
                        mol_type = other DNA
                        organism = Zea mays
SEQUENCE: 5
atggcggcgg cggccgtggt gttcgacgcc gaggcgctga gccgggagga gcacatcccg  60
gcgcagttcg tgtggcccac cgaggagcgg gcgccggcgg gcggcgtgga ggaggtcgcc  120
atccccgtgg tcgacctcgg cgagttcctc cgccgcgggg tgctcccgcg cggcgtggcg  180
gaggcgtgcg agcgccacgg cgtcttccag gtggtgaacc acggcgtggg cgccgcgctg  240
ctcgccgagg cctaccgctg ttgcgacgcc ttttacgcgc tcccgctcgc ggacaagcag  300
cgcgcgcagc gccggcacgg ggagaaccac ggctacgcca gcagcttcac gggccgcttc  360
cactgctgcc tgccgtggaa ggagacgctg tccttcaact gccccgccgg tgccgggact  420
gcgcgcgccg tcgtcggcta cttcgtcgac gtcctcggcg aggactaccg ccacatgggg  480
gaggtgtacc aggagtactg cgacgcgatg acgcgtctgg cgctggacgt gacggaggtg  540
ctggcggcag cgctggggct ggaccgcggc gcactgcgcg gcttcttcga gggcggcgac  600
tccgtcatgc ggctgaacca ctacccggcg tgccggcagc cgcacctgac gctggggacg  660
ggcccgcacc gggacccgac gtcgctgacg ctgctgcacc aggacgacgt gggcgggctg  720
caggtgcgcg ccggcggcgg gccgtggcgc gcggtgcggc cccgcgcgga cgcgttcgtg  780
gtcaacattg gcgacacctt cgccgcgctc accgacgggc gtcacaccag ctgcctgcac  840
cgcgccgtgg tgaccggcgg cggctcccgc cggtcgctcg ccttcttcct caacccgccg  900
ctggaccgcg tcgtccgccc gccgggcgcg ctcctccagg agaacaagca ggcgggccgc  960
ccgcgcgcgt tcccggactt cacgtggcgc gagttcctcg agttcacgca gaagcactac  1020
cggtcggacg cgggcaccat ggacgccttc gtgtcgtgga tcgcgggagg ccgccgccac  1080
catggcggac aggaggaggg caactga                                      1107

SEQ ID NO: 6            moltype = AA  length = 368
FEATURE                 Location/Qualifiers
source                  1..368
                        mol_type = protein
                        organism = Zea mays
SEQUENCE: 6
MAAAAVVFDA EALSREEHIP AQFVWPTEER APAGGVEEVA IPVVDLGEFL RRGVLPRGVA  60
EACERHGVFQ VVNHGVGAAL LAEAYRCCDA FYALPLADKQ RAQRRHGENH GYASSFTGRF  120
HCCLPWKETL SFNCPAGAGT ARAVVGYFVD VLGEDYRHMG EVYQEYCDAM TRLALDVTEV  180
LAAALGLDRG ALRGFFEGGD SVMRLNHYPA CRQPHLTLGT GPHRDPTSLT LLHQDDVGGL  240
QVRAGGGPWR AVRPRADAFV VNIGDTFAAL TDGRHTSCLH RAVVTGGGSR RSLAFFLNPP  300
LDRVVRPPGA LLQENKQAGR PRAFPDFTWR EFLEFTQKHY RSDAGTMDAF VSWIAGGRRH  360
HGGQEEGN                                                           368

SEQ ID NO: 7            moltype = DNA  length = 1522
FEATURE                 Location/Qualifiers
source                  1..1522
                        mol_type = other DNA
                        organism = Zea mays
SEQUENCE: 7
gcacactcgc agctcgcaca tctcatggtg tcctaagaac ggcaagagcc agctctgcct  60
agcagcagcg cacagccaca tccatggacg ccagcccgac cccaccgctc cccctccgcg  120
ccccaactcc cagcattgac ctccccgctg gcaaggacag ggccgacgcg gcggctaaca  180
aggccgcggc tgtgttcgac ctgcgccggg agcccaagat cccggagcca ttcctgtggc  240
cgcacgaaga ggcgcggccg acctcggccg cggagctgga ggtgccggtg gtggacgtgg  300
gcgtgctgcg caatggcgac ggcgcggggc tccgccgcgc cgcggcgcaa gtggcggcgg  360
cgtgcgcgac gcacgggttc ttccaggtgt gcgggcacgg cgtggacgcg gcgctggggc  420
gcgccgcgct ggacggcgcc agcgacttct tccggctgcc gctggctgag aagcagcggg  480
cccggcgcgt ccccggcacc gtgtccgggt acacgagcgc gcacgccgac cggttcgcgt  540
ccaagctccc ctggaaggag accctgtcct tcggcttcca cgacggcgcc gcggcgcccg  600
tcgtcgtgga ctacttcacc ggcaccctcg gccaagattt cgagccagtg gggcgggtgt  660
accagaggta ctgcgaggag atgaaggagc tgtcgctgac gatcatggag ctgctggagc  720
tgagcctggg cgtggagcgc ggctactacc gggagttctt cgaggacagc cgctccatca  780
tgcggtgcaa ctactacccg ccgtgcccgg tgccggagcg cacgctgggc acgggcccgc  840
actgcgaccc cacggcgctg accatcctcc tgcaggacga cgtcggcggg ctggaggtcc  900
tggtggacgg cgagtggcgc cccgtccggc ccgtcccagg cgccatggtc atcaacatcg  960
gcgacacctt catggcgctg tccaacgggc ggtacaagag ctgcctgcac cgcgcggtgg  1020
tgaaccggcg gcaggagcgg caatcgctgg ccttcttcct gtgcccgcgc gaggaccggg  1080
tggtgcgccc gccggccagc gccgcgccgc ggcagtaccc ggacttcacc tgggccgacc  1140
tcatgcgctt cacgcagcgc cactaccgcg ccgacacccg cacgctggac gccttcaccc  1200
gctggctctc ccacggcccg gcggcggcgg ctccctgcac ctaacgagcc ggccgtctct  1260
ttcgccgggg cccgcgcggg gttcgcccac gtggtgatca ggtggcagac atgtggccca  1320
cgggccccgc gccgccttcc ccatttttgg acgaccctac tgctactact actagtgtac  1380
atatgcaaaa aaatacatat atatataggt actttctcta atatttttat atataagcaa  1440
ggcggcctgg tgttcttttc tttgttttgt cgacaactgt ttgatcccat cctatggacg  1500
atggatagtt caatgtttgt ac                                           1522

SEQ ID NO: 8            moltype = DNA  length = 1161
FEATURE                 Location/Qualifiers
source                  1..1161
```

```
                        mol_type = other DNA
                        organism = Zea mays
SEQUENCE: 8
atggacgcca gcccgacccc accgctcccc ctccgcgccc caactcccag cattgacctc  60
cccgctggca aggacagggc cgacgcggcg gctaacaagg ccgcggctgt gttcgacctg  120
cgccgggagc ccaagatccc ggagccattc ctgtggccgc acgaagaggc gcggccgacc  180
tcggccgcgg agctggaggt gccggtggtg gacgtgggcg tgctgcgcaa tggcgacggc  240
gcggggctcc gccgcgccgc ggcgcaagtg gcggcggcgt gcgcgacgca cgggttcttc  300
caggtgtgcg ggcacggcgt ggacgcggcg ctggggcgcg ccgcgctgga cggcgccagc  360
gacttcttcc ggctgccgct ggctgagaag cagcgggccc ggcgcgtccc cggcaccgtg  420
tccgggtaca cgagcgcgca cgccgaccgg ttcgcgtcca agctcccctg gaaggagacc  480
ctgtccttcg gcttccacga cggcgccgcg gcgcccgtcg tcgtggacta cttcaccggc  540
accctcggcc aagatttcga gccagtgggg cgggtgtacc agaggtactg cgaggagatg  600
aaggagctgt cgctgacgat catggagctg ctggagctga gcctgggcgt ggagcgcggc  660
tactaccggg agttcttcga ggacagccgc tccatcatgc ggtgcaacta ctacccgccg  720
tgcccggtgc cggagcgcac gctgggcacg ggcccgcact gcgaccccac ggcgctgacc  780
atcctcctgc aggacgacgt cggcgggctg gaggtcctgg tggacggcga gtggcgcccc  840
gtccggcccg tcccaggcgc catggtcatc aacatcggcg acaccttcat ggcgctgtcc  900
aacgggcggt acaagagctg cctgcaccgc gcggtggtga accggcggca ggagcggcaa  960
tcgctggcct tcttcctgtg cccgcgcgag gaccgggtgg tgcgcccgcc ggccagcgcc  1020
gcgccgcggc agtacccgga cttcacctgg gccgacctca tgcgcttcac gcagcgccac  1080
taccgcgccg acacccgcac gctggacgcc ttcacccgct ggctctccca cggcccggcg  1140
gcggcggctc cctgcaccta a                                              1161

SEQ ID NO: 9            moltype = AA  length = 386
FEATURE                 Location/Qualifiers
source                  1..386
                        mol_type = protein
                        organism = Zea mays
SEQUENCE: 9
MDASPTPPLP LRAPTPSIDL PAGKDRADAA ANKAAAVFDL RREPKIPEPF LWPHEEARPT  60
SAAELEVPVV DVGVLRNGDG AGLRRAAAQV AAACATHGFF QVCGHGVDAA LGRAALDGAS  120
DFFRLPLAEK QRARRVPGTV SGYTSAHADR FASKLPWKET LSFGFHDGAA APVVVDYFTG  180
TLGQDFEPVG RVYQRYCEEM KELSLTIMEL LELSLGVERG YYREFFEDSR SIMRCNYYPP  240
CPVPERTLGT GPHCDPTALT ILLQDDVGGL EVLVDGEWRP VRPVPGAMVI NIGDTFMALS  300
NGRYKSCLHR AVVNRRQERQ SLAFFLCPRE DRVVRPPASA APRQYPDFTW ADLMRFTQRH  360
YRADTRTLDA FTRWLSHGPA AAAPCT                                         386

SEQ ID NO: 10           moltype = DNA  length = 1457
FEATURE                 Location/Qualifiers
source                  1..1457
                        mol_type = other DNA
                        organism = Zea mays
SEQUENCE: 10
taatcacctc atcacaggtc cccccagcct cactctcgcg ccggctcaag gtacattgcg  60
tgtcctagcc aagacacgca gctcatctca gcctcacacg cacagcaaga gcgaggcgtg  120
attcgccatg ggcggcctca ctatggacca ggccttcgtg caggcccccg agcaccgccc  180
caagcccatc gtcaccgagg ccaccggcat ccctctcatc gacctctcgc ctctggccgc  240
cagcggcggc gccgtggacg cgctggccgc cgaggtgggc gcggcgagcc gggactgggg  300
cttcttcgtg gtcgtgggcc acggcgtgcc cgcagagacc gtggcgcgcg cgacggaggc  360
gcagcgagcg ttcttcgcgc tgccggcaga gcggaaggcc gccgtgcgga ggaacgaggc  420
ggagccgctc gggtactacg agtcggagca caccaagaac gtgagggact ggaaggaggt  480
gtacgacctc gtgccgcgcg agccgccgcc gccggcagcc gtggccgacg gcgagcttgt  540
gttcgataac aagtggcccc aggatctacc gggcttcaga gaggcgctgg aggagtacgc  600
gaaagcgatg gaagagctgg cgttcaagct gctggagctg atcgcccgga gcctgaagct  660
gaggcccgac cggctgcacg gcttcttcaa ggaccagacg accttcatcc ggctgaacca  720
ctaccctcct tgcccgagcc ccgacctggc cctcggcgtg ggcggcaca aggacgccgg  780
cgccctgacc atcctgtacc aggacgacgt cggggggctc gacgtccggc ggcgctccga  840
cggcgagtgg gtccgcgtca ggcccgtgcc cgactcgttc atcatcaacg tcggcgacct  900
catccaggta cgagagcgcg gagcaccggg tgtcggtgaa ctcggcgagg gagaggttct  960
ccatgcccta cttcttcaac ccggcgacct acaccatggt ggagccggtg gaggagctgg  1020
tgagcaagga cgatccgccc aggtacgacg cctacaactg ggcgacttc ttcagcacca  1080
ggaagaacag caacttcaag aagctcaacg tggagaacat tcagatcgcg catttcaaga  1140
agagcctcgt cctcgcctaa ctactgctac tgctaggatc catgccattg ccatgtcgtc  1200
ttcagattca gagcacgcca tgtcgtcgct agcttcgtgg tagaacaaat aatgatgtgc  1260
gtgctgtgtg taagcatgga tatggatgtg aatatgtaat atgatgagca ctcctacttt  1320
ggtatgtttg ggaataacag acttgtgttg gtctggttca ttatttgtaa gaaaatcaaa  1380
aagagttagt agggcaggag gctaaccaca gtcatgctgc accacatccc tggtggaaag  1440
ctggccgggt tacgcta                                                   1457

SEQ ID NO: 11           moltype = DNA  length = 1116
FEATURE                 Location/Qualifiers
source                  1..1116
                        mol_type = other DNA
                        organism = Zea mays
SEQUENCE: 11
atgggcggcc tcactatgga ccaggccttc gtgcaggccc ccgagcaccg ccccaagccc  60
atcgtcaccg aggccaccgg catccctctc atcgacctct cgcctctggc cgccagcggc  120
ggcgccgtgg acgcgctggc cgccgaggtg ggcgcggcga gccgggactg ggcttcttc  180
```

```
gtggtcgtgg gccacggcgt gcccgcagag accgtggcgc gcgcgacgga ggcgcagcga  240
gcgttcttcg cgctgccggc agagcggaag gccgccgtgc ggaggaacga ggcggagccg  300
ctcgggtact acgagtcgga gcacaccaag aacgtgaggg actggaagga ggtgtacgac  360
ctcgtgccgc gcgagccgcc gccgccggca gccgtggccg acggcgagct tgtgttcgat  420
aacaagtggc cccaggatct accgggcttc agagaggcgc tggaggagta cgcgaaagcg  480
atggaagagc tggcgttcaa gctgctggag ctgatcgccc ggagcctgaa gctgaggccc  540
gaccggctgc acggcttctt caaggaccag acgaccttca tccggctgaa ccactaccct  600
ccttgcccga gccccgacct ggccctcggc gtggggcggc acaaggacgc cggcgccctg  660
accatcctgt accaggacga cgtcgggggg ctcgacgtcc ggcggcgctc cgacggcgag  720
tgggtccgcg tcaggcccgt gcccgactcg ttcatcatca acgtcggcga cctcatccag  780
gtacgagagc gcggagcacc gggtgtcggt gaactcggcg agggagaggt tctccatgcc  840
ctacttcttc aacccggcga cctacaccat ggtggagccg gtggaggagc tggtgagcaa  900
ggacgatccg cccaggtacg acgcctacaa ctggggcgac ttcttcagca ccaggaagaa  960
cagcaacttc aagaagctca acgtggagaa cattcagatc gcgcatttca agaagagcct  1020
cgtcctcgcc taactactgc tactgctagg atccatgcca ttgccatgtc gtcttcagat  1080
tcagagcacg ccatgtcgtc gctagcttcg tggtag                            1116

SEQ ID NO: 12           moltype = AA  length = 371
FEATURE                 Location/Qualifiers
source                  1..371
                        mol_type = protein
                        organism = Zea mays
SEQUENCE: 12
MGGLTMDQAF VQAPEHRPKP IVTEATGIPL IDLSPLAASG GAVDALAAEV GAASRDWGFF  60
VVVGHGVPAE TVARATEAQR AFFALPAERK AAVRRNEAEP LGYYESEHTK NVRDWKEVYD  120
LVPREPPPPA AVADGELVFD NKWPQDLPGF REALEEYAKA MEELAFKLLE LIARSLKLRP  180
DRLHGFFKDQ TTFIRLNHYP PCPSPDLALG VGRHKDAGAL TILYQDDVGG LDVRRRSDGE  240
WVRVRPVPDS FIINVGDLIQ VRERGAPGVG ELGEGEVLHA LLLQPGDLHH GGAGGGAGEQ  300
GRSAQVRRLQ LGRLLQHQEE QQLQEAQRGE HSDRAFQEEP RPRLTTATAR IHAIAMSSSD  360
SEHAMSSLAS W                                                       371

SEQ ID NO: 13           moltype = DNA  length = 1733
FEATURE                 Location/Qualifiers
source                  1..1733
                        mol_type = other DNA
                        organism = Zea mays
SEQUENCE: 13
atgaggccgc gcctccctcc aaatgttccc tccctgcctt cgtctttgtc gttgctcgca  60
aactccctgt cctcccctgt tacaaatacc cccacccgcc cggacagctt ccctgcatac  120
ttgcagctcg cacatctcat ggtgtcgcag gaacgacaag agccagctgt gcctagcagc  180
agcagcagca gcgccaagcg cgcagccacg tccatggacg ccagcccggc cccgccgctc  240
ctcctccgcg cccccactcc cagccccagc attgacctcc ccgctggcaa ggacaaggcc  300
gacgcggcgg ccagcaaggc cggcgcggcc gtgttcgacc tgcgccggga gcccaagatc  360
cccgcgccat tcctgtggcc gcaggaagag gcgcggccgt cctcggccgc ggagctggag  420
gtgccgatgg tggacgtggg cgtgctgcgc aatggcgacc gcgcggggct gcggcgcgcc  480
gcggcgcagg tggccgcggc gtgcgcgacg cacgggttct tccaggtgtg cgggcacggc  540
gtggacgcgg cgctggggcg cgccgcgctg gacggcgcca gcgacttctt ccggctgccg  600
ctcgccgaga agcagcgcgc ccggcgcgtc cccggcaccg tgtccgggta cacgagcgcg  660
cacgccgacc ggttcgcggc caagctcccc tggaaggaga ccctgtcgtt cggctaccac  720
gacggcgccg cgtcgcctgt cgtcgtggac tacttcgtcg gcaccctcgg ccaggatttc  780
gagccaatgg ggtgggtgta ccagaggtac tgcgaggaga tgaaggagct gtcgctgacg  840
atcatggagc tgctggagct gagcctgggc gtggagctgc gcggctacta ccgggagttc  900
ttcgaggaca gccggtccat catgcggtgc aactactacc cgccgtgccc ggagccggag  960
cgcacgctgg gcacgggccc gcactgcgac cccacggcgc tcaccatcct cctgcaggac  1020
gacgtgggcg ggctggaggt gctggtggac ggtgagtggc gccccgtccg gcccgtcccg  1080
ggcgccatgg tcatcaacat cggcgacacc ttcatggcgc tgtcgaacgg gaggtacaag  1140
agctgcctgc accgcgcggt ggtgaaccag cggcgggcgc ggcggtcgct ggccttcttc  1200
ctgtgcccgc gcgaggaccg ggtggtgcgc ccgccggcca gtgctgcgcc gcggcgctac  1260
ccggacttca cctgggccga cctcatgcgc ttcacgcagc gccactaccg cgccgacacc  1320
cgcacgctgg acgccttcac ccgctggctc tcccacggcc cggcccaggc ggcggcgcct  1380
ccctgcacct agcgagccgg gccaaggccg tctctttcgc cccacgtgcg cgcccagctg  1440
ggcaggtggc cagacacgcg gcccgcgggc cccgcgccgc cttgccattt tttgacgctg  1500
gccctactgc tgtgctacta gtgtacatat gcaagagtac atatatatat atatatatac  1560
gtattttcta tatattatat ataaaagcaa ggcggcccgg tgcccttctc ttgttttgtc  1620
cacaactgtt tgatcccatt attctatgga ccatggatac ttcaatgttt gtactaagac  1680
cgtgaacgtg ggattctttt ccttcctctg tgttttttct gagaaaaatt aaa         1733

SEQ ID NO: 14           moltype = DNA  length = 1392
FEATURE                 Location/Qualifiers
source                  1..1392
                        mol_type = other DNA
                        organism = Zea mays
SEQUENCE: 14
atgaggccgc gcctccctcc aaatgttccc tccctgcctt cgtctttgtc gttgctcgca  60
aactccctgt cctcccctgt tacaaatacc cccacccgcc cggacagctt ccctgcatac  120
ttgcagctcg cacatctcat ggtgtcgcag gaacgacaag agccagctgt gcctagcagc  180
agcagcagca gcgccaagcg cgcagccacg tccatggacg ccagcccggc cccgccgctc  240
ctcctccgcg cccccactcc cagccccagc attgacctcc ccgctggcaa ggacaaggcc  300
gacgcggcgg ccagcaaggc cggcgcggcc gtgttcgacc tgcgccggga gcccaagatc  360
```

cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtccgggta cacgagcgcg 660
cacgccgacc ggttcgcggc caagctcccc tggaaggaga ccctgtcgtt cggctaccac 720
gacggcgccg cgtcgcctgt cgtcgtggac tacttcgtcg gcaccctcgg ccaggatttc 780
gagccaatgg ggtgggtgta ccagaggtac tgcgaggaga tgaaggagct gtcgctgacg 840
atcatggagc tgctggagct gagcctgggc gtggagctgc gcggctacta ccgggagttc 900
ttcgaggaca gccggtccat catgcggtgc aactactacc cgccgtgccc ggagccggag 960
cgcacgctgg gcacgggccc gcactgcgac cccacggcgc tcaccatcct cctgcaggac 1020
gacgtgggcg ggctggaggt gctggtggac ggtgagtggc gccccgtccg gcccgtcccg 1080
ggcgccatgg tcatcaacat cggcgacacc ttcatggcgc tgtcgaacgg gaggtacaag 1140
agctgcctgc accgcgcggt ggtgaaccag cggcgggcgc ggcggtcgct ggccttcttc 1200
ctgtgcccgc gcgaggaccg ggtggtgcgc ccgccggcca gtgctgcgcc gcggcgctac 1260
ccggacttca cctgggccga cctcatgcgc ttcacgcagc gccactaccg cgccgacacc 1320
cgcacgctgg acgccttcac ccgctggctc tcccacggcc cggcccaggc ggcggcgcct 1380
ccctgcacct ag 1392

SEQ ID NO: 15 moltype = AA length = 463
FEATURE Location/Qualifiers
source 1..463
mol_type = protein
organism = Zea mays
SEQUENCE: 15
MRPRLPPNVP SLPSSLSLLA NSLSSPVTNT PTRPDSFPAY LQLAHLMVSQ ERQEPAVPSS 60
SSSSAKRAAT SMDASPAPPL LLRAPTPSPS IDLPAGKDKA DAAASKAGAA VFDLRREPKI 120
PAPFLWPQEE ARPSSAAELE VPMVDVGVLR NGDRAGLRRA AAQVAAACAT HGFFQVCGHG 180
VDAALGRAAL DGASDFFRLP LAEKQRARRV PGTVSGYTSA HADRFAAKLP WKETLSFGYH 240
DGAASPVVVD YFVGTLGQDF EPMGWVYQRY CEEMKELSLT IMELLELSLG VELRGYYREF 300
FEDSRSIMRC NYYPPCPEPE RTLGTGPHCD PTALTILLQD DVGGLEVLVD GEWRPVRPVP 360
GAMVINIGDT FMALSNGRYK SCLHRAVVNQ RRARRSLAFF LCPREDRVVR PPASAAPRRY 420
PDFTWADLMR FTQRHYRADT RTLDAFTRWL SHGPAQAAAP PCT 463

SEQ ID NO: 16 moltype = DNA length = 1510
FEATURE Location/Qualifiers
source 1..1510
mol_type = other DNA
organism = Zea mays
SEQUENCE: 16
aaagagcgcg cgacggcggc ccctgggaga gccatgcgag actggaggcg gaaccgcgca 60
cgacaccaag ctgccgcgcc ggactgctgc acgcaagcgc agcgcaggac cgaccgacct 120
ccgtaggcac gcacggcgcc ggcggcatgg cggagcacct cctgtcgacg gccgtgcacg 180
acacgctgcc ggggagctac gtgcggccgg agccggagcg cccgcgcctc gcggaggtcg 240
tgaccggcgc gcgcatcccc gtcgtggacc tgggcagccc cgaccgcggc gcggtcgtgg 300
ccgccgtcgg cgacgcctgc cgctcgcacg gcttcttcca ggtcgtcaac cacgggatac 360
acgccgccct ggtcgcggcg gtgatggccg cggggcgcgg cttcttccgg ctgccccccg 420
aggagaaggc caagctctac tccgacgacc ccgccaggaa gatccggctg tccaccagct 480
tcaacgtgcg caaggagacg gtgcacaact ggcgcgacta cctccgcctg cactgccatc 540
ccctcgacga gttcctgccc gattggccgt ccaacccgcc cgatttcaag gagaccatgg 600
gcacctactg caaggaggtc cgggagctcg ggttcaggct gtacgccgcg atctcggaga 660
gcctgggcct agaggcgagc tacatgaagg aagcgctggg ggagcaggag cagcacatgg 720
cggtcaactt ctacccgccg tgcccggagc cggagctcac ctacggcctc ccggcgcaca 780
ccgaccccaa cgcgctcacc atcctgctca tggacccgga cgtcgccggc ctgcaggtgc 840
tccacgccgg ccagtgggtc gccgtcaacc cgcagcccgg cgcgctcatc atcaacatcg 900
gcgaccagct gcaggcgctg agcaacgggc agtaccggag cgtgtggcac cgcgcggtgg 960
tgaactcgga ccgggagcgc atgtccgtgg cgtcgttcct gtgcccgtgc aaccacgtcg 1020
tgctcggccc cgcgcggaag ctcgtcaccg aggacacccc ggccgtgtac aggaactaca 1080
cgtacgacaa gtactacgcc aagttctgga gcaggaacct ggaccaggag cactgcctcg 1140
agctcttcag aacctagcga atcggatacg gatggatgga tacattacat acgcgccctc 1200
tgtttttctc catgacgtta gaagaacacg ttctgcaatg tttgtccatt caaggtggta 1260
tcaatcaagg ctgtggtcgt tgcaattctt ccgctccata tacatgatta aatgctttga 1320
aagaaaaaga aaaaaaagaa acacaagtat tatggcacta ctagtgtttt taggaacaag 1380
gaaagagggg ttgcccctgc tggctatata tattaaatat aaataaaggt aaggctgtag 1440
acattggtga ataagagaaa gtatttgagt ttctctattg tcactccaga acagactcct 1500
ttgcctcgat 1510

SEQ ID NO: 17 moltype = DNA length = 1011
FEATURE Location/Qualifiers
source 1..1011
mol_type = other DNA
organism = Zea mays
SEQUENCE: 17
atggcggagc acctcctgtc gacggccgtg cacgacacgc tgccggggag ctacgtgcgg 60
ccggagccgg agcgcccgcg cctcgcggag gtcgtgaccg gcgcgcgcat ccccgtcgtg 120
gacctgggca gccccgaccg cggcgcggtc gtggccgccg tcggcgacgc ctgccgctcg 180
cacggcttct tccaggtcgt caaccacggg atacacgccg ccctggtcgc ggcggtgatg 240
gccgcggggc gcggcttctt ccggctgccc cccgaggaga aggccaagct ctactccgac 300
gaccccgcca ggaagatccg gctgtccacc agcttcaacg tgcgcaagga gacggtgcac 360

```
aactggcgcg actacctccg cctgcactgc catcccctcg acgagttcct gcccgattgg  420
ccgtccaacc cgcccgattt caaggagacc atgggcacct actgcaagga ggtccgggag  480
ctcgggttca ggctgtacgc cgcgatctcg gagagcctgg gcctagaggc gagctacatg  540
aaggaagcgc tgggggagca ggagcagcac atggcggtca acttctaccc gccgtgcccg  600
gagccggagc tcacctacgg cctcccggcg cacaccgacc ccaacgcgct caccatcctg  660
ctcatggacc cggacgtcgc cggcctgcag gtgctccacg ccggccagtg ggtcgccgtc  720
aacccgcagc ccggcgcgct catcatcaac atcggcgacc agctgcaggc gctgagcaac  780
gggcagtacc ggagcgtgtg gcaccgcgcg gtggtgaact cggaccggga gcgcatgtcc  840
gtggcgtcgt tcctgtgccc gtgcaaccac gtcgtgctcg gccccgcgcg gaagctcgtc  900
accgaggaca ccccggccgt gtacaggaac tacacgtacg acaagtacta cgccaagttc  960
tggagcagga acctggacca ggagcactgc ctcgagctct tcagaaccta g           1011

SEQ ID NO: 18          moltype = AA  length = 336
FEATURE                Location/Qualifiers
source                 1..336
                       mol_type = protein
                       organism = Zea mays
SEQUENCE: 18
MAEHLLSTAV HDTLPGSYVR PEPERPRLAE VVTGARIPVV DLGSPDRGAV VAAVGDACRS  60
HGFFQVVNHG IHAALVAAVM AAGRGFFRLP PEEKAKLYSD DPARKIRLST SFNVRKETVH  120
NWRDYLRLHC HPLDEFLPDW PSNPPDFKET MGTYCKEVRE LGFRLYAAIS ESLGLEASYM  180
KEALGEQEQH MAVNFYPPCP EPELTYGLPA HTDPNALTIL LMDPDVAGLQ VLHAGQWVAV  240
NPQPGALIIN IGDQLQALSN GQYRSVWHRA VVNSDRERMS VASFLCPCNH VVLGPARKLV  300
TEDTPAVYRN YTYDKYYAKF WSRNLDQEHC LELFRT                            336

SEQ ID NO: 19          moltype = DNA  length = 1387
FEATURE                Location/Qualifiers
source                 1..1387
                       mol_type = other DNA
                       organism = Zea mays
SEQUENCE: 19
gttttctttt tgaacgtaac tgacagaagc tatctgccta gctacggcgt gtcggttgct  60
tgtctcacca aagcagcgac atggaagcct gacagctcgt cgcgtcgcgc catttccacc  120
caacaaagcg gcggcgccag cacgcactgc ttctgcttgt gcgtgctcct ccgttccggg  180
cacgcctcta aagtctatac agcctcgaat ccatcccggc cgccgctcct gggggatact  240
acagcgagcc gaagcgggga tggcggagat ccctgtgatc gacctgcgcg tcgccggctc  300
ggcggccgag gagtccgcgc ggctgcgggc cgcgtgcgag cgcctgggct gcttccgggt  360
gaccggccac ggcgtgccct cggtgctcct ggcagagatg aaggccgccg tgcgcgcgct  420
cttcgacctc cccgacgacg ccaagcgccg caacgccgac gtcatcaccg gcagcggcta  480
cgtcgccccc agcccgacca acccgctcta cgaggccttc gggctcctcg acgccgccgt  540
gcccaccgac gtcgacgcct tttgcgcgct cctcgacgcg ccgcccaaca tcagggagac  600
cgtcaaggcc tacgcggaga agatgcacga tgtgatcgtt ggcgtcgccc gcgagctggc  660
gtctagcctg gggctagtcg aggagcactc gttccaggac tggccgtgcc agttccgcat  720
caacaggtac aactacacgc gggagacggt gggctcctcc ggcgtgcaga cccacacgga  780
ctcgggcttc ctcaccgtgc tccatgagga cgagtgtgtc ggcggcctcg aggtcctgga  840
cccgggcacc ggcgagttcg tgcccgtgga ccccgtcgcg ggctcctttc tcgtaaacat  900
cggcgacgtc ggcacggcgt ggagcaacgg gaggctgcac aacgtgaagc accgggtgcg  960
gtgcgtcgca cccgtgccgc gcatctccat cgccatgttc ctgctcgcac ccaaggacga  1020
cagcgtgagc gcaccggcgg cgttcgtgga cgcggaccac ccgcgcaggt acaaggtgtt  1080
caactacaac gactatcgga ggctcagact gtccaccggc gagcacgcag gcgaggcgct  1140
cgcacggatg gcggcgtgac gtggctggag ctgcaaattg gattggaagc cgagacaagc  1200
cgttagttat ttaccatgcc cgtgcgttca ccgcacacaa tcatattcaa aagccataaa  1260
ataaaaaata attttaatat cagtcaacat atggtttaaa tatcatatgg agtacaaatat 1320
tccgaatttt tttttgtaat ttagtctgtc ttttgaaaaa aatgcacatc tagacctccg  1380
gatgact                                                            1387

SEQ ID NO: 20          moltype = DNA  length = 900
FEATURE                Location/Qualifiers
source                 1..900
                       mol_type = other DNA
                       organism = Zea mays
SEQUENCE: 20
atggcggaga tccctgtgat cgacctgcgc gtcgccggct cggcggccga ggagtccgcg  60
cggctgcggg ccgcgtgcga gcgcctgggc tgcttccggg tgaccggcca cggcgtgccc  120
tcggtgctcc tggcagagat gaaggccgcc gtgcgcgcgc tcttcgacct ccccgacgac  180
gccaagcgcc gcaacgccga cgtcatcacc ggcagcggct acgtcgcccc cagcccgacc  240
aacccgctct acgaggcctt cgggctcctc gacgccgccg tgcccaccga cgtcgacgcc  300
ttttgcgcgc tcctcgacgc gccgcccaac atcagggaga ccgtcaaggc ctacgcggag  360
aagatgcacg atgtgatcgt tggcgtcgcc cgcgagctgg cgtctagcct ggggctagtc  420
gaggagcact cgttccagga ctggccgtgc cagttccgca tcaacaggta caactacacg  480
cgggagacgg tgggctcctc cggcgtgcag acccacacgg actcgggctt cctcaccgtg  540
ctccatgagg acgagtgtgt cggcggcctc gaggtcctgg acccgggcac cggcgagttc  600
gtgcccgtgg accccgtcgc gggctccttt ctcgtaaaca tcggcgacgt cggcacggcg  660
tggagcaacg ggaggctgca caacgtgaag caccgggtgc ggtgcgtcgc acccgtgccg  720
cgcatctcca tcgccatgtt cctgctcgca cccaaggacg acagcgtgag cgcaccggcg  780
gcgttcgtgg acgcggacca cccgcgcagg tacaaggtgt tcaactacaa cgactatcgg  840
aggctcagac tgtccaccgg cgagcacgca ggcgaggcgc tcgcacggat ggcggcgtga  900

SEQ ID NO: 21          moltype = AA  length = 299
```

```
FEATURE                Location/Qualifiers
source                 1..299
                       mol_type = protein
                       organism = Zea mays
SEQUENCE: 21
MAEIPVIDLR VAGSAAEESA RLRAACERLG CFRVTGHGVP SVLLAEMKAA VRALFDLPDD  60
AKRRNADVIT GSGYVAPSPT NPLYEAFGLL DAAVPTDVDA FCALLDAPPN IRETVKAYAE  120
KMHDVIVGVA RELASSLGLV EEHSFQDWPC QFRINRYNYT RETVGSSGVQ THTDSGFLTV  180
LHEDECVGGL EVLDPGTGEF VPVDPVAGSF LVNIGDVGTA WSNGRLHNVK HRVRCVAPVP  240
RISIAMFLLA PKDDSVSAPA AFVDADHPRR YKVFNYNDYR RLRLSTGEHA GEALARMAA   299

SEQ ID NO: 22          moltype = DNA  length = 1496
FEATURE                Location/Qualifiers
source                 1..1496
                       mol_type = other DNA
                       organism = Zea mays
SEQUENCE: 22
gtcggtctct tgtctcacca aaccggcgac atggtacatg gaggccagcc cgtcgcttgg  60
cgccacaagt ctcggtgccg tccgtccgac aagcggcgcc agcgcacgct ggctgctcgt  120
gcacgcctct aaatacggcc ccggacccgc caccaagcga aggccaatcc cgtccgccgc  180
cccccaccaa ccacgaacca cgcaagcgaa cccggccggc gcggggcagc ggcgatggcg  240
gagatcccgg tgatcgacct gcgcctcgcc ggctcgtcgc ccgacgagtc ggcgcggctg  300
cgcgacgcgt gcgagcgcct gggctgcttt cgggtgaccg gccacggcgc gcccgcgggg  360
ctcctggccg acatgaaggc cgccgtgcgc gcgctcttcg acctccccga cgacgccaag  420
cgccgcaacg ccgacgtcat ccccggcagc ggctacgtcg cgccctgccc cgccaacccg  480
ctctacgagg ccttcgggct cctcgacgcc gccgcgcccg ccgacgtcga cgccttctgc  540
gcgcgcctcg acgcgccgcc caaagtcagg gagaccgtca agacctacgc ggagaagatg  600
cacgacgtga tcgtcggcgt cgccggcgag ctggccacca gcctggggct gggcctggag  660
gagcactcgt tccaggactg gccgtgccag ttccgcatca acaggtacaa ctacacgcag  720
gagacggtgg gctcctccgg cgtgcagacc cacacggact cgggcttcct caccgtgctc  780
caggaggacg agtgcgtcgg cggcctcgag gtgctggacc ccgccgcggg tgagttcgtg  840
cccgtggacc ccgtcgccgg ctccttcctc gtcaacatcg gcgacgtcgg cacggcgtgg  900
agcaacggga ggctccacaa cgtgaagcac cgggtgcggt gcgtcgcgcc cgtgccgcgc  960
atctccatcg ccatgttcct gctggcgccc aaggacgacc gcgtgagcgc cccggaggcg  1020
ttggtcgacg cgggccaccc gcgtcggtac aagccgttca actacgacga ctaccggagg  1080
ctccggctgt ccaccggcga gcgcgcaggc gaggcgctcg cgcggatggc ggcgtgatgt  1140
cgtcacgcac gtgcaagccg ttaattatag gctcgcgcat gcatacgcct acacgagagg  1200
ttgtctcgtt aagccgttct attaaaatgt gtgggggaga aagatgacta ccgtggtgcc  1260
atgtggattg ctatcgggtc tgatcaataa aatcttgcaa cacttgcacg tgcgattcca  1320
tatcctagca cgggtgggcg ccacgctagt aggtagagac cggagcggcc aaaaaatggc  1380
tacagcacca gtaggtgaac tctcaagcaa cactggctat cccacttctg acgttgtctc  1440
tctcatcact atgtatgacc agcgaatgaa gtgtttaaaa atctgacgcc gtgaaa      1496

SEQ ID NO: 23          moltype = DNA  length = 903
FEATURE                Location/Qualifiers
source                 1..903
                       mol_type = other DNA
                       organism = Zea mays
SEQUENCE: 23
atggcggaga tcccggtgat cgacctgcgc ctcgccggct cgtcgcccga cgagtcggcg  60
cggctgcgcg acgcgtgcga gcgcctgggc tgctttcggg tgaccggcca cggcgcgccc  120
gcggggctcc tggccgacat gaaggccgcc gtgcgcgcgc tcttcgacct ccccgacgac  180
gccaagcgcc gcaacgccga cgtcatcccc ggcagcggct acgtcgcgcc ctgccccgcc  240
aacccgctct acgaggcctt cgggctcctc gacgccgccg cgcccgccga cgtcgacgcc  300
ttctgcgcgc gcctcgacgc gccgcccaaa gtcagggaga ccgtcaagac ctacgcggag  360
aagatgcacg acgtgatcgt cggcgtcgcc ggcgagctgg ccaccagcct ggggctgggc  420
ctggaggagc actcgttcca ggactggccg tgccagttcc gcatcaacag gtacaactac  480
acgcaggaga cggtgggctc ctccggcgtg cagacccaca cggactcggg cttcctcacc  540
gtgctccagg aggacgagtg cgtcggcggc ctcgaggtgc tggacccgc cgccggtgag  600
ttcgtgcccg tggaccccgt cgccggctcc ttcctcgtca acatcggcga cgtcggcacg  660
gcgtggagca acgggaggct ccacaacgtg aagcaccggg tgcggtgcgt cgcgcccgtg  720
ccgcgcatct ccatcgccat gttcctgctg gcgcccaagg acgaccgcgt gagcgccccg  780
gaggcgttgg tcgacgcggg ccacccgcgt cggtacaagc cgttcaacta cgacgactac  840
cggaggctcc ggctgtccac cggcgagcgc gcaggcgagg cgctcgcgcg gatggcggcg  900
tga                                                                903

SEQ ID NO: 24          moltype = AA  length = 300
FEATURE                Location/Qualifiers
source                 1..300
                       mol_type = protein
                       organism = Zea mays
SEQUENCE: 24
MAEIPVIDLR LAGSSPDESA RLRDACERLG CFRVTGHGAP AGLLADMKAA VRALFDLPDD  60
AKRRNADVIP GSGYVAPCPA NPLYEAFGLL DAAAPADVDA FCARLDAPPK VRETVKTYAE  120
KMHDVIVGVA GELATSLGLG LEEHSFQDWP CQFRINRYNY TQETVGSSGV QTHTDSGFLT  180
VLQEDECVGG LEVLDPAAGE FVPVDPVAGS FLVNIGDVGT AWSNGRLHNV KHRVRCVAPV  240
PRISIAMFLL APKDDRVSAP EALVDAGHPR RYKPFNYDDY RRLRLSTGER AGEALARMAA  300

SEQ ID NO: 25          moltype = DNA  length = 1614
```

```
FEATURE                Location/Qualifiers
source                 1..1614
                       mol_type = other DNA
                       organism = Zea mays
SEQUENCE: 25
accacacgaa ttgcacatct ccacagctca cgattccaac actagctaca tatatatgta  60
gctttctagg ctactatata cactcaccac caagtgtgaa gtgtgtatat atagtgacag  120
ctactgcaat atatacatac gcgtcaccta tatattagcc aagctagcta tatgagcttg  180
gttgcggcgc caatggcgat cgtcgacgtg gccaacgccc agctgcagca agcagcagca  240
gcagctgcca agaaagacga ggacggccat gagcagcagg agtcgtccta cgactacggc  300
gcgctgatga aaggcgtgag gcacctgtcg gacagcggca ttaccaggct gcccgacagg  360
tacgtcctgc ccgcgtccga ccgccccggc gtccttgccg tctcgtcgtc cgtggcgggc  420
agcggcaggg tcaagctccc tgtcgtcaac ctcgccggcc tccgcgaccc ctgccagcgc  480
gccgccgtgc tggccacgct cgacgccgcg tgccgggagt acggcttctt tcaggtggta  540
aaccacgggt tcgggagcga cgtgagcggc gggatgctgg acgtggcgca gcgcttcttc  600
gagctgccgc tggccgagcg agcgcggcac atgtcggcgg acgtgcgggc gccggtgcgc  660
tacggcacca gcttcaacca ggccaaggac gacgtgctct gctggcgcga cttcctcaag  720
ctcgtctgcc agccgctgca ggcggtgctc ccgtactggc cccagcagcc ggcggacctc  780
agggacgtgg ccaccaggta cgccacggcg agccaccggc tgttcatgga ggtcatggag  840
gcggcgctgg aggccctggg catccccacg gccggcggcg tgctcgggga gctggcagcg  900
tcgtcgtcgc acatgatgac ggtgaactgc tacccggcgt gcccgcagcc tgagctcacg  960
ctggggatgc cctcgcactc ggactacggc ctcttcacgt tcgtcctgca ggaccacgtc  1020
gagggcctcc aggtcatgca cgacggccgc tggctcacca tcgaccccat cccgggatcg  1080
ttcgtcgtca acgtcggcga ccacctagag atctacagca acgggcggta caagagcgcg  1140
ctgcaccggg tgcacgtgaa ctccacgcgg ccgcgcatct cggtggcgtc gttccacagc  1200
ctgccggcgg agcgagtgat cgggccggcg ccggagctgg tggacgacga ggccggcaac  1260
ccgcggcggt acatggacac cgacttcgct accttcctcg cctacctcgc atccgcggac  1320
ggcaagaaca agaccttcct ccagtcaagg aagctgcctg ctgctgctcc tccatgcctc  1380
tagctaacta gatagctgct tattaatctg acagaataaa attaatcagt tcagcgcaca  1440
attccacaag cgaaaacaaa cctggatttg ttttaattag ctctgccctt cattattaca  1500
ttcaagctag ctcttggtca acgcatgcac acaagcttga gcattgactg gtccctttc  1560
aatcggttgc attgtactcc ctccgtacca aaattggttg tcgctatagt attt        1614

SEQ ID NO: 26          moltype = DNA  length = 1212
FEATURE                Location/Qualifiers
source                 1..1212
                       mol_type = other DNA
                       organism = Zea mays
SEQUENCE: 26
atgagcttgg ttgcggcgcc aatggcgatc gtcgacgtgg ccaacgccca gctgcagcaa  60
gcagcagcag cagctgccaa gaaagacgag gacggccatg agcagcagga gtcgtcctac  120
gactacggcg cgctgatgaa aggcgtgagg cacctgtcgg acagcggcat taccaggctg  180
cccgacaggt acgtcctgcc cgcgtccgac cgccccggcg tccttgccgt ctcgtcgtcc  240
gtggcgggca gcggcagggt caagctccct gtcgtcaacc tcgccggcct ccgcgacccc  300
tgccagcgcg ccgccgtgct ggccacgctc gacgccgcgt gccgggagta cggcttcttt  360
caggtggtaa accacgggtt cgggagcgac gtgagcggcg ggatgctgga cgtggcgcag  420
cgcttcttcg agctgccgct ggccgagcga gcgcggcaca tgtcggcgga cgtgcgggcg  480
ccggtgcgct acggcaccag cttcaaccag gccaaggacg acgtgctctg ctggcgcgac  540
ttcctcaagc tcgtctgcca gccgctgcag gcggtgctcc cgtactggcc ccagcagccg  600
gcggacctca gggacgtggc caccaggtac gccacggcga gccaccggct gttcatggag  660
gtcatggagg cggcgctgga ggccctgggc atccccacgg ccggcggcgt gctcggggag  720
ctggcagcgt cgtcgtcgca catgatgacg gtgaactgct acccggcgtg cccgcagcct  780
gagctcacgc tggggatgcc ctcgcactcg gactacggcc tcttcacgtt cgtcctgcag  840
gaccacgtcg agggcctcca ggtcatgcac gacggccgct ggctcaccat cgaccccatc  900
ccgggatcgt tcgtcgtcaa cgtcggcgac cacctagaga tctacagcaa cgggcggtac  960
aagagcgcgc tgcaccgggt gcacgtgaac tccacgcggc cgcgcatctc ggtggcgtcg  1020
ttccacagcc tgccggcgga gcgagtgatc gggccggcgc cggagctggt ggacgacgag  1080
gccggcaacc cgcggcggta catggacacc gacttcgcta ccttcctcgc ctacctcgca  1140
tccgcggacg gcaagaacaa gaccttcctc cagtcaagga agctgcctgc tgctgctcct  1200
ccatgcctct ag                                                      1212

SEQ ID NO: 27          moltype = AA  length = 403
FEATURE                Location/Qualifiers
source                 1..403
                       mol_type = protein
                       organism = Zea mays
SEQUENCE: 27
MSLVAAPMAI VDVANAQLQQ AAAAAAKKDE DGHEQQESSY DYGALMKGVR HLSDSGITRL  60
PDRYVLPASD RPGVLAVSSS VAGSGRVKLP VVNLAGLRDP CQRAAVLATL DAACREYGFF  120
QVVNHGFGSD VSGGMLDVAQ RFFELPLAER ARHMSADVRA PVRYGTSFNQ AKDDVLCWRD  180
FLKLVCQPLQ AVLPYWPQQP ADLRDVATRY ATASHRLFME VMEAALEALG IPTAGGVLGE  240
LAASSSHMMT VNCYPACPQP ELTLGMPSHS DYGLFTFVLQ DHVEGLQVMH DGRWLTIDPI  300
PGSFVVNVGD HLEIYSNGRY KSALHRVHVN STRPRISVAS FHSLPAERVI GPAPELVDDE  360
AGNPRRYMDT DFATFLAYLA SADGKNKTFL QSRKLPAAAP PCL                    403

SEQ ID NO: 28          moltype = DNA  length = 1863
FEATURE                Location/Qualifiers
source                 1..1863
                       mol_type = other DNA
```

```
                         organism = Zea mays
SEQUENCE: 28
tgccaccata ccactagtgc aaggtcctag atttacactt ggtgctacac cttgcttcgc  60
ccccttcctt ccttccttcc ttccttccct ccttccttgg tctctaggca gctagcagtg  120
tggtgctgct gccggccgcc tattggccgc ctgggactgg gatccattaa ttactgcgcg  180
cgcgcggcta accaaccaat cccagcgtgc gtaatctatt gcccacatgc cgacgccgtc  240
gcacctcaac aagaacccgc gctacctgga cttccgggcg gcgcggcggg tgccggagtc  300
gcacgcctgg ccgggcctgc acgaccaccc cgtcgtggac ggcggcgcgc cgggccccga  360
cgccgtgccg gtggtggacc tgggcgccgc ggacccggcg ccggcgccgg cggcggcggt  420
ggcccgcgcc gccgagcaat ggggcgcgtt cctgctcacg ggccacggcg tccccgcgga  480
cctgctggcg cgcgtggagg accggatcgc caccatgttc gcgctgccgg ccgacgacaa  540
gatgcgcgcc gtgcgcgggc ccggcgacgc ctgcggctac ggctccccgc ccatctcctc  600
cttcttctcc aagtgcatgt ggtccgaggg ctacaccttc tcgccggcct ccctccgcgc  660
cgacctccgc aagctctggc ccaaggccgg cgacgactac accagcttct gtgatgtgat  720
ggaggagttc cacaagcaca tgcgcgccct cgcggacaag ctgctggagc tgttcctcat  780
ggcgctgggg ctcaccgacg agcaggccag cgccgtcgag gccgagcgga ggatcgccga  840
gacgatgacc gccaccatgc atctcaactg gtacccgagg tgcccggacc cgcggcgcgc  900
gctggggctg atcgcgcaca ccgactcggg cttcttcacc ttcgtgatgc agagcctcgt  960
gcccgggctg cagctcttcc gccacgcccc ggaccggtgg gtggcggtgc cggccgtgcc  1020
gggcgccttc gtcgtcaacg tgggcgacct cttccacatc ctcaccaacg gccggttcca  1080
cagcgtgtac caccgcgccg tcgtgaaccg ggacctcgac aggatctcgc tcggctactt  1140
cctcggcccg ccgccgcacg ccaaggtggc gccgctgcgc gaggccgtgc cgcccggccg  1200
ggcccccgcg taccgcgccg tcacgtggcc cgagtacatg ggcgtccgca agaaggcctt  1260
caccaccggc gcctccgcgc tcaagatggt cgccctcgcc gccgccgccg acctcgacga  1320
cgacggcgac gccgccgtcg tccatcagca gcagcagcta gtcgtctcgt cgtagccgag  1380
accgatcgcc ggagactgat gctgatgatg atgcatatat acatgagaga aatcgtcgag  1440
tagactagcc gattgcaaaa gcaaccccag ctgccgaaac ctggcatatc gatcccattc  1500
tctgctgcgc acatgtatgc atgcatgcgc ttcgtccgtt cgactcgtgt gtgcttgctt  1560
gcttgcgcgt gcagcagaac taattccgtt ccgcagctag ctgctctgct ctgctctgct  1620
ggaatgtaat taagtagtag tatatggtag tagagaaaag attagctagg cgatcgatat  1680
agatgacggg ccggggaaga agacgaatta attaagatcg atcgacgacg acgagctgtg  1740
cgtggctggc tgtgttcttc tctagcctag ttacagaggc cggctgctgc tgcttccaat  1800
cgggctgctt gtcgctactg acgatcgtta gtggatccat taactaatct ggaattctgg  1860
att                                                               1863

SEQ ID NO: 29            moltype = DNA  length = 1149
FEATURE                  Location/Qualifiers
source                   1..1149
                         mol_type = other DNA
                         organism = Zea mays
SEQUENCE: 29
atgccgacgc cgtcgcacct caacaagaac ccgcgctacc tggacttccg ggcggcgcgg  60
cgggtgccgg agtcgcacgc ctggccgggc ctgcacgacc accccgtcgt ggacggcggc  120
gcgccgggcc ccgacgccgt gccggtggtg gacctgggcg ccgcggaccc ggcgccggcg  180
ccggcggcgg cggtggcccg cgccgccgag caatggggcg cgttcctgct cacgggccac  240
ggcgtccccg cggacctgct ggcgcgcgtg gaggaccgga tcgccaccat gttcgcgctg  300
ccggccgacg acaagatgcg cgccgtgcgc gggcccggcg acgcctgcgg ctacggctcc  360
ccgcccatct cctccttctt ctccaagtgc atgtggtccg agggctacac cttctcgccg  420
gcctccctcc gcgccgacct ccgcaagctc tggcccaagg ccggcgacga ctacaccagc  480
ttctgtgatg tgatggagga gttccacaag cacatgcgcg ccctcgcgga caagctgctg  540
gagctgttcc tcatggcgct ggggctcacc gacgagcagg ccagcgccgt cgaggccgag  600
cggaggatcg ccgagacgat gaccgccacc atgcatctca actggtaccc gaggtgcccg  660
gacccgcggc gcgcgctggg gctgatcgcg cacaccgact cgggcttctt caccttcgtg  720
atgcagagcc tcgtgcccgg gctgcagctc ttccgccacg ccccggaccg gtgggtggcg  780
gtgccggccg tgccgggcgc cttcgtcgtc aacgtgggcg acctcttcca catcctcacc  840
aacggccggt tccacagcgt gtaccaccgc gccgtcgtga accgggacct cgacaggatc  900
tcgctcggct acttcctcgg cccgccgccg cacgccaagg tggcgccgct gcgcgaggcc  960
gtgccgcccg gccgggcccc cgcgtaccgc gccgtcacgt ggcccgagta catgggcgtc  1020
cgcaagaagg ccttcaccac cggcgcctcc gcgctcaaga tggtcgccct cgccgccgcc  1080
gccgacctcg acgacgacgg cgacgccgcc gtcgtccatc agcagcagca gctagtcgtc  1140
tcgtcgtag                                                         1149

SEQ ID NO: 30            moltype = AA  length = 382
FEATURE                  Location/Qualifiers
source                   1..382
                         mol_type = protein
                         organism = Zea mays
SEQUENCE: 30
MPTPSHLNKN PRYLDFRAAR RVPESHAWPG LHDHPVVDGG APGPDAVPVV DLGAADPAPA  60
PAAAVARAAE QWGAFLLTGH GVPADLLARV EDRIATMFAL PADDKMRAVR GPGDACGYGS  120
PPISSFFSKC MWSEGYTFSP ASLRADLRKL WPKAGDDYTS FCDVMEEFHK HMRALADKLL  180
ELFLMALGLT DEQASAVEAE RRIAETMTAT MHLNWYPRCP DPRRALGLIA HTDSGFFTFV  240
MQSLVPGLQL FRHAPDRWVA VPAVPGAFVV NVGDLFHILT NGRFHSVYHR AVVNRDLDRI  300
SLGYFLGPPP HAKVAPLREA VPPGRAPAYR AVTWPEYMGV RKKAFTTGAS ALKMVALAAA  360
ADLDDDGDAA VVHQQQQLVV SS                                          382

SEQ ID NO: 31            moltype = DNA  length = 1439
FEATURE                  Location/Qualifiers
source                   1..1439
```

```
                         mol_type = other DNA
                         organism = Zea mays
SEQUENCE: 31
gacctccatt ttgattatct ctatcctgta cgtgccgaga gtccttcaaa gccgacgacg  60
agacgacgat gcagtcgtcg tcgtcatcag cctcgacgcc ggctgccgct tccggcctcg  120
tcttcgatct cgggtctgcg gcgggcgtgc cggagacaca cgcgtggccg ggggtgaacg  180
agtacccgtc ggtggagtcc gctggccgcg acgtggtccc ggtggtggac atgggggtgg  240
cctgcccgga cgcgacgcgg gcgttggcgc gcgccgcaga cgagtggggc gtgtttctgc  300
tcgtcggcca cggcgtgccc cgggaagtgg cggcgcgtgc cgaggagcag gtcgcgcgcc  360
tgttcgtgct cccggctcct gacaaggccc gcgcggggcg ccgcccccggg gagcccacgg  420
ccaccggcta cggcaggccg cccctggcac tccgcttctc caagctcatg tggtccgagg  480
ggtacacgtt ccgcgccgcc accgtccgcg aagagttccg ccgcgtctgg cccgacggcg  540
gcgacgacta cctccgcttc tgcgacgtga tggaggagta cgacagagag atgagggctc  600
tcggtggcag gctgctcgac ctcttcttca tggcgctcgg cctcaccgac gtccagttcg  660
ccaccggcga gacggagcgg aggatccgcg agacctggac ggcgacgatg cacccaatcc  720
tgtgtccgga accggagcgc gccatcgggc tgacggcgca cacggactcg ggcttcatca  780
cgctcatcat gcagagcccc gtgcccgggc tgcagctgct ccgccgcggg ccggaccggt  840
gggtgacggt gccggcgccg ccgggcgcgc tcatcgtcat gctcggcgac ctgttccagg  900
tgctcacgaa cggccgcttc cggagcccta tccaccgcgc cgtcgtaagc cgagagcgcg  960
agcggatctc cgtgccctac ttcctctgcc cgccggagga catgacggtg gcgccgctcg  1020
cgtccgctct gctgccgggg aggaaggccg tgttccgggc cgtgacgtgg ccagagtaca  1080
tggaggtcaa gcacaaggtg ttcggcacgg atgcgccggc cctggagatg ctgcagctgc  1140
aggtggatga ggaagaacaa ggtgaaaggg ccgccaccac ctaagcccta aggaactact  1200
agctgaatcc ataaactaat aaagaattcg tgaataaggg cgttggaaga ctggacacaa  1260
cacaagagag ttgctatata tcgtatttct gaaatttaag gcaaatatct tagttaaaaa  1320
actggtatat ttaaatagac aatatatatc taaaataaag atagttcacc atttttacgg  1380
tcgaacaatg ataaagttat atattgtctg aatagtaaca aattaaagat ttccaggag   1439

SEQ ID NO: 32            moltype = DNA  length = 1116
FEATURE                  Location/Qualifiers
source                   1..1116
                         mol_type = other DNA
                         organism = Zea mays
SEQUENCE: 32
atgcagtcgt cgtcgtcatc agcctcgacg ccggctgccg cttccggcct cgtcttcgat  60
ctcgggtctg cggcgggcgt gccggagaca cacgcgtggc cgggggtgaa cgagtacccg  120
tcggtggagt ccgctggccg cgacgtggtc ccggtggtgg acatgggggt ggcctgcccg  180
gacgcgacgc gggcgttggc gcgcgccgca gacgagtggg gcgtgtttct gctcgtcggc  240
cacggcgtgc cccgggaagt ggcggcgcgt gccgaggagc aggtcgcgcg cctgttcgtg  300
ctcccggctc ctgacaaggc ccgcgcgggg cgccgccccg gggagcccac ggccaccggc  360
tacggcaggc cgcccctggc actccgcttc tccaagctca tgtggtccga ggggtacacg  420
ttccgcgccg ccaccgtccg cgaagagttc cgccgcgtct ggcccgacgg cggcgacgac  480
tacctccgct tctgcgacgt gatggaggag tacgacagag agatgagggc tctcggtggc  540
aggctgctcg acctcttctt catggcgctc ggcctcaccg acgtccagtt cgccaccggc  600
gagacggagc ggaggatccg cgagacctgg acggcgacga tgcacccaat cctgtgtccg  660
gaaccggagc gcgccatcgg gctgacggcg cacacggact cgggcttcat cacgctcatc  720
atgcagagcc ccgtgcccgg gctgcagctg ctccgccgcg ggccggaccg gtgggtgacg  780
gtgccggcgc cgccgggcgc gctcatcgtc atgctcggcg acctgttcca ggtgctcacg  840
aacggccgct tccggagccc tatccaccgc gccgtcgtaa gccgagagcg cgagcggatc  900
tccgtgccct acttcctctg cccgccggag gacatgacgg tggcgccgct cgcgtccgct  960
ctgctgccgg ggaggaaggc cgtgttccgg gccgtgacgt ggccagagta catggaggtc  1020
aagcacaagg tgttcggcac ggatgcgccg gccctggaga tgctgcagct gcaggtggat  1080
gaggaagaac aaggtgaaag ggccgccacc acctaa                            1116

SEQ ID NO: 33            moltype = AA  length = 371
FEATURE                  Location/Qualifiers
source                   1..371
                         mol_type = protein
                         organism = Zea mays
SEQUENCE: 33
MQSSSSSAST PAAASGLVFD LGSAAGVPET HAWPGVNEYP SVESAGRDVV PVVDMGVACP  60
DATRALARAA DEWGVFLLVG HGVPREVAAR AEEQVARLFV LPAPDKARAG RRPGEPTATG  120
YGRPPLALRF SKLMWSEGYT FRAATVREEF RRVWPDGGDD YLRFCDVMEE YDREMRALGG  180
RLLDLFFMAL GLTDVQFATG ETERRIRETW TATMHPILCP EPERAIGLTA HTDSGFITLI  240
MQSPVPGLQL LRRGPDRWVT VPAPPGALIV MLGDLFQVLT NGRFRSPIHR AVVSRERERI  300
SVPYFLCPPE DMTVAPLASA LLPGRKAVFR AVTWPEYMEV KHKVFGTDAP ALEMLQLQVD  360
EEEQGERAAT T                                                       371

SEQ ID NO: 34            moltype = DNA  length = 4095
FEATURE                  Location/Qualifiers
source                   1..4095
                         mol_type = genomic DNA
                         organism = Zea mays
SEQUENCE: 34
taaatttgtg atccttgtga agttgttata tcatgaattg tgaacttgtt gcatttgtga  60
tcttttgtca actttgttgt attgtgaagt ttgatatgtt taccgatcgt attttagatt  120
tcgatcgtta ccggtgtatt ttccgcacca aacttttgtt tccgatgttt tcgaaatacc  180
gatatcgttt ccgtttctat agttaccctt ttcaatttta tttccgatta aaaatatgaa  240
aacggtaatg gttttagtgt ttatcgaccg ttttcatctc taatcatccc tgccggtgaa  300
```

-continued

```
gtttaatttt tcccttggct aaagagatgc aagctgctgt aaaatacgtt aaaacaggca  360
aggcagcccc agcagccagc atcgcgtgcc cgtctatgta catcagtgga tacgtagcat  420
ctctagtgag taatataacg attgcatttg gctggaggac gtatgttata taagtatgtc  480
atttaccagt tgcattagta tcttccctaa ctcctataat aactctcttc gtggaatgga  540
cgtagacgta tgctatataa gtattaaaaa atagtttttt aagctggtgt cctcaatttt  600
gctattgttc tcgtttttat ctttagttgt gtcacaaatt taatccgtac aacaaatcaa  660
aaataccata cccttcttat attaattttc taacataaca tttgtttaga tattttcagt  720
cgtgaaaata caattctaat tctaacgtcg tagtatcaaa tcaaaccatc cagaatttga  780
ccaagcttaa ttataaaaaa tataaaattt atgatactga atagatagca ttagatttgt  840
tatataatat atttttataa aataccattt ttatggtata aatattggta ctcctttact  900
ttaaactata gatagttttg actaaggatg caactagaat tgcatcctct tttcactgca  960
ccttcattag ttttaatatt tatttagatg ggcccttgca aactgtagat atcatctctt  1020
gcaacattct ttctatagca ccacgaaaat gtattgcggc tttgaaatta taattgaatt  1080
agttgtatca tttctttcac cgatgcgtta aattcaaaat taagtgttat atttcttcat  1140
aatttgttaa atatatagac cctataatcc accattattt actataatag catacattaa  1200
cattggtttt agcctacact acgacactcg aggcattgaa ttttcctcta tcaaagaatt  1260
atatgtgtag tagtattgtt cttgacaaaa agggggatta aaattaaact accaatattg  1320
atacttatct tatcacatcc atgaatacaa tcaacactct tacaaaagat aagatacaag  1380
attaaaaagt accatgataa tacattaaga ttattagcaa tgcattaaat taaataaatg  1440
tgcaagtgaa tcatgatttt agttttatct attttacttt taaaatatga tattctctga  1500
ctacttctaa gcataaatgt gattctaagt catgaccgat cgtgcttatt cagaaaaatg  1560
aaggagacac agatttctat aaaaaaaggt tgtcatggga ctattgggtc aaccatctta  1620
ttcatttggg aaaataagtt tagaacacat caacccattt tagatgttga gtttggccct  1680
aatggtccat tgaccttact tttgtgggtt gacatagacc atctatccca agttattgtt  1740
gtgtcacatt ccctgatatc atgaatctat attttagctt tccgttttca tatttttagt  1800
cgttacatat tttttatccg cgtactagat taaaactcta gttgttgcaa tacattttgt  1860
tcattttttt ctatttcttc tttactaaca acatattcta gttcctagct acattcttaa  1920
gtaccatagt gctataaaca ttttttatcc tacattattc cacttaagaa attgaatttt  1980
ctgcataaaa aaattatatg tccagtagtg ttgtcttata aaagcataaa gtgattaaaa  2040
ttaaaaccat tattgatatc ttatttttca aaaaaaaata taagcttata gaaagtgaat  2100
taatttcatg gtaaattaat atagtttaaa ttgaattatt agtgttatta ctatgtttat  2160
tatcaatgaa acatttttca tggttgatat aacttagtgt tacttatttt agtatttttt  2220
atataattct agttaacttt tagtttttga tttaaaaaaa cgagaattgt gtccttttgt  2280
ggagtgagta taaagaaagt aatatctgtt catcataatt tggtttttta aggtacgtga  2340
aacttgcttt atatttggac tcaagctatg tctaaataca tagtaaaaaa gcaatatttc  2400
tagaaaagac aaaacatctt ataatttaga atcaaggaaa tatatagatt ttatgtgcag  2460
tgagaagcca tttacaatgg aacgttcaac gttgggccaa tagatatttt gcgatatgat  2520
gatgggcata tttttgcatg gttgtccctc cactagctat agtttgatga tacgatacgc  2580
tgcacacacc attgggttgt accatgttag tgtagcaaca gtagaaaccc aattgtggcc  2640
gtgaaccatg ataatactag gtagagtgct agctagaggt ttcaggctat tgatgcgtga  2700
attaaacttt ctgttgtgtt gcgaggaaac gagtattgtg aaatatttga aacggttttt  2760
tttgtgaaag atttgaaacg gtatttttgt tgtgaaataa agatcaaggc taaataaatt  2820
caaactaata aaacatatta attgacggcc tgaagccccc gcccccatgg ccccatgcca  2880
tagcatcagg tcccacatga catgaggccg cgcctccctc tatgttggct ccctgccttc  2940
gccgttgtcg tcgctcccga actccctctc ctcccctgtt acaaataccc ccacccgccc  3000
ggacagcttc cctgcacact cgcagctcgc acatctcatg gtgtcctaag aacggcaaga  3060
gccagctctg cctagcagca gcgcacagcc acatccatgg acgccagccc gaccccaccg  3120
ctccccctcc gcgccccaac tcccagcatt gacctccccg ctggcaagga cagggccgac  3180
gcggcggcta acaaggccgc ggctgtgttc gacctgcgcc gggagcccaa gatcccggag  3240
ccattcctgt ggccgcacga agaggcgcgg ccgacctcgg ccgcggagct ggaggtgccg  3300
gtggtggacg tgggcgtgct gcgcaatggc gacggcgcgg ggctccgccg cgccgcggcg  3360
caagtggcgg cggcgtgcgc gacgcacggg ttcttccagg tgtgcgggca cggcgtggac  3420
gcggcgctgg ggcgcgccgc gctggacggc gccagcgact tcttccggct gccgctggct  3480
gagaagcagc gggcccggcg cgtccccggc accgtgtccg ggtacacgag cgcgcacgcc  3540
gaccggttcg cgtccaagct cccctggaag gagaccctgt ccttcggctt ccacgacggc  3600
gccgcggcgc ccgtcgtcgt ggactacttc accggcaccc tcggccaaga tttcgagcca  3660
gtggggtgag taaagaagaa gatggcgccg aatttacatt tataagtagg accagcagaa  3720
gcccctgccc ctgggggcct tagcattgca ttcgactgat gaatacgcat ggcaggcggg  3780
tgtaccagag gtactgcgag gagatgaagg agctgtcgct gacgatcatg gagctgctgg  3840
agctgagcct gggcgtggag cgcggctact accgggagtt cttcgaggac agccgctcca  3900
tcatgcggtg caactactac ccgccgtgcc cggtgccgga gcgcacgctg ggcacgggcc  3960
cgcactgcga ccccacggcg ctgaccatcc tcctgcagga cgacgtcggc gggctggagg  4020
tcctggtgga cggcgagtgg cgccccgtcc ggcccgtccc aggcgccatg gtcatcaaca  4080
tcggcgacac cttca                                                  4095
```

```
SEQ ID NO: 35          moltype = DNA  length = 7404
FEATURE                Location/Qualifiers
source                 1..7404
                       mol_type = genomic DNA
                       organism = Zea mays
SEQUENCE: 35
cctattttgt gtctaatact cttcttatat taattgtttg gtcaaacttt agataaattt  60
gactaatgat gcaattaaaa ctgcatcacc tttactaagg tactgcttta tatgtttcga  120
caaaattttc aattattctc tatgtgtttt aatctttgcg ctacacctcc attgatttaa  180
atactcattt attttaaacc ataacttaaa ttatatcgga tctttgcatc ctttctatgg  240
caccatacat gaatcgatat tttggctgca aatttttaat catgttagtt ttagcatttt  300
ttcatatcca tgtgttaagt ttgaatcatg tgttgttttt atataattta ttgaaaatat  360
agatcctaaa cttcactaat acttacaaca atagcatcat catgtgtttt aatccacgcc  420
acaacactca aggcattgaa ttttcttcta ccaaagagtt gtatgtgtgt attgttcttt  480
```

```
aaaaaataga gtgattataa ttaaactacc agtattcata tgtaaaatgt atagacatct  540
aaaataaaat ttgcaaaaaa cattgttgca gactttcaat ataattaaga atgggtttta  600
gggtcatgat atatggtttg ttaaagaaac ttgttttttt ttgcaattga taaactataa  660
aatacatttt cactattgtg tgcatatgta cttggtatac atagtggcat atatcatttt  720
tgtttacttt gaggtttgaa ttatctatgt taaaattgga taacatagat acattggtgt  780
gcgtcctttg gcccatttac ttgactgagg agcaatacta taaagtaaaa catatttgga  840
tattttatct taaactccta gcataatatt gatttaatta tgaacaaata tatgtttagg  900
tgatagtttc atgggtggta aactatataa gaaggcttac catgatcttt gcaaactcta  960
ggctatgaaa gagttccatg atttgtctta gaagcataga caaaacagtg ataatgatct  1020
aaatcacact tatggcactg atgaccatat atgcaaagct aaatgcatgt taagttgtat  1080
tatatcatat gtttacaatg actatcgcat ataacgagga atacattgtc tatatagata  1140
gctattactg tagtagtgcc aaatgttgga caacatgaat cataatcttc aaacctagag  1200
aaattgtagt cagtcgtaca catatcgtct agtaagttgt ctatactttt tatttattgt  1260
atcaaatttt attgttatct tgcttgcttg tttgtttgta ccatagacac aatatggtca  1320
aaaagtggtc aatcgattcg aagaagattg caattgacga gtgctaacag ttgatccttt  1380
tgttgtgcac gctagcggag tagcatgaaa agagtaaaat atgaaattag cgttctaaac  1440
tgtttgtgct ataggtactt cgtatttaat ggagtgacta actataggaa ggtgagagct  1500
cagaagtcag caccctcaca cagagttcta gagttagtgg tcatcgaacc acgacaaact  1560
acatgatgag cagaagaggc aacatcaaga ctatgatcaa tagtttcggg tcaatgaatg  1620
acatcgtgat gagtatttat ctaactatat agaacaacaa cacatgatgt tttaagtaag  1680
ttcaactgat cttctattgc tatctttaag tatttaacgt agcgaataat gtttatcta   1740
tttcattcat aaataatgtt gtgacaaaag gggataacca tcacttttac catgttctag  1800
ataccacaac catctccacc atcataatgg gttcttcatt ggtgcttgga cctcaaataa  1860
tcatatctat agccaactta gctcaattct aataaaatta ggcaacttgg cttcattgta  1920
gcaaaaatag ccaacttagc tcaattttat ctaaacttag ctaatctagc acaacttaga  1980
tcaatattag gaaaaactaa tcaatctaat ctagctcaac tatagcgaaa gatagatatt  2040
gtagcataac ttagtagatc tatctcaaat tttagcaaaa actaatcaat ttagataaac  2100
tctataaaat tttaatcatt atgacttatt tccaactaat tgtaacttgc atgattttta  2160
tgttccttct ttataattag caacacctaa agacacgaat gatgaggggt ctaacgcatt  2220
cattaaccag ttgttaaata atactctagg tagatgataa gaactctaat tattctatga  2280
atctaagcta aaagatgttt aatatttaag tattggtgtt tattatgtta tttagaacga  2340
ttcatgttac ttaaagattt gttatgattt ttaaatatga ttatgataat ttatgtggtg  2400
tggattaact tgtgaacata tgtgatgtag atgaatatgt atgttgtgga tggaaccata  2460
tgaatatata tacacactca tatactattc gttggtgtag gtaaagcttc atccatcggt  2520
aattactaaa tggtcttcag tcattaccac taggtgaagc ttcacacgac cgataattat  2580
tgaagaacgc tcattaattt ccggtaatgg cttattggcc ttcactagtc ggtgaaaatt  2640
agctattttt ataccaataa aaattagcta atatatgtaa accaggtcta atttttatgg  2700
gcctcttacc gaccaaaatt gattagatta ttgttacaat agttttagtc aaaagctagc  2760
tatgctataa aaattttgaa ttaaagtgag tttcgtaata aaaattgcat acttttaaaa  2820
taaaataatt aaaaaacagt ttttagaaat acaatcaaac accttatgct ataaaaaaat  2880
tgtaatgtac ctacaaatat ataatacttt actttaaaat aggcctgtgc cttctcggct  2940
ctatatgggc tgcctccaac gaagcgccat ggccatgggc tccactgtgt cgggtcccac  3000
atgaggccgc gcctccctcc aaatgttccc tccctgcctt cgtctttgtc gttgctcgca  3060
aactccctgt cctcccctgt tacaaatacc cccacccgcc cggacagctt ccctgcatac  3120
ttgcagctcg cacatctcat ggtgtcgcag gaacgacaag agccagctgt gcctagcagc  3180
agcagcagca gcgccaagcg cgcagccacg tccatggacg ccagcccggc cccgccgctc  3240
ctcctccgcg cccccactcc cagccccagc attgacctcc ccgctggcaa ggacaaggcc  3300
gacgcggcgg ccagcaaggc cggcgcggcc gtgttcgacc tgcgccggga gcccaagatc  3360
cccgcgccat tcctgtggcc gcaggaagag gcgcggccgt cctcggccgc ggagctggag  3420
gtgccgatgg tggacgtggg cgtgctgcgc aatggcgacc gcgcggggct gcggcgcgcc  3480
gcggcgcagg tggccgcggc gtgcgcgacg cacgggttct tccaggtgtg cgggcacggc  3540
gtggacgcgg cgctggggcg cgccgcgctg gacggcgcca gcgacttctt ccggctgccg  3600
ctcgccgaga agcagcgcgc ccggcgcgtc cccggcaccg tgtccgggta cacgagcgcg  3660
cacgccgacc ggttcgcggc caagctcccc tggaaggaga ccctgtcgtt cggctaccac  3720
gacggcgccg cgtcgcctgt cgtcgtggac tacttcgtcg gcaccctcgg ccaggatttc  3780
gagccaatgg ggtaagtaag gtagtaagaa ggagcgccgg tttacattta ccgcacgtcg  3840
gcgtgcggtc gagtcgggac tcgggagacg tatgaacccc cgtcccgtcc catgcatgtg  3900
tggcaggtgg gtgtaccaga ggtactgcga ggagatgaag gagctgtcgc tgacgatcat  3960
ggagctgctg gagctgagcc tgggcgtgga gctgcgcggc tactaccggg agttcttcga  4020
ggacagccgg tccatcatgc ggtgcaacta ctacccgccg tgcccggagc cggagcgcac  4080
gctgggcacg ggcccgcact gcgaccccac ggcgctcacc atcctcctgc aggacgacgt  4140
gggcgggctg gaggtgctgg tggacggtga gtggcgcccc gtccggcccg tcccgggcgc  4200
catggtcatc aacatcggcg acaccttcat ggtaacgaaa cgaaagcgct cgctcctctg  4260
ttttccttgg ccgctcttgt cctgtgtgta tattcagttg agctctctct gtgctgttat  4320
ttcccgaatc ctagtggacc taaacgggca ggttattaca gcacgcacac gtaggcatgt  4380
catgtagcta gtacatacat agcgatgccg atgcaaatgc aatagagaca tgcgttcgag  4440
ttggttccta tctcggcggg ctacggcagg tacacgcggc cgcggcgcgc tctctctagt  4500
ctatccgcgg ccgcgcccag gccgatcgag gcttccgggg gagagttgcg acaagagaac  4560
ggaccgaggg ggtcggctag cggtagcaag ttccctgttg gtttgtggcg ttggagcgtt  4620
gcggagaggc ttgcgcggcg gcggggacgt cgacggggac gtggcgggga gacgatacga  4680
tgggtgccgg gcaggtttcc gaattccaaa cgtttttgtg gcgtgcgtcc atggggcgcc  4740
cccaaacttc ggacgtttcc ggcgctccaa caaatcttct cgcttcacac gtcaccgtcg  4800
tcccggattc atttgcctcg tcgctccacc attcgctgct ctcctctcca cgtactctta  4860
ccctgacctt tgggaaagaa ctgaacattc gagatgcaca acagttcaaa tataacatat  4920
gcagcacaag atcgttcgac tgctatccga caagccaaca acgtgcccag tagaactgaa  4980
tgtacctgtg atttccagca ctaacttaca gcaacgttgt gaaaaaacaa aaacgaaaac  5040
aaacggcaga aaaaacagat gtattgttct acagttacac caaatatttt ctggtccttt  5100
cagcaccaac aagagccata cgcatatcta gaagacaaaa ttcctctaat ttcacccta   5160
cgtggtagca gttcctcctc aacacagttc acgtgctagc gtcgagttct ttggccgcc   5220
```

```
acatcgactt ctcgacgcag agcaggccct cgctgccctt ggtgtaggtc atccgcacct  5280
cccactgcac ggacttggcc atgctctcca gctcatttat cgtgtccgcg gtgtccctca  5340
cgatcagctt gccctgtggc ctcagtacac ggtcgacctc ggcgaaaact gcagccagtt  5400
tgcatctgta aacaggcaac acagattttt agtatctaaa acactgcagg caaacgccac  5460
aggttttagt cgcaagaagc aataaaagca tgcaaacaat gctacgtgta cgtatcaaag  5520
gaacatgtca aaactcgttg catgaacgat cattgatgtt tccttgctga actagtcaca  5580
tcagtctgct tcaacttctg ggtttcacta gtagatatac cagaagggta gaataatgtg  5640
aagagcaaga aatacagacc tctttctgag ctttgagaac agatggtccg cgtgcagaag  5700
gtcatacgtt cttgggtaag tgctgaaaga ctcgcaccag tcatggtaca tgccaaacaa  5760
accgcgctcg tagatgatgg gcagcgtgtc tggtgaatcg atcggcacga tattcatgac  5820
ccagaccttt tggtccctca gagctgcagc aaaactgcca tgcaacaatg taaagcatta  5880
gtcaagaaga aggtgtacag tgcatttctc cttgtcaaca gtcttcagta acaaaaaaaa  5940
agtgttatgc ttgactgaat ctttcaaaga aatatgcttg atgacttatg gtggacaagt  6000
tgcctgttat agtgttatgt tttaattaac tatgtgccag cttgggtaac tagtagttat  6060
gtagtgtgat ctgaattacc aaaatataaa taaataaata aacatgccca agaaactacg  6120
aaaaccattt acttaccctc catagacagc tctcatgtcc atgacatttc tcactttgga  6180
ccagtcaatt cccatgccat tcacatacga tttacttaca acccgtttcc agtgggcatt  6240
atctgcctca aaatcttcat ttgcaggctt tccatagaca ccaaccttgg aaccatcaat  6300
ccagaaaggg gtcttctcaa gcctttgcgg ccataactct ggccattttg atcctcggac  6360
ttttgagcca ccaggcagtt tgtgcatgca tgcttccaac ggtacattcc tgcaaatcaa  6420
aaggctgtgt aagcaaagca gagaagcact tttctccatt gaaaatatac tcttctcaaa  6480
gaaccgaaac cataccaagc agcatctgca tcatcagatt ccttgcacaa tggcgggctg  6540
ttttcagatc ttttctcata gcaaatattg tccattggtt tctgatatat gaccatacca  6600
acttggttta acttatcctt agtcttgttg accatcttcc agcacatgga ctttgtcaaa  6660
gtagacatgg ctgaaaaggg tatgtggcca catgttatgt tagaaataaa attcaatttt  6720
gaacagttgg tccatagcat gtattttgaa caaatgcaat ccttctccat ccatgaaaga  6780
agttgaccct tcatacttag gattattcag tactttcact catgtctgct gaatttgttc  6840
tcttggtagt tgctatacaa gaaaggggga agtacagagt agctaaactt atacaagcta  6900
tagtctgata tttgtatgaa acataaattt tggtatggat gtcttattaa aatgggaggt  6960
tgtataatat ttttctagcc tacctcaact tgcttgagac taaaaggctt tgttgttgtt  7020
gttgaggctg tatggtgctt tgactttaca aatcaagtta tcagctaccc tacttatgga  7080
tatacacctc tcataaaatg atggtaagaa gtttcgatat gtcacattaa cataagaact  7140
tcattcagtt agggtacaac gaagttaagt agttacggaa ataccattcc aaatctcaac  7200
atcctctggg agcttttggt aaacaggagt ggcagaccag acaaagtaac caccagggcg  7260
taacaagcgg ttcaattcca gcaaaagcat gccacctaaa agtagcgagc cagcaataag  7320
attcagttct atagcaaatc aataaatgaa aggaggacat gtcaatatgt aaccagcagg  7380
acaaaccttc gatgtgccaa ggga                                          7404

SEQ ID NO: 36           moltype = DNA  length = 1788
FEATURE                 Location/Qualifiers
source                  1..1788
                        mol_type = genomic DNA
                        organism = Zea mays
SEQUENCE: 36
aatcccagcg tgcgtaatct attgcccaca tgccgacgcc gtcgcacctc aacaagaacc  60
cgcgctacct ggacttccgg gcggcgcggc gggtgccgga gtcgcacgcc tggccgggcc  120
tgcacgacca ccccgtcgtg gacggcggcg cgccgggccc cgacgccgtg ccggtggtgg  180
acctgggcgc cgcggacccg gcgccggcgc cggcggcggc ggtggcccgc gccgccgagc  240
aatggggcgc gttcctgctc acgggccacg gcgtccccgc ggacctgctg gcgcgcgtgg  300
aggaccggat cgccaccatg ttcgcgctgc cggccgacga caagatgcgc gccgtgcgcg  360
ggcccggcga cgcctgcggc tacggctccc cgcccatctc ctccttcttc tccaagtgca  420
tgtggtccga gggctacacc ttctcgccgg cctccctccg cgccgacctc cgcaagctct  480
ggcccaaggc cggcgacgac tacaccagct tctggtacgt tgcgttgcgt gcttgtgtgc  540
gcgcacacct gccgaccgcg gccacaccgt acgcaaccca cgcgtacgta cgtgcgctag  600
ctacctgctt cgctcgcttc gctcctctcg cctcgccatg catatgcacg tacggccgta  660
caggtacagc agcaggtcac acgcacgaac gcacgcacgc accagcaccg atatgataca  720
tcatcgacgt gtcgtccccc cgtctaaggc catgcatgca tgcaagcacg cctagctagc  780
ccttttggct tgctagctga cgaggggagc taggacgagc atacttactg tgcgcgtcat  840
gctcaattgc tcacactata ctactacttg ttactacagt gatgtgatgg aggagttcca  900
caagcacatg cgcgccctcg cggacaagct gctggagctg ttcctcatgg cgctggggct  960
caccgacgag caggccagcg ccgtcgaggc cgagcggagg atcgccgaga cgatgaccgc  1020
caccatgcat ctcaactggt gggtatatat tattgtctgt catgttgtcg tcgtcgtacg  1080
cgttgcggtt gggtgtacat gtatataaca caaacaacaa aaaactaacg ccgtgccgac  1140
gacgacgacg atcatcaggt acccgaggtg cccggacccg cggcgcgcgc tggggctgat  1200
cgcgcacacc gactcgggct tcttcacctt cgtgatgcag agcctcgtgc ccggctgca  1260
gctcttccgc cacgccccgg accggtgggt ggcggtgccg gccgtgccgg gcgccttcgt  1320
cgtcaacgtg ggcgacctct tccacatcct caccaacggc cggttccaca gcgtgtacca  1380
ccgcgccgtc gtgaaccggg acctcgacag gatctcgctc ggctacttcc tcggcccgcc  1440
gccgcacgcc aaggtggcgc cgctgcgcga ggccgtgccg cccggccggg cccccgcgta  1500
ccgcgccgtc acgtggcccg agtacatggg cgtccgcaag aaggccttca ccaccggcgc  1560
ctccgcgctc aagatggtcg ccctcgccgc cgccgccgac ctcgacgacg acggcgacgc  1620
cgccgtcgtc catcagcagc agcagctagt cgtctcgtcg tagccgagac cgatcgccgg  1680
agactgatgc tgatgatgat gcatatatac atgagagaaa tcgtcgagta gactagccga  1740
ttgcaaaagc aaccccagct gccgaaacct ggcatatcga tcccattc              1788

SEQ ID NO: 37           moltype = DNA  length = 1698
FEATURE                 Location/Qualifiers
source                  1..1698
                        mol_type = genomic DNA
```

```
                        organism = Zea mays
SEQUENCE: 37
cgtgccgaga gtccttcaaa gccgacgacg agacgacgat gcagtcgtcg tcgtcatcag  60
cctcgacgcc ggctgccgct tccggcctcg tcttcgatct cgggtctgcg gcgggcgtgc  120
cggagacaca cgcgtggccg ggggtgaacg agtacccgtc ggtggagtcc gctggccgcg  180
acgtggtccc ggtggtggac atgggggtgg cctgcccgga cgcgacgcgg gcgttggcgc  240
gcgccgcaga cgagtggggc gtgtttctgc tcgtcggcca cggcgtgccc cgggaagtgg  300
cggcgcgtgc cgaggagcag gtcgcgcgcc tgttcgtgct cccggctcct gacaaggccc  360
gcgcggggcg ccgccccggg gagcccacgg ccaccggcta cggcaggccg cccctggcac  420
tccgcttctc caagctcatg tggtccgagg ggtacacgtt ccgcgccgcc accgtccgcg  480
aagagttccg ccgcgtctgg cccgacggcg gcgacgacta cctccgcttc tggtacgtac  540
gagcgccatg tcacgtgctt gtgctttcat gcctcgtacc gtcgtcgtgc tgtacgtgtt  600
atgtttatcg gccggtacgt cacgcgtgct acactggtta acgacgtgag cgtgcccacg  660
ttgactgcat gcatgtgcat gcgcgcgccc agcgacgtga tggaggagta cgacagagag  720
atgagggctc tcggtggcag gctgctcgac ctcttcttca tggcgctcgg cctcaccgac  780
gtccagttcg ccaccggcga gacggagcgg aggatccgcg agacctggac ggcgacgatg  840
cacccaatcc tgtacgtacg tcaaaaacga atatctgacc aatgcaaacg tttttctgca  900
atgccagtca tccactcatc ctgtacgtac ctctggactc tgcttgtcca tctactgatg  960
acacgtatgg taggtacccc aggtgtccgg aaccggagcg cgccatcggg ctgacggcgc  1020
acacggactc gggcttcatc acgctcatca tgcagagccc cgtgcccggg ctgcagctgc  1080
tccgccgcgg gccggaccgg tgggtgacgg tgccggcgcc gccgggcgcg ctcatcgtca  1140
tgctcggcga cctgttccag gtgctcacga acggccgctt ccggagccct atccaccgcg  1200
ccgtcgtaag ccgagagcgc gagcggatct ccgtgcccta cttcctctgc ccgccggagg  1260
acatgacggt ggcgccgctc gcgtccgctc tgctgccggg gaggaaggcc gtgttccggg  1320
ccgtgacgtg gccagagtac atggaggtca agcacaaggt gttcggcacg gatgcgccgg  1380
ccctggagat gctgcagctg caggtggatg aggaagaaca aggtgaaagg gccgccacca  1440
cctaagccct aaggaactac tagctgaatc cataaactaa taaagaattc gtgaataagg  1500
gcgttggaag actggacaca acacaagaga gttgctatat atcgtatttc tgaaatttaa  1560
ggcaaatatc ttagttaaaa aactggtata tttaaataga caatatatat ctaaaataaa  1620
gatagttcac catttttacg gtcgaacaat gataaagtta tatattgtct gaatagtaac  1680
aaattaaaga tttccagg                                               1698

SEQ ID NO: 38           moltype = DNA  length = 4095
FEATURE                 Location/Qualifiers
source                  1..4095
                        mol_type = genomic DNA
                        organism = Zea mays
SEQUENCE: 38
cggtctaagt gaccgtttga gagaggaaaa gggttgaaag agacccggtc tttgtgacca  60
cctcaacggg gagtaggttt ataagaaccg aacctcggta aaacgaatca ccgtgtcatc  120
cgccttattt gcttgtgatt tgttttcgcc ctctctttcg gactcgttta tatttctaac  180
gctaaccccg acttgtagtt gtgcttaaag tttgtaaatt tcagattcgc cctattcacc  240
ccctctaggc gactttcata taaatattgg gagaaatatg aaaaacaaat gaaggtcgaa  300
cgagtcagag acaccataaa aaagaggtcg tcttaactag ggtgctaaac ctcaacattg  360
tagtagatct tagtactgag tttgacatct ttgacaccaa caagatggtg atacgttact  420
ttctacgtta acttgggtag gtatatcgac tatagtggcc tataacacta ggctatgtaa  480
tatgatattg tgttgagtct ttataaacat gatttttttt aaaaaaaaga gctaaaataa  540
aaaatagaaa tcgacggtac gatgcaagtt cttctcaaga caaccaaacg cacccttgcc  600
cctttattga aattgaagta tgtgctttat caaatgttta aatactaatt ataagtatta  660
aatataattt aattataata ctaattatat agataaagac taaataacaa gacaaattta  720
ttaaatataa ttaattcatt attaacaaat acttaatgta gcacgatcga atcatggact  780
aattagtctt gatagactcg tcttaccatt taatcataat tagttttgta tactgtttat  840
aatatttcta actagctagt attaaacttt tgatgtaacc taactaaagt ttagtcacgc  900
caatacataa ggactcggat cgttcgatca cccatgacat cacgtatact aagagcatct  960
ccaaaagctc tccagaagtc tcccctaaat ctattttttt gggaaaaaca caaaaacatg  1020
tctccaacag ttcccttaaa gcgcccccaa ctttttcata gcccttaaaa ctccctcatt  1080
tgtagctaca aatgaggggt tttttgggct ccccagaaac aaactgttga tttaagggat  1140
ctgttggaga aaggattaaa atttaccctc acttattatt tagatgtccc ttaaaactga  1200
ttttgaggag tcgttttatg tagagctctt ggagatgctc taacacaccg agcacaaccg  1260
catcatcaat caaaacaacc caaagtttgt tcggtacaag tcatcagcct gtgtacacac  1320
atcagcctcg gccccgggag aagcgctagc aaacaaggtt cacctaaaaa tccatccaga  1380
ttcattgaat ccaaccagca caaacgtccc atttattaat cacctcatca caggtccccc  1440
cagcctcact ctcgcgccgg ctcaaggtac attgcgtgtc ctagccaaga cacgcagctc  1500
atctcagcct cacacgcaca gcaagagcga ggcgtgattc gccatgggcg gcctcactat  1560
ggaccaggcc ttcgtgcagg cccccgagca ccgccccaag cccatcgtca ccgaggccac  1620
cggcatccct ctcatcgacc tctcgcctct ggccgccagc ggcggcgccg tggacgcgct  1680
ggccgccgag gtgggcgcgg cgagccggga ctggggcttc ttcgtggtcg tgggccacgg  1740
cgtgcccgca gagaccgtgg cgcgcgcgac ggaggcgcag cgagcgttct tcgcgctgcc  1800
ggcagagcgg aaggccgccg tgcggaggaa cgaggcggag ccgctcgggt actacgagtc  1860
ggagcacacc aagaacgtga gggactggaa ggaggtgtac gacctcgtgc cgcgcgagcc  1920
gccgccgccg gcagccgtgg ccgacggcga gcttgtgttc gataacaagt ggccccagga  1980
tctaccgggc ttcaggtgac gaaattaact atatatccct ttcgatcata gttgcgttaa  2040
taaattaagg gaatcgtgag cgtacgtacg taagtttccg cagagaggcg ctggaggagt  2100
acgcgaaagc gatggaagag ctggcgttca agctgctgga gctgatcgcc cggagcctga  2160
agctgaggcc cgaccggctg cacggcttct tcaaggacca gacgaccttc atccggctga  2220
accactaccc tccttgcccg agccccgacc tggccctcgg cgtggggcgg cacaaggacg  2280
ccggcgccct gaccatcctg taccaggacg acgtcggggg gctcgacgtc cggcggcgct  2340
ccgacggcga gtgggtccgc gtcaggcccg tgcccgactc gttcatcatc aacgtcggcg  2400
acctcatcca ggtacgtgcc cacctgatga actgagctga acgtaggttg catgcactgc  2460
```

```
atgtgtatag gcttctcaga tcgcttcgtg tggcgtaagg tgtggagcaa cgacaggtac  2520
gagagcgcgg agcaccgggt gtcggtgaac tcggcgaggg agaggttctc catgccctac  2580
ttcttcaacc cggcgaccta caccatggtg gagccggtgg aggagctggt gagcaaggac  2640
gatccgccca ggtacgacgc ctacaactgg ggcgacttct tcagcaccag gaagaacagc  2700
aacttcaaga agctcaacgt ggagaacatt cagatcgcgc atttcaagaa gagcctcgtc  2760
ctcgcctaac tactgctact gctaggatcc atgccattgc catgtcgtct tcagattcag  2820
agcacgccat gtcgtcgcta gcttcgtggt agaacaaata atgatgtgcg tgctgtgtgt  2880
aagcatggat atggatgtga atatgtaata tgatgagcac tcctactttg gtatgtttgg  2940
gaataacaga cttgtgttgg tctggttcat tatttgtaag aaaatcaaaa agagttagta  3000
gggcaggagg ctaaccacag tcatgctgca ccacatccct ggtggaaagc tggccgggtt  3060
acgctacgct cgtgcagcca gattactgca gggccgggat atgcttccgg tggaaggaag  3120
gggacggtgg ctgaggacca tggggctgga gcctgggaga gaggtcgagc tagaagaaag  3180
ggggagagag aagacgcaca acgaagatgg gtcagccagg gatttcgacc caagggggag  3240
ctagtggatt ttgggagaaa acagaaaaga gaaaagagaa aagaagaaaa atttgttggt  3300
gtgaacacaa ggttgatttg tcttttctta tttggattga tgatgagtcg tggactaacc  3360
gacccgtgag ctattgtgtc gtataatcat gtctctcggt ttctggtgtg caggtttgaa  3420
gcacagagac ggtggtcgac gcaaaggtga acgtcatgca ggttcgtgcc gatggaccgg  3480
gagcagtgaa agacgagcgt tgggacttga acaagggacc agagtcgccg gatgactagc  3540
cgcagtggct gacgcctgga acacgcatag acgtgaggac gtggtagagc aggtgaaaat  3600
cgcctagagg ggggggggt gaatagacaa aacctaaaaa ttataaactt tgaacacaaa  3660
ctttacctga ggttaccgtt agaacgagta ttaatgaaat cggagtgcgg aaggcaagtt  3720
cttcttgcta cgagttgctt aatcaatatt gataactttg ggagtcaact caaaatgatc  3780
acaagcaaaa gaactagaga gagaggagag gaagaatcaa ctcgcaaagt aatgatcaac  3840
acaaatgaac acaatgattt atttctcgag gtttggttcc gaagaaccta ctccccgttc  3900
aggagtccac ataggacatg tctctttcaa ccctttctct ctctcaaatg gtcacataga  3960
ctggttcagt tgagagcacc tagagggggg tgaataggtg atcttgtaaa atcaaacact  4020
aatagccaca aaacttagtt taaagtgtta gtacggctaa gtagctttga agcgagttat  4080
tgtgaacaca acaat                                                    4095

SEQ ID NO: 39          moltype = DNA  length = 21
FEATURE                Location/Qualifiers
source                 1..21
                       mol_type = other DNA
                       note = suppression oligo
                       organism = synthetic construct
SEQUENCE: 39
ctccatcatg cggtgcaact a                                             21

SEQ ID NO: 40          moltype = RNA  length = 21
FEATURE                Location/Qualifiers
source                 1..21
                       mol_type = other RNA
                       note = suppression oligo
                       organism = synthetic construct
SEQUENCE: 40
tagttgcacc gcatgatgga g                                             21

SEQ ID NO: 41          moltype = DNA  length = 19
FEATURE                Location/Qualifiers
source                 1..19
                       mol_type = other DNA
                       note = suppression oligo
                       organism = synthetic construct
SEQUENCE: 41
ggtactgcga ggagatgaa                                                19

SEQ ID NO: 42          moltype = RNA  length = 21
FEATURE                Location/Qualifiers
source                 1..21
                       mol_type = other RNA
                       note = suppression oligo
                       organism = synthetic construct
SEQUENCE: 42
ttcatctcct cgcagtacct a                                             21

SEQ ID NO: 43          moltype = DNA  length = 19
FEATURE                Location/Qualifiers
source                 1..19
                       mol_type = other DNA
                       note = suppression oligo
                       organism = synthetic construct
SEQUENCE: 43
caggcgccat ggtcatcaa                                                19

SEQ ID NO: 44          moltype = RNA  length = 21
FEATURE                Location/Qualifiers
source                 1..21
                       mol_type = other RNA
                       note = suppression oligo
```

```
                         organism = synthetic construct
SEQUENCE: 44
ttgatgacca tggcgcctgg a                                              21

SEQ ID NO: 45            moltype = DNA  length = 19
FEATURE                  Location/Qualifiers
source                   1..19
                         mol_type = other DNA
                         note = suppression oligo
                         organism = synthetic construct
SEQUENCE: 45
tcatgcggtg caactacta                                                 19

SEQ ID NO: 46            moltype = RNA  length = 21
FEATURE                  Location/Qualifiers
source                   1..21
                         mol_type = other RNA
                         note = suppression oligo
                         organism = synthetic construct
SEQUENCE: 46
tagtagttgc accgcatgat a                                              21

SEQ ID NO: 47            moltype = DNA  length = 19
FEATURE                  Location/Qualifiers
source                   1..19
                         mol_type = other DNA
                         note = suppression oligo
                         organism = synthetic construct
SEQUENCE: 47
tcgctcgcct tcttcctca                                                 19

SEQ ID NO: 48            moltype = RNA  length = 21
FEATURE                  Location/Qualifiers
source                   1..21
                         mol_type = other RNA
                         note = suppression oligo
                         organism = synthetic construct
SEQUENCE: 48
tgaggaagaa ggcgagcgac a                                              21

SEQ ID NO: 49            moltype = DNA  length = 19
FEATURE                  Location/Qualifiers
source                   1..19
                         mol_type = other DNA
                         note = suppression oligo
                         organism = synthetic construct
SEQUENCE: 49
tccaacgggc ggtacaaga                                                 19

SEQ ID NO: 50            moltype = RNA  length = 21
FEATURE                  Location/Qualifiers
source                   1..21
                         mol_type = other RNA
                         note = suppression oligo
                         organism = synthetic construct
SEQUENCE: 50
tcttgtaccg cccgttggac c                                              21

SEQ ID NO: 51            moltype = DNA  length = 19
FEATURE                  Location/Qualifiers
source                   1..19
                         mol_type = other DNA
                         note = suppression oligo
                         organism = synthetic construct
SEQUENCE: 51
gcatcaacag gtacaacta                                                 19

SEQ ID NO: 52            moltype = RNA  length = 21
FEATURE                  Location/Qualifiers
source                   1..21
                         mol_type = other RNA
                         note = suppression oligo
                         organism = synthetic construct
SEQUENCE: 52
tagttgtacc tgttgatgcg a                                              21

SEQ ID NO: 53            moltype = DNA  length = 19
FEATURE                  Location/Qualifiers
source                   1..19
```

```
                         mol_type = other DNA
                         note = suppression oligo
                         organism = synthetic construct
SEQUENCE: 53
tggacgatgg atagttcaa                                                19

SEQ ID NO: 54            moltype = RNA  length = 21
FEATURE                  Location/Qualifiers
source                   1..21
                         mol_type = other RNA
                         note = suppression oligo
                         organism = synthetic construct
SEQUENCE: 54
ttgaactatc catcgtccat c                                             21

SEQ ID NO: 55            moltype = DNA  length = 19
FEATURE                  Location/Qualifiers
source                   1..19
                         mol_type = other DNA
                         note = suppression oligo
                         organism = synthetic construct
SEQUENCE: 55
tggaccatgg atacttcaa                                                19

SEQ ID NO: 56            moltype = RNA  length = 21
FEATURE                  Location/Qualifiers
source                   1..21
                         mol_type = other RNA
                         note = suppression oligo
                         organism = synthetic construct
SEQUENCE: 56
ttgaagtatc catggtccat c                                             21

SEQ ID NO: 57            moltype = DNA  length = 19
FEATURE                  Location/Qualifiers
source                   1..19
                         mol_type = other DNA
                         note = suppression oligo
                         organism = synthetic construct
SEQUENCE: 57
gcaaggtcct agatttaca                                                19

SEQ ID NO: 58            moltype = RNA  length = 21
FEATURE                  Location/Qualifiers
source                   1..21
                         mol_type = other RNA
                         note = suppression oligo
                         organism = synthetic construct
SEQUENCE: 58
tgtaaatcta ggaccttgca a                                             21

SEQ ID NO: 59            moltype = DNA  length = 19
FEATURE                  Location/Qualifiers
source                   1..19
                         mol_type = other DNA
                         note = suppression oligo
                         organism = synthetic construct
SEQUENCE: 59
cagagtacat ggaggtcaa                                                19

SEQ ID NO: 60            moltype = RNA  length = 21
FEATURE                  Location/Qualifiers
source                   1..21
                         mol_type = other RNA
                         note = suppression oligo
                         organism = synthetic construct
SEQUENCE: 60
ttgacctcca tgtactctgg a                                             21

SEQ ID NO: 61            moltype = DNA  length = 19
FEATURE                  Location/Qualifiers
source                   1..19
                         mol_type = other DNA
                         note = suppression oligo
                         organism = synthetic construct
SEQUENCE: 61
ccatgcccta cttcttcaa                                                19

SEQ ID NO: 62            moltype = RNA  length = 21
```

```
FEATURE                 Location/Qualifiers
source                  1..21
                        mol_type = other RNA
                        note = suppression oligo
                        organism = synthetic construct
SEQUENCE: 62
ttgaagaagt agggcatgga a                                            21

SEQ ID NO: 63           moltype = DNA  length = 19
FEATURE                 Location/Qualifiers
source                  1..19
                        mol_type = other DNA
                        note = suppression oligo
                        organism = synthetic construct
SEQUENCE: 63
acatggcggt caacttcta                                               19

SEQ ID NO: 64           moltype = RNA  length = 21
FEATURE                 Location/Qualifiers
source                  1..21
                        mol_type = other RNA
                        note = suppression oligo
                        organism = synthetic construct
SEQUENCE: 64
tagaagttga ccgccatgtg a                                            21

SEQ ID NO: 65           moltype = DNA  length = 726
FEATURE                 Location/Qualifiers
source                  1..726
                        mol_type = genomic DNA
                        organism = Rice tungro bacilliform virus
SEQUENCE: 65
tcctacaaaa gggagtagta atatttaatg agcttgaagg aggatatcaa ctctctccaa  60
ggtttattgg agacctttat gctcatggtt ttattaaaca aataaacttc acaaccaagg  120
ttcctgaagg gctaccgcca atcatagcgg aaaaacttca agactataag ttccctggat  180
caaataccgt cttaatagaa cgagagattc ctcgctggaa cttcaatgaa atgaaaagag  240
aaacacagat gaggaccaac ttatatatct tcaagaatta tcgctgtttc tatggctatt  300
caccattaag gccatacgaa cctataactc ctgaagaatt tgggtttgat tactacagtt  360
gggaaaatat ggttgatgaa gacgaaggag aagttgtata catctccaag tatactaaga  420
ttatcaaagt cactaaagag catgcatggg cttggccaga acatgatgga gacacaatgt  480
cctgcaccac atcaatagaa gatgaatgga tccatcgtat ggacaatgct taaagaagct  540
ttatcaaaag caactttaag tacgaatcaa taaagaagga ccagaagata taaagcggga  600
acatcttcac atgctaccac atggctagca tctttacttt agcatctcta ttattgtaag  660
agtgtataat gaccagtgtg cccctggact ccagtatata aggagcacca gagtagtgta  720
atagat                                                             726

SEQ ID NO: 66           moltype = DNA  length = 165
FEATURE                 Location/Qualifiers
source                  1..165
                        mol_type = genomic DNA
                        organism = Rice tungro bacilliform virus
SEQUENCE: 66
acgaatcaat aaagaaggac cagaagatat aaagctggaa catcttcaca tgctaccaca  60
tggctagcat ctttacttta gcatctctat tattgtaaga gtgtataatg accagtgtgc  120
ccctggactc cagtatataa ggagcaccag agtagtgtaa tagat                  165

SEQ ID NO: 67           moltype = DNA  length = 2000
FEATURE                 Location/Qualifiers
source                  1..2000
                        mol_type = genomic DNA
                        organism = Zea mays
SEQUENCE: 67
ctgcaatata tacaccaaaa gtattataaa ctgtcatata tatgaccaaa accttttttat  60
tttagaaaag tatattaatc atggtatatt aatcaaagtt gttgttgggg ctgcaaaaat  120
catacccttc ttccacaagc tgttccttga actgcaggta ctcaggaact ctcagctcct  180
caacagcgag ctcactgacg ttgaccctca catactccca gacaccaggc ctagggcgga  240
tggcaagtgc aacccatggg gggatgacaa tcgcctcctg taagataata gagctagaat  300
gattaaagaa ggtgcacact acaaaaggaa cagtgctgtc cagcgagatc tgaatctgat  360
gcaaacctga gctgccctca ggacatcctc aaaagcacca tccttgagct tctcgcgctc  420
agcctcaggg atcgcattgt tgtactcggc aatgatctgg tggggctgca gcataccctt  480
tccaaggttt ttcagcctgc gcaaaacgat gtgccaaata acatcagact atgccagatc  540
tataaactca tcaaacatat acaatttcaa gaaatagttt agacgtatga tcagcagtca  600
gtagcgtggg aacatatgca acatagcgaa gaggcacaac agcaaattca ttcgaaaaaa  660
tgaaaacaaa gattcctctc ttttaactga acttctcgaa acccctttca tgcctacaca  720
tccgatctag tcagatgcct atgcgttcat gctgaacaga acgtgtcaga actaagcata  780
aactggttag caagcattat cgtattcgat agacccttta gtaacaagct atacattggg  840
taagttcaga ctccaatcat tctgttcaga aacatcgtat tgaatataaa actaaagaac  900
acacatgcag gtgcagccag atctaacagc agtttacagt cggtactaaa aaaagcatgg  960
tgtatgtatg tatcatcagt atccagtact aggtttcgac aaaatcctgg atgctaatta  1020
```

```
aatactcatc ttattaggga acacaggaac attatgtcta cagcattgaa tgatggccac  1080
atcatgctag atctaacaat acataatatg atggaactgg tcttaaaaag tcgcattcgc  1140
tcaaataata cccgtagcaa aataaatgta aacttgcaga cgaagcgggg gaaatgaggg  1200
cagacctggt gaagacggcg acaagctcat tggggtgggc agagagtgag tcgccaatgc  1260
gctccctgac gctgtggagg cggctcagga cacggtcacc tgcaccttcc cccattgctg  1320
tcctcttcct ggatcctcag gcctgcacag cgaaaccgaa acggaagcgg aagcttcagt  1380
cagcagagaa aactgaaacc gaaaaacggt tcagatccgt tgacataaaa gctgcgatga  1440
catcctaaaa ctaaaacccc tccagcaaga cataaaccca actgccaaca accagtcttt  1500
taagtctcga cacacccttg acgctgcgcc acgaaactat attgcaggca agaaaccaac  1560
agaacctaac tctggaaggg gggaaagaaa cggcagacag gagcaagacc caaaaaaaaa  1620
cgactcagat cctggtacta tagtcctagt acctagacca gaaagaagaa acaaccaata  1680
caacaagagg catacaagaa ctgaatcgat gaactgaaac gcttcagagg accgaggaat  1740
ggcggagaag ggaggcgcct atttatacag atctgacgag agaaccgaac aaaaacacat  1800
cgatgggaac catggagaag aaaagggctg gccgcatggc accaatggcc tcggcctcca  1860
aaaagccgtt gaatccaaag caggcgagga cgaagcgtga cgcggcaggg tacttctcta  1920
gaaaagcacg gcatcagcaa ggtggggggg ctggggttcc ttattgcagg caatcacgag  1980
gtgattagca caaacggaag                                             2000

SEQ ID NO: 68          moltype = DNA  length = 2000
FEATURE                Location/Qualifiers
source                 1..2000
                       mol_type = genomic DNA
                       organism = Oryza sativa
SEQUENCE: 68
ctgaaatata catcagagat attacaatga catatatatc gataaaagaa aaataataaa  60
attaagtttt aaattttaag aatatatgtt tttagtatcc caattatgca gatttcatac  120
ccttcttcca caagctgttc cttgaactgc aagtactcgg ggactgtcag caactcaaca  180
gcgagctcgc tcacattgac cctcacatac tcccagacac cggcctcgg gcggatggca   240
agggcaaccc atggggagat aacaatcccc tcctgcatga taaaaaaacaa ttacaagtta 300
agttagagca agcggtagag taaagatgga tctctgtgat gcaatgaaat ctgaatctga  360
ttcaaacctg tgcactcctc aggacatcct caaaagcacc gtccttcagc ttctcacgat  420
cagcctcaga gattgcgttg ttgtactcag caatgatctg gtgggcctga agcattccct  480
ttccgaggtt aaccagcctg cgcaaataac agtgtcaaca aaaatatcag gccagatcta  540
tcaactcagc ctataaatat ctcaataaga taattttagc acttgagcat ttgcgcataa  600
taagaaaatt tgctattagc cacttaaaaa gaccatatat gatctgtttg cattgagatg  660
aattaaaaat ttcattgtag atatgaaatg attagttttg accatttaat tggacttaat  720
gaaatatgcg cgataatcag atctacgcgc tcgcgccaat agatctagta agatgtaggt  780
tttttatttt ttttgtgaaa ctttgctacc acaacaagca tctgtaccag tgcagaattc  840
attacttgta ttcagtttgt aaaccgtata tataatataa ataacatgca catgcagtca  900
gatctagcac taccagtcca cagtaatcca aaactacatt tgtatatttc atcattattc  960
agtagtacta ggtttgtaca aaatcttggc tgcagaaggc cgcacttaaa tattcattct  1020
aatcagaaac ttaaaaaaaa agtgactaca aaatgattgc atccaattca gtaaatatga  1080
gccattcctg gccagatcta acaatctcaa caacaaagat cctatatgaa catctccttc  1140
taaaagaaaa tacagtaaca tctgaaggca gtagactaga aaccaacaaa atctaatgct  1200
gggaaatcac taaatcagca cgaacctggt gaagacggcg acgagctcat tggggtgggc  1260
ggagagggag tcgccgatgc gctccctgac gctgtggagg cggctcagga cgcggtcgcc  1320
ggcagcttcc cccattgctc tcctcttcct cttggctcct caagcctgcg tgcacaacca  1380
accaccatca tcagatacat ccagacccag tcaacacaat cactccagga aaaaaaaaag  1440
tcaagccata aaccccaacc aaaaaccacg cctttgacaa acactggaag aaaaagaaaa  1500
tcgcagcttt ttcacaagca atctagaaga aaagaaaaag aaaagactac atagcagcta  1560
taattgactg agaagcatac aggaatcaaa caatggagaa ggggagggag gaagaacaat  1620
gatgctccag gctgaggacc gaggaactgg gtgaagcggg gtaggcgcgt atttatgcag  1680
atctgaggag agaaaccacc aaaacaatcc gatggtttca acgaaaaaga tcgtcgcttc  1740
ttgctgcacc agctcaccca tagccgttga gatcgaagct aagctagcag cagcaaagct  1800
ggaacgaaga gtgacgcatt caagctcctc tcctctcctc tcctctcctc cggagcacga  1860
ggccagcatg ggatggattg gggtttcttg ttggccatgg caaaggagga ggtcattaac  1920
gttgacacgg cgtaatttaa ttaaatctta tcttaaaata tgatttaagt ggtagtaaca  1980
aggaagatta atactatgaa                                             2000

SEQ ID NO: 69          moltype = DNA  length = 2000
FEATURE                Location/Qualifiers
source                 1..2000
                       mol_type = genomic DNA
                       organism = Oryza sativa
SEQUENCE: 69
gctgtttaag aaaaacagaa gtaaaattca gtcactgtta ttttgcttca gttataatct  60
gcaaatcgtc gttctggtac ttactgtcca tcaacaagct gttccttgaa tgccaagtac  120
tcagaaacac tcagctcttc cactgccaac tcacttacat tcacccgaat gtagtcccag  180
acaccaggcc ttggcctgat ggccagtgca acccagggcg gcagcacaat ggcttcctac  240
atacagtcaa ggaagtaagt tagaaagact ggtatttgac tttgagttga ctatcataac  300
catcctggct cattgccaaa tttacctgag cagcccggag aatgtcttca aagggagcat  360
atttctcttt gtcagcttcg atcaaggcat cgaactccgc aagcagctgg tgacgctgga  420
gcattccctt tccctggtta acatacctgc atagagtgat atttaagaaa tagaaccaat  480
gcttagatct cacatccttt ctgcggctga actatgttaa tggcactacc acataaacct  540
gatttttact tcttattttt aagaccacat gatctgtact taatctagct atgaacaaac  600
aatatttcaa catcatctaa gattcatgac tcaagacaaa aatgttagag ctcatcacag  660
attattatag ataccatcat taaaactaaa gagatgcata accttgtcag ctaagaattt  720
gtaacatact aacatgttat cgtttcacat ctgggttgac taagaactaa ccaactgtat  780
ggataaaatc attgaaaact caaaacaatt agtagcaggt tccaagaaga cacaagatat  840
```

```
tatattgaga tcttcaccta gagaagagtg caatcaactc attgggatga gacgagaagg  900
tggcaccgag gcgttcgcgg agactgtgga ggcgagctag cttggcagcc atgactcaat  960
ttcaggaact gcaaagaaag gttacactta gcaacacgta ccaaaaccac tcacttgcac  1020
aagaataatt agtcaacagc catcactaag cattgcaaga ctatctctga acaggaaagc  1080
catgctaaat caacactaat aacatcacac aaaagcattg gaagatcaaa acataactaa  1140
aaacagctgt ttcatctaca caactgaaag catctatggt ttacgaagca gagtgcgagt  1200
actgattcaa aataaatcaa cctgaaccaa tatactctga caatgttttc aaagggataa  1260
aagaaccagc tttatcaaat ggatttgttg ggttttagta agtatcattg agataccgat  1320
ggcatatctc aaactttgca aaattataat ggcatggttc caaattaccc tttagtatta  1380
gcaccagtta gatcctaatt cctaaatccg ataggacaga gcgaaagatc cctggagata  1440
tgaagatttg gctacagatt aagcagagcc aacatgaagt tccgaatatt atgaatccgc  1500
aagcggggag atcaaagaga agaatacgga aggtcgcgac tccatgaaag aatccaacca  1560
aaaacccaaa gatttttctc agttcaaaaa aaaaaaaccc ttcatttttg gttcgccatc  1620
caccgacagg caccaagaca ttcctcagga agcaaaaaag attaagcaga acaagtgata  1680
agcaagacac agtatcaacg gactacgagt cgagaaaatc actgaggcgc gattcttact  1740
gcaccaagta aaaaaaaatt tgggggcaaa aagaactctg caatggggcg gagcaacgtg  1800
gcagcaaaac taaaggtcga ggatttgagg ttttttgccg gtttcctcg aaaccccgaa  1860
tccgctcata gtaaacccac taaactgcag cagaaacccc cctcttggtt cagatttacc  1920
gaaagcagta aacccaagaa catgtcagca aaaactcctg caagattcag ctgacgaccc  1980
accaaagaat cgcaagaaat                                              2000

SEQ ID NO: 70           moltype = DNA  length = 2000
FEATURE                 Location/Qualifiers
source                  1..2000
                        mol_type = genomic DNA
                        organism = Oryza sativa
SEQUENCE: 70
tggcggacgc gccacgcaca aacacaaacc tgcacacccc tgtgtcagag gaggagaggc  60
caagaaagga aatcgagtgg aggaagtgag gagcggcgga gacgtaggag gaggaggggg  120
agatggaaat ggaaagccgc gcgagagagg aggcgcgtgc tggatgggag gaggaggagg  180
aggtggtggg tttgtgtttg gagagacgag cgagagaggc gaagcattta aagggaggaa  240
gagggggaga gagagagaga gagagagaga gagagagaga gagagagaaa ggaggaatat  300
aataaagggt ggtgcacctg ccaactgcta tgctcaccaa cactttgtac acacccagtt  360
acaccccctt gcctttatta tttccagtgc agtaataact tcaacaatta ttgaaatgaa  420
aatggaatta atggagttag tatcggatta gcgacacgct tgccgagctt ctagacggtg  480
cgattatttc agcgggaacg actttctgta ggtgaattta atagaggagt gttttaaatc  540
cactcgacgt tgtaatagct ggtttaattc gtttgtactg tcgagtagtt atccaaaatc  600
aattttggat atttaaaaga aaaaaaaaca gatccgaagt attggaccta ctggcaaata  660
ggaattttgc tatatatagg tgtgcgttca tttataatgg agtagcatgg agttttatta  720
atccagtaaa tgttttcatt gatttaatta atataacgaa tttcgcttga ggccatattt  780
gttaaacgct tttatctcta tcatcattca tcctaccagt aaagagcacc ggagatcgca  840
cttcatttaa atatatgtcc atgttggata aaccatagtt tattatagtg ttcttttata  900
tgttttgtgg ggaatttaga ttgtttaata tggcatacat atccatccat cattattata  960
ttctaacaca actggataag tgttctaaac tattgtagaa taactttgta gtatgatcga  1020
tcttgtggaa taaaaaaagt ctgacaataa cctttcataa aggaatatga atacccgtaa  1080
tcaacgcatc aaatcattca cggtgtacgc ctagcgaatt cgttggcgag tgctcgtgcg  1140
gccgtgggct cgctgtgatg catgcatggc tctctggcta cgtcgagata gcgattagta  1200
gcaaaattaa gcaagccact tattaattaa tctttggaga tatcatatga ttaaggcatt  1260
aattcgtacg tactcgtcgt cagcgttttc tgcaaagtcc actacagttt tttctttctt  1320
tgctgaaaat gctgatgtgt tggagatgga gtgacgtgca caacctgccg ccacgtggat  1380
ggttgctgga gcctacgtgt catcttaatt tgaacaaaaa aaaaagagga ataatacatc  1440
aatacatttt cgaatttcag ttctgccatt gaccagtaat acacatgtcg gcctcacatt  1500
ttaccctgat cttagtaacg ggtggtcgcc tggtcggtca ctgaaaaaag ttcaggaaat  1560
tatagtcaaa ctgaaacgaa catattcact ccttaaaaaa actaaatctt tttatatatt  1620
tgtgatattg taaaatagct acgggataat gatatagata tatatagtga taagggatag  1680
atggatcgag atatggagtt gtgctttctt taatttccac tacttgggct accatattat  1740
ggtagttggt atgaaaagat acacagcagt atagtgatgt gatcaatgac atgtatatct  1800
cacatgctcc catgttggag tcaaattttg ctagactaaa atccaattcc aagcagtccc  1860
tagccaagaa caaacaaaat tcagtgaggt cactgctgca ccaaggactg catgcatgca  1920
ggagaagggc attttctctt ttttcttttg gagactcgat tcaattcggt cggtcggtcg  1980
caatggtcag cttaattaaa                                              2000

SEQ ID NO: 71           moltype = DNA  length = 2000
FEATURE                 Location/Qualifiers
source                  1..2000
                        mol_type = genomic DNA
                        organism = Oryza sativa
SEQUENCE: 71
tgtgaaaggt ggcggcacca gcttagccgc agcttctctc gtcgtctccc tgaaacgaga  60
gggaggaagt tggtagcgtg atatatttag gcatgtcatc tcttgtataa gaagtcttat  120
ctgtgctaat tcacacggtt ctctaatctc tctccattct gtttttgtaa attggttcag  180
tagatagcgt agggttatgc ttatatatac tccgtgaagt atatatttaa aaattagtca  240
cacgtaaagt actatacatg ttttatcgtc taataacaat aaaaacacta atcataaaat  300
ttttttaaat aatacgaatg gttaaacgtt gaatatgaac cgtgcaaaac tatatttatt  360
ttgtaacaga gaaaatattt cacattaatt agattgttgt tttatggaag gttggagagc  420
tgcgccgccg ttgcgcagac ctaggaggct gcttataagt tataatcaat caattcacgg  480
atgccggctg ggacgcggcc catcgtccgg gaagacgaca actcaacgca aaaagccgat  540
atgcctccaa attgccattg ccacctctac ggctgtttat actgctccaa atcaaaagcg  600
tccatggaag aatctagtat ttcccgcaaa gacgatgatg atatgcagga ttggatatat  660
```

```
aggggggttgt tgcatgattg ctagaactcc cgtttccgaa gttgttcgtc catttttaaa  720
gctgccaaat aggaatttat tttgttttca agtgtaatag agttctgtcc agatgagtga  780
attataattt ggttcacatt ttatttgcta agtttcagtt tgaacattct caaataactt  840
ttttcttcac tttttaaccg agtaacttag ttattttttc cgtttggacc acccaacaat  900
ttgttgctaa gtgcatctca cccgtcaaat aattcctttg aatccaaatt caattatatc  960
ccaaaaaataa aaaacttctg aattccacat caattcaaac cccaaccatt ttaatttctc  1020
tccatatttt ccatttctct atttttacct ttctcttttt tccatctatt tatttttttc  1080
cttttctatt tctttctttc tccttccttt ctctgtttcc ttcttcttct cctcggctag  1140
gcccgagcca gcccgtgccg cctcgcgcca accctgtgcc gccttacgcc gcgcttgcgt  1200
gcgctcgcgc ccacctcgtg cccaacccgc gcacgccaca cgcacacacg aggacgatcg  1260
acggacgaat gcaatcatat ccccttcctt actcagctag aaggctcaag aaccgcaact  1320
ttgatctctt ccaccctctc aaatccgccc caacccctgc tgactcaatc gccattaccg  1380
gaggaaaaat ccccgaaacc ctattaccgg cgccactaac agagctccaa aattcgtcgc  1440
ataattcgaa aatattctga aattgaaggt aaaaatggaa tctacatgcg aagtactccc  1500
tttcccctcc aatccgtcac tggaacgccg ccggcgccgc ctcccgctgc cactgccctg  1560
tttggccgcc gacagccgca cggcgcgccg ctgctccagg ccgccctagc ttcaaccacc  1620
gccacctttg gctccgcctc cctcctctta tgctcaccaa gcccgcctcc ctcgccggag  1680
atcgccggaa ccaccgccgc catggccgcc accgcctcct gcttctggcc gccgccgcca  1740
gcctcgccac cggcgcctat gccaccgccg accacggaaa cggagtccct acaccttggg  1800
gaccacaaaa ccggcggcat ccctcccaaa accggcctcc tccaccgccg gcgttcgtgg  1860
gattccggcc agttctgtgc agagcgagag aagaagagga aaaatagatt ttcctattga  1920
aagataaatc agaaaattcc tttttctttt cctatcaagt tgaccatccg tttgacctca  1980
aaatcaaaat ctgagaccta                                              2000

SEQ ID NO: 72          moltype = DNA  length = 786
FEATURE                Location/Qualifiers
source                 1..786
                       mol_type = genomic DNA
                       organism = Zea mays
SEQUENCE: 72
gacatggagg tggaaggcct gacgtagata gagaagatgc tcttagcttt cattgtcttt  60
cttttgtagt catctgattt acctctctcg tttatacaac tggtttttta aacactcctt  120
aactttcaa attgtctctt tctttaccct agactagata attttaatgg tgattttgct  180
aatgtggcgc catgttagat agaggtaaaa tgaactagtt aaaagctcag agtgataaat  240
caggctctca aaaattcata aactgttttt taaatatcca aatattttta catggaaaat  300
aataaaattt agtttagtat taaaaaattc agttgaatat agttttgtct tcaaaaatta  360
tgaaactgat cttaattatt tttccttaaa accgtgctct atctttgatg tctagtttga  420
gacgattata taatttttttt tgtgcttaac tacgacgagc tgaagtacgt agaaatacta  480
gtggagtcgt gccgcgtgtg cctgtagcca ctcgtacgct acagcccaag cgctagagcc  540
caagaggccg gaggtggaag gcgtcgcggc actatagcca ctcgccgcaa gagcccaaga  600
gaccggagct ggaaggatga gggtctgggt gttcacgaat tgcctggagg caggaggctc  660
gtcgtccgga gccacaggcg tggagacgtc cgggataagg tgagcagccg ctgcgatagg  720
ggcgcgtgtg aaccccgtcg cgccccacgg atggtataag aataaaggca ttccgcgtgc  780
aggatt                                                             786

SEQ ID NO: 73          moltype = DNA  length = 1160
FEATURE                Location/Qualifiers
source                 1..1160
                       mol_type = genomic DNA
                       organism = Zea mays
SEQUENCE: 73
atgtgctggt gccccataag gtaggcacct aggtctgtgt ttgaagcatc gacagatttg  60
taaacatgtt cctatgaacc tatttctgat tgataatttg tcaaaactca tcatttgtct  120
tcatccttgc ctgcttgcgt tcacgtgaca aagtacgtgt atgtcttcgg cctttgctgt  180
gtatgtttcg cattgcttag atgtggtgaa agaacatcag aagatgcatt gatggcgtgc  240
ttaaaccagt gatgtgctcc aggtgttcct gcagtctgca gagatattta ctcttgtagt  300
cttgttgaca gcacagttgt atgtgatttc ttggatgtaa tgtaaaccaa atgaaagata  360
ggaacagttc gtcctcttcc gtatacgaag gtcactgtat catttgtcgt ggcacaagat  420
gatctgcagg caggactgca acatggtttc ttggactgtc ctgaatgccc gttcttgttc  480
tttagttgag ccagagcagc agcctggtgt cggtgcctga gacctgacga agcacacggc  540
aaacaaacaa gtcgcagcag ctagcagggg cgttgccatc gccacaagcc cccaagagac  600
ccgccgagga aaagaaaaaa aaactacggc cgccgttgcc aagccgagcg tgcgaaccga  660
tccacggatg ggagatcaga gatcacccac cgcaggcggg cggcagtggc tggcgaggtg  720
cgtcccacaga acctgctgca ggtccctgtc cgtcccggcg accccttttc taggcgagca  780
actccccatg gcagagctgc acgcagcagg gcccgtcgtt ggttgcagct ttaacccttt  840
ttgttttaac catacaatgc agagtcgcag aggtgaaaca ggacggaaat tacagaaaag  900
atggtggtgt gccagcagcc ccagcatgaa gaagatcagg acaaaagaaa agcttgtgat  960
tggtgacagc aacaggattg gattggagcc aagctaggca gtgagaggca ggcagcaaga  1020
cgcgtcagcc actgaaatcc agagggcaac ctcggcctca caactcatat ccccttgtgc  1080
tgttgcgcgc cgtggttagc caggtgtgct gcaggcctcc tccttgttta tatatgggag  1140
atgctctcac cctctaaggt                                              1160

SEQ ID NO: 74          moltype = DNA  length = 1532
FEATURE                Location/Qualifiers
source                 1..1532
                       mol_type = genomic DNA
                       organism = Oryza sativa
SEQUENCE: 74
tagtcctcta atatatgaaa ttttgatata ggtaaagaag ggtattgcaa ggataagaat  60
```

```
gtaaaaagaa ataagagtaa tccttaccga taatagtatt ccttctctac cgttaaaagt  120
taaacctgtg cgtgtagcat tttaatccag gatctatcga atccgtccct cgttggcgtg  180
ggcgacgaac acgtgcagaa gaagctttcc ccagaaagca cctcaccgcc tcgccgtctg  240
gcagactggc acgcggggcc ctaccctcgc tgcgcctggg cccgtccgcc ttctgcacac  300
tgtcacgccc ccacccgctc gccgcctcgc gcctctctct ccgcctccgc cgcggccgcc  360
cgacgtgata gcgacacgta ggactcgcca aacacaaaaa atccatcgcg atttttggaa  420
ttttgttaca aaccaaatcc cgcattagag atttaatttg atttaattta attacgtagg  480
agtaccagat aaggagatcg agttaaaaaa gctaacggcg cggcgtggtt atctccgaat  540
cggctgtggc tccccgcgtc ggcgtcggcg cggcggcggc gcgccggccg aaccctggcc  600
gtcggatcgg gcgtcgtcct gggccccacg cgccacgggc ggctgtcgtt tgctcctcgg  660
agcggggtgg gcccaccatg gccaccacca caggtcgcgg tcgcggctga cctggcggtg  720
gtcccgtgct cgcggtgttt tttttttttc actctctttc tctcggtgga cagtagcggg  780
ggccgcggcc cgcgggggca gagattgcaa aaacagcgga aacggaagat tgcaaaattg  840
caactgcttt cctgttttta attcgggatc aaaaagattc tttcgtcggg gtccccgtgc  900
cattgttgta ttgcgcgtag gtccttgctt gtaaaagata atctccttaa ttttttcttt  960
gtactactag tgtatatgca gtaagaatat accatgagta aaatgaacca caaaactaat  1020
tacgatatac cattctcatg tagacgttct cttttctttt gctagtcata cgtgcatata  1080
taaccaaaca aaaaaatgtt tgaagtactc ctatccaatt tattactcca gtagacaaca  1140
aaagaaaatg tttgaagtaa taactgatcc atggtacagt agggttgtcg tcaatcttgt  1200
gtttctttca ttccattgta cttacaatcg tactccagct agcacagcac aatgggctta  1260
agctttggac cccaaattct gatcttgtcg gggacccgta cgaaaatact cccgtagaga  1320
tgcagatacc gtcacaacct acaaccaacg aatgttaaga aaacaaaggg aaaaaaaaag  1380
aggcgaattc ggaggagaaa aaacggtggc taaaatatag tgcgggtgtg gggacgcgac  1440
gcgagcgacg aaagaggaga gaggatgggt tggcctgccc ccccctcccc tgtctataaa  1500
tgcagaggcg ccgagtgccc tagtcgccgc tc                                1532

SEQ ID NO: 75          moltype = DNA  length = 841
FEATURE                Location/Qualifiers
source                 1..841
                       mol_type = genomic DNA
                       organism = Oryza sativa
SEQUENCE: 75
tcgaggtcat tcatatgctt gagaagagag tcgggatagt ccaaaataaa acaaaggtaa  60
gattacctgg tcaaaagtga aaacatcagt taaaaggtgg tataaagtaa aatatcggta  120
ataaaaggtg gcccaaagtg aaatttactc ttttctacta ttataaaaat tgaggatgtt  180
tttgtcggta ctttgatacg tcatttttgt atgaattggt ttttaagttt attcgctttt  240
ggaaatgcat atctgtattt gagtcgggtt ttaagttcgt ttgcttttgt aaatacagag  300
ggatttgtat aagaaatatc tttagaaaaa cccatatgct aatttgacat aatttttgag  360
aaaaatatat attcaggcga attctcacaa tgaacaataa taagattaaa atagctttcc  420
cccgttgcag cgcatgggta ttttttctag taaaaataaa agataaactt agactcaaaa  480
catttacaaa aacaacccct aaagttccta aagcccaaag tgctatccac gatccatagc  540
aagcccagcc caacccaacc caacccaacc caccccagtc cagccaactg gacaatagtc  600
tccacacccc cccactatca ccgtgagttg tccgcacgca ccgcacgtct cgcagccaaa  660
aaaaaaaaga aagaaaaaaa agaaaaagaa aaaacagcag gtgggtccgg gtcgtggggg  720
ccggaaacgc gaggaggatc gcgagccagc gacgaggccg gccctccctc cgcttccaaa  780
gaaacgcccc ccatcgccac tatatacata cccccccctc tcctcccatc cccccaaccc  840
t                                                                  841

SEQ ID NO: 76          moltype = DNA  length = 1392
FEATURE                Location/Qualifiers
source                 1..1392
                       mol_type = genomic DNA
                       organism = Oryza sativa
SEQUENCE: 76
ctcgaggtca ttcatatgct tgagaagaga gtcgggatag tccaaaataa aacaaaggta  60
agattacctg gtcaaaagtg aaaacatcag ttaaaaggtg gtataagtaa aatatcggta  120
ataaaaggtg gcccaaagtg aaatttactc ttttctacta ttataaaaat tgaggatgtt  180
ttgtcggtac tttgatacgt catttttgta tgaattggtt tttaagttta ttcgcgattt  240
tggaaatgca tatctgtatt tgagtcgggt tttaagttcg tttgcttttg taaatacaga  300
gggatttgta taagaaatat ctttaaaaaa acccatatgc taatttgaca taatttttga  360
gaaaaatata tattcaggcg aattctcaca atgaacaata ataagattaa aatagcttgc  420
ccccgttgca gcgatgggta ttttttctag taaaataaaa gataaactta gactcaaaac  480
atttacaaaa acaaccccta aagtcctaaa gcccaaagtg ctatgcacga tccatagcaa  540
gcccagccca acccaaccca acccaaccca ccccagtgca gccaactggc aaatagtctc  600
cacaccccgg cactatcacc gtgagttgtc cgcaccaccg cacgtctcgc agccaaaaaa  660
aaaaaaagaa agaaaaaaaa gaaaaagaaa aaacagcagg tgggtccggg tcgtgggggc  720
cggaaaagcg aggaggatcg cgagcagcga cgaggccggc cctccctccg cttccaaaga  780
aacgcccccc atcgccacta tatacatacc ccccctctc ctcccatccc cccaacccta  840
ccaccaccac caccaccacc tcctcccccc tcgctgccgg acgacgagct cctccccccct  900
ccccctccgc cgccgccggt aaccaccccg cgtccctctc ctctttcttt ctccgttttt  960
tttttccgtc tcgtctcgat ctttggcctt ggtagtttgg gggcgagagg cggcttcgtc  1020
gcccagatcg gtgcgcggga ggggcgggat ctcgcggctg ggtctcggcg tgcggccgga  1080
tcctcgcggg gaatggggct ctcggatgta gatctgatcc gccgttgttg ggggagatga  1140
tggggcgttt aaaatttcgc catgctaaac aagatcagga agaggggaaa agggcactat  1200
ggtttatatt tttatatatt tctgctgctg ctcgtcaggc ttagatgtgc tagatctttc  1260
tttcttcttt ttgtgggtag aatttgaatc cctcagcatt gttcatcggt agtttttctt  1320
ttcatgattt gtgacaaatg cagcctcgtg cggagctttt ttgtaggtag aagatggctg  1380
acgccgagga ta                                                      1392
```

```
SEQ ID NO: 77          moltype = DNA  length = 743
FEATURE                Location/Qualifiers
source                 1..743
                       mol_type = genomic DNA
                       organism = Oryza sativa
SEQUENCE: 77
gaattcccgg acctccatgc ctacatcaac taatttgatt ccttgagttt acgtttagtg  60
atatgtctat ttttagagct tgttggggct tcggcctcag ctctagccag ccaaacatgt  120
tctaccaagt accctatgtt ggcatgatat agtgatgcat tataacaata aatgagcgag  180
ggattgctgg ctgaaaaagc tatactagct gcatttggtt atagttaacc gaactattaa  240
ttgcgtgtac aacaaaataa aaaaaatgca tgttgcacat tctttcatta acattatgtt  300
ttggtagtgt gaattagaaa tttgattgac agtagatcga caaacatagt ttcaatatgc  360
ttaagttagt tatgacttta acatatcagt ctccttgata ttttcgtttt agattcgtct  420
ctctactagt gtgtatgtcc accttccata gcagtgaagg gttccattcc atccctggta  480
aaaaaaaatc aaccactact atttatttcc taaaaagcaa aatgataaaa tatcattttt  540
ttaataaaaa taaaaaaatt ttggggtaca taattgatgt tgccccttgg gattaacctt  600
aaaaaagggc gaattttcta gggtttggcc aagttttgca atgcaccaaa ttattcccct  660
tgggccggcc gccaccccaa aaaaaacccc aacccccaac tttccattga aggccgggcc  720
cccttaaatc ctcatccccc caa                                          743

SEQ ID NO: 78          moltype = DNA  length = 144
FEATURE                Location/Qualifiers
source                 1..144
                       mol_type = genomic DNA
                       organism = Oryza sativa
SEQUENCE: 78
taaaaaaggg cgaattttct agggtttggc caagttttgc aatgcaccaa attattcccc  60
ttgggccggc cgccacccca aaaaaaaccc caaccccCaa ctttccattg aaggccgggc  120
cccccttaaat cctcatcccc ccaa                                        144

SEQ ID NO: 79          moltype = DNA  length = 612
FEATURE                Location/Qualifiers
source                 1..612
                       mol_type = genomic DNA
                       organism = Cauliflower mosaic virus
SEQUENCE: 79
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga gg                                                      612

SEQ ID NO: 80          moltype = DNA  length = 837
FEATURE                Location/Qualifiers
source                 1..837
                       mol_type = genomic DNA
                       organism = Coix lacryma-jobi
SEQUENCE: 80
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc caccccctccc agcttccttc gccacat    837

SEQ ID NO: 81          moltype = DNA  length = 947
FEATURE                Location/Qualifiers
source                 1..947
                       mol_type = genomic DNA
                       organism = Oryza sativa
SEQUENCE: 81
aatccgaaaa gtttctgcac cgttttcacg tcctaactaa caatataggg aacgtgtgct  60
aaatataaaa tgagacctta tatatgtagc gctgataact agaactatgt aagaaaaact  120
catccaccta ctttagtggc aatcgggcta aataaaaaag agtcgctaca ctagtttcgt  180
tttccttagt aattaagtgg gaaaatgaaa tcattattgc ttagaatata cgttcacatc  240
```

```
tctgtcatga agttaaatta ttcgaggtag ccataattgt catcaaactc ttcttgaata  300
aaaaaatctt tctagctgaa ctcaatgggt aaagagagat attttttttt aaaaaaaaat  360
agaatgaaga tattctgaac gtatcggcaa agatttaaac atataattat ataattttat  420
agtttgtgca ttcgttatat cgcacgtcat taaggacatg tcttactcca tctcaatttt  480
tatttagtaa ttaaagacaa ttgacttatt tttattattt atctttttttc gattagatgc  540
aaggtactta cgcacacact ttgtgctcat gtgcatgtgt gagtgcacct cctcaataca  600
cgttcaacta gcgacacatc tccaatatca ctcgcctatt taatacattt aggtagcaat  660
atctgaattc aagcactcca ccatcaccag accactttta ataatatcta aaatacaaaa  720
aataatttta cagaatagca tgaaaagtat gaaacgaact atttaggttt ttcacataca  780
aaaaaaaaaa gaattttgct cgtgcgcgag cgccaatctc ccatattggg cacacaggca  840
acaacagagt ggctgcccac agaacaaccc acaaaaaacg atgatctaac ggaggacagc  900
aagtccgcaa caacctttta acagcaggct ttgcggccag gagagag               947

SEQ ID NO: 82          moltype = DNA  length = 721
FEATURE                Location/Qualifiers
source                 1..721
                       mol_type = genomic DNA
                       organism = Mirabilis mosaic virus
SEQUENCE: 82
tggagattca gaaaaatctc catcaacaaa taatccaagt aaggattaat ggattgatca  60
acatccttac cgctatgggt aagattgatg aaaagtcaaa aacaaaaatc aattatgcac  120
accagcatgt gttgatcacc agctattgtg ggacaccaat ttcgtccaca gacatcaaca  180
tcttatcgtc ctttgaagat aagataataa tgttgaagat aagagtggga gccaccacta  240
aaacattgct ttgtcaaaag ctaaaaaaga tgatgcccga cagccacttg tgtgaagcat  300
gtgaagccgg tccctccact aagaaaaatta gtgaagcatc ttccagtggt ccctccactc  360
acagctcaat cagtgagcaa caggacgaag gaaatgacgt aagccatgac gtctaatccc  420
acaagaattt ccttatataa ggaacacaaa tcagaaggaa gagatcaatc gaaatcaaaa  480
tcggaatcga aatcaaaatc ggaatcgaaa tctctcatct ctctctacct tctctctaaa  540
aaacacttag atgtgtgagt aatcacccac ttggggttgt aatatgtagt agtaaataag  600
ggaaccttag ggtataccat tgttgtaata ttattttcag tatcaataaa ataatctttc  660
agtttatctt atattcattt gtgtgacacc gtattcccat aaaaccgatc ctaatctctc  720
c                                                                  721

SEQ ID NO: 83          moltype = DNA  length = 352
FEATURE                Location/Qualifiers
source                 1..352
                       mol_type = genomic DNA
                       organism = Peanut chlorotic streak virus
SEQUENCE: 83
acagagggat ttctctgaag atcatgtttg ccagctatgc gaacaatcat cgggagatct  60
tgagccaatc aaagaggagt gatgtagacc taaagcaata atggagccat gacgtaaggg  120
cttacgccat tacgaaataa ttaaaggctg atgtgacctg tcggtctctc agaaccttta  180
ctttttatat ttggcgtgta tttttaaatt tccacggcaa tgacgatgtg acctgtgcat  240
ccgctttgcc tataaataag ttttagtttg tattgatcga cacgatcgag aagacacggc  300
catttggacg atcatttgag agtctaaaag aacgagtctt gtaatatgtt tt          352

SEQ ID NO: 84          moltype = DNA  length = 1648
FEATURE                Location/Qualifiers
source                 1..1648
                       mol_type = other DNA
                       organism = Sorghum bicolor
SEQUENCE: 84
cactcgcaca tctcatggtg tcccaagaac ggcaagagcc agcactgcct ctgcctagca  60
acagcagcag cgccaagcga gcagccgcgt ccatggacgc cagcagcccg gccccgccgc  120
tcctcctccg cgcccccact cccagtccca gcattgacct ccccgctgcc gctggcaagg  180
ccgcggccgt gttcgacctg cggcgggagc ccaagatccc ggcgccattc ctgtggccgc  240
acgaggaggc gcgcccgacc tcggccgcgg agctggaggt tccggtggtg gacgtgggcg  300
tgctgcgcaa tggcgaccgc gcggggctgc ggcgcgccgc ggcgcaggtg gcctcggcgt  360
gcgcgacgca cgggttcttc caggtgtgcg ggcacggcgt ggacgcggcc ctggggcgcg  420
ccgcgctgga cggcgccagc gacttcttcc ggctgccgct ggccgacaag cagcgcgccc  480
ggcgcgtccc cggcaccgtg tccgggtaca cgagcgcgca cgccgaccgg ttcgcgtcca  540
agctcccctg gaaggagacc ctgtccttcg gcttccacga cggcgccgcg tcgcccgtcg  600
tcgtggacta cttcaccggc accctcggcc aagatttcga gccaatgggg cgggtgtacc  660
agaggtactg cgagaagatg aaggagctgt cgctgacgat catggagctg ctggagctga  720
gcctgggcgt ggagcgcggc tactaccggg agttcttcga ggacagccgc tccatcatgc  780
ggtgcaacta ctacccgccg tgcccggagc cggagcgcac gctgggcacg ggcccgcact  840
gcgaccctac ggcgctgacc atcctcctgc aggacgacgt cggcgggctg gaggtgctgg  900
tggacggcga gtggcgcccc gtccggcccg tcccaggcgc catggtcatc aacatcggcg  960
acaccttcat ggcgctgtcg aacgggcggt acaagagctg cctgcaccgc gcggtggtga  1020
accagcggca ggagcggcgg tcgctggcct tcttcctgtg cccgcgcgag gaccgggtgg  1080
tgcggccgcc ggccagcagc gccacgccgc ggcagtaccc ggacttcacc tgggccgacc  1140
tcatgcgctt cacgcagcgc cactaccgcg ccgacacccg cacgctggac gccttcaccc  1200
gctggctctc ccacggccca gtcccagccc aggaggcggc ggctccctgc acctagcgag  1260
cgagcgagcc gggccaaaca aacaaggggc aaaggccatc tctttcgccg gggcccgcgc  1320
gcggggttcg cccacgtgcg cgcccaggtg ggcgctggcc gcgggcaggt ggcggacatg  1380
tggcctgcgg gccccgcgcc gccttcccat ttttggacgc tgccgcgcat gccgcatgcg  1440
tgcgtcgacg gccctactac ttctactact gctactgcga ctactagtgt acatacgcaa  1500
aaatacatat atacgtattt tctatatata tatatataag caaggcggcc ccccggtgac  1560
cttttctttg tttttgtcga caactgtgtt ttgatcccat tctagctgtt ctatggacca  1620
```

```
tggatggttc gttcaatgtt tgtacgta                                  1648

SEQ ID NO: 85          moltype = DNA  length = 1242
FEATURE                Location/Qualifiers
source                 1..1242
                       mol_type = other DNA
                       organism = Sorghum bicolor
SEQUENCE: 85
atggtgtccc aagaacggca agagccagca ctgcctctgc ctagcaacag cagcagcgcc  60
aagcgagcag ccgcgtccat ggacgccagc agcccggccc cgccgctcct cctccgcgcc  120
cccactccca gtcccagcat tgacctcccc gctgccgctg gcaaggccgc ggccgtgttc  180
gacctgcggc gggagcccaa gatcccggcg ccattcctgt ggccgcacga ggaggcgcgc  240
ccgacctcgg ccgcggagct ggaggttccg gtggtggacg tgggcgtgct gcgcaatggc  300
gaccgcgcgg ggctgcggcg cgccgcggcg caggtggcct cggcgtgcgc gacgcacggg  360
ttcttccagg tgtgcgggca cggcgtggac gcggccctgg ggcgcgccgc gctggacggc  420
gccagcgact tcttccggct gccgctggcc gacaagcagc gcgcccggcg cgtccccggc  480
accgtgtccg ggtacacgag cgcgcacgcc gaccggttcg cgtccaagct cccctggaag  540
gagaccctgt ccttcggctt ccacgacggc gccgcgtcgc ccgtcgtcgt ggactacttc  600
accggcaccc tcggccaaga tttcgagcca atggggcggg tgtaccagag gtactgcgag  660
aagatgaagg agctgtcgct gacgatcatg gagctgctgg agctgagcct gggcgtggag  720
cgcggctact accgggagtt cttcgaggac agccgctcca tcatgcggtg caactactac  780
ccgccgtgcc cggagccgga gcgcacgctg ggcacgggcc cgcactgcga ccctacggcg  840
ctgaccatcc tcctgcagga cgacgtcggc gggctggagg tgctggtgga cggcgagtgg  900
cgccccgtcc ggcccgtccc aggcgccatg gtcatcaaca tcggcgacac cttcatggcg  960
ctgtcgaacg ggcggtacaa gagctgcctg caccgcgcgg tggtgaacca gcggcaggag  1020
cggcggtcgc tggccttctt cctgtgcccg cgcgaggacc gggtggtgcg gccgccggcc  1080
agcagcgcca cgccgcggca gtacccggac ttcacctggg ccgacctcat gcgcttcacg  1140
cagcgccact accgcgccga cacccgcacg ctggacgcct tcacccgctg gctctcccac  1200
ggcccagtcc cagcccagga ggcggcggct ccctgcacct ag                  1242

SEQ ID NO: 86          moltype = AA  length = 413
FEATURE                Location/Qualifiers
source                 1..413
                       mol_type = protein
                       organism = Sorghum bicolor
SEQUENCE: 86
MVSQERQEPA LPLPSNSSSA KRAAASMDAS SPAPPLLLRA PTPSPSIDLP AAAGKAAAVF  60
DLRREPKIPA PFLWPHEEAR PTSAAELEVP VVDVGVLRNG DRAGLRRAAA QVASACATHG  120
FFQVCGHGVD AALGRAALDG ASDFFRLPLA DKQRARRVPG TVSGYTSAHA DRFASKLPWK  180
ETLSFGFHDG AASPVVVDYF TGTLGQDFEP MGRVYQRYCE KMKELSLTIM ELLELSLGVE  240
RGYYREFFED SRSIMRCNYY PPCPEPERTL GTGPHCDPTA LTILLQDDVG GLEVLVDGEW  300
RPVRPVPGAM VINIGDTFMA LSNGRYKSCL HRAVVNQRQE RRSLAFFLCP REDRVVRPPA  360
SSATPRQYPD FTWADLMRFT QRHYRADTRT LDAFTRWLSH GPVPAQEAAA PCT        413

SEQ ID NO: 87          moltype = DNA  length = 12906
FEATURE                Location/Qualifiers
source                 1..12906
                       mol_type = genomic DNA
                       organism = Sorghum bicolor
SEQUENCE: 87
cactcgcaca tctcatggtg tcccaagaac ggcaagagcc agcactgcct ctgcctagca  60
acagcagcag cgccaagcga gcagccgcgt ccatggacgc cagcagcccg gccccgccgc  120
tcctcctccg cgcccccact cccagtccca gcattgacct ccccgctgcc gctggcaagg  180
ccgcggccgt gttcgacctg cggcgggagc ccaagatccc ggcgccattc ctgtggccgc  240
acgaggaggc gcgcccgacc tcggccgcgg agctggaggt tccggtggtg gacgtgggcg  300
tgctgcgcaa tggcgaccgc gcggggctgc ggcgcgccgc ggcgcaggtg gcctcggcgt  360
gcgcgacgca cgggttcttc caggtgtgcg ggcacggcgt ggacgcggcc ctggggcgcg  420
ccgcgctgga cggcgccagc gacttcttcc ggctgccgct ggccgacaag cagcgcgccc  480
ggcgcgtccc cggcaccgtg tccgggtaca cgagcgcgca cgccgaccgg ttcgcgtcca  540
agctcccctg gaaggagacc ctgtccttcg gcttccacga cggcgccgcg tcgcccgtcg  600
tcgtggacta cttcaccggc accctcggcc aagatttcga gccaatgggg taagcgaagc  660
accgatttac atttaccgcg cgtcggcccc tgaggcctgg gtcttagtct tagcactgca  720
tatacggtcg gtagctctgg atatgatacg tatatatgaa accccgttcc aatcccatgc  780
acggtgtaca caggcgggtg taccagaggt actgcgagaa gatgaaggag ctgtcgctga  840
cgatcatgga gctgctggag ctgagcctgg gcgtggagcg cggctactac cgggagttct  900
tcgaggacag ccgctccatc atgcggtgca actactaccc gccgtgcccg gagccggagc  960
gcacgctggg cacgggcccg cactgcgacc ctacggcgct gaccatcctc ctgcaggacg  1020
acgtcggcgg gctggaggtg ctggtggacg gcgagtggcg ccccgtccgg cccgtcccag  1080
gcgccatggt catcaacatc ggcgacacct tcatggtaac ccctgctctg ttttttcttg  1140
tcctcctctt gtcctgtgtg tgtgtatatt cacttctctc tgttttttttg ccccgaatcc  1200
tagtggacct aactggacgg attacagcac gcacacgtag gcatgtcatg tagcagcagt  1260
ctgcagcact gtagtactta gcgatgcaat agagacatgc gttccagtcg gttccatctc  1320
ggtgggctac agctacagtc ctacacggac gcggctcgta gtcgtaggga cgggcgcgtt  1380
ctctgtatcc acacacggct gcgcccaggc cgaggcttcc gccgcgggaa agttgcgaca  1440
acagaacggg gtttgtgccg ttggagcgtt gcggagaggc agaggcttgg ggggacgggg  1500
gcgcgatacg ctgcgatggg tgggtgaccg aggcgacgct ttcggcgggg gcccgggcct  1560
gcccaggtgc gcgcggcctc gtcgccttcc cctgtttttt tgatgccgcc gctcggtcct  1620
cggtgttctg gctccgcccg cccgctcgct gggtgcccat cccatctgat ccgatccgct  1680
ccgctccgcg gtggcggtcc tatgcgatgc cgccgcacga gcgcgggggg ccgcccgtgg  1740
```

```
aggagtagaa agtggtacaa ggttggttgg aacttggaat tgtggggggt tactgctgct  1800
ggtggctgct gctttgcaac ttgccaggct gctgcctgtt gccccccgcg ttttctagcc  1860
gtttccgctc gcgatccggc acgcggcgcc cacaccgggg ctccagctcg gccccttggc  1920
cgtgtaggta gcaggcactt gcatctgtcc gttcgacacg atgattcttg tgcactgtgt  1980
acgtatgtac taaccctttc tggtatgatg tacgcatggc atgcaggcgc tgtcgaacgg  2040
gcggtacaag agctgcctgc accgcgcggt ggtgaaccag cggcaggagc ggcggtcgct  2100
ggccttcttc ctgtgcccgc gcgaggaccg ggtggtgcgg ccgccggcca gcagcgccac  2160
gccgcggcag tacccggact tcacctgggc cgacctcatg cgcttcacgc agcgccacta  2220
ccgcgccgac acccgcacgc tggacgcctt cacccgctgg ctctcccacg gcccagtccc  2280
agcccaggag gcggcggctc cctgcaccta gcgagcgagc gagccgggcc aaacaaacaa  2340
ggggcaaagg ccatctcttt cgccggggcc cgcgcgcggg gttcgcccac gtgcgcgccc  2400
aggtgggcgc tggccgcggg caggtggcgg acatgtggcc tgcgggcccc gcgccgcctt  2460
cccatttttg gacgctgccg cgcatgccgc atgcgtgcgt cgacggccct actacttcta  2520
ctactgctac tgcgactact agtgtacata cgcaaaaata catatatacg tatttctat  2580
atatatatat ataagcaagg cggccccccg gtgacctttt ctttgttttt gtcgacaact  2640
gtgttttgat cccattctag ctgttctatg gaccatggat ggttcgttca atgtttgtac  2700
gtactccacg taaccaaact actctagtgg actagtagat cgggctcatg tgatgaaact  2760
ggaccgacgc ggacgtcacg tgcgtcaccc gcgtctggta gcggtagcgc acgagcgccg  2820
aatgtttcct gggcccgcaa gagaatcgct tctcatctcc tctcaccatg aatggggaaa  2880
aatgctgcgt cgaaagttcc agacgtttcc aaattccaaa cggttttgtg gcgtccgatc  2940
catggggcgc cccaaacttc caagacgttt tcaggttcca aatcttcgtg ctccacatca  3000
ccttcttccc agattcattt gcctcgtcgc ttgctctcct gtgttattca cgggtcccac  3060
tgttgccccg tctgcgagaa agaaatttat tagagttgaa gcattcgaca tttcgactga  3120
ctgattgtta gtatcactaa attttgtgca catgtttctt tggtcattca tctctggata  3180
tttttttag ataatggata taaatatcgg gcctctacat ctgaggaagt acacagccaa  3240
ttattttcat ctctggacat gggacgatgg aagaggcaga tagatttagg agacccttca  3300
attcagaatt tcaggtgcac aaggcctgcc tggcttgccc ggattcttgt ttcggacatg  3360
accaactagg ccgcactact tgcactgata gctggagaaa aaacaaaact ttgcaaacag  3420
caggattatc tacaagggaa actccatcca cgtgaaccag catttcaggg agagatgcga  3480
caaaaaaaaa gaggcggcaa caaaaaaatc ttactgcaat tttatctctg cattgaacct  3540
cttccaacca tgccgcatcc tgtactgttt tgtatctttc ccggtggtcc gttgcgttct  3600
cacgcagttg ataacatgca gtcacgcacc accgaatcca gtgtactagg ggtagtgact  3660
tgtcacgcgg aacaacaggt cggtagcacc aagcaagtcg ctgtagactt gggcgtttaa  3720
caacgacttg cacaacagtt caaatatagc atatgcaatt atgcacaaga ttgttcgact  3780
gctatccgac aaactgaaga agctgcccaa ttgaacagaa tgtaccagtg atttccagca  3840
cactatctta cagcagcgtt gagaatgaaa caacaaatgg gggaaaacag atgtgtatta  3900
ttctacagtt acaccaaaga gtttgtcctt tcagcatcaa caagaatcat atgcatatct  3960
agtgacaaaa attcctctaa ttttacccta cttggtaaca gttctcttca acacatatat  4020
ttcacgtgct tgcatcgagt tccttgggcc gccacatcga cttctcgacg caaagcaagc  4080
cctcgttgcc cttggtgtag gtcattcgca cctcccactg cagggacttg gccatgcttt  4140
ccagttcgtt tattgtgtcc gcagtgtccc tcacaatcag tttgccttgg ggcctcagta  4200
cacgatcaac ctcggcaaaa actgccatca atttgcatct gtaaacaagc aacacagatt  4260
tagcatctgt aaacaccaca ggtttcattg caagaagcat aaagcatgca aacatgctac  4320
ttgtacatgt caaagaaaca tgtcaaactc aaacacatga aaatcattat tattgttttc  4380
ttgctgaact gatcacatta gttggtttca atttctgagt tccactagta atctatacca  4440
gaaggataga ataatgtcaa gaacaagaga tacaaacctc tttgtgagct ttgagaatag  4500
atggtccgcg tgcagaaggt cataagttct tgggtaagtg ctcaaagact cgcaccagtc  4560
atggtacata ccaaacaaac cacgctcgta aatgatgggc agtgtgtctg gtgaatcaat  4620
cggcacaata ttcatgaccc agaccttttg gtccctcaga gctgcagcaa aactgccatg  4680
caacgatgta aagcattagt aaaaatattg ggttttttaa accaaaacca agaaagataa  4740
ttcctccagc ttaactgaaa gaaagaaaga aaaaaactgc ttaatgactt atggtggaca  4800
agttgcctgt tatgttttat gatagctatg tgccagcttg gctaactggt agttatgtag  4860
tgtgatctga attaccaaaa aagagaagaa aaaaaaatca tgcccaagaa actgagaaag  4920
acacccattt acttaccctc catacacagc tctcatgtcc attacatttc tcactttgga  4980
ccagtcaatt cccatgccat tcacatacga tttacttaca accctttttcc agtgagcatt  5040
atctgcctcg aaatcttcat ttgcaggctt tccatagacc ccaaccttgg aaccatcaat  5100
ccagaaagga gtcttctcaa gcctttgtgg ccaaaactct ggccatttttg accctcgaac  5160
tttcgagcca acaggcagtt tgtgcatgca tgcttccaaa ggtacattcc tgcaaatcaa  5220
aagattgtgt aagcaaagca gaggaagcac ttcgccgcat tgaaaatacg ttcttctcaa  5280
agaaacaaaa ccataccaag ctgcatctgc atcatcagat tccttgcaca atggtgggtt  5340
gttttcggat cttttctcat agcaaatgtt gtccattggt ttctgaaata tgaccatacc  5400
aacttgattt aacttatcct tagtcttgtt gaccatcttc cagcacatgg actttgtcaa  5460
agtggacatc gctgaaaaga ttaaggggtc atatgttatg atagaaataa aattcaattt  5520
tgcactgttg gtacatagca tctgttttga acaaatgcaa tccttcctta tccatgaaag  5580
aagttaaccc ctgatactta ggattattca gtactttcac tcatgaactg ctgaatttgt  5640
tctgccagta gttgctatac tagaaatgtt cagtgtacca aacataaatt tggtacgggt  5700
tccttattaa agatgggagg ctgtatggta tttcgacgta acaaatcaag ttagcagcta  5760
ccctacttat ggatatacac ttctcaaaat gaatatacat agttttgata ggtgacatta  5820
attaatataa gaacttcatg cagttagggt gaaactaaac taagcagtta cggaaatacc  5880
attccaaatc tcaacatcct ctgggagctt ttggtaaaca ggagtggcag accagacaaa  5940
gtaaccacca gggcgtaaca agcggttcaa ttccagcaaa agcatgccac ctaaaaggag  6000
tcagtaataa gattcagttc tatagcaaat caataaatga aaggaagaca tgtcaccaac  6060
aagacaaacc ttcaatgtgc caagggaccc tgcagcgagc gcaatgaatg acatcaaaga  6120
ctctgctggg gtatggaagt ctcttggtgc ccatcacagc tgatattgct ggaattcccc  6180
tttctaatgc aaattgtact tgagcttcat gctcatcttt cggagcaaaa gacatggtaa  6240
gcacatctct atcaaacatg tagcctccaa agctggcaac tccacaaccg acatctagaa  6300
tgacgcggct tcgtttgccc catgcaatat caggcagtgc ctgtgaatga cagtttaatc  6360
agcatatgat gaaagcaagt gtgataatat caagttcaaa gatgcaacat gaaactttca  6420
taatcatgga cagtactaag cttgcttgat agattaatgt atggatgaga ctaaaaaaaa  6480
```

-continued

```
ggaaagttgt atccatcaga acgagaggct gaaaacacat ggctggctgt gaaagcctga  6540
tgtcgtttag tctagcataa acaaactgtc ctcagcatgt agatttccat agggtggcat  6600
ttgacaaatt atgattgtgg actagcgaat caatcactga ttctcaaaag tgtgagacag  6660
atgagttcaa gtctaagggg tgactaatat gggatgctgg gatgatgatg atgatatata  6720
cctgctgaat agtatcaata tagtggaggg caccattctt gaactgagtc ccaccccccag  6780
ggaacaggag gtagtcacct gatactttaa cccaattttg atgtcccttg tactctgcga  6840
gcctagtgtg aggaacattg ctgtaccata cctgcaaaaa gcagcacaag atggtaataa  6900
gtaaacagag atcttggtca gctaaagatg attcagtgtc gtacaattta gaatagacag  6960
aatcaccttg tccctgctcc ttggccactc aattgggcgt ttatatcctt ctgggagtgg  7020
aacaaggcag gtaggaggct cctcagggca atgcctctca cgatgttcat aatgtttagt  7080
agttcgaagc ttcttgatag ccttctcgtt gtcaaggcaa ggtatgtaat ctgtcgaggc  7140
actgctatta catagtttcc aggaatagct agtcgcatca cctgaagact ttgatgacgc  7200
ttggacttcc ttttcattct tggactctgc agcctgtgtg gggaatgaac cattctgggt  7260
atttgactcc ttcagaagct ctgattgggc cccatcagga aatacctcgt tggagtttga  7320
gctctgatcc ttctctccat tttcttccac cttctcttct atctgaggtt gctcctcctg  7380
agtggcatca ccttcaggct tctcttcttg atcatccttg ctctctccat caggtttttc  7440
atcaccactc tcatttgtga tttcatcatc tttcttctcc ccactcttct ccccgtcacc  7500
atcgttcttc atgtcatctg accgcccttc tgattttcca tttgcatcat caaacatatc  7560
cttggtctca gctttctctg tcggcacttc cggctccttc tcttcaggct tctcctctgg  7620
cttctcagtg aacttctctt ccatcgtggc atccttgtta ttcggctcct ccggcatcgt  7680
ggcatcattg ttgtcggtgt cctcaaattt ctcagaacct tcaccagcat tgtcctgtga  7740
ggccccaaaa ttgacaggcg caggctgctg cttcaccacc ggcttcttat tcgaggagat  7800
ctccagcggg aagacagtgg acgaggtcat catccacgcg ccgaccaggc agagcgccac  7860
aaagacgacg accgtggtgg tcgtgcagaa cgacgacgac gtcgaggacg gccggcggcc  7920
gtccatcttc ccacctcggc caaatgccat tagtgcctgg cgaacatgta ccagagcacc  7980
gaccttcacg cgatttatct ccaccaacta ctgctggacc aagaaccccc aaaaaaatcg  8040
cacctttgtc tgctttgtgc tgctacagcc gcgcggcacc tgaagcaaac cacaaaaaaa  8100
acttaaatcg ccgcggacat aaatcaaggt gctggatcta aagaacaaac gctggatcta  8160
ctcaagcaac aacggaagga agatccgcta ttggtgctag tattagcttc ttgtttccta  8220
gtactacagc ggctctttcc cagtataaga acacgggaaa acgcggagaa atccccccttc  8280
gtggccaaac atggaaagaa aattagtaaa gcgtgtgctt taaaaccccc tcgttctgtt  8340
ccttccgcgg agagctaccg catcttccaa ttgagctggt tctcagctgg gcgcaaaacg  8400
cgcactaatc aatgtccgat tccatccaca aagaaaaaaa agacgggaac agctaatcca  8460
gcagctcgct cgctagctag ctagctcatc ggcggaagga cggaaccagc tttgctggat  8520
ccaggacagc aagagtgtgc aaggagaaag aacggagcag caatgcggat tgcggaggcg  8580
gtggattggt acctcgccgg aaccgaccgg agtggtcgcg gtggccctcc gcgcggatct  8640
cgaagaggag cgaggaaggg gaaggcggat gcgcgtcctt gggttctctg ccaccgcact  8700
gggcctcgcc gcgttataaa ggcgggcggg cgggcgggca gcgcagtgtg agtggagtgc  8760
aatctgttgt gtagtgtgtg aagaggcgga agcggaagcg gaggagatgg gttcgcatta  8820
gacgaccgta cgtaattata cgctatacta gtacttgggt tagattactc gggagatctt  8880
ggccaaaatg tccggtctga gtgtttggta gttttatgga tttgcccttt taagatgttg  8940
gtatttctcc gggagcttag aaagaagaaa tggcgatgct ttaggccttg tttagatgcg  9000
aaaaaaattt ggatttcgct actgtggcat ttttatttgt ttgtagcaaa tattgtccaa  9060
acacggacta actaagattc atctcgcgat ttacagttaa actgtacaat tagtttttat  9120
tttcatttat atttaatgtt tcatggatgt gtcgaaagat acgatatgat agaaaatttt  9180
gaaaactttt tagttattga ggttaactaa acaatgcctt aattgagaat ttactcgagc  9240
aaaaagagtt aggtcagtct cagtggagag tttcatggtg ttgtttccaa gactgccata  9300
tcatgtgaaa tgaaatgaaa cttggttgaa acactcactc tcaatggaga gtttcatttt  9360
atagtttcat gggcatttaa tttcaatact catagagagt tgatatcgtg ccaactcatt  9420
tcttctctct cttcttaaat acacagtcat atcatcaaaa aaaatcctat gtagcaacat  9480
atttaatgca aataaaactc atatggtgga ctgtaggagt agcattaggc caagggcaca  9540
cacacggtca cggtgtgagt gcgacggtgc gagtgggccc gcggcggtag taagtgcgtg  9600
cgcgcccggc gcccccctcc gcggcgacga cgcagcggca gcgcgtcgtc cagtgcaccg  9660
tctgctgttc ggcgctgcgg gtcctccgcg ccacggcgca gtgaaccggg cgcgtgcatc  9720
ccgggagcgg cggcttggca ctcccctgct tgtcggtggc ggccgtcggc atcgctcggc  9780
cccggagcgt cacgaggctg ctgattggga gcgagagcga gtagtggggc tggttgggga  9840
caatcccatt cccacccggc ccaccaggct gggactggcc cactagtcac tagtgggtgg  9900
ctcatgggtg tgggtgggct ggctaatgcc gcctgcccaa caaccaaccc aacccctgtg  9960
gacgctggta ccggtagttg ccgcgccatg gtggactgct gccgcctgat gcctttgcct  10020
gccacgctcc acgagttgag gcgcaccaaa ctgtgctgtg ctcctgattt gtgctaatcg  10080
gccgacgcgt accattcttt ctttctttcg tctacgcgca gagaggccgg ttgactgttt  10140
cttcgttgga gggccatgtt gactcgtact aataataaaa ataataatac taggttgact  10200
ttttcaattc caacgcagca gtgcaaagct gcccacctat gagcacaggt ccttttttaa  10260
ctccgttttt gtacgtacac acgtactgtc cagcctgtgt ctaataatct taccaaaaac  10320
ctgtcatctc actatcaacc aatcaggctc tccgcctgtt cgtcgaggaa cagcagttgt  10380
tttccctact ccaacataga gtacactatg gacgcacatt accatgccag cttgagctta  10440
gcattgccca ccgttggata actgccatgc cattctcagg ccctgtttag ttcccatcta  10500
aaaatttttc atccattcca tcgaatcttt ggacacatgc atggaacatt aaatgtagat  10560
aaaaaaataa actaattaca cagtttagtt gagaatcgcg agacgaatct tttaagtcta  10620
gttactccat aattagcctt aagtgctaca gtaatccaca tatactaatg acagattaat  10680
tatgcttaat aaatttgtct tacagtttcc tgacgagcta tgtaatttgt tttttttatta  10740
gtttctaaaa acccctcccg acatccttcc gacatatccg atgtgacaac caaaaaattt  10800
tcatcttcaa tctaaacagg ccctcactct catcatctca tgccggggca gcaggtccgt  10860
cgtcaggtct gtcgtcccgt cccgtgccgt ctgaagcaac aggcgagaga aacgccgttc  10920
catcggtttg ccgagcgtgc agaggataga gctatactcg atccggagag gattgtgaaa  10980
cgaagcacgg ttaagcagtg ccgcgcacgt gctgctctgc tcctggatcc gatccagatc  11040
gactcggggc gtctcggcct cagcggcgat ggcaatcatc gcgcgcgctg ctggagctgg  11100
acgttttcgt cttgcattgc aggaggcgga acagaacgga gaaagccacg gcgcgctttg  11160
ccgacgccac gcgctgacac gagggacccg ttcagcggcc agcacgcagc ctaatcatgc  11220
```

```
ctgtcggggg gagctcatcc gttcctgaat ttgggtcatg ctccagtatc aggtattcag  11280
gtactagtac tcctgagcca tgtgctgcga caaaaaagcg aggctcctgt agtagagcct  11340
tgtttactta caaaattttt tacattctca gttatattaa atcttgtgac acatgcataa  11400
agcattaaat atacataaaa gaaataatta tttacacagt tacttataat ttgcgaaacg  11460
aatcttttaa gactggttag tttatgatta gataatattt attaaataca aatgaaagta  11520
atattattta tattttgcaa aaagtaaata agacctaggt agctaggcca acgtgagcat  11580
gtcggacccg gaccggttcg ttctacggcg cgtcccgcaa acctgcagcc aggtagtagt  11640
agtacaccgt gcacgggaga ggtgcgccat gcatgctcgg gcaaaagatc atagagaaag  11700
gtgcagcgtt tcagttgcac acctgaccga gtgacgcctc gccttgtttg gctttgttcc  11760
caaaattttt taaaattcct catcacatta aatctttgaa cgaatatatg gagcattaaa  11820
tataaataaa agaaataatt aatcatacaa tttgtctgta atttgcgaga cgaatctttt  11880
gagcctagtt agtttataat taaataatat ttgttaaata caaacgaaaa tgctacgtta  11940
gccaaaacta aaatttttct ccaaacgtga cccagcacct tccgatcaat catcactcag  12000
cgggtcacgt cagaagatca gatggacctt gccgtccggg cctgtctctc ggcctcctcc  12060
ccatctggaa cgaacagagg tccagtcctg tttcgagtcg agctgagtcg atcagatggg  12120
cctaaatagg ccgaagacgt aggcaaaggg cccgctgatt tatctgattc ttctaggacc  12180
gtgcatgcgc ggatgggcct aggtggaaac ccaacagatg tgaggcttca aagaggaaga  12240
agtccgttac acatggagag ttagtctata atgggataat atttaccaca aacaaataaa  12300
aatactacag tagcgaaatc caaaattttt cacatctaaa caaggcccta gatgttttgt  12360
cagtgccaga ccagagaaaa tctcgtcttc tgctgtcaat agctttgatg attcctggcg  12420
gcagaggtaa agcttgcctg ggccttgttt agttccgaaa agtgaaaagt tttcggtact  12480
gtagcacttt tgtttgttcg tgacaaatat catccaatta tggactaact agaattaaaa  12540
gattcgtctc gtgatctaca gctaaactgt gtaattagtt tttgttttcg tctatattta  12600
atgtttcatg catgtgccac aagattcgat gtgacggaga attttgaaaa tttttttggtt  12660
ttcagagtga actaaacaag gcccagatgt aattgaccat gccatcgagc gcgagttgac  12720
tagagtgagt cggccctgat ggttaagtag tgcagactgc caagtggaca accgtctatc  12780
aactttgcag agtggggcga atgcactgag gatgttggag aggggcaagc caaggtaaac  12840
ttgaggaaag atgcttgttg acactgtagt atgtgaacaa tcctgtttaa ttttgtgtcc  12900
tcgacg                                                             12906

SEQ ID NO: 88           moltype = DNA  length = 1790
FEATURE                 Location/Qualifiers
source                  1..1790
                        mol_type = other DNA
                        organism = Setaria italica
SEQUENCE: 88
tctcatggtg tcccaagcac agcaagagcc agctctgcct cacagcagca gcaccgccaa  60
gcgcgcagcc gcgtcactca tggacgcccg cccggcccag cctctcctcc tccgcgcccc  120
gactcccagc attgacctcc ccgcgtccaa gccggacagg gccgccgcgg cggccggcaa  180
ggccgccgcc gcctccgtgt tcgacctgcg gcgggagccc aagatcccgg cgccattcgt  240
gtggccgcac gacgacgcgc ggccggcgtc ggcggcggag ctggacgtgc cgttggtgga  300
cgtgggcgtg ctgcgcaatg gcgaccgcgc ggggctgcgg cgcgctgcgg cgcaggtggc  360
cgcggcgtgc gcgacgcacg ggttcttcca ggtgtgcggg cacggcgtgg gcgcggacct  420
ggcgcgcgcg gcgctggacg gcgccagtga cttcttccgg ctgccgctgg cggagaagca  480
gcgcgcccgg cgcgtcccgg ggaccgtgtc cgggtacacg agcgcgcacg ccgaccggtt  540
cgcgtccaag ctcccctgga aggagaccct ctccttcggg ttccacgacg gcgccgcgtc  600
gcccgtcgtc gtcgactact tcgccggcac cctcgggcag gacttcgagg cagtggggcg  660
ggtgtaccag aggtactgcg aggagatgaa ggctctgtcg ctgacgatca tggagctcct  720
ggagctgagc ctgggcgtgg agcgcggcta ctaccgcgac ttcttcgagg acagccgctc  780
catcatgcgg tgcaactact acccgccgtg cccggagccg gagcgcacgc tgggcacggg  840
cccgcactgc gaccccaccg cgctgaccat cctcctccag gacgacgtcg gcgggctcga  900
ggtcctcgtc gacggcgact ggcgccccgt ccgccccgtc cccggcgcca tggtcatcaa  960
catcggcgac accttcatgg ctctgtccaa cgggcggtac aagagctgcc tgcaccgggc  1020
ggtggtgaac cagcggcagg agcggcggtc gctggccttc ttcctgtgcc cgcgcgagga  1080
ccgggtggtg cgcccgccgg ccagcggcgc cgtcggcgag gcgccccgcc gctacccgga  1140
cttcacctgg gccgacctca tgcgcttcac gcagcgccac taccgcgccg acacccgcac  1200
gctggacgcc ttcacacgct ggctctccca cggcccggcc caggacgcgc cagtggcggc  1260
ggcggcttcc acctagctag cggcgcggat ccgaccgagc ccattgacga cgccgtccct  1320
ttccgccgcc gccggggccc gcgcgggggt tcaccccacg tgcgcgccca ggtgggcgag  1380
gtggcggcct cgtggcccgc gggccccgcg ccgccttccc atttttgggc gctgccgccc  1440
cgcgcgcatg ccggatgcgt gcgtccacgg cctactgctg ctactagtgt acatatacaa  1500
acatacatat atacgtagta taaatatata agcaagcggc ccggtgcccc ttttcgtttt  1560
cttgttttgt cgatcacaat ctctggattc gatggatgga taaatgtttg tacgcatgca  1620
tgtagatggg ctcatgaaat ttcagaatct ggaacggacg aggagctcac gtgcctcttc  1680
cgtgtctggt agcggtagct gcgtgccaaa tgtctggtgg gcccaaagaa attctagtgc  1740
cacccgtccg gatccggcat ccgaaagttc ccgacggttc gacacccgaa             1790

SEQ ID NO: 89           moltype = DNA  length = 1272
FEATURE                 Location/Qualifiers
source                  1..1272
                        mol_type = other DNA
                        organism = Setaria italica
SEQUENCE: 89
atggtgtccc aagcacagca agagccagct ctgcctcaca gcagcagcac cgccaagcgc  60
gcagccgcgt cactcatgga cgcccgcccg gcccagcctc tcctcctccg cgccccgact  120
cccagcattg acctccccgc gtccaagccg gacagggccg ccgcggcggc cggcaaggcc  180
gccgccgcct ccgtgttcga cctgcggcgg gagcccaaga tcccggcgcc attcgtgtgg  240
ccgcacgacg acgcgcggcc ggcgtcggcg gcggagctgg acgtgccgtt ggtggacgtg  300
ggcgtgctgc gcaatggcga ccgcgcgggg ctgcggcgcg ctgcggcgca ggtggccgcg  360
```

```
gcgtgcgcga cgcacgggtt cttccaggtg tgcgggcacg gcgtgggcgc ggacctggcg  420
cgcgcggcgc tggacggcgc cagtgacttc ttccggctgc cgctggcgga gaagcagcgc  480
gcccggcgcg tcccggggac cgtgtccggg tacacgagcg cgcacgccga ccggttcgcg  540
tccaagctcc cctggaagga gaccctctcc ttcgggttcc acgacggcgc cgcgtcgccc  600
gtcgtcgtcg actacttcgc cggcaccctc gggcaggact tcgaggcagt ggggcgggtg  660
taccagaggt actgcgagga gatgaaggct ctgtcgctga cgatcatgga gctcctggag  720
ctgagcctgg gcgtggagcg cggctactac cgcgacttct tcgaggacag ccgctccatc  780
atgcggtgca actactaccc gccgtgcccg gagccggagc gcacgctggg cacgggcccg  840
cactgcgacc ccaccgcgct gaccatcctc ctccaggacg acgtcggcgg gctcgaggtc  900
ctcgtcgacg gcgactggcg ccccgtccgc cccgtccccg gcgccatggt catcaacatc  960
ggcgacacct tcatggctct gtccaacggg cggtacaaga gctgcctgca ccgggcggtg  1020
gtgaaccagc ggcaggagcg gcggtcgctg gccttcttcc tgtgcccgcg cgaggaccgg  1080
gtggtgcgcc cgccggccag cggcgccgtc ggcgaggcgc cccgccgcta cccggacttc  1140
acctgggccg acctcatgcg cttcacgcag cgccactacc gcgccgacac ccgcacgctg  1200
gacgccttca cacgctggct ctcccacggc ccggcccagg acgcgccagt ggcggcggcg  1260
gcttccacct ag                                                    1272

SEQ ID NO: 90          moltype = AA  length = 423
FEATURE                Location/Qualifiers
source                 1..423
                       mol_type = protein
                       organism = Setaria italica
SEQUENCE: 90
MVSQAQQEPA LPHSSSTAKR AAASLMDARP AQPLLLRAPT PSIDLPASKP DRAAAAAGKA  60
AAASVFDLRR EPKIPAPFVW PHDDARPASA AELDVPLVDV GVLRNGDRAG LRRAAAQVAA  120
ACATHGFFQV CGHGVGADLA RAALDGASDF FRLPLAEKQR ARRVPGTVSG YTSAHADRFA  180
SKLPWKETLS FGFHDGAASP VVVDYFAGTL GQDFEAVGRV YQRYCEEMKA LSLTIMELLE  240
LSLGVERGYY RDFFEDSRSI MRCNYYPPCP EPERTLGTGP HCDPTALTIL LQDDVGGLEV  300
LVDGDWRPVR PVPGAMVINI GDTFMALSNG RYKSCLHRAV VNQRQERRSL AFFLCPREDR  360
VVRPPASGAV GEAPRRYPDF TWADLMRFTQ RHYRADTRTL DAFTRWLSHG PAQDAPVAAA  420
AST                                                              423

SEQ ID NO: 91          moltype = DNA  length = 2888
FEATURE                Location/Qualifiers
source                 1..2888
                       mol_type = genomic DNA
                       organism = Setaria italica
SEQUENCE: 91
tctcatggtg tcccaagcac agcaagagcc agctctgcct cacagcagca gcaccgccaa  60
gcgcgcagcc gcgtcactca tggacgccg cccggcccag cctctcctcc tccgcgcccc  120
gactcccagc attgacctcc ccgcgtccaa gccggacagg gccgccgcgg cggccggcaa  180
ggccgccgcc gcctccgtgt tcgacctgcg gcgggagccc aagatcccgg cgccattcgt  240
gtggccgcac gacgacgcgc ggccggcgtc ggcggcggag ctggacgtgc cgttggtgga  300
cgtgggcgtg ctgcgcaatg gcgaccgcgc ggggctgcgg cgcgctgcgg cgcaggtggc  360
cgcggcgtgc gcgacgcacg ggttcttcca ggtgtgcggg cacggcgtgg gcgcggacct  420
ggcgcgcgcg gcgctggacg gcgccagtga cttcttccgg ctgccgctgg cggagaagca  480
gcgcgcccgg cgcgtcccgg ggaccgtgtc cgggtacacg agcgcgcacg ccgaccggtt  540
cgcgtccaag ctcccctgga aggagaccct ctccttcggg ttccacgacg gcgccgcgtc  600
gcccgtcgtc gtcgactact tcgccggcac cctcgggcag gacttcgagg cagtggggta  660
agtatgtagg aatgaacttg gcacgcattg catccacatg gcgtgctgat cgaacgagct  720
gagccaaccg gcatgcacac atggcgtggc aggcgggtgt accagaggta ctgcgaggag  780
atgaaggctc tgtcgctgac gatcatggag ctcctggagc tgagcctggg cgtggagcgc  840
ggctactacc gcgacttctt cgaggacagc cgctccatca tgcggtgcaa ctactacccg  900
ccgtgcccgg agccggagcg cacgctgggc acgggcccgc actgcgaccc caccgcgctg  960
accatcctcc tccaggacga cgtcggcggg ctcgaggtcc tcgtcgacgg cgactggcgc  1020
cccgtccgcc ccgtccccgg cgccatggtc atcaacatcg gcgacacctt catggtacgg  1080
ccgccgctaa tccatccttt tgttgctctt atctcctctg gcgagtgcga gtaacgaaag  1140
cgctagctcc cctgctcctt gtcctgctct gtttcccaag tcctaatgga gctaaccggg  1200
cagactgcaa cacgcacgcg taggcatgtc acgtagccac cacttgcact gtgctgcgca  1260
gcgacgacgc aacgcggacg tgcgttcgag tcggttccat ctcggcgccg ctacacgcgg  1320
ccgcggctcc tagcctccta gggctccctg atccctatcc ccgagccctt ccgcgggaaa  1380
agttcgttgg cgacggcaga ggagagccga cgggtccgtg ccgttggagc gtggcggcag  1440
gagaggccgg gagggtgttt tgttgcgttg cgcggcggcg cggaggatgc gatggcgcgg  1500
gcgggcggcg ctttcggcgg tggcccccgc gacccacgtg cgcgcgcggt ctcgtcgcct  1560
tccctgtttt ggtgccacct ctctgtgtcc gggaatgggt tggcttagcg gcgaccgaga  1620
ccgggcggtg gtctggcctg ctcccggcgc ccatcccgcc tggtctctca tcctgctcct  1680
cctatgcgcg agggggcctg tagcggctgg agtacaagca gattggttgg gttgggttgc  1740
tgctgcttgg ctgttgcccg cccgctttct agccgtttcc gctcgccatc cggcacgcgg  1800
cgcccacgcc ggggctccag ctcggcccct ttggccgtgt gggtggcagg cacccctgca  1860
tcgtctcgtg cgtccggttt ccgcgcctgg ccccccgcct tgaggtttcc ctgtgctttt  1920
gacaagactt tcgtagatat atgtgtgtgt atgtgtgtgt gtgcgtgcgc gcgtgtgtgt  1980
atatatatat ataaataaat aacatctgtg aatgatggat tacacgtgta gctgaccggc  2040
tgattgtgtt cgcgtgtgtg tcttcgatgc attgcaggct ctgtccaacg ggcggtacaa  2100
gagctgcctg caccgggcgg tggtgaacca gcggcaggag cggcggtcgc tggccttctt  2160
cctgtgcccg cgcgaggacc gggtggtgcg cccgccggcc agcggcgccg tcggcgaggc  2220
gccccgccgc tacccggact tcacctgggc cgacctcatg cgcttcacgc agcgccacta  2280
ccgcgccgac acccgcacgc tggacgcctt cacacgctgg ctctcccacg gcccggccca  2340
ggacgcgcca gtggcggcgg cggcttccac ctagctagcg gcgcggatcc gaccgagccc  2400
attgacgacg ccgtcccttt ccgccgccgc cggggcccgc gcgggggttc accccacgtg  2460
```

```
cgcgcccagg tgggcgaggt ggcggcctcg tggcccgcgg gccccgcgcc gccttcccat  2520
ttttgggcgc tgccgccccg cgcgcatgcc ggatgcgtgc gtccacggcc tactgctgct  2580
actagtgtac atatacaaac atacatatat acgtagtata aatatataag caagcggccc  2640
ggtgcccctt ttcgttttct tgttttgtcg atcacaatct ctggattcga tggatggata  2700
aatgtttgta cgcatgcatg tagatgggct catgaaattt cagaatctgg aacggacgag  2760
gagctcacgt gcctcttccg tgtctggtag cggtagctgc gtgccaaatg tctggtgggc  2820
ccaaagaaat tctagtgcca cccgtccgga tccggcatcc gaaagttccc gacggttcga  2880
cacccgaa                                                           2888

SEQ ID NO: 92          moltype = DNA  length = 1567
FEATURE                Location/Qualifiers
source                 1..1567
                       mol_type = other DNA
                       organism = Oryza sativa
SEQUENCE: 92
tgcccagaca gctcgccctg cacacacaca cacactcaca ctcacacacg ctctcaactc  60
actcccgctc aacacagcgc tcacttctca tctccaatct catggtggcc gagcacccca  120
cgccaccaca gccgcaccaa ccaccgccca tggactccac cgccggctct ggcattgccg  180
ccccggcggc ggcggcggtg tgcgacctga ggatggagcc caagatcccg gagccattcg  240
tgtggccgaa cggcgacgcg aggccggcgt cggcggcgga gctggacatg cccgtggtcg  300
acgtgggcgt gctccgcgac ggcgacgccg aggggctgcg ccgcgccgcg gcgcaggtgg  360
ccgccgcgtg cgccacgcac gggttcttcc aggtgtccga gcacggcgtc gacgccgctc  420
tggcgcgcgc cgcgctcgac ggcgccagcg acttcttccg cctcccgctc gccgagaagc  480
gccgcgcgcg ccgcgtcccg ggcaccgtgt ccggctacac cagcgcccac gccgaccgct  540
tcgcctccaa gctcccatgg aaggagaccc tctccttcgg cttccacgac cgcgccgccg  600
cccccgtcgt cgccgactac ttctccagca ccctcggccc cgacttcgcg ccaatgggga  660
gggtgtacca gaagtactgc gaggagatga aggagctgtc gctgacgatc atggaactcc  720
tggagctgag cctgggcgtg gagcgaggct actacaggga gttcttcgcg gacagcagct  780
caatcatgcg gtgcaactac tacccgccat gcccggagcc ggagcggacg ctcggcacgg  840
gcccgcactg cgaccccacc gccctcacca tcctcctcca ggacgacgtc ggcggcctcg  900
aggtcctcgt cgacggcgaa tggcgccccg tcagccccgt ccccggcgcc atggtcatca  960
acatcggcga caccttcatg gcgctgtcga acgggaggta taagagctgc ctgcacaggg  1020
cggtggtgaa ccagcggcgg gagcggcggt cgctggcgtt cttcctgtgc ccgcgggagg  1080
acagggtggt gcggccgccg ccgagcgccg ccacgccgca gcactacccg gacttcacct  1140
gggccgacct catgcgcttc acgcagcgcc actaccgcgc cgacacccgc acgctcgacg  1200
ccttcacgcg ctggctcgcg ccgccggccg ccgacgccgc cgcgacggcg caggtcgagg  1260
cggccagctg atcgccgaac ggaacgaaac ggaacgaaca gaagccgatt tttggcgggg  1320
cccacgccca cgtgaggccc cacgtggaca gtgggcccgg gcggaggtgg cacccacgtg  1380
gaccgcgggc cccgcgccgc cttccaattt tggaccctac cgctgtacat attcatatat  1440
tgcaagaaga agcaaaacgt acgtgtgggt tgggttgggc ttctctctat tactaaaaaa  1500
aatataatgg aacgacggat gaatggatgc ttatttattt atctaaattg aattcgaatt  1560
cggctca                                                            1567

SEQ ID NO: 93          moltype = DNA  length = 1170
FEATURE                Location/Qualifiers
source                 1..1170
                       mol_type = other DNA
                       organism = Oryza sativa
SEQUENCE: 93
atggtggccg agcaccccac gccaccacag ccgcaccaac caccgcccat ggactccacc  60
gccggctctg gcattgccgc cccggcggcg gcggcggtgt gcgacctgag gatggagccc  120
aagatcccgg agccattcgt gtggccgaac ggcgacgcga ggccggcgtc ggcggcggag  180
ctggacatgc ccgtggtcga cgtgggcgtg ctccgcgacg gcgacgccga ggggctgcgc  240
cgcgccgcgg cgcaggtggc cgccgcgtgc gccacgcacg ggttcttcca ggtgtccgag  300
cacggcgtcg acgccgctct ggcgcgcgcc gcgctcgacg gcgccagcga cttcttccgc  360
ctcccgctcg ccgagaagcg ccgcgcgcgc cgcgtcccgg gcaccgtgtc cggctacacc  420
agcgcccacg ccgaccgctt cgcctccaag ctcccatgga aggagaccct ctccttcggc  480
ttccacgacc gcgccgccgc ccccgtcgtc gccgactact tctccagcac cctcggcccc  540
gacttcgcgc caatggggag ggtgtaccag aagtactgcg aggagatgaa ggagctgtcg  600
ctgacgatca tggaactcct ggagctgagc ctgggcgtgg agcgaggcta ctacagggag  660
ttcttcgcgg acagcagctc aatcatgcgg tgcaactact acccgccatg cccggagccg  720
gagcggacgc tcggcacggg cccgcactgc gaccccaccg ccctcaccat cctcctccag  780
gacgacgtcg gcggcctcga ggtcctcgtc gacggcgaat ggcgccccgt cagccccgtc  840
cccggcgcca tggtcatcaa catcggcgac accttcatgg cgctgtcgaa cgggaggtat  900
aagagctgcc tgcacagggc ggtggtgaac cagcggcggg agcggcggtc gctggcgttc  960
ttcctgtgcc cgcgggagga cagggtggtg cggccgccgc cgagcgccgc cacgccgcag  1020
cactacccgg acttcacctg ggccgacctc atgcgcttca cgcagcgcca ctaccgcgcc  1080
gacacccgca cgctcgacgc cttcacgcgc tggctcgcgc cgccggccgc cgacgccgcc  1140
gcgacggcgc aggtcgaggc ggccagctga                                   1170

SEQ ID NO: 94          moltype = AA  length = 389
FEATURE                Location/Qualifiers
source                 1..389
                       mol_type = protein
                       organism = Oryza sativa
SEQUENCE: 94
MVAEHPTPPQ PHQPPPMDST AGSGIAAPAA AAVCDLRMEP KIPEPFVWPN GDARPASAAE  60
LDMPVVDVGV LRDGDAEGLR RAAAQVAAAC ATHGFFQVSE HGVDAALARA ALDGASDFFR  120
LPLAEKRRAR RVPGTVSGYT SAHADRFASK LPWKETLSFG FHDRAAAPVV ADYFSSTLGP  180
```

-continued

```
DFAPMGRVYQ KYCEEMKELS LTIMELLELS LGVERGYYRE FFADSSSIMR CNYYPPCPEP  240
ERTLGTGPHC DPTALTILLQ DDVGGLEVLV DGEWRPVSPV PGAMVINIGD TFMALSNGRY  300
KSCLHRAVVN QRRERRSLAF FLCPREDRVV RPPPSAATPQ HYPDFTWADL MRFTQRHYRA  360
DTRTLDAFTR WLAPPAADAA ATAQVEAAS                                    389

SEQ ID NO: 95          moltype = DNA  length = 3140
FEATURE                Location/Qualifiers
source                 1..3140
                       mol_type = genomic DNA
                       organism = Oryza sativa
SEQUENCE: 95
tgcccagaca gctcgccctg cacacacaca cacactcaca ctcacacacg ctctcaactc  60
actcccgctc aacacagcgc tcacttctca tctccaatct catggtggcc gagcacccca  120
cgccaccaca gccgcaccaa ccaccgccca tggactccac cgccggctct ggcattgccg  180
ccccggcggc ggcggcggtg tgcgacctga ggatggagcc caagatcccg gagccattcg  240
tgtggccgaa cggcgacgcg aggccggcgt cggcggcgga gctggacatg cccgtggtcg  300
acgtgggcgt gctccgcgac ggcgacgccg aggggctgcg ccgcgccgcg gcgcaggtgg  360
ccgccgcgtg cgccacgcac gggttcttcc aggtgtccga gcacggcgtc gacgccgctc  420
tggcgcgcgc cgcgctcgac ggcgccagcg acttcttccg cctcccgctc gccgagaagc  480
gccgcgcgcg ccgcgtcccg ggcaccgtgt ccggctacac cagcgcccac gccgaccgct  540
tcgcctccaa gctcccatgg aaggagaccc tctccttcgg cttccacgac cgcgccgccg  600
cccccgtcgt cgccgactac ttctccagca ccctcggccc cgacttcgcg ccaatggggt  660
aattaaaacg atggtggacg acattgcatt tcaaattcaa aacaaattca aaacacaccg  720
accgagatta tgctgaattc aaacgcgttt gtgcgcgcag gagggtgtac cagaagtact  780
gcgaggagat gaaggagctg tcgctgacga tcatggaact cctggagctg agcctgggcg  840
tggagcgagg ctactacagg gagttcttcg cggacagcag ctcaatcatg cggtgcaact  900
actacccgcc atgcccggag ccggagcgga cgctcggcac gggcccgcac tgcgacccca  960
ccgccctcac catcctcctc caggacgacg tcggcggcct cgaggtcctc gtcgacggcg  1020
aatggcgccc cgtcagcccc gtccccggcg ccatggtcat caacatcggc gacaccttca  1080
tggtaaacca tctcctattc tcctctcctc tgttctcctc tgcttcgaag caacagaaca  1140
agtaattcaa gctttttttt ctctctcgcg cgaaattgac gagaaaaata agatcgtggt  1200
aggggcgggg ctttcagctg aaagcgggaa gaaaccgacc tgacgtgatt tctctgttcc  1260
aatcacaaac aatggaatgc cccactcctc catgtgttat gatttatctc acatcttata  1320
gttaatagga gtaagtaaca agctactttt ttcatattat agttcgtttg attttttttt  1380
tttaaagttt ttttagtttt atccaaattt attgaaaaac ttagcaacgt ttataatacc  1440
aaattagtct catttagttt aatattgtat atattttgat aatatattta tgttatatta  1500
aaaatattac tatatttttc tataaacatt attaaaagcc atttataata taaaatggaa  1560
ggagtaatta atatggatct cccccgacat gagaatattt tccgatggtg tgacgacgcc  1620
atgtaagctt cggtgggcct ggacggccag aggtgccaac agccacgtcc aacaacccct  1680
gggtcccccc ctaacactcc aaacagtagt gagtagtgtc tcgtcgcgtt ttagtatttg  1740
atgacaaaca aagtgtgagt tgagttagcc accaccaact tgcacacgag cacatacatt  1800
tgtgtccatt ctcgccagtc acttccatct ctagtcctaa ctcctatcta gcgatgtaag  1860
cggataattt catcatccgt atataaacct gtttgttata gttaatttcc tatataatac  1920
tataacagta tacattttaa aagaaaacaa aattaggata aacaggccct gctcctatcc  1980
atccatggca cttggaagga ccagactcgg tcatgccatg ccaagccaag atatgggtta  2040
tggaagagta gagaagagga gagatgagag ataagcatgc gttctcctcc tcgttggatg  2100
tgtattttgg agggatttgt gtagtagtag cagcggcgcc gcggggacgg atgcggatgg  2160
tggcgctttc ggtggcgttt tcccgggggg gttttggttt ggcgcttggg ggggatggca  2220
tggcgcggcg tgcggctgca cgccacacac acgcgcgcgc acgcacgtac gtcgtcgtcg  2280
ccgcgggcgg acggtagctt agggtggtgt gttccgcgcg cgggcgcgga ttgttccatg  2340
ccgatcgatt tggcgccacc ctcgccgcgg ctcttgtcgc gtcgtgcgcc tctctcgcgc  2400
ggtttgtcct tgtcgcgttg ctcagccggc gacgggggca cggacattgg cgatgtagcc  2460
ctgcacgtgt cggcctctcc gttgatgaat gatgatgtat gtatgtattt ttttttgtct  2520
gaaggaattt gtggggaatt gttgtgtgtg caggcgctgt cgaacgggag gtataagagc  2580
tgcctgcaca gggcggtggt gaaccagcgg cgggagcggc ggtcgctggc gttcttcctg  2640
tgcccgcggg aggacagggt ggtgcggccg ccgccgagcg ccgccacgcc gcagcactac  2700
ccggacttca cctgggccga cctcatgcgc ttcacgcagc gccactaccg cgccgacacc  2760
cgcacgctcg acgccttcac gcgctggctc gcgccgccgg ccgccgacgc cgccgcgacg  2820
gcgcaggtcg aggcggccag ctgatcgccg aacggaacga aacggaacga acagaagccg  2880
atttttggcg gggcccacgc ccacgtgagg ccccacgtgg acagtgggcc cgggcggagg  2940
tggcacccac gtggaccgcg ggccccgcgc cgccttccaa ttttggaccc taccgctgta  3000
catattcata tattgcaaga agaagcaaaa cgtacgtgtg ggttgggttg ggcttctctc  3060
tattactaaa aaaaatataa tggaacgacg gatgaatgga tgcttattta tttatctaaa  3120
ttgaattcga attcggctca                                              3140

SEQ ID NO: 96          moltype = DNA  length = 1170
FEATURE                Location/Qualifiers
source                 1..1170
                       mol_type = other DNA
                       organism = Triticum aestivum
SEQUENCE: 96
atggacacca gccctgcaac tcccctgctc ctccagcctc ctgctcccag cattgacccg  60
ttcgccgcca aggcggccgt caacaagggc ggcggcgcgg caaccgcggt gtacgacctc  120
cggagggagc cgaagatccc cgccccgttc gtgtggccgc acgccgaggt gcgccccacc  180
acggcccagg agctggccgt gccggtggtg gacgtgggcg tgctgcgcaa tggcgacgcc  240
gcggggctcc gccgcgccgt ggcgcaggtg gccgcggcgt gcgccacgca cgggttcttc  300
caggtgtccg ggcacggcgt ggacgaggcc ctggcgcgcg cggcgctgga cggcgcgagc  360
ggcttcttcc ggctgccgct ggccgagaag cagcgcgcgc ggcgcgtccc ggggaccgtg  420
tccgggtaca cgagcgcgca cgccgaccgg ttcgcctcca agctcccctg gaaggagacc  480
```

```
ctctccttcg gcttccacga ccgcgccggc gccgcgcccg tcgtggtgga ctacttcacc  540
agcaccctcg ggccggacta cgagccaatg gggagggtgt accaggagta ctgcgggaag  600
atgaaggagc tgtcgctgag gatcatggag ctgctggagc tgagccaggg cgtggagaag  660
cgcgggtact accgggagtt cttcgcggac agcagctcca tcatgcggtg caactactac  720
ccgccgtgcc cggagccgga gcgcacgctg ggcacgggcc cgcactgcga ccccacggcg  780
ctcaccatcc tactgcagga cgacgtgggc gggctggagg tcctcgtcga cggcgactgg  840
cgccccgtcc gccccgtccc cggcgccatg gtcatcaaca tcggcgacac cttcatggcg  900
ctgtcgaacg ggcggtacaa gagctgcctg caccgcgcgg tggtgaaccg gcggcaggag  960
cggcggtcgc tggccttctt cctgtgcccg cgcgaggacc gcgtggtgcg gccgccgccg  1020
ggcctgagga gcccgcggcg gtacccggac ttcacctggg ctgacctcat gcgcttcacg  1080
cagcgccact accgcgccga cacgcgcacc ctcgacgcct tcacccagtg gttctcctcc  1140
tcctcctcct cggcccagga ggcggcctga                                  1170
```

```
SEQ ID NO: 97          moltype = AA  length = 389
FEATURE                Location/Qualifiers
source                 1..389
                       mol_type = protein
                       organism = Triticum aestivum
SEQUENCE: 97
MDTSPATPLL LQPPAPSIDP FAAKAAVNKG GGAATAVYDL RREPKIPAPF VWPHAEVRPT  60
TAQELAVPVV DVGVLRNGDA AGLRRAVAQV AAACATHGFF QVSGHGVDEA LARAALDGAS  120
GFFRLPLAEK QRARRVPGTV SGYTSAHADR FASKLPWKET LSFGFHDRAG AAPVVVDYFT  180
STLGPDYEPM GRVYQEYCGK MKELSLRIME LLELSQGVEK RGYYREFFAD SSSIMRCNYY  240
PPCPEPERTL GTGPHCDPTA LTILLQDDVG GLEVLVDGDW RPVRPVPGAM VINIGDTFMA  300
LSNGRYKSCL HRAVVNRRQE RRSLAFFLCP REDRVVRPPP GLRSPRRYPD FTWADLMRFT  360
QRHYRADTRT LDAFTQWFSS SSSSAQEAA                                   389
```

```
SEQ ID NO: 98          moltype = DNA  length = 3050
FEATURE                Location/Qualifiers
source                 1..3050
                       mol_type = genomic DNA
                       organism = Triticum aestivum
SEQUENCE: 98
ctcatggtgc tccagaccgc tcagcaagaa ccatccctga cgcgtccgcc tcactgcagc  60
gtcgccagcg cgcgctcgcc ggcggccatg gacaccagcc ctgcaactcc cctgctcctc  120
cagcctcctg ctcccagcat tgacccgttc gccgccaagg cggccgtcaa caagggcggc  180
ggcgcggcaa ccgcggtgta cgacctccgg agggagccga agatccccgc cccgttcgtg  240
tggccgcacg ccgaggtgcg ccccaccacg gcccaggagc tggccgtgcc ggtggtggac  300
gtgggcgtgc tgcgcaatgg cgacgccgcg gggctccgcc gcgccgtggc gcaggtggcc  360
gcggcgtgcg ccacgcacgg gttcttccag gtgtccgggc acggcgtgga cgaggccctg  420
gcgcgcgcgg cgctggacgg cgcgagcggc ttcttccggc tgccgctggc cgagaagcag  480
cgcgcgcggc gcgtcccggg gaccgtgtcc gggtacacga gcgcgcacgc cgaccggttc  540
gcctccaagc tcccctggaa ggagaccctc tccttcggct tccacgaccg cgccggcgcc  600
gcgcccgtcg tggtggacta cttcaccagc accctcgggc cggactacga gccaatgggg  660
taatatatcc acccgcccac acccctatcc ggccagcacg aatccatccc cgccactgca  720
ttttttttcct tttgtttccg cgcgaccgta cgttcgatcg gcgcccacgt acgtacgtgc  780
gtacgcagta gcagtacttg aagccgccgt actacgtgct gagtagtgac aactgaacac  840
gtgcaggagg gtgtaccagg agtactgcgg gaagatgaag gagctgtcgc tgaggatcat  900
ggagctgctg gagctgagcc agggcgtgga gaagcgcggg tactaccggg agttcttcgc  960
ggacagcagc tccatcatgc ggtgcaacta ctacccgccg tgcccggagc cggagcgcac  1020
gctgggcacg ggcccgcact gcgaccccac ggcgctcacc atcctactgc aggacgacgt  1080
gggcgggctg gaggtcctcg tcgacggcga ctggcgcccc gtccgccccg tccccggcgc  1140
catggtcatc aacatcggcg acaccttcat ggtaattact cctctctcag cgttgctttc  1200
gctgattaat tgcagaaaca gtagtcaact acccatgctc tgttccgctg tgctctgctt  1260
cccaacgagc gaaccggccc ataaaaactg ccttgctgtc ttggaaccaa gaggaaaggg  1320
accgtgggag cctaccgaca cgacgtgatt gcactctgct tcctaacaag cgagccgccg  1380
gtagggctat caccgtaagg gctcctttga ttcaaaggaa tttcttagga tttctgaagg  1440
attgaaatcc ttaggatttt ttcctatgtt ggtacttcga ttcataggat tgaatcccat  1500
aggatttttt tcctatgaaa tcttctgtac tacatttcat aggaaatcta acatccactc  1560
caacctttttt ttatatttcc tttgtttttc atgtgccatc aaacactcct tgttaatcct  1620
ataggattca agtgggcatg ccactccaat cctatacttt tcccattcct acgttttcaa  1680
aatcctacga atcaaagagg ccctaaagct gctgacatga cgtgattttt tttttctttt  1740
ctttctttct ttctcagctc caatcaacgc tggttattag atcattagag tggacaggtt  1800
gaattaacat gcagtagtta gtagttagca gccacaaacg ggtcccgttc tctgaagtct  1860
gaactgacat aagtcctgat catcgaccat tctttgcttc ctaggacgat gcctgttgga  1920
acttgcgtcc aatgcccgtt agggagtggt aattgtcatc acttttagac tcgtcgattc  1980
cactgatgaa gacgtagcac atggatgagc caacgtatcc gtttctagtg gtctcgaaaa  2040
gtagggtttc attcattcta tctatctatc cgtccgtcca aaagggctgc gatgcgagca  2100
cttgagtcgg agccaatcag agcgcgagaa aagatagggg gggtagcaag ccatgtcgga  2160
ggggcgtttg cttccggcag gtttggattc ttgtggtagg cgggcggctc tgtacagtag  2220
cggcggtgac ggtgaggtgg cggcgctttc ggtggcgggc caacccaggt gcatgcacgc  2280
gcgctcgtcg ttttcccgcc tgaatctgcc gctgcgccca tggcaagggg gtgggtgctg  2340
ccgccgggcg atggagtaga tcacggtcgc cgtcgggctc ggccagttga tcacggttcg  2400
ttcgtgcggt actaggttcc ccccacggcac tgtgactgca tcgttccggc cctcgccatt  2460
ggcgatcggg caatctcctg ttcatccgtc gctgttgatt cctcggccac gatagaccat  2520
gcgcgtgccg gtcgtcgccc cgtcgcgctc gcttcacgtg ctcgtcgcgt ggctcccgtc  2580
ccacacgagg ccgccgcttt ctgacccagt ggagcgcgtg atttacagtt tatatatgtc  2640
gctgcatttt tctttttgtg tgctgctcat tttgcttgga cggagaccgg gaacgattag  2700
ccacggatct aacgcgttgt tgcttgtttt caatgcatgc atgcaggcgc tgtcgaacgg  2760
```

```
gcggtacaag agctgcctgc accgcgcggt ggtgaaccgg cggcaggagc ggcggtcgct  2820
ggccttcttc ctgtgcccgc gcgaggaccg cgtggtgcgg ccgccgccgg gcctgaggag  2880
cccgcggcgg tacccggact tcacctgggc tgacctcatg cgcttcacgc agcgccacta  2940
ccgcgccgac acgcgcaccc tcgacgcctt cacccagtgg ttctcctcct cctcctcctc  3000
ggcccaggag gcggcctgat tctgctctgc cacgaaacga tcggtccaca             3050

SEQ ID NO: 99          moltype = DNA  length = 1486
FEATURE                Location/Qualifiers
source                 1..1486
                       mol_type = other DNA
                       organism = Hordeum vulgare
SEQUENCE: 99
gaccagtagc atatagtttt tcttgtgttt gccatggtgg acgtgtcgaa ctttgtagaa  60
gccaatggca atgcagcagt atcgattcct gccatggaag ttgctgggag tcctcacgtc  120
ccgttcgttc ctcgggacgc gaacgcgaca gacagcaaga atgccaagga cgtcctcgac  180
ctctggcggc agcagaaaca aatcccggct cccttcatct ggccccacgc cgacgcgcgg  240
ccgtcgtcga tcttggagct ggacgtgccc gtggtcgaca tcggcgcggc cctgcacagc  300
gccgccggga tggcccgcgc cgcggcgcag gtggccgagg catgcgcgag ccacggcttc  360
ttccaggtga ccgggcacgg cgtcgacccc gcgctggccc aagcagcgct cgacggcgca  420
gcggacttct tccgcctgcc gctcgccacc aagcagcgcg cccgccgatc cccggggacc  480
gtcaaagggt acgcctccgc ccacgccgac cgcttcgccg ccaagcttcc ctggaaggag  540
actctctcct tcatccacaa ccacgtccac gaggacgtcg gcgcccgcgc aagcagtcac  600
gtcgtcgact acttcacctc cgcccttggc gacgacttca tgcacctagg ggaggtgtac  660
caggagtact gtgaggcgat ggaggacgcg tcgctggcga taatggaggt gctgggggtg  720
agcctggggc tggggagagg gtactacagg gacttcttcg ccgacggcag ctccatcatg  780
aggtgcaact actacccgcg gtgcccggag ccggaccgga cgctggggac ggggccgcac  840
tgcgacccgt cggcgctgac catcctgctg caggacggcg aggtggacgg gctccaggtg  900
ctcgtcgacg gcgcatggcg ctccgtgcgg cccaagcccg gcgagctcgt cgtaaacatc  960
ggcgacacct tcatggcgct gtcgaacggc cggtacaaga gctgcctcca ccgcgcggtg  1020
gtgcaccggg agaaggagcg ccggtcgctg gcctacttcc tcgcccccgcg ggaggaccgg  1080
gtggttcgcc cgccgccttc gccggcgccg gcgccgcggc tctacccgga cttcacctgg  1140
gcggagctca tgcgattcac gcagcgccac taccgcgccg acgcccgcac gctcgacgcc  1200
ttcgcgtgct ggctcgacct gcccagctgc ccccaccacgc cccaggccca agggactgtc  1260
tagtgtctgt gatgtatcat ctgtctcagc tgttgtatac gaccacttgt gtctgctagc  1320
tctgcgcttg tgtttcttat gtgagctaac taactaaata gtgtgtatat ttcttgccgc  1380
gccttatgca agccctagtc tagaacatgt aataattaac ttaagcatat acgttgatct  1440
ttggtgtatt tttcatattt ccttcataat gaataatcta ttatgc                 1486

SEQ ID NO: 100         moltype = DNA  length = 1230
FEATURE                Location/Qualifiers
source                 1..1230
                       mol_type = other DNA
                       organism = Hordeum vulgare
SEQUENCE: 100
atggtggacg tgtcgaactt tgtagaagcc aatggcaatg cagcagtatc gattcctgcc  60
atggaagttg ctgggagtcc tcacgtcccg ttcgttcctc gggacgcgaa cgcgacagac  120
agcaagaatg ccaaggacgt cctcgacctc tggcggcagc agaaacaaat cccggctccc  180
ttcatctggc cccacgccga cgcgcggccg tcgtcgatct tggagctgga cgtgcccgtg  240
gtcgacatcg gcgcggccct gcacagcgcc gccgggatgg cccgcgccgc ggcgcaggtg  300
gccgaggcat gcgcgagcca cggcttcttc caggtgaccg ggcacggcgt cgaccccgcg  360
ctggcccaag cagcgctcga cggcgcagcg gacttcttcc gcctgccgct cgccaccaag  420
cagcgcgccc gccgatcccc ggggaccgtc aaagggtacg cctccgccca cgccgaccgc  480
ttcgccgcca agcttccctg gaaggagact ctctccttca tccacaacca cgtccacgag  540
gacgtcggcg cccgcgcaag cagtcacgtc gtcgactact tcacctccgc ccttggcgac  600
gacttcatgc acctagggga ggtgtaccag gagtactgtg aggcgatgga ggacgcgtcg  660
ctggcgataa tggaggtgct gggggtgagc ctggggctgg ggagagggta ctacagggac  720
ttcttcgccg acggcagctc catcatgagg tgcaactact acccgcggtg cccggagccg  780
gaccggacgc tggggacggg gccgcactgc gacccgtcgg cgctgaccat cctgctgcag  840
gacggcgagg tggacgggct ccaggtgctc gtcgacggcg catggcgctc cgtgcggccc  900
aagcccggcg agctcgtcgt aaacatcggc gacaccttca tggcgctgtc gaacggccgg  960
tacaagagct gcctccaccg cgcggtggtg caccgggaga aggagcgccg gtcgctggcc  1020
tacttcctcg ccccgcggga ggaccgggtg gttcgcccgc cgccttcgcc ggcgccggcg  1080
ccgcggctct acccggactt cacctgggcg gagctcatgc gattcacgca gcgccactac  1140
cgcgccgacg cccgcacgct cgacgccttc gcgtgctggc tcgacctgcc cagctgcccc  1200
accacgcccc aggcccaagg gactgtctag                                   1230

SEQ ID NO: 101         moltype = AA  length = 409
FEATURE                Location/Qualifiers
source                 1..409
                       mol_type = protein
                       organism = Hordeum vulgare
SEQUENCE: 101
MVDVSNFVEA NGNAAVSIPA MEVAGSPHVP FVPRDANATD SKNAKDVLDL WRQQKQIPAP  60
FIWPHADARP SSILELDVPV VDIGAALHSA AGMARAAAQV AEACASHGFF QVTGHGVDPA  120
LAQAALDGAA DFFRLPLATK QRARRSPGTV KGYASAHADR FAAKLPWKET LSFIHNHVHE  180
DVGARASSHV VDYFTSALGD DFMHLGEVYQ EYCEAMEDAS LAIMEVLGVS LGLGRGYYRD  240
FFADGSSIMR CNYYPRCPEP DRTLGTGPHC DPSALTILLQ DGEVDGLQVL VDGAWRSVRP  300
KPGELVVNIG DTFMALSNGR YKSCLHRAVV HREKERRSLA YFLAPREDRV VRPPSPAPA   360
PRLYPDFTWA ELMRFTQRHY RADARTLDAF ACWLDLPSCP TTPQAQGTV              409
```

SEQ ID NO: 102 moltype = DNA length = 1423
FEATURE Location/Qualifiers
source 1..1423
mol_type = other DNA
organism = Sorghum bicolor
SEQUENCE: 102
cctctcatca caggccccag cctcactctt ctcacagcaa gacatcgcag cctcacaacc 60
acacagcaac gtgatcgcca tgggcgggct caccatggag caggccttcg tgcaggcccc 120
cgagcaccgc cccaagccca ccgtcaccga ggccaccggc atcctggtca tcgacctctc 180
gcctctcacc gccagcgaca ccgacgcggc cgcggtggac gcgctggccg ccgaggtggg 240
cgcggcgagc cgggactggg gcttcttcgt ggtggttggc cacggcgtgc ccgcggagac 300
cgtggcgcgc gcgacggcgg cgcagcgcgc gttcttcgcg ctgccggcgg agcggaaggc 360
cgccgtgcgg aggagcgagg cggagccgct cgggtactac gagtcggagc acaccaagaa 420
cgtcagggac tggaaggagg tgttcgacct cgtcccgcgc gatccgccgc cgccagcagc 480
cgtggccgac ggcgagctcg tcttcaagaa caagtggccc caggatctgc cgggcttcag 540
agaggcgctg gaggagtacg cggcagcgat ggaggagctg tcgttcaagc tgctggagct 600
gatcgcccgg agcttgaagc tgaggcccga ccggctgcac ggcttcttca aggaccagac 660
gacgttcatc cggctgaacc actaccctcc atgcccgagc ccggacctgg cgctgggagt 720
ggggcggcac aaggacgcgg gggcgctgac catcctgtac caggacgaag tgggcgggct 780
ggacgtccgg cggcgctcct ccgacggcgg cggcggcgag tgggtgcggg tgaggcccgt 840
gccggagtcg ttcgtcatca acgtcggcga cctcgtccag gtgtggagca acgacaggta 900
cgagagcgcg gagcaccggg tgtcggtgaa ctcggcgagg gagaggttct ccatgcccta 960
cttcttcaac ccggcgagct acaccatggt ggagccggtg gaggagctgg tgagcgacga 1020
cgacccgccc aggtacgacg cctacagctg gggcgagttc ttcagcacca ggaagaacag 1080
caacttcaag aagctcagcg tggagaacat tcagatcgcg catttcaaga agaccctcgt 1140
cctcgcctag ataagcagca ggatactaca ggtctacagg actaggacaa gccgatcgag 1200
gtgaccggcc gtcgtcttca gattcagtat atgcgtgtcg ccgttcgtgt tagaacaaat 1260
taataatgtg cgcgctgtgt gctgtgtgtg tggagtaaaa aaaaactaaa catggatgtg 1320
catgttcaaa aaaaaaaaca tggatgcgag tatgtttggg aataataaca ggcttgtgac 1380
ggtctggttt atttgcaaat tcaaaccgaa ttggttgatc ttc 1423

SEQ ID NO: 103 moltype = DNA length = 1071
FEATURE Location/Qualifiers
source 1..1071
mol_type = other DNA
organism = Sorghum bicolor
SEQUENCE: 103
atgggcgggc tcaccatgga gcaggccttc gtgcaggccc ccgagcaccg ccccaagccc 60
accgtcaccg aggccaccgg catcctggtc atcgacctct cgcctctcac cgccagcgac 120
accgacgcgg ccgcggtgga cgcgctggcc gccgaggtgg gcgcggcgag ccgggactgg 180
ggcttcttcg tggtggttgg ccacggcgtg cccgcggaga ccgtggcgcg cgcgacggcg 240
gcgcagcgcg cgttcttcgc gctgccggcg gagcggaagg ccgccgtgcg gaggagcgag 300
gcggagccgc tcgggtacta cgagtcggag cacaccaaga acgtcaggga ctggaaggag 360
gtgttcgacc tcgtcccgcg cgatccgccg ccgccagcag ccgtggccga cggcgagctc 420
gtcttcaaga acaagtggcc ccaggatctg ccgggcttca gagaggcgct ggaggagtac 480
gcggcagcga tggaggagct gtcgttcaag ctgctggagc tgatcgcccg gagcttgaag 540
ctgaggcccg accggctgca cggcttcttc aaggaccaga cgacgttcat ccggctgaac 600
cactaccctc catgcccgag cccggacctg gcgctgggag tggggcggca caaggacgcg 660
ggggcgctga ccatcctgta ccaggacgaa gtgggcgggc tggacgtccg gcggcgctcc 720
tccgacggcg gcggcggcga gtgggtgcgg gtgaggcccg tgccggagtc gttcgtcatc 780
aacgtcggcg acctcgtcca ggtgtggagc aacgacaggt acgagagcgc ggagcaccgg 840
gtgtcggtga actcggcgag ggagaggttc tccatgccct acttcttcaa cccggcgagc 900
tacaccatgg tggagccggt ggaggagctg gtgagcgacg acgacccgcc caggtacgac 960
gcctacagct ggggcgagtt cttcagcacc aggaagaaca gcaacttcaa gaagctcagc 1020
gtggagaaca ttcagatcgc gcatttcaag aagaccctcg tcctcgccta g 1071

SEQ ID NO: 104 moltype = AA length = 356
FEATURE Location/Qualifiers
source 1..356
mol_type = protein
organism = Sorghum bicolor
SEQUENCE: 104
MGGLTMEQAF VQAPEHRPKP TVTEATGILV IDLSPLTASD TDAAAVDALA AEVGAASRDW 60
GFFVVVGHGV PAETVARATA AQRAFFALPA ERKAAVRRSE AEPLGYYESE HTKNVRDWKE 120
VFDLVPRDPP PPAAVADGEL VFKNKWPQDL PGFREALEEY AAAMEELSFK LLELIARSLK 180
LRPDRLHGFF KDQTTFIRLN HYPPCPSPDL ALGVGRHKDA GALTILYQDE VGGLDVRRRS 240
SDGGGGEWVR VRPVPESFVI NVGDLVQVWS NDRYESAEHR VSVNSARERF SMPYFFNPAS 300
YTMVEPVEEL VSDDDPPRYD AYSWGEFFST RKNSNFKKLS VENIQIAHFK KTLVLA 356

SEQ ID NO: 105 moltype = DNA length = 1499
FEATURE Location/Qualifiers
source 1..1499
mol_type = genomic DNA
organism = Sorghum bicolor
SEQUENCE: 105
cctctcatca caggccccag cctcactctt ctcacagcaa gacatcgcag cctcacaacc 60
acacagcaac gtgatcgcca tgggcgggct caccatggag caggccttcg tgcaggcccc 120
cgagcaccgc cccaagccca ccgtcaccga ggccaccggc atcctggtca tcgacctctc 180

```
gcctctcacc gccagcgaca ccgacgcggc cgcggtggac gcgctggccg ccgaggtggg  240
cgcggcgagc cgggactggg gcttcttcgt ggtggttggc cacggcgtgc ccgcggagac  300
cgtggcgcgc gcgacggcgg cgcagcgcgc gttcttcgcg ctgccggcgg agcggaaggc  360
cgccgtgcgg aggagcgagg cggagccgct cgggtactac gagtcggagc acaccaagaa  420
cgtcagggac tggaaggagg tgttcgacct cgtcccgcgc gatccgccgc cgccagcagc  480
cgtggccgac ggcgagctcg tcttcaagaa caagtggccc caggatctgc cgggcttcag  540
gtgacgaaat caacttatct tttcgatcat attttaccat ttaatagttt aacaataatt  600
gaactttttt ttgcagagag gcgctggagg agtacgcggc agcgatggag gagctgtcgt  660
tcaagctgct ggagctgatc gcccggagct tgaagctgag gcccgaccgg ctgcacggct  720
tcttcaagga ccagacgacg ttcatccggc tgaaccacta ccctccatgc ccgagcccgg  780
acctggcgct gggagtgggg cggcacaagg acgcgggggc gctgaccatc ctgtaccagg  840
acgaagtggg cgggctggac gtccggcgga gctcctccga cggcggcggc ggcgagtggg  900
tgcgggtgag gcccgtgccg gagtcgttcg tcatcaacgt cggcgacctc gtccaggtgt  960
ggagcaacga caggtacgag agcgcggagc accgggtgtc ggtgaactcg gcgagggaga  1020
ggttctccat gccctacttc ttcaacccgg cgagctacac catggtggag ccggtggagg  1080
agctggtgag cgacgacgac ccgcccaggt acgacgccta cagctggggc gagttcttca  1140
gcaccaggaa gaacagcaac ttcaagaagc tcagcgtgga gaacattcag atcgcgcatt  1200
tcaagaagac cctcgtcctc gcctagataa gcagcaggat actacaggtc tacaggacta  1260
ggacaagccg atcgaggtga ccggccgtcg tcttcagatt cagtatatgc gtgtcgccgt  1320
tcgtgttaga acaaattaat aatgtgcgcg ctgtgtgctg tgtgtgtgga gtaaaaaaaa  1380
actaaacatg gatgtgcatg ttcaaaaaaa aaaacatgga tgcgagtatg tttgggaata  1440
ataacaggct tgtgacggtc tggtttattt gcaaattcaa accgaattgg ttgatcttc   1499
```

```
SEQ ID NO: 106          moltype = DNA  length = 1490
FEATURE                 Location/Qualifiers
source                  1..1490
                        mol_type = other DNA
                        organism = Setaria italica
SEQUENCE: 106
accccacaca cacacccgca ctgcatgcgg cgtcctagct aatcagtcgc tgctggcagc  60
ctcacaagtc acacaactcc gacgcaggaa agctcgatcc atcgccatgg gcggcttctc  120
catggatcag tccttcgtgc aggcccccga gcaccgcccc aagcccaccg tcaccgaggc  180
cacgggcatc ccgctcatcg acctctcgcc actcaccggc ggtggcggcg gcgacgcggc  240
cgccgtggac gcgctggccg ccgaggtggg cgcggcgagc cgggactggg gcttcttcgt  300
ggtggtgggg cacggtgtgc cggcggagac cgtggcgcgc gccacggagg cgcagcgcgc  360
gttcttcgcc ctgccggcgg agcggaaagc cgccgtgcgg aggagcgagg cggagccgct  420
cgggtactac gagtcggagc acaccaagaa cgtcagggac tggaaggagg tgtacgacct  480
cgtcccgggc gggcttcagc cgccgatagc cgtggccgac ggcgaggtcg tgttcgaaaa  540
caagtggccc gaagacctgc cgggattcag agaggcgttg gaggagtaca tgcaagcgat  600
ggaagagctg gcattcaaga tactggagct gatcgcccgg agcctgaacc tgaggcctga  660
cagactgcac ggcttcttca aggaccagac caccttcatc cggctcaacc actaccctcc  720
ctgcccgagc cccgacctcg ccctcggcgt cggccggcac aaggacgccg gagcactgac  780
catcctctac caggacgacg tcggcgggct cgacgtccgg cgccgttccg acggcgattg  840
ggtccgcgtc aagcctgtcc ccgactcctt catcatcaac gtcggcgacc tcatccaggt  900
ttggagcaac gacaggtacg agagcgcgga gcaccgggtt acggtgaact cggccaagga  960
gaggttctcc aggccctact tcttcaaccc ggcgggctac accatggtgg agccggtgga  1020
ggagctggtg agcgaggagg acccgccccg gtacgacgcc tacaactggg gcaacttctt  1080
cagcaccagg aagaacagca acttcaagaa gctgagcgtg gagaacatcc agatcgcgca  1140
tttcaagagg agcgtcgccg cctaggatac gcacagaaag atcccatatg ctgacttgct  1200
gatgaggcga caggcggccg tgtcgtcttc agattcagag actgggagta aacatttgtg  1260
cggtgttctg taatcgtgat gtgacgagaa ctttagatat atgtttggaa ataacagcct  1320
tgtgttggtc tggcttatcc gcaaagtcaa gattttcttc tacattttgg gattattgtt  1380
ggtaagcatt aagcaacgtc cagttcttac ttcttagctc gatcagtgga cgtaggaccg  1440
gcctctgatg acaagggtga tttatgagaa atgtcatgta tatatgttcc             1490
```

```
SEQ ID NO: 107          moltype = DNA  length = 1059
FEATURE                 Location/Qualifiers
source                  1..1059
                        mol_type = other DNA
                        organism = Setaria italica
SEQUENCE: 107
atgggcggct tctccatgga tcagtccttc gtgcaggccc ccgagcaccg ccccaagccc  60
accgtcaccg aggccacggg catcccgctc atcgacctct cgccactcac cggcggtggc  120
ggcggcgacg cggccgccgt ggacgcgctg gccgccgagg tgggcgcggc gagccgggac  180
tggggcttct tcgtggtggt ggggcacggt gtgccggcgg agaccgtggc gcgcgccacg  240
gaggcgcagc gcgcgttctt cgccctgccg gcggagcgga aagccgccgt gcggaggagc  300
gaggcggagc cgctcgggta ctacgagtcg gagcacacca agaacgtcag ggactggaag  360
gaggtgtacg acctcgtccc gggcgggctt cagccgccga tagccgtggc cgacggcgag  420
gtcgtgttcg aaaacaagtg gcccgaagac ctgccgggat tcagagaggc gttggaggag  480
tacatgcaag cgatggaaga gctggcattc aagatactgg agctgatcgc ccggagcctg  540
aacctgaggc ctgacagact gcacggcttc ttcaaggacc agaccacctt catccggctc  600
aaccactacc ctccctgccc gagccccgac ctcgccctcg gcgtcggccg gcacaaggac  660
gccggagcac tgaccatcct ctaccaggac gacgtcggcg ggctcgacgt ccggcgccgt  720
tccgacggcg attgggtccg cgtcaagcct gtccccgact ccttcatcat caacgtcggc  780
gacctcatcc aggtttggag caacgacagg tacgagagcg cggagcaccg ggttacggtg  840
aactcggcca aggagaggtt ctccaggccc tacttcttca acccggcggg ctacaccatg  900
gtggagccgg tggaggagct ggtgagcgag gaggacccgc cccggtacga cgcctacaac  960
tggggcaact tcttcagcac caggaagaac agcaacttca agaagctgag cgtggagaac  1020
atccagatcg cgcatttcaa gaggagcgtc gccgcctag                          1059
```

```
SEQ ID NO: 108          moltype = AA  length = 352
FEATURE                 Location/Qualifiers
source                  1..352
                        mol_type = protein
                        organism = Setaria italica
SEQUENCE: 108
MGGFSMDQSF VQAPEHRPKP TVTEATGIPL IDLSPLTGGG GGDAAAVDAL AAEVGAASRD  60
WGFFVVVGHG VPAETVARAT EAQRAFFALP AERKAAVRRS EAEPLGYYES EHTKNVRDWK  120
EVYDLVPGGL QPPIAVADGE VVFENKWPED LPGFREALEE YMQAMEELAF KILELIARSL  180
NLRPDRLHGF FKDQTTFIRL NHYPPCPSPD LALGVGRHKD AGALTILYQD DVGGLDVRRR  240
SDGDWVRVKP VPDSFIINVG DLIQVWSNDR YESAEHRVTV NSAKERFSRP YFFNPAGYTM  300
VEPVEELVSE EDPPRYDAYN WGNFFSTRKN SNFKKLSVEN IQIAHFKRSV AA          352

SEQ ID NO: 109          moltype = DNA  length = 1886
FEATURE                 Location/Qualifiers
source                  1..1886
                        mol_type = genomic DNA
                        organism = Setaria italica
SEQUENCE: 109
accccacaca cacacccgca ctgcatgcgg cgtcctagct aatcagtcgc tgctggcagc  60
ctcacaagtc acacaactcc gacgcaggaa agctcgatcc atcgccatgg gcggcttctc  120
catggatcag tccttcgtgc aggcccccga gcaccgcccc aagcccaccg tcaccgaggc  180
cacgggcatc ccgctcatcg acctctcgcc actcaccggc ggtggcggcg gcgacgcggc  240
cgccgtggac gcgctggccg ccgaggtggg cgcggcgagc cgggactggg gcttcttcgt  300
ggtggtgggg cacggtgtgc cggcggagac cgtggcgcgc gccacggagg cgcagcgcgc  360
gttcttcgcc ctgccggcgg agcggaaagc cgccgtgcgg aggagcgagg cggagccgct  420
cgggtactac gagtcggagc acaccaagaa cgtcagggac tggaaggagg tgtacgacct  480
cgtcccgggc gggcttcagc cgccgatagc cgtggccgac ggcgaggtcg tgttcgaaaa  540
caagtggccc gaagacctgc cgggattcag gtgaatcaac ttgcgcatat tgttgtttct  600
ggcattgcat atgatcgtcg tgccagtatg ttttgacaat atttttgttt tcatattttt  660
ggtgaagatg ggaaaatctt tgttgaaata atcagggaat tttcacatct ttttttaatc  720
aaagatagaa taggttcggt tactgaattt tgatgatgga cagaaaaagc tgtgttttca  780
ctttccatct cagcgatgtt tttttgtgga tgaattctcc taaatttttg tcttttcatg  840
ttaaaacttg aacgggaatt ctcgcagaga ggcgttggag gagtacatgc aagcgatgga  900
agagctggca ttcaagatac tggagctgat cgcccggagc ctgaacctga ggcctgacag  960
actgcacggc ttcttcaagg accagaccac cttcatccgg ctcaaccact accctccctg  1020
cccgagcccc gacctcgccc tcggcgtcgg ccggcacaag gacgccggag cactgaccat  1080
cctctaccag gacgacgtcg gcgggctcga cgtccggcgc cgttccgacg gcgattgggt  1140
ccgcgtcaag cctgtccccg actccttcat catcaacgtc ggcgacctca tccaggtaca  1200
acaaacaaaa acacacgtca ttctcaaatc ttttcgtgct gttaatgctc attcacgaat  1260
tgatatctta catgaacgac tgagactttt tcaggtttgg agcaacgaca ggtacgagag  1320
cgcggagcac cgggttacgg tgaactcggc caaggagagg ttctccaggc cctacttctt  1380
caacccggcg ggctacacca tggtggagcc ggtggaggag ctggtgagcg aggaggaccc  1440
gccccggtac gacgcctaca actggggcaa cttcttcagc accaggaaga acagcaactt  1500
caagaagctg agcgtggaga acatccagat cgcgcatttc aagaggagcg tcgccgccta  1560
ggatacgcac agaaagatcc catatgctga cttgctgatg aggcgacagg cggccgtgtc  1620
gtcttcagat tcagagactg ggagtaaaca tttgtgcggt gttctgtaat cgtgatgtga  1680
cgagaacttt agatatatgt ttggaaataa cagccttgtg ttggtctggc ttatccgcaa  1740
agtcaagatt ttcttctaca ttttgggatt attgttggta agcattaagc aacgtccagt  1800
tcttacttct tagctcgatc agtggacgta ggaccggcct ctgatgacaa gggtgattta  1860
tgagaaatgt catgtatata tgttcc                                      1886

SEQ ID NO: 110          moltype = DNA  length = 1379
FEATURE                 Location/Qualifiers
source                  1..1379
                        mol_type = other DNA
                        organism = Oryza sativa
SEQUENCE: 110
aagccacacg cacacacaca cacacgctga cacacgagac gaacacttgt gctacagctt  60
ctcgccacca gctactgatc gaccatgggc ggcctctcca tggaccaggc gttcgtgcag  120
gcccccgagc accgccccaa ggcgtccgtc gccgaggccg acggcatccc ggtcatcgac  180
ctctcccctc tcctcgccgc cggcgatggc gacgccgacg gggtggacgc gctcgcggcg  240
gaggtcggga gggcgagccg ggactggggc ttcttcgtgg tggtgcgcca cggtgtgccc  300
gcggaggcgg tggcgcgcgc ggcggaggcg cagaggacgt tcttcgcgct gccgccggag  360
cggagggcgg ccgtggcgcg gagcgaggcg gcgccgatgg ggtactacgc gtccgagcac  420
accaagaacg tcagggactg gaaggaggtg ttcgacctcg tcccgcgcca gacgccgccg  480
ccgccgacga ccgccgtggc cgacggcgac ctggtgttcg acaacaagtg gcccgacgac  540
ctgccgggat tcagggaggc aatggaggag tacggcgaag cggtggagga gctggcgttc  600
aagctgctgg agctgatcgc caggagcctc ggcctgagac ccgaccgcct ccatggcttc  660
ttcaaggacg accagaccac cttcatccgg ctcaaccact accctccctg cccgagcccc  720
gacctcgccc tcggcgtcgg ccgccacaag gacgccggcg cgctcaccgt gctctaccag  780
gacgatgtcg gcggcctcga cgtccgccgc cgatccgacg gcgagtgggt gcgcgtcagg  840
cccgtccctc actccttcat catcaacgtc ggcgacatca tccaggtgtg gagcaatgac  900
aggtacgaga gcgcggagca ccgggtggcg gtgaacgtgg agaaggagag gttctccatc  960
cctttcttct tcaacccggc gggccacacc atggtggagc cactggagga ggtcgtgagc  1020
gacgagagcc cggccaggta caacccctac aactggggcg aattcttcag caccaggaag  1080
aacagcaact tcaagaagct ggacgtggag aacgtccaga tcacgcattt caggaagaat  1140
taacgcgccg gctagatcat gttcagtaaa ttttcagatg atgatgcgtg gacaaccata  1200
```

```
tagcctttgc gtcataagtt aataatgtct gtgacagtat atcatgtaaa caatcgtatg  1260
atgtggcttc tctatctgcc ggtgatggta atgtgacatt gtagaagagg gtttgtgaga  1320
tacttccttc acttaacttt tacgaatgaa tatagacaac cacaacatcc ttgtcgtga   1379

SEQ ID NO: 111         moltype = DNA  length = 1059
FEATURE                Location/Qualifiers
source                 1..1059
                       mol_type = other DNA
                       organism = Oryza sativa
SEQUENCE: 111
atgggcggcc tctccatgga ccaggcgttc gtgcaggccc ccgagcaccg ccccaaggcg  60
tccgtcgccg aggccgacgg catcccggtc atcgacctct cccctctcct cgccgccggc  120
gatggcgacg ccgacggggt ggacgcgctc gcggcggagg tcgggagggc gagccgggac  180
tggggcttct tcgtggtggt gcgccacggt gtgcccgcgg aggcggtggc gcgcgcggcg  240
gaggcgcaga ggacgttctt cgcgctgccg ccggagcgga gggcggccgt ggcgcggagc  300
gaggcggcgc cgatggggta ctacgcgtcc gagcacacca agaacgtcag ggactggaag  360
gaggtgttcg acctcgtccc gcgccagacg ccgccgccgc cgacgaccgc cgtggccgac  420
ggcgacctgg tgttcgacaa caagtggccc gacgacctgc cgggattcag ggaggcaatg  480
gaggagtacg gcgaagcggt ggaggagctg gcgttcaagc tgctggagct gatcgccagg  540
agcctcggcc tgagacccga ccgcctccat ggcttcttca aggacgacca gaccaccttc  600
atccggctca accactaccc tccctgcccg agccccgacc tcgccctcgg cgtcggccgc  660
cacaaggacg ccggcgcgct caccgtgctc taccaggacg atgtcggcgg cctcgacgtc  720
cgccgccgat ccgacggcga gtgggtgcgc gtcaggcccg tccctcactc cttcatcatc  780
aacgtcggcg acatcatcca ggtgtggagc aatgacaggt acgagagcgc ggagcaccgg  840
gtggcggtga acgtggagaa ggagaggttc tccatccctt tcttcttcaa cccggcgggc  900
cacaccatgg tggagccact ggaggaggtc gtgagcgacg agagcccggc caggtacaac  960
ccctacaact ggggcgaatt cttcagcacc aggaagaaca gcaacttcaa gaagctggac  1020
gtggagaacg tccagatcac gcatttcagg aagaattaa                        1059

SEQ ID NO: 112         moltype = AA  length = 352
FEATURE                Location/Qualifiers
source                 1..352
                       mol_type = protein
                       organism = Oryza sativa
SEQUENCE: 112
MGGLSMDQAF VQAPEHRPKA SVAEADGIPV IDLSPLLAAG DGDADGVDAL AAEVGRASRD  60
WGFFVVVRHG VPAEAVARAA EAQRTFFALP PERRAAVARS EAAPMGYYAS EHTKNVRDWK  120
EVFDLVPRQT PPPPTTAVAD GDLVFDNKWP DDLPGFREAM EEYGEAVEEL AFKLLELIAR  180
SLGLRPDRLH GFFKDDQTTF IRLNHYPPCP SPDLALGVGR HKDAGALTVL YQDDVGGLDV  240
RRRSDGEWVR VRPVPHSFII NVGDIIQVWS NDRYESAEHR VAVNVEKERF SIPFFFNPAG  300
HTMVEPLEEV VSDESPARYN PYNWGEFFST RKNSNFKKLD VENVQITHFR KN          352

SEQ ID NO: 113         moltype = DNA  length = 2027
FEATURE                Location/Qualifiers
source                 1..2027
                       mol_type = genomic DNA
                       organism = Oryza sativa
SEQUENCE: 113
aagccacacg cacacacaca cacacgctga cacacgagac gaacacttgt gctacagctt  60
ctcgccacca gctactgatc gaccatgggc ggcctctcca tggaccaggc gttcgtgcag  120
gcccccgagc accgccccaa ggcgtccgtc gccgaggccg acggcatccc ggtcatcgac  180
ctctcccctc tcctcgccgc cggcgatggc gacgccgacg gggtggacgc gctcgcggcg  240
gaggtcggga gggcgagccg ggactggggc ttcttcgtgg tggtgcgcca cggtgtgccc  300
gcggaggcgg tggcgcgcgc ggcggaggcg cagaggacgt tcttcgcgct gccgccggag  360
cggagggcgg ccgtggcgcg gagcgaggcg gcgccgatgg ggtactacgc gtccgagcac  420
accaagaacg tcagggactg gaaggaggtg ttcgacctcg tcccgcgcca gacgccgccg  480
ccgccgacga ccgccgtggc cgacggcgac ctggtgttcg acaacaagtg gcccgacgac  540
ctgccgggat tcaggtcagg tcaccacatc gatcgatcgt cttcttcatc ctcgcatcaa  600
ttcagttcaa cctcatcgaa ttcttgagca gggaggcaat ggaggagtac ggcgaagcgg  660
tggaggagct ggcgttcaag ctgctggagc tgatcgccag gagcctcggc ctgagacccg  720
accgcctcca tggcttcttc aaggacgacc agaccacctt catccggctc aaccactacc  780
ctccctgccc gagccccgac ctcgccctcg gcgtcggccg ccacaaggac gccggcgcgc  840
tcaccgtgct ctaccaggac gatgtcggcg gcctcgacgt ccgccgccga tccgacggcg  900
agtgggtgcg cgtcaggccc gtccctcact ccttcatcat caacgtcggc gacatcatcc  960
aggtactttt ttttttgagc agctacatat ttatcaacaa atttcttct  aacaatttat  1020
cggacataaa tatattacaa tgaaagaata attgtatcat aacttgtgtg tccttatatg  1080
taagttttag aaatcctata gtaacatggt attttcgcga aagcggagat tgtgagaccg  1140
tatcttttca cccatgcgcg tcatatgatt ttttttttctt gccaacttaa ataaatttca  1200
aagtaaatct aatagattaa aattatgtga aacttacata taagtttttct acggtaacac  1260
gctattttca cgaaacggag gtcgttccaa gttgaatgaa tcttgaagta aatctaacga  1320
tttaaaatta tgtgcataca cgttatatta cagttatata caagttataa tataattaca  1380
ctacaattat aacggtattc atagttgaca aacttttaaa agagaattag ttaataaata  1440
tataacaaca ttgtagttta attgttacta tttgacatca tttttatttg cattttgaat  1500
ttgactgaaa aaattgagag tgcgcttgtc caggtgtgga gcaatgacag gtacgagagc  1560
gcggagcacc gggtggcggt gaacgtggag aaggagaggt tctccatccc tttcttcttc  1620
aacccggcgg gccacaccat ggtggagcca ctggaggagg tcgtgagcga cgagagcccg  1680
gccaggtaca acccctacaa ctggggcgaa ttcttcagca ccaggaagaa cagcaacttc  1740
aagaagctgg acgtggagaa cgtccagatc acgcatttca ggaagaatta acgcgccggc  1800
tagatcatgt tcagtaaatt ttcagatgat gatgcgtgga caaccatata gcctttgcgt  1860
```

```
cataagttaa taatgtctgt gacagtatat catgtaaaca atcgtatgat gtggcttctc  1920
tatctgccgg tgatggtaat gtgacattgt agaagagggt ttgtgagata cttccttcac  1980
ttaactttta cgaatgaata tagacaacca caacatcctt gtcgtga               2027

SEQ ID NO: 114         moltype = DNA  length = 1747
FEATURE                Location/Qualifiers
source                 1..1747
                       mol_type = other DNA
                       organism = Triticum aestivum
SEQUENCE: 114
tcactcaagg ccacaacaca ctcgccagtc catcgccacc atacgtgaca acttgagtta  60
cttgatctgt tgctcatcga tctcgacatc gccatgggcg gcctctccat ggaccaggcc  120
ttcgtgcagg cccccgagca tcgcaccaag gcgaacctcg ccgacgcggc cggcatcccg  180
gtcatcgacc tctcccctct cgccgccggc gacaaggccg gcctggacgc cctcgcggcc  240
gaggtgggca gggcgagccg tgactgggg ttcttcgtgg tggtgcgcca cggcgtgccg  300
gcggagacgg tggcgcgggc gctggaggcg cagagggcct tcttcgcgct gcccgcggac  360
cggaaggcgg ccgtgcggag ggacgaggcg gcgccgctgg ggtactacga gtcggagcac  420
accaagaacg tcagggactg gaaggaggtg ttcgacctcg tcccccgcga gccgccgccg  480
cctgccgcgg ttgccgacgg cgagctcatg ttcgagaaca agtggcccga ggacctgccg  540
gggttcagag aggctctcga agagtacgag aaagcgatgg aggagctggc gttcaagctg  600
ctggagctga tcgcccggag cctgggactg agaccggacc ggctgcacgg cttcttcaag  660
gaccagacca ccttcatccg gctgaaccac tacccgccct gccccagccc cgacctcgcc  720
ctcggcgtcg gtcgccacaa ggacgccggc gcgctcacca tcctctacca ggacgacgtc  780
ggcgggctcg acgtccggcg ccgctccgac ggcgagtggg tgcgcgtcag gcctgtcccg  840
gactcctacg tcatcaacgt cggcgacatc atccaggtgt ggagcaacga caggtacgag  900
agcgcggagc acagggtgtc ggtgaactcg cacaaggaga ggttctccat gccctacttc  960
ttcgaccccg ggagcgacgc catgatcgag ccgttggagg agatggtgag cgacgaaagg  1020
ccggccaggt acgacgccta caactggggc aacttcttca gcaccaggaa gaacagcaac  1080
ttcaggaagc tcgccgtcga aaacgtccag atcgcacact tcagaaagga ccgaccttaa  1140
atgaaggatc cctcatgaat tcatgatcct tccgctctcc tcagtgatcc tagtgctaca  1200
actacaagca tctccccgtt tgtagtaatc atatataaat aagtattccc tccgtaaact  1260
aatataagag catttaaaac actactctag tgatctaaat gctcttatat tagtttacag  1320
agagagtatt gtgtattaat aatgactttc tctgtttcaa aataagtgat gacgtggttt  1380
tagttcaatt ttttttagag aggaggcatc tgacgggcct taaactgagg accttagagt  1440
acaaacaagg ttcgacgaaa gtaagtttaa gggatacaag gccgtagcca acaaaacgcg  1500
acgcagcgcg caatctaaaa tcagcgtgct gtcaaggtag ctggagacgt ccatgccgtt  1560
aatctctctc aagaagctcg ccgaagctca gtgcaccttg cgtgcactct tgtgaagagc  1620
accttcacgt gtcctttgtc ctgagatttt gtcaacagtt tccatgactg caagaaaaac  1680
actagtttgt ataatagctc agcgggatgt cgaatgaatt gcccctcaat caaagcttta  1740
tttctag                                                            1747

SEQ ID NO: 115         moltype = DNA  length = 1047
FEATURE                Location/Qualifiers
source                 1..1047
                       mol_type = other DNA
                       organism = Triticum aestivum
SEQUENCE: 115
atgggcggcc tctccatgga ccaggccttc gtgcaggccc ccgagcatcg caccaaggcg  60
aacctcgccg acgcggccgg catcccggtc atcgacctct cccctctcgc cgccggcgac  120
aaggccggcc tggacgccct cgcggccgag gtgggcaggg cgagccgtga ctgggggttc  180
ttcgtggtgg tgcgccacgg cgtgccggcg gagacggtgg cgcgggcgct ggaggcgcag  240
agggccttct tcgcgctgcc cgcggaccgg aaggcggccg tgcggaggga cgaggcggcg  300
ccgctggggt actacgagtc ggagcacacc aagaacgtca gggactggaa ggaggtgttc  360
gacctcgtcc cccgcgagcc gccgccgcct gccgcggttg ccgacggcga gctcatgttc  420
gagaacaagt ggcccgagga cctgccgggg ttcagagagg ctctcgaaga gtacgagaaa  480
gcgatggagg agctggcgtt caagctgctg gagctgatcg cccggagcct gggactgaga  540
ccggaccggc tgcacggctt cttcaaggac cagaccacct tcatccggct gaaccactac  600
ccgccctgcc ccagccccga cctcgccctc ggcgtcggtc gccacaagga cgccggcgcg  660
ctcaccatcc tctaccagga cgacgtcggc gggctcgacg tccggcgccg ctccgacggc  720
gagtgggtgc gcgtcaggcc tgtcccggac tcctacgtca tcaacgtcgg cgacatcatc  780
caggtgtgga gcaacgacag gtacgagagc gcggagcaca gggtgtcggt gaactcgcac  840
aaggagaggt tctccatgcc ctacttcttc gaccccggga gcgacgccat gatcgagccg  900
ttggaggaga tggtgagcga cgaaaggccg gccaggtacg acgcctacaa ctggggcaac  960
ttcttcagca ccaggaagaa cagcaacttc aggaagctcg ccgtcgaaaa cgtccagatc  1020
gcacacttca gaaaggaccg accttaa                                      1047

SEQ ID NO: 116         moltype = AA  length = 348
FEATURE                Location/Qualifiers
source                 1..348
                       mol_type = protein
                       organism = Triticum aestivum
SEQUENCE: 116
MGGLSMDQAF VQAPEHRTKA NLADAAGIPV IDLSPLAAGD KAGLDALAAE VGRASRDWGF  60
FVVVRHGVPA ETVARALEAQ RAFFALPADR KAAVRRDEAA PLGYYESEHT KNVRDWKEVF  120
DLVPREPPPP AAVADGELMF ENKWPEDLPG FREALEEYEK AMEELAFKLL ELIARSLGLR  180
PDRLHGFFKD QTTFIRLNHY PPCPSPDLAL GVGRHKDAGA LTILYQDDVG GLDVRRRSDG  240
EWVRVRPVPD SYVINVGDII QVWSNDRYES AEHRVSVNSH KERFSMPYFF DPGSDAMIEP  300
LEEMVSDERP ARYDAYNWGN FFSTRKNSNF RKLAVENVQI AHFRKDRP                348
```

```
SEQ ID NO: 117          moltype = DNA  length = 1863
FEATURE                 Location/Qualifiers
source                  1..1863
                        mol_type = genomic DNA
                        organism = Triticum aestivum
SEQUENCE: 117
tcactcaagg ccacaacaca ctcgccagtc catcgccacc atacgtgaca acttgagtta  60
cttgatctgt tgctcatcga tctcgacatc gccatgggcg gcctctccat ggaccaggcc  120
ttcgtgcagg cccccgagca tcgcaccaag gcgaacctcg ccgacgcggc cggcatcccg  180
gtcatcgacc tctcccctct cgccgccggc gacaaggccg gcctggacgc cctcgcggcc  240
gaggtgggca gggcgagccg tgactggggg ttcttcgtgg tggtgcgcca cggcgtgccg  300
gcggagacgg tggcgcgggc gctggaggcg cagagggcct tcttcgcgct gcccgcggac  360
cggaaggcgg ccgtgcggag ggacgaggcg gcgccgctgg ggtactacga gtcggagcac  420
accaagaacg tcagggactg gaaggaggtg ttcgacctcg tcccccgcga gccgccgccg  480
cctgccgcgg ttgccgacgg cgagctcatg ttcgagaaca agtggcccga ggacctgccg  540
gggttcaggt acggtcatca actcaatcaa ttctgcgacc ccgagagaaa tggttcacta  600
ttattcgtgg ttcatacgta tgattcagac gttaatctcg atgcaaattg atttgtgcat  660
gcagagaggc tctcgaagag tacgagaaag cgatggagga gctggcgttc aagctgctgg  720
agctgatcgc ccggagcctg ggactgagac cggaccggct gcacggcttc ttcaaggacc  780
agaccacctt catccggctg aaccactacc cgccctgccc cagccccgac ctcgccctcg  840
gcgtcggtcg ccacaaggac gccggcgcgc tcaccatcct ctaccaggac gacgtcggcg  900
ggctcgacgt ccggcgccgc tccgacggcg agtgggtgcg cgtcaggcct gtcccggact  960
cctacgtcat caacgtcggc gacatcatcc aggtgtggag caacgacagg tacgagagcg  1020
cggagcacag ggtgtcggtg aactcgcaca aggagaggtt ctccatgccc tacttcttcg  1080
accccgggag cgacgccatg atcgagccgt tggaggagat ggtgagcgac gaaaggccgg  1140
ccaggtacga cgcctacaac tggggcaact tcttcagcac caggaagaac agcaacttca  1200
ggaagctcgc cgtcgaaaac gtccagatcg cacacttcag aaaggaccga ccttaaatga  1260
aggatccctc atgaattcat gatccttccg ctctcctcag tgatcctagt gctacaacta  1320
caagcatctc cccgtttgta gtaatcatat ataaataagt attccctccg taaactaata  1380
taagagcatt taaaacacta ctctagtgat ctaaatgctc ttatattagt ttacagagag  1440
agtattgtgt attaataatg actttctctg tttcaaaata agtgatgacg tggttttagt  1500
tcaatttttt ttagagagga ggcatctgac gggccttaaa ctgaggacct tagagtacaa  1560
acaaggttcg acgaaagtaa gtttaaggga tacaaggccg tagccaacaa aacgcgacgc  1620
agcgcgcaat ctaaaatcag cgtgctgtca aggtagctgg agacgtccat gccgttaatc  1680
tctctcaaga agctcgccga agctcagtgc accttgcgtg cactcttgtg aagagcacct  1740
tcacgtgtcc tttgtcctga gattttgtca acagtttcca tgactgcaag aaaaacacta  1800
gtttgtataa tagctcagcg ggatgtcgaa tgaattgccc ctcaatcaaa gctttatttc  1860
tag                                                                1863

SEQ ID NO: 118          moltype = AA  length = 349
FEATURE                 Location/Qualifiers
source                  1..349
                        mol_type = protein
                        organism = Hordeum vulgare
SEQUENCE: 118
MGGLSMGQAF VQAPEHRTKP TLADADGIPV IDLSPLAAGD EAGVDALAAE VGRASRDWGF  60
FVVVRHGVPA ETVARALEAQ RAFFALPAER KAAVRRDEAA PLGYYESEHT KNVRDWKEVF  120
DFVPREPPPP AAVADGELVF ENKWPEDLPG FRVAFEEYAK AMEELAFKLL ELIARSLGLT  180
PDRLNGFFKD HQTTFIRLNH YPPCPSPDLA LGVGRHKDAG ALTVLYQDDV GGLDVRHRSD  240
GEWVRVRPVP DSYVINVGDI IQVWSNDRYE SAEHRVSVNS DKERFSMPYF FNPGSDAMVE  300
PLEEMVSDER PARYDAYNWG HFFSTRKNSN FKKLDVENVQ IAHFRKLHL              349

SEQ ID NO: 119          moltype = DNA  length = 1963
FEATURE                 Location/Qualifiers
source                  1..1963
                        mol_type = other DNA
                        organism = Sorghum bicolor
SEQUENCE: 119
tataaatacc acgccatgta cttctctgct tctacacttc tccagcttct ctcatgccat  60
accactagtg caaggtccta gatttacact tggtgctaca gcttcttcct ccctccctcc  120
cctctctagg cagctagcac gcagcgcagc acacgaaaca tctattgacc ggccgcctcc  180
gccggggatc cataattact atactaccaa tcggccagcg tcatgccgac gccgtcgcac  240
ctcgcgaacc cgcgctactt cgacttccgt gcggcgcggc gggtgccgga gacgcacgcc  300
tggccggggc tgcacgacca ccccgtcgtg gacggcggcg cgccggggcc agacgccgtc  360
cccgtggtgg acctcgcggg ggcggcggac gagccgagag ccgcggtggt ggcccaagtg  420
gcgcgcgccg ccgagcaatg gggcgcgttc ctgctcacgg ggcacggcgt ccccgcggag  480
ctgctggcgc gcgtcgagga ccggatcgcc accatgttcg cgctgccagc ggacgacaag  540
atgcgcgccg tgcgcgggcc tggcgacgcc tgcggctacg gctccccgcc catctcctcc  600
ttcttctcca agtgcatgtg gtcggaggga tacaccttct cgccggccaa cctccgcgcc  660
gacctccgca agctctggcc taaggccggc gacgactaca ccagcttctg tgatgtgatg  720
gaggagttcc acaagcacat gcgtgccctc gcggacaagc tgctggagct gttcctcatg  780
gcgctggggc tcaccgacga gcaggtcggc ggcgtggagg cggagcggag gatcgccgag  840
acgatgaccg ccaccatgca cctcaactgg taccctcggt gcccggaccc gcgccgcgcg  900
ctggggctga tcgcgcacac cgactcgggc ttcttcacct tcgtgctgca gagcctcgtc  960
ccggggctgc agctcttccg ccacgccccg gaccggtggg tggcggtgcc ggcggtaccg  1020
ggcgccttcg tcgtcaacgt gggcgacctc ttccacatcc tcaccaacgg ccggttccac  1080
agcgtgtacc accgcgccgt cgtgaaccgg gacctcgaca ggatatctct cggctacttc  1140
ctcggcccgc cgccgcacgc caaggtggcg ccgctaaggg aggccgtgcc gcccggccgc  1200
acccccgcgt accgcgccgt cacgtggccc gagtacatgg gcgtccgcaa gaaggccttc  1260
```

```
accaccggcg catccgcgct caagatggtc gccctcgccg ccgccgccgc cgccgccgac  1320
ctcgacgatg acgccggtgc tggcgccgcc gccgaacctg tcgtccatca gcagctactc  1380
gtctcgtcgt agccgatcga tcgccggatc ggtcgagact gatgatgatg atgcatatat  1440
actcgtcgat ggagtagaca gactaatcaa gcaaccctga aactatgaat gcatgcgtgc  1500
gcttcgtgct tgcttgcgca tgcagctagc aggcttcatt ccgttccgca gctgctctgc  1560
tccaacctgc tctgctggat tgatgtatat ggtagaagaa ttaagagatc gatggatgac  1620
ggaggaagaa gaagacgaag acgacgatga ggaaaaggac acgctgtacg tagctggttc  1680
ttctagtcta gtttacagca ggccgggcgg ccggctgctg cttccaatcg agtttgtcgt  1740
tactgacgat tgttagtgga tcgattaact aatctggaat tctggattat taatataatg  1800
catgtggttt ggcatctggc gtaaagcagg taatggtacc tagccagtag ccagtagcca  1860
ggctggtcaa tgataggtct ataccctgat cctgtactgt tgtttctttc ggtctttctg  1920
agagagaaaa aaaacgaata tatggcgtac tcaattcatc aaa                    1963

SEQ ID NO: 120          moltype = DNA  length = 1170
FEATURE                 Location/Qualifiers
source                  1..1170
                        mol_type = other DNA
                        organism = Sorghum bicolor
SEQUENCE: 120
atgccgacgc cgtcgcacct cgcgaacccg cgctacttcg acttccgtgc ggcgcggcgg  60
gtgccggaga cgcacgcctg gccggggctg cacgaccacc ccgtcgtgga cggcggcgcg  120
ccggggccag acgccgtccc cgtggtggac ctcgcggggg cggcggacga gccgagagcc  180
gcggtggtgg cccaagtggc gcgcgccgcc gagcaatggg gcgcgttcct gctcacgggg  240
cacggcgtcc ccgcggagct gctggcgcgc gtcgaggacc ggatcgccac catgttcgcg  300
ctgccagcgg acgacaagat gcgcgccgtg cgcgggcctg gcgacgcctg cggctacggc  360
tccccgccca tctcctcctt cttctccaag tgcatgtggt cggagggata caccttctcg  420
ccggccaacc tccgcgccga cctccgcaag ctctggccta aggccggcga cgactacacc  480
agcttctgtg atgtgatgga ggagttccac aagcacatgc gtgccctcgc ggacaagctg  540
ctggagctgt tcctcatggc gctggggctc accgacgagc aggtcggcgg cgtggaggcg  600
gagcggagga tcgccgagac gatgaccgcc accatgcacc tcaactggta ccctcggtgc  660
ccggacccgc gccgcgcgct ggggctgatc gcgcacaccg actcgggctt cttcaccttc  720
gtgctgcaga gcctcgtccc ggggctgcag ctcttccgcc acgccccgga ccggtgggtg  780
gcggtgccgg cggtaccggg cgccttcgtc gtcaacgtgg gcgacctctt ccacatcctc  840
accaacggcc ggttccacag cgtgtaccac cgcgccgtcg tgaaccggga cctcgacagg  900
atatctctcg gctacttcct cggcccgccg ccgcacgcca aggtggcgcc gctaagggag  960
gccgtgccgc ccggccgcac ccccgcgtac cgcgccgtca cgtggcccga gtacatgggc  1020
gtccgcaaga aggccttcac caccggcgca tccgcgctca agatggtcgc cctcgccgcc  1080
gccgccgccg ccgccgacct cgacgatgac gccggtgctg gcgccgccgc cgaacctgtc  1140
gtccatcagc agctactcgt ctcgtcgtag                                  1170

SEQ ID NO: 121          moltype = AA  length = 389
FEATURE                 Location/Qualifiers
source                  1..389
                        mol_type = protein
                        organism = Sorghum bicolor
SEQUENCE: 121
MPTPSHLANP RYFDFRAARR VPETHAWPGL HDHPVVDGGA PGPDAVPVVD LAGAADEPRA  60
AVVAQVARAA EQWGAFLLTG HGVPAELLAR VEDRIATMFA LPADDKMRAV RGPGDACGYG  120
SPPISSFFSK CMWSEGYTFS PANLRADLRK LWPKAGDDYT SFCDVMEEFH KHMRALADKL  180
LELFLMALGL TDEQVGGVEA ERRIAETMTA TMHLNWYPRC PDPRRALGLI AHTDSGFFTF  240
VLQSLVPGLQ LFRHAPDRWV AVPAVPGAFV VNVGDLFHIL TNGRFHSVYH RAVVNRDLDR  300
ISLGYFLGPP PHAKVAPLRE AVPPGRTPAY RAVTWPEYMG VRKKAFTTGA SALKMVALAA  360
AAAAADLDDD AGAGAAAEPV VHQQLLVSS                                   389

SEQ ID NO: 122          moltype = DNA  length = 2321
FEATURE                 Location/Qualifiers
source                  1..2321
                        mol_type = genomic DNA
                        organism = Sorghum bicolor
SEQUENCE: 122
tataaatacc acgccatgta cttctctgct tctacacttc tccagcttct ctcatgccat  60
accactagtg caaggtccta gatttacact tggtgctaca gcttcttcct ccctccctcc  120
cctctctagg cagctagcac gcagcgcagc acacgaaaca tctattgacc ggccgcctcc  180
gccggggatc cataattact atactaccaa tcggccagcg tcatgccgac gccgtcgcac  240
ctcgcgaacc cgcgctactt cgacttccgt gcggcgcggc gggtgccgga gacgcacgcc  300
tggccggggc tgcacgacca ccccgtcgtg gacggcggcg cgccggggcc agacgccgtc  360
cccgtggtgg acctcgcggg ggcggcggac gagccgagag ccgcggtggt ggcccaagtg  420
gcgcgcgccg ccgagcaatg gggcgcgttc ctgctcacgg ggcacggcgt ccccgcggag  480
ctgctggcgc gcgtcgagga ccggatcgcc accatgttcg cgctgccagc ggacgacaag  540
atgcgcgccg tgcgcgggcc tggcgacgcc tgcggctacg gctccccgcc catctcctcc  600
ttcttctcca agtgcatgtg gtcggaggga tacaccttct cgccggccaa cctccgcgcc  660
gacctccgca agctctggcc taaggccggc gacgactaca ccagcttctg gtacgtgcac  720
ccgccggccg cgcgccgcca cacaccgtac ccacacacgt gcgcgctcgc gcctagctac  780
tagtagctgc tttgctttgc ttacctttga ttctcgcctt tgccatgcat atgcatgatg  840
cacgtacagg tactgcaggt acaacatgtc acacgcacgc acgcacgcac aacccatagt  900
ccgatacgat acatcatcga tcgacgtgtc gtcaccgtct aaggccatgc atgcatgcaa  960
gcacacgcct agaccttttt agcatgctgg ctgacgagga gtatactagc taataagcta  1020
cttgtcactg cgcgtcttgc ttaattacac tagtgcatat ttctacagtg atgtgatgga  1080
ggagttccac aagcacatgc gtgccctcgc ggacaagctg ctggagctgt tcctcatggc  1140
```

```
gctggggctc accgacgagc aggtcggcgg cgtggaggcg gagcggagga tcgccgagac  1200
gatgaccgcc accatgcacc tcaactggta ccctcggtgc ccggacccgc gccgcgcgct  1260
ggggctgatc gcgcacaccg actcgggctt cttcaccttc gtgctgcaga gcctcgtccc  1320
ggggctgcag ctcttccgcc acgccccgga ccggtgggtg gcggtgccgg cggtaccggg  1380
cgccttcgtc gtcaacgtgg gcgacctctt ccacatcctc accaacggcc ggttccacag  1440
cgtgtaccac cgcgccgtcg tgaaccggga cctcgacagg atatctctcg gctacttcct  1500
cggcccgccg ccgcacgcca aggtggcgcc gctaagggag gccgtgccgc ccggccgcac  1560
ccccgcgtac cgcgccgtca cgtggcccga gtacatgggc gtccgcaaga aggccttcac  1620
caccggcgca tccgcgctca agatggtcgc cctcgccgcc gccgccgccg ccgccgacct  1680
cgacgatgac gccggtgctg gcgccgccgc cgaacctgtc gtccatcagc agctactcgt  1740
ctcgtcgtag ccgatcgatc gccggatcgg tcgagactga tgatgatgat gcatatatac  1800
tcgtcgatgg agtagacaga ctaatcaagc aaccctgaaa ctatgaatgc atgcgtgcgc  1860
ttcgtgcttg cttgcgcatg cagctagcag gcttcattcc gttccgcagc tgctctgctc  1920
caacctgctc tgctggattg atgtatatgg tagaagaatt aagagatcga tggatgacgg  1980
aggaagaaga agacgaagac gacgatgagg aaaaggacac gctgtacgta gctggttctt  2040
ctagtctagt ttacagcagg ccgggcggcc ggctgctgct tccaatcgag tttgtcgtta  2100
ctgacgattg ttagtggatc gattaactaa tctggaattc tggattatta atataatgca  2160
tgtggtttgg catctggcgt aaagcaggta atggtaccta gccagtagcc agtagccagg  2220
ctggtcaatg ataggtctat accctgatcc tgtactgttg tttctttcgg tctttctgag  2280
agagaaaaaa aacgaatata tggcgtactc aattcatcaa a                     2321

SEQ ID NO: 123          moltype = DNA  length = 1796
FEATURE                 Location/Qualifiers
source                  1..1796
                        mol_type = other DNA
                        organism = Setaria italica
SEQUENCE: 123
actagtgcaa ggtcctagat ttacacttgg tgcttgcttg tttcttccta gttgctactg  60
gtagcacgca gtggctggct ggccgtaatc tattgtctgg gctcgatcgg tgattaggaa  120
gtagccaaag caagctaagg ccgccgccgc cgccgccatg ccgacgccgt cgcacctcaa  180
gaacccgctc tacttcgact tccgcgccgc gcggcgggtg ccggagtccc acgcctggcc  240
ggggctcgac gaccaccccg tggtggacgg cggcggcgcg ccggggtccc cggacgccgt  300
gccggtggtg gacctgcgcg agccgggcgc cgcggcggtg gcccgcgtgg cgcgcgccgc  360
cgagcagtgg ggcgcgttcc tgctcaccgg ccacggcgtc cccgcggagc tcctggcgcg  420
cgtcgaggac cgcgtcgcgt gcatgttcgc gctgccggcc gccgacaaga tgcgcgccgt  480
gcgcgggccg ggggacgcct gcggctacgg ctcgccgccc atctcctcct tcttctccaa  540
gtgcatgtgg tccgagggct acaccttctc gccggcctcc ctccgccgcg acctccgcaa  600
gctctggccc aaggccggcg acgactacga cagcttctgt gacgtgatgg aggagttcca  660
caaggagatg cgcgccctcg ccgacaggct cctggagctg ttcctcaggg cgctcgggct  720
caccggcgag caggtcggcg ccgtcgaggc ggagcggagg atcggcgaga cgatgaccgc  780
caccatgcac ctcaactggt atccgaggtg cccggacccg cggcgcgcgc tggggctgat  840
cgcgcacacg gactcgggct tcttcacctt cgtgctgcag agcctcgtgc cggggctgca  900
gctgttccgg cacggcccca accggtgggt ggcggtgccg gccgtgccgg gcgccttcgt  960
cgtcaacgtc ggcgacctct tccacatcct cacgaacggc cgcttccaca gcgtgtacca  1020
ccgcgccgtc gtcaaccggg acctcgaccg gatatcgctc ggctacttcc tcggcccgcc  1080
gccccacgcc aaggtggcgc cgctccggga ggtcgtgccg ccgggccggg cccccgccta  1140
ccgcgccgtc acgtggcccg agtacatggg cgtccgcaag aaggccttca ccaccggcgc  1200
ctccgcgctc aagatggtcg ccgccgccgc cgccgccacc gaatccgacg acaccgacgc  1260
agccgccgcc gccgttcacc agccgccggt cgtcgtctca tcgtagccga tcgatcgccg  1320
gaaacacaga cgatgcatac cgtaccccga gcaatctaat caaaacaagg catccattct  1380
cgcgcgcatg cagcggccag ccgggcttcc gcagctgctc ggcctcctct gctggctgtg  1440
gaaatggaaa attttaatct gagatgaaga cgaagacgaa gacgaaacgg agaggaaaag  1500
gacatgctgt agctgtttct tctagttgcg caggccgctc ccagtcgagt ttgtcgttac  1560
tgacgattat tactctgatg aaaactaatc tgaattaatg catgtagttt ggcaatttgg  1620
tactaaaggt aggcacctag ccaggctggt caatgatagg tctataacct gatcctgttc  1680
tctgttgttt tcctttgtct gagaaaaaat ggaaataatt gatccggccg gacgggtgta  1740
ctgataggtg atgctgaatt gctgatgcaa gaggttgcga gctgcagtga gcagca      1796

SEQ ID NO: 124          moltype = DNA  length = 1149
FEATURE                 Location/Qualifiers
source                  1..1149
                        mol_type = other DNA
                        organism = Setaria italica
SEQUENCE: 124
atgccgacgc cgtcgcacct caagaacccg ctctacttcg acttccgcgc cgcgcggcgg  60
gtgccggagt cccacgcctg gccggggctc gacgaccacc ccgtggtgga cggcggcggc  120
gcgccggggt ccccggacgc cgtgccggtg gtggacctgc gcgagccggg cgccgcggcg  180
gtggcccgcg tggcgcgcgc cgccgagcag tggggcgcgt tcctgctcac cggccacggc  240
gtccccgcgg agctcctggc gcgcgtcgag gaccgcgtcg cgtgcatgtt cgcgctgccg  300
gccgccgaca agatgcgcgc cgtgcgcggg ccgggggacg cctgcggcta cggctcgccg  360
cccatctcct ccttcttctc caagtgcatg tggtccgagg gctacacctt ctcgccggcc  420
tccctccgcc gcgacctccg caagctctgg cccaaggccg gcgacgacta cgacagcttc  480
tgtgacgtga tggaggagtt ccacaaggag atgcgcgccc tcgccgacag gctcctggag  540
ctgttcctca gggcgctcgg gctcaccggc gagcaggtcg gcgccgtcga ggcggagcgg  600
aggatcggcg agacgatgac cgccaccatg cacctcaact ggtatccgag gtgcccggac  660
ccgcggcgcg cgctggggct gatcgcgcac acggactcgg gcttcttcac cttcgtgctg  720
cagagcctcg tgccggggct gcagctgttc cggcacggcc ccaaccggtg ggtggcggtg  780
ccggccgtgc cgggcgcctt cgtcgtcaac gtcggcgacc tcttccacat cctcacgaac  840
ggccgcttcc acagcgtgta ccaccgcgcc gtcgtcaacc gggacctcga ccggatatcg  900
```

```
ctcggctact tcctcggccc gccgccccac gccaaggtgg cgccgctccg ggaggtcgtg  960
ccgccgggcc gggcccccgc ctaccgcgcc gtcacgtggc ccgagtacat gggcgtccgc  1020
aagaaggcct tcaccaccgg cgcctccgcg ctcaagatgg tcgccgccgc cgccgccgcc  1080
accgaatccg acgacaccga cgcagccgcc gccgccgttc accagccgcc ggtcgtcgtc  1140
tcatcgtag                                                          1149

SEQ ID NO: 125         moltype = AA  length = 382
FEATURE                Location/Qualifiers
source                 1..382
                       mol_type = protein
                       organism = Setaria italica
SEQUENCE: 125
MPTPSHLKNP LYFDFRAARR VPESHAWPGL DDHPVVDGGG APGSPDAVPV VDLREPGAAA  60
VARVARAAEQ WGAFLLTGHG VPAELLARVE DRVACMFALP AADKMRAVRG PGDACGYGSP  120
PISSFFSKCM WSEGYTFSPA SLRRDLRKLW PKAGDDYDSF CDVMEEFHKE MRALADRLLE  180
LFLRALGLTG EQVGAVEAER RIGETMTATM HLNWYPRCPD PRRALGLIAH TDSGFFTFVL  240
QSLVPGLQLF RHGPNRWVAV PAVPGAFVVN VGDLFHILTN GRFHSVYHRA VVNRDLDRIS  300
LGYFLGPPPH AKVAPLREVV PPGRAPAYRA VTWPEYMGVR KKAFTTGASA LKMVAAAAAA  360
TESDDTDAAA AAVHQPPVVV SS                                           382

SEQ ID NO: 126         moltype = DNA  length = 2146
FEATURE                Location/Qualifiers
source                 1..2146
                       mol_type = genomic DNA
                       organism = Setaria italica
SEQUENCE: 126
actagtgcaa ggtcctagat ttacacttgg tgcttgcttg tttcttccta gttgctactg  60
gtagcacgca gtggctggct ggccgtaatc tattgtctgg gctcgatcgg tgattaggaa  120
gtagccaaag caagctaagg ccgccgccgc cgccgccatg ccgacgccgt cgcacctcaa  180
gaacccgctc tacttcgact tccgcgccgc gcggcgggtg ccggagtccc acgcctggcc  240
ggggctcgac gaccaccccg tggtggacgg cggcggcgcg ccggggtccc cggacgccgt  300
gccggtggtg gacctgcgcg agccgggcgc cgcggcggtg gcccgcgtgg cgcgcgccgc  360
cgagcagtgg ggcgcgttcc tgctcaccgg ccacggcgtc cccgcggagc tcctggcgcg  420
cgtcgaggac cgcgtcgcgt gcatgttcgc gctgccggcc gccgacaaga tgcgcgccgt  480
gcgcgggccg gggacgcct  gcggctacgg ctcgccgccc atctcctcct tcttctccaa  540
gtgcatgtgg tccgagggct acaccttctc gccggcctcc ctccgccgcg acctccgcaa  600
gctctggccc aaggccggcg acgactacga cagcttctgg tacgtcgtcg tctatagcta  660
gtagctagcc gccggcacac gtgcgcctga cctgctccgc catgcatggt gcacgtatgc  720
agatcgatca cacgcaccga tcgatcgacg tgtcccggtc aaggccatgc atgcatgcaa  780
gcaaccaaca gcacgcctcc tgatactgct tgttgcttac accgttggta tgtgcctgtt  840
gcctacagtg acgtgatgga ggagttccac aaggagatgc gcgccctcgc cgacaggctc  900
ctggagctgt tcctcagggc gctcgggctc accggcgagc aggtcggcgc cgtcgaggcg  960
gagcggagga tcggcgagac gatgaccgcc accatgcacc tcaactggta tgtgccatgc  1020
catgaccacc tgcgtctatg aactaacgga agcttccatc gcgtgtccat gacgatttag  1080
aagctgtagt ccagagcttg agacaaacga aacgaagctt acatggtggc gtgacgtgtc  1140
gcgtgcaggt atccgaggtg cccggacccg cggcgcgcgc tggggctgat cgcgcacacg  1200
gactcgggct tcttcacctt cgtgctgcag agcctcgtgc cggggctgca gctgttccgg  1260
cacggcccca accggtgggt ggcggtgccg gccgtgccgg gcgccttcgt cgtcaacgtc  1320
ggcgacctct tccacatcct cacgaacggc cgcttccaca gcgtgtacca ccgcgccgtc  1380
gtcaaccggg acctcgaccg gatatcgctc ggctacttcc tcggcccgcc gccccacgcc  1440
aaggtggcgc cgctccggga ggtcgtgccg ccgggccggg cccccgccta ccgcgccgtc  1500
acgtggcccg agtacatggg cgtccgcaag aaggccttca ccaccggcgc ctccgcgctc  1560
aagatggtcg ccgccgccgc cgccgccacc gaatccgacg acaccgacgc agccgccgcc  1620
gccgttcacc agccgccggt cgtcgtctca tcgtagccga tcgatcgccg gaaacacaga  1680
cgatgcatac cgtaccccga gcaatctaat caaaacaagg catccattct cgcgcgcatg  1740
cagcggccag ccgggcttcc gcagctgctc ggcctcctct gctggctgtg gaaatggaaa  1800
attttaatct gagatgaaga cgaagacgaa gacgaaacgg agaggaaaag gacatgctgt  1860
agctgtttct tctagttgcg caggccgctc ccagtcgagt ttgtcgttac tgacgattat  1920
tactctgatg aaaactaatc tgaattaatg catgtagttt ggcaatttgg tactaaaggt  1980
aggcacctag ccaggctggt caatgatagg tctataacct gatcctgttc tctgttgttt  2040
tcctttgtct gagaaaaaat ggaaataatt gatccggccg gacgggtgta ctgataggtg  2100
atgctgaatt gctgatgcaa gaggttgcga gctgcagtga gcagca                 2146

SEQ ID NO: 127         moltype = DNA  length = 1933
FEATURE                Location/Qualifiers
source                 1..1933
                       mol_type = other DNA
                       organism = Oryza sativa
SEQUENCE: 127
actactcatt ccactattgt aaagtcatag aaaaaattta tatagagaga aaaaattagt  60
gttgttattg ttactggctt tctgccagac gagacgagcg agcgcgcgag tgtgttgctc  120
tctggtcatc gtcgtcgtcg tcgcgatgcc gacgccgtcg cacttgaaga acccgctctg  180
cttcgacttc cgggcggcga ggcgggtgcc ggagacgcac gcgtggccgg ggctggacga  240
ccacccggtg gtggacggcg gcggcggcgg cggcgaggac gcggtgccgg tggtggacgt  300
cggggcgggc gacgcggcgg cgcgggtggc gcgggcggcg gagcagtggg gcgcgttcct  360
tctggtcggg cacggcgtgc cggcggcgct gctgtcgcgc gtcgaggagc gcgtcgcccg  420
cgtgttctcc ctgccggcgt cggagaagat gcgcgccgtc cgcggccccg gcgagccctg  480
cggctacggc tcgccgccca tctcctcctt cttctccaag ctcatgtggt ccgagggcta  540
caccttctcc ccttcctccc tccgctccga gctccgccgc ctctggccca agtccggcga  600
```

```
cgactacctc ctcttctgtg acgtgatgga ggagtttcac aaggagatgc ggcggctagc  660
cgacgagttg ctgaggttgt tcttgagggc gctggggctc accggcgagg aggtcgccgg  720
agtcgaggcg gagaggagga tcggcgagag gatgacggcg acggtgcacc tcaactggta  780
cccgaggtgc ccggagccgc ggcgagcgct ggggctcatc gcgcacacgg actcgggctt  840
cttcaccttc gtgctccaga gcctcgtccc ggggctgcag ctgttccgtc gagggcccga  900
ccggtgggtg gcggtgccgg cggtggcggg ggccttcgtc gtcaacgtcg gcgacctctt  960
ccacatcctc accaacggcc gcttccacag cgtctaccac cgcgccgtcg tgaaccgcga  1020
ccgcgaccgg gtctcgctcg gctacttcct cggcccgccg ccggacgccg aggtggcgcc  1080
gctgccggag gccgtgccgg ccggccggag ccccgcctac cgcgctgtca cgtggccgga  1140
gtacatggcc gtccgcaaga aggccttcgc caccggcggc tccgccctca agatggtctc  1200
caccgacgcc gccgccgccg ccgacgaaca cgacgacgtc gccgccgccg ccgacgtcca  1260
cgcataagct atagctacta gctacctcga tctcacgcaa aaaaaaaaag aaacaattaa  1320
tagagcaaaa aaaaaaagaa gagaaaatgg tggtacttgt gtttaaggtt tcctccatgc  1380
aaaatggttt gcatgcatgc atgcaaagct agcatctgca gctgcaagaa ttacaagagc  1440
agagaagcag acagctagat ggagataatt aattaattaa ttaatctaat taagcatgca  1500
ataattaaga ttattattct gatttcagaa ctgaaaaaaa aagtgtggtt aattaattat  1560
tggttaggct taattttatc tagatgtaga aaaagaatca agatcttcaa gcaagagaga  1620
agaggatcga agaagaagga aaagaaaacg aaaaggacat gctgtgttgt ctcttctagt  1680
tgtaccctgg ctgctgatta agtgctttgt tttgttgctg caagcttgtc gttactgatt  1740
attagttagt tatgcatcta attgattaaa ctaatctgtt tggcattttg gctcgagcta  1800
agctatagcc aggctggtca atgataggaa cttgtacaat ttaagcaatt gaacctgatc  1860
ctgtactggc atgtatgtat atatgcaagt gatgagaacc actagctagt atagctagac  1920
atgtatttgt ata                                                     1933

SEQ ID NO: 128          moltype = DNA  length = 1122
FEATURE                 Location/Qualifiers
source                  1..1122
                        mol_type = other DNA
                        organism = Oryza sativa
SEQUENCE: 128
atgccgacgc cgtcgcactt gaagaacccg ctctgcttcg acttccgggc ggcgaggcgg  60
gtgccggaga cgcacgcgtg gccggggctg gacgaccacc cggtggtgga cggcggcggc  120
ggcggcggcg aggacgcggt gccggtggtg gacgtcgggg cgggcgacgc ggcggcgcgg  180
gtggcgcggg cggcggagca gtggggcgcg ttccttctgg tcgggcacgg cgtgccggcg  240
gcgctgctgt cgcgcgtcga ggagcgcgtc gcccgcgtgt tctccctgcc ggcgtcggag  300
aagatgcgcg ccgtccgcgg ccccggcgag ccctgcggct acggctcgcc gcccatctcc  360
tccttcttct ccaagctcat gtggtccgag ggctacacct tctccccttc ctccctccgc  420
tccgagctcc gccgcctctg gcccaagtcc ggcgacgact acctcctctt ctgtgacgtg  480
atggaggagt ttcacaagga gatgcggcgg ctagccgacg agttgctgag gttgttcttg  540
agggcgctgg ggctcaccgg cgaggaggtc gccggagtcg aggcggagag gaggatcggc  600
gagaggatga cggcgacggt gcacctcaac tggtacccga ggtgcccgga gccgcggcga  660
gcgctggggc tcatcgcgca cacggactcg ggcttcttca ccttcgtgct ccagagcctc  720
gtcccggggc tgcagctgtt ccgtcgaggg cccgaccggt gggtggcggt gccggcggtg  780
gcgggggcct tcgtcgtcaa cgtcggcgac ctcttccaca tcctcaccaa cggccgcttc  840
cacagcgtct accaccgcgc cgtcgtgaac cgcgaccgcg accgggtctc gctcggctac  900
ttcctcggcc cgccgccgga cgccgaggtg gcgccgctgc cggaggccgt gccggccggc  960
cggagccccg cctaccgcgc tgtcacgtgg ccggagtaca tggccgtccg caagaaggcc  1020
ttcgccaccg gcggctccgc cctcaagatg gtctccaccg acgccgccgc cgccgccgac  1080
gaacacgacg acgtcgccgc cgccgccgac gtccacgcat aa                    1122

SEQ ID NO: 129          moltype = AA  length = 373
FEATURE                 Location/Qualifiers
source                  1..373
                        mol_type = protein
                        organism = Oryza sativa
SEQUENCE: 129
MPTPSHLKNP LCFDFRAARR VPETHAWPGL DDHPVVDGGG GGGEDAVPVV DVGAGDAAAR  60
VARAAEQWGA FLLVGHGVPA ALLSRVEERV ARVFSLPASE KMRAVRGPGE PCGYGSPPIS  120
SFFSKLMWSE GYTFSPSSLR SELRRLWPKS GDDYLLFCDV MEEFHKEMRR LADELLRLFL  180
RALGLTGEEV AGVEAERRIG ERMTATVHLN WYPRCPEPRR ALGLIAHTDS GFFTFVLQSL  240
VPGLQLFRRG PDRWVAVPAV AGAFVVNVGD LFHILTNGRF HSVYHRAVVN RDRDRVSLGY  300
FLGPPPDAEV APLPEAVPAG RSPAYRAVTW PEYMAVRKKA FATGGSALKM VSTDAAAAAD  360
EHDDVAAAAD VHA                                                     373

SEQ ID NO: 130          moltype = DNA  length = 2040
FEATURE                 Location/Qualifiers
source                  1..2040
                        mol_type = genomic DNA
                        organism = Oryza sativa
SEQUENCE: 130
actactcatt ccactattgt aaagtcatag aaaaaattta tatagagaga aaaaattagt  60
gttgttattg ttactggctt tctgccagac gagacgagcg agcgcgcgag tgtgttgctc  120
tctggtcatc gtcgtcgtcg tcgcgatgcc gacgccgtcg cacttgaaga acccgctctg  180
cttcgacttc cgggcggcga ggcgggtgcc ggagacgcac gcgtggccgg ggctggacga  240
ccacccggtg gtggacggcg gcggcggcgg cggcgaggac gcggtgccgg tggtggacgt  300
cggggcgggc gacgcggcgg cgcgggtggc gcgggcggcg gagcagtggg gcgcgttcct  360
tctggtcggg cacggcgtgc cggcggcgct gctgtcgcgc gtcgaggagc gcgtcgcccg  420
cgtgttctcc ctgccggcgt cggagaagat gcgcgccgtc cgcggccccg gcgagccctg  480
cggctacggc tcgccgccca tctcctcctt cttctccaag ctcatgtggt ccgagggcta  540
```

```
caccttctcc ccttcctccc tccgctccga gctccgccgc ctctggccca agtccggcga  600
cgactacctc ctcttctggt atatatacat atatactctc ccatgcattc catgcacata  660
cactctacgt atatatctac ctctacgtat atatctacgt attgatctac gtataatata  720
cgcagtgacg tgatggagga gtttcacaag gagatgcggc ggctagccga cgagttgctg  780
aggttgttct tgagggcgct ggggctcacc ggcgaggagg tcgccggagt cgaggcggag  840
aggaggatcg gcgagaggat gacggcgacg gtgcacctca actggtaccc gaggtgcccg  900
gagccgcggc gagcgctggg gctcatcgcg cacacggact cgggcttctt caccttcgtg  960
ctccagagcc tcgtcccggg gctgcagctg ttccgtcgag ggcccgaccg gtgggtggcg  1020
gtgccggcgg tggcgggggc cttcgtcgtc aacgtcggcg acctcttcca catcctcacc  1080
aacggccgct tccacagcgt ctaccaccgc gccgtcgtga accgcgaccg cgaccgggtc  1140
tcgctcggct acttcctcgg cccgccgccg gacgccgagg tggcgccgct gccggaggcc  1200
gtgccggccg gccggagccc cgcctaccgc gctgtcacgt ggccggagta catggccgtc  1260
cgcaagaagg ccttcgccac cggcggctcc gccctcaaga tggtctccac cgacgccgcc  1320
gccgccgccg acgaacacga cgacgtcgcc gccgccgccg acgtccacgc ataagctata  1380
gctactagct acctcgatct cacgcaaaaa aaaaaagaaa caattaatag agcaaaaaaa  1440
aaaagaagag aaaatggtgg tacttgtgtt taaggtttcc tccatgcaaa atggtttgca  1500
tgcatgcatg caaagctagc atctgcagct gcaagaatta caagagcaga gaagcagaca  1560
gctagatgga gataattaat taattaatta atctaattaa gcatgcaata attaagatta  1620
ttattctgat ttcagaactg aaaaaaaaag tgtggttaat taattattgg ttaggcttaa  1680
ttttatctag atgtagaaaa agaatcaaga tcttcaagca agagagaaga ggatcgaaga  1740
agaaggaaaa gaaaacgaaa aggacatgct gtgttgtctc ttctagttgt accctggctg  1800
ctgattaagt gctttgtttt gttgctgcaa gcttgtcgtt actgattatt agttagttat  1860
gcatctaatt gattaaacta atctgtttgg cattttggct cgagctaagc tatagccagg  1920
ctggtcaatg ataggaactt gtacaattta agcaattgaa cctgatcctg tactggcatg  1980
tatgtatata tgcaagtgat gagaaccact agctagtata gctagacatg tatttgtata  2040
```

```
SEQ ID NO: 131         moltype = DNA  length = 1332
FEATURE                Location/Qualifiers
source                 1..1332
                       mol_type = other DNA
                       organism = Hordeum vulgare
SEQUENCE: 131
acactcactc ctcaatccat ccgtctccac cattgctcgc tagctcgagc tctactagct  60
agcactgcaa agtcagccgg gccggagttg atttggtcct tgttagcttg accgatcgta  120
tacgtatcgc caggatgccg acgccgtcgc acctgagcaa ggacccgcac tacttcgact  180
tccgggcggc gcggcgggtg ccggagacac acgcgtggcc ggggctgcac gaccacccgg  240
tggtggacgg cggcggcgcg ggcggagggc cggacgcggt gccggtggtg gacatgcgcg  300
acccgtgcgc cgcggaggcg gtggcgctgg ccgcgcagga ctggggcgcc ttcctcttgc  360
agggccacgg cgtcccgttg gagctgctgg cccgcgtgga ggccgcgata gcgggcatgt  420
tcgcgctgcc ggcgtcggag aagatgcgcg ccgtgcggcg gcccggcgac tcgtgcggct  480
acgggtcgcc gcccatctcc tccttcttct ccaagtgcat gtggtccgag ggctacacct  540
tctccccggc caacctccgc tccgacctcc gcaagctctg gcccaaggcc ggccacgact  600
accgccactt ctgtgccgtg atggaggagt tccacaggga gatgcgcgtt ctggccgaca  660
agctgctgga gctgttcctg gtggccctcg ggctcaccgg cgagcaggtc gccgccgtcg  720
agtcggagca caagatcgcc gagaccatga ccgccacaat gcacctcaac tggtacccca  780
agtgcccgga cccgaagcga gcgctgggcc tgatcgcgca cacggactcg ggcttcttca  840
ccttcgtgct ccagagcctg gtgcccgggc tgcagctgtt ccggcacggc cccgaccgtt  900
gggtgacggt gcccgccgtg ccgggcgcca tggtcgtcaa cgtcggcgac ctcttccaca  960
tcctcaccaa tggccgcttc cacagcgtct accaccgcgc cgtcgtcaac cgcgacagcg  1020
accggatatc gctggggtac ttcctcggcc cgcccgccca cgttaaggtg gcgccgctca  1080
gggaggccct cgccggcacg cccgctgcct accgcgccgt cacgtggccc gagtacatgg  1140
gcgtgcgcaa gaaggccttc accaccggcg cctccgcgct caagatggtc gccatctcca  1200
ccgacgacgc cgccgacgtc ctccccgacg tcctctcgtc gtagatcggc gccggccatc  1260
acccggccgg ccaagagacc gatctataca aacaattagt gaacaaaaaa aaaaaaaaaa  1320
aaaaaaaaaa aa                                                     1332
```

```
SEQ ID NO: 132         moltype = DNA  length = 1110
FEATURE                Location/Qualifiers
source                 1..1110
                       mol_type = other DNA
                       organism = Hordeum vulgare
SEQUENCE: 132
atgccgacgc cgtcgcacct gagcaaggac ccgcactact tcgacttccg ggcggcgcgg  60
cgggtgccgg agacacacgc gtggccgggg ctgcacgacc acccggtggt ggacggcggc  120
ggcgcgggcg gagggccgga cgcggtgccg gtggtggaca tgcgcgaccc gtgcgccgcg  180
gaggcggtgg cgctggccgc gcaggactgg ggcgccttcc tcttgcaggg ccacggcgtc  240
ccgttggagc tgctggcccg cgtggaggcc gcgatagcgg gcatgttcgc gctgccggcg  300
tcggagaaga tgcgcgccgt gcggcggccc ggcgactcgt gcggctacgg gtcgccgccc  360
atctcctcct tcttctccaa gtgcatgtgg tccgagggct acaccttctc cccggccaac  420
ctccgctccg acctccgcaa gctctggccc aaggccggcc acgactaccg ccacttctgt  480
gccgtgatgg aggagttcca cagggagatg cgcgttctgg ccgacaagct gctggagctg  540
ttcctggtgg ccctcgggct caccggcgag caggtcgccg ccgtcgagtc ggagcacaag  600
atcgccgaga ccatgaccgc cacaatgcac ctcaactggt accccaagtg cccggacccg  660
aagcgagcgc tgggcctgat cgcgcacacg gactcgggct tcttcacctt cgtgctccag  720
agcctggtgc ccgggctgca gctgttccgg cacggccccg accgttgggt gacggtgccc  780
gccgtgccgg gcgccatggt cgtcaacgtc ggcgacctct tccacatcct caccaatggc  840
cgcttccaca gcgtctacca ccgcgccgtc gtcaaccgcg acagcgaccg gatatcgctg  900
ggtacttcc tcggcccgcc cgcccacgtt aaggtggcgc cgctcaggga ggccctcgcc  960
ggcacgcccg ctgcctaccg cgccgtcacg tggcccgagt acatgggcgt gcgcaagaag  1020
```

```
gccttcacca ccggcgcctc cgcgctcaag atggtcgcca tctccaccga cgacgccgcc  1080
gacgtcctcc ccgacgtcct ctcgtcgtag                                   1110

SEQ ID NO: 133          moltype = AA  length = 369
FEATURE                 Location/Qualifiers
source                  1..369
                        mol_type = protein
                        organism = Hordeum vulgare
SEQUENCE: 133
MPTPSHLSKD PHYFDFRAAR RVPETHAWPG LHDHPVVDGG GAGGGPDAVP VVDMRDPCAA  60
EAVALAAQDW GAFLLQGHGV PLELLARVEA AIAGMFALPA SEKMRAVRRP GDSCGYGSPP  120
ISSFFSKCMW SEGYTFSPAN LRSDLRKLWP KAGHDYRHFC AVMEEFHREM RVLADKLLEL  180
FLVALGLTGE QVAAVESEHK IAETMTATMH LNWYPKCPDP KRALGLIAHT DSGFFTFVLQ  240
SLVPGLQLFR HGPDRWVTVP AVPGAMVVNV GDLFHILTNG RFHSVYHRAV VNRDSDRISL  300
GYFLGPPAHV KVAPLREALA GTPAAYRAVT WPEYMGVRKK AFTTGASALK MVAISTDDAA  360
DVLPDVLSS                                                          369

SEQ ID NO: 134          moltype = DNA  length = 1653
FEATURE                 Location/Qualifiers
source                  1..1653
                        mol_type = other DNA
                        organism = Triticum aestivum
SEQUENCE: 134
cacgagatcc atccgtctcc accattgctc gctagctcga gctcctagct agtactgcaa  60
agtcagccgg ggagttgatt tggtccttct tggcttgacc gatcgtacgt gccgccagga  120
tgccgacgcc ggcgcacctg agcaaggacc cgcgctactt cgacttccgg gcggcgcggc  180
gggtgccgga gacgcacgcg tggcccgggc tgcacgacca ccccgtggtg gacggcagcg  240
gcgcgggcgg agggccggac gcggtgccgg tggtggacat gcgcgacccg tgcgcggcgg  300
aggcggtggc gctggcggcg caggactggg gcgccttcct cctggagggc cacggcgtcc  360
cgttggagct gctggcgcgc gtggaggccg cgatcgcggg catgttcgcg ctgccggcgt  420
cggagaagat gcgcgccgtg cggcggcccg gcgactcgtg cggctacggg tcgccgccca  480
tctcctcctt cttctccaag tgcatgtggt ccgagggcta caccttctcc ccggccaacc  540
tccgctccga cctccgcaag ctctggccca aggccggcca cgactaccgc cacttctgcg  600
ccgtgatgga ggagttccac agggagatgc gcgcgctggc cgacaagctg ctggagctgt  660
tcctggtggc cctcgggctc accggcgagc aggtcgccgc cgtcgagtcc gagcagaaga  720
tcgccgagac catgaccgcc acaatgcacc tcaactggta ccccaagtgc ccggacccga  780
agcgggcgct gggcctgatc gcgcacacgg actcgggctt cttcaccttc gtgctgcaga  840
gccttgtgcc cgggctgcag ctgttccggc acggccccga ccggtgggtg acggtgcccg  900
ccgtgccggg ggccatggtc gtcaacgtcg gcgacctctt ccagatcctc accaacggcc  960
gcttccacag cgtctaccac cgcgccgtcg tcaaccgcga cagcgaccgg atatcgctcg  1020
gctacttcct cggcccgccc gcccacgtca aggtggcgcc gctcagggag gccctggccg  1080
gcacgcccgc cgcctaccgc gccgtcacgt ggcccgagta catgggcgtg cgcaagaagg  1140
ccttcaccac cggcgcctcc gcgctcaaga tggtcgccat ctccactgac aacgacgccg  1200
ccaaccacac ggacgacctg atctcgtcgt agatcggcgc cggccatcac cggccggcca  1260
agggatcgat ctacacacac aattagtgaa caaaaaaatg ccagagatgg tgcatggtgg  1320
gctggtagct tagctgaggt agctaggagg aagagcgcgc gtgcggctgt cgttcgtgcg  1380
gctgttcccg caaaaaaaaa aaaggtttcc tccatatatg tctccatgca gaactgcaga  1440
tgctggtggt ggatgcgtcc atgcagcagg gaacgaacta attgtaagaa aatcaagcaa  1500
acttagttct acatctgtaa ttaagtatgc atgccacttg gtttaattca attcaagtgc  1560
agaaaaaatt atgatgggaa aaaaaaagac atgnnnnnnn aaaaaaaaaa aaaaaaaaaa  1620
aaaaaaaaaa aaaaaaaaaa naaaaaaaaa aaa                               1653

SEQ ID NO: 135          moltype = DNA  length = 1113
FEATURE                 Location/Qualifiers
source                  1..1113
                        mol_type = other DNA
                        organism = Triticum aestivum
SEQUENCE: 135
atgccgacgc cggcgcacct gagcaaggac ccgcgctact tcgacttccg ggcggcgcgg  60
cgggtgccgg agacgcacgc gtggcccggg ctgcacgacc accccgtggt ggacggcagc  120
ggcgcgggcg gagggccgga cgcggtgccg gtggtggaca tgcgcgaccc gtgcgcggcg  180
gaggcggtgg cgctggcggc gcaggactgg ggcgccttcc tcctggaggg ccacggcgtc  240
ccgttggagc tgctggcgcg cgtggaggcc gcgatcgcgg gcatgttcgc gctgccggcg  300
tcggagaaga tgcgcgccgt gcggcggccc ggcgactcgt gcggctacgg gtcgccgccc  360
atctcctcct tcttctccaa gtgcatgtgg tccgagggct acaccttctc cccggccaac  420
ctccgctccg acctccgcaa gctctggccc aaggccggcc acgactaccg ccacttctgc  480
gccgtgatgg aggagttcca cagggagatg cgcgcgctgg ccgacaagct gctggagctg  540
ttcctggtgg ccctcgggct caccggcgag caggtcgccg ccgtcgagtc cgagcagaag  600
atcgccgaga ccatgaccgc cacaatgcac ctcaactggt accccaagtg cccggacccg  660
aagcgggcgc tgggcctgat cgcgcacacg gactcgggct tcttcacctt cgtgctgcag  720
agccttgtgc ccgggctgca gctgttccgg cacggccccg accggtgggt gacggtgccc  780
gccgtgccgg gggccatggt cgtcaacgtc ggcgacctct tccagatcct caccaacggc  840
cgcttccaca gcgtctacca ccgcgccgtc gtcaaccgcg acagcgaccg gatatcgctc  900
ggctacttcc tcggcccgcc cgcccacgtc aaggtggcgc cgctcaggga ggccctggcc  960
ggcacgcccg ccgcctaccg cgccgtcacg tggcccgagt acatgggcgt gcgcaagaag  1020
gccttcacca ccggcgcctc cgcgctcaag atggtcgcca tctccactga caacgacgcc  1080
gccaaccaca cggacgacct gatctcgtcg tag                               1113

SEQ ID NO: 136          moltype = AA  length = 370
```

```
FEATURE                Location/Qualifiers
source                 1..370
                       mol_type = protein
                       organism = Triticum aestivum
SEQUENCE: 136
MPTPAHLSKD PRYFDFRAAR RVPETHAWPG LHDHPVVDGS GAGGGPDAVP VVDMRDPCAA  60
EAVALAAQDW GAFLLEGHGV PLELLARVEA AIAGMFALPA SEKMRAVRRP GDSCGYGSPP  120
ISSFFSKCMW SEGYTFSPAN LRSDLRKLWP KAGHDYRHFC AVMEEFHREM RALADKLLEL  180
FLVALGLTGE QVAAVESEQK IAETMTATMH LNWYPKCPDP KRALGLIAHT DSGFFTFVLQ  240
SLVPGLQLFR HGPDRWVTVP AVPGAMVVNV GDLFQILTNG RFHSVYHRAV VNRDSDRISL  300
GYFLGPPAHV KVAPLREALA GTPAAYRAVT WPEYMGVRKK AFTTGASALK MVAISTDNDA  360
ANHTDDLISS                                                         370

SEQ ID NO: 137         moltype = DNA  length = 1884
FEATURE                Location/Qualifiers
source                 1..1884
                       mol_type = genomic DNA
                       organism = Triticum aestivum
SEQUENCE: 137
tatatataca gctccttgta cttctctcgt tcttacactc actcctcaat ccatccgtct  60
ccaccattgc tcgctagctc gagctcctag ctagtactgc aaagtcagcc ggggagttga  120
tttggtcctt cttggcttga ccgatcgtac gtgccgccag gatgccgacg ccggcgcacc  180
tgagcaagga cccgcgctac ttcgacttcc gggcggcgcg gcgggtgccg gagacgcacg  240
cgtggcccgg gctgcacgac caccccgtgg tggacggcag cggcgcgggc ggagggccgg  300
acgcggtgcc ggtggtggac atgcgcgacc cgtgcgcggc ggaggcggtg gcgctggcgg  360
cgcaggactg gggcgccttc ctcctggagg gccacggcgt cccgttggag ctgctggcgc  420
gcgtggaggc cgcgatcgcg ggcatgttcg cgctgccggc gtcggagaag atgcgcgccg  480
tgcggcggcc cggcgactcg tgcggctacg ggtcgccgcc catctcctcc ttcttctcca  540
agtgcatgtg gtccgagggc tacaccttct ccccggccaa cctccgctcc gacctccgca  600
agctctggcc caaggccggc cacgactacc gccacttctg gtacgtacgc cggccgccga  660
tgcgcatata cacgtcatag tacggcacct acctaactgg ctctggccaa ccgtccgtac  720
acacgtgaag gggcgacgtg tccgactccg accatgcatg catgcacgcg cgcgaaactt  780
gttactcctg ttctgctatg gcagcagcta gccgcgtgtg tccgttcgta ggagtagtta  840
cttacacagt tacacttacg ccgtccgtcg tgttcctcga cgtgcagcgc cgtgatggag  900
gagttccaca gggagatgcg cgcgctggcc gacaagctgc tggagctgtt cctggtggcc  960
ctcgggctca ccggcgagca ggtcgccgcc gtcgagtccg agcagaagat cgccgagacc  1020
atgaccgcca caatgcacct caactggtac gttccactac tactccagta gtacaagtac  1080
aatatataga atacaaatgg cagcagccac gacgacacgt actccaccat gcagcaaagc  1140
atatattgtc ggtgcggcgg ttgacacgga gttgtgtcgt gtcgttgatt cacaggtacc  1200
ccaagtgccc ggacccgaag cgggcgctgg gcctgatcgc gcacacggac tcgggcttct  1260
tcaccttcgt gctgcagagc cttgtgcccg ggctgcagct gttccggcac ggccccgacc  1320
ggtgggtgac ggtgcccgcc gtgccggggg ccatggtcgt caacgtcggc gacctcttcc  1380
agatcctcac caacggccgc ttccacagcg tctaccaccg cgccgtcgtc aaccgcgaca  1440
gcgaccggat atcgctcggc tacttcctcg gcccgcccgc ccacgtcaag gtggcgccgc  1500
tcagggaggc cctggccggc acgcccgccg cctaccgcgc cgtcacgtgg cccgagtaca  1560
tgggcgtgcg caagaaggcc ttcaccaccg gcgcctccgc gctcaagatg gtcgccatct  1620
ccactgacaa cgacgccgcc aaccacacgg acgacctgat ctcgtcgtag atcggcgccg  1680
gccatcaccg gccggccaag ggatcgatct acacacacaa ttagtgaaca aaaaaatgcc  1740
agagatggtg catggtgggc tggtagctta gctgaggtag ctaggaggaa gagcgcgcgt  1800
gcggctgtcg ttcgtgcggc tgttcccgca aaaaaaaaaa ggtttcctcc atatakgtcc  1860
ccakscaaaa tsgmaawgct gggg                                         1884

SEQ ID NO: 138         moltype = RNA  length = 20
FEATURE                Location/Qualifiers
source                 1..20
                       mol_type = other RNA
                       note = suppression oligo
                       organism = synthetic construct
SEQUENCE: 138
acgggttctt ccaggtgtgc                                              20

SEQ ID NO: 139         moltype = RNA  length = 20
FEATURE                Location/Qualifiers
source                 1..20
                       mol_type = other RNA
                       note = suppression oligo
                       organism = synthetic construct
SEQUENCE: 139
cacgggttct tccaggtgtg                                              20

SEQ ID NO: 140         moltype = RNA  length = 20
FEATURE                Location/Qualifiers
source                 1..20
                       mol_type = other RNA
                       note = suppression oligo
                       organism = synthetic construct
SEQUENCE: 140
cattgacctc cccgctggca                                              20
```

```
SEQ ID NO: 141          moltype = RNA  length = 20
FEATURE                 Location/Qualifiers
source                  1..20
                        mol_type = other RNA
                        note = suppression oligo
                        organism = synthetic construct
SEQUENCE: 141
ccagcgggga ggtcaatgct                                              20

SEQ ID NO: 142          moltype = RNA  length = 20
FEATURE                 Location/Qualifiers
source                  1..20
                        mol_type = other RNA
                        note = suppression oligo
                        organism = synthetic construct
SEQUENCE: 142
cccagcattg acctccccgc                                              20

SEQ ID NO: 143          moltype = RNA  length = 20
FEATURE                 Location/Qualifiers
source                  1..20
                        mol_type = other RNA
                        note = suppression oligo
                        organism = synthetic construct
SEQUENCE: 143
cgcgctcgtg tacccggaca                                              20

SEQ ID NO: 144          moltype = RNA  length = 20
FEATURE                 Location/Qualifiers
source                  1..20
                        mol_type = other RNA
                        note = suppression oligo
                        organism = synthetic construct
SEQUENCE: 144
ctcccggcgc aggtcgaaca                                              20

SEQ ID NO: 145          moltype = RNA  length = 20
FEATURE                 Location/Qualifiers
source                  1..20
                        mol_type = other RNA
                        note = suppression oligo
                        organism = synthetic construct
SEQUENCE: 145
gtgtacccgg acacggtgcc                                              20

SEQ ID NO: 146          moltype = RNA  length = 20
FEATURE                 Location/Qualifiers
source                  1..20
                        mol_type = other RNA
                        note = suppression oligo
                        organism = synthetic construct
SEQUENCE: 146
tgcagggaag ctgtccgggc                                              20

SEQ ID NO: 147          moltype = RNA  length = 20
FEATURE                 Location/Qualifiers
source                  1..20
                        mol_type = other RNA
                        note = suppression oligo
                        organism = synthetic construct
SEQUENCE: 147
ttcttccagg tgtgcgggca                                              20

SEQ ID NO: 148          moltype = RNA  length = 20
FEATURE                 Location/Qualifiers
source                  1..20
                        mol_type = other RNA
                        note = suppression oligo
                        organism = synthetic construct
SEQUENCE: 148
agatccccgc gccattcctg                                              20

SEQ ID NO: 149          moltype = RNA  length = 20
FEATURE                 Location/Qualifiers
source                  1..20
                        mol_type = other RNA
                        note = suppression oligo
                        organism = synthetic construct
SEQUENCE: 149
```

```
atgcagggaa gctgtccggg                                              20

SEQ ID NO: 150          moltype = RNA  length = 20
FEATURE                 Location/Qualifiers
source                  1..20
                        mol_type = other RNA
                        note = suppression oligo
                        organism = synthetic construct
SEQUENCE: 150
attcctgtgg ccgcaggaag                                              20

SEQ ID NO: 151          moltype = RNA  length = 20
FEATURE                 Location/Qualifiers
source                  1..20
                        mol_type = other RNA
                        note = suppression oligo
                        organism = synthetic construct
SEQUENCE: 151
cagcggggag gtcaatgctg                                              20

SEQ ID NO: 152          moltype = RNA  length = 20
FEATURE                 Location/Qualifiers
source                  1..20
                        mol_type = other RNA
                        note = suppression oligo
                        organism = synthetic construct
SEQUENCE: 152
caggaatggc gcggggatct                                              20

SEQ ID NO: 153          moltype = RNA  length = 20
FEATURE                 Location/Qualifiers
source                  1..20
                        mol_type = other RNA
                        note = suppression oligo
                        organism = synthetic construct
SEQUENCE: 153
gactacttcg tcggcaccct                                              20

SEQ ID NO: 154          moltype = RNA  length = 20
FEATURE                 Location/Qualifiers
source                  1..20
                        mol_type = other RNA
                        note = suppression oligo
                        organism = synthetic construct
SEQUENCE: 154
gccaggattt cgagccaatg                                              20

SEQ ID NO: 155          moltype = RNA  length = 20
FEATURE                 Location/Qualifiers
source                  1..20
                        mol_type = other RNA
                        note = suppression oligo
                        organism = synthetic construct
SEQUENCE: 155
ggaacatttg gagggaggcg                                              20

SEQ ID NO: 156          moltype = RNA  length = 20
FEATURE                 Location/Qualifiers
source                  1..20
                        mol_type = other RNA
                        note = suppression oligo
                        organism = synthetic construct
SEQUENCE: 156
gggaggtcaa tgctggggct                                              20

SEQ ID NO: 157          moltype = RNA  length = 20
FEATURE                 Location/Qualifiers
source                  1..20
                        mol_type = other RNA
                        note = suppression oligo
                        organism = synthetic construct
SEQUENCE: 157
ttggctcgaa atcctggccg                                              20

SEQ ID NO: 158          moltype = RNA  length = 20
FEATURE                 Location/Qualifiers
source                  1..20
                        mol_type = other RNA
                        note = suppression oligo
```

```
                        organism = synthetic construct
SEQUENCE: 158
acgggttctt ccaggtgtgc                                               20

SEQ ID NO: 159          moltype = RNA  length = 20
FEATURE                 Location/Qualifiers
source                  1..20
                        mol_type = other RNA
                        note = suppression oligo
                        organism = synthetic construct
SEQUENCE: 159
cacgggttct tccaggtgtg                                               20

SEQ ID NO: 160          moltype = RNA  length = 20
FEATURE                 Location/Qualifiers
source                  1..20
                        mol_type = other RNA
                        note = suppression oligo
                        organism = synthetic construct
SEQUENCE: 160
cattgacctc cccgctggca                                               20

SEQ ID NO: 161          moltype = RNA  length = 20
FEATURE                 Location/Qualifiers
source                  1..20
                        mol_type = other RNA
                        note = suppression oligo
                        organism = synthetic construct
SEQUENCE: 161
ccagcgggga ggtcaatgct                                               20

SEQ ID NO: 162          moltype = RNA  length = 20
FEATURE                 Location/Qualifiers
source                  1..20
                        mol_type = other RNA
                        note = suppression oligo
                        organism = synthetic construct
SEQUENCE: 162
cccagcattg acctccccgc                                               20

SEQ ID NO: 163          moltype = RNA  length = 20
FEATURE                 Location/Qualifiers
source                  1..20
                        mol_type = other RNA
                        note = suppression oligo
                        organism = synthetic construct
SEQUENCE: 163
cgcgctcgtg tacccggaca                                               20

SEQ ID NO: 164          moltype = RNA  length = 20
FEATURE                 Location/Qualifiers
source                  1..20
                        mol_type = other RNA
                        note = suppression oligo
                        organism = synthetic construct
SEQUENCE: 164
ctcccggcgc aggtcgaaca                                               20

SEQ ID NO: 165          moltype = RNA  length = 20
FEATURE                 Location/Qualifiers
source                  1..20
                        mol_type = other RNA
                        note = suppression oligo
                        organism = synthetic construct
SEQUENCE: 165
gtgtacccgg acacggtgcc                                               20

SEQ ID NO: 166          moltype = RNA  length = 20
FEATURE                 Location/Qualifiers
source                  1..20
                        mol_type = other RNA
                        note = suppression oligo
                        organism = synthetic construct
SEQUENCE: 166
tgcagggaag ctgtccgggc                                               20

SEQ ID NO: 167          moltype = RNA  length = 20
FEATURE                 Location/Qualifiers
source                  1..20
```

mol_type = other RNA
note = suppression oligo
organism = synthetic construct
SEQUENCE: 167
ttcttccagg tgtgcgggca 20

SEQ ID NO: 168 moltype = DNA length = 8406
FEATURE Location/Qualifiers
source 1..8406
mol_type = genomic DNA
organism = Zea mays
SEQUENCE: 168
catcatatgg tctgttatat tgagaaggat atatttacaa gcattgagga tgcaaagaaa 60
ttggattatt ttcaaggcat gagaacccgt aggaatctac ctcatactag tggtatgtac 120
caattactaa tattattaaa tttattcaac attacctttg aagtcgtgtt tgtaatatca 180
tttccttcaa agttctggag caagaaacac tgatgttgat gttgacatta tacatttgaa 240
atgagctaca tcatagcttg tatgtcatct ttaacattta tgacaacgtt gtttcgctgt 300
acaatttttc tttatatgct actattagag tttatggtcg cttcgaccta ggtcttagcc 360
aatttctgag tccaccacta actacgagaa catttacttg tgtttcttca attcgccaac 420
atgttgccgc acgtcgttgt taccgtgagt tttttcccta ccctccatag aatattggag 480
tgagaacaaa aaggttgttt tggtttacaa gaacgtgtca tgtttctact cgaaaaccat 540
gcggtcagtg cgggtgggct aggtatgtag ctgcgccgtc gcgctgtccg tggcgtgcgt 600
gcactcggtg tcggactcgg acggcgggca gccctcgggc gccggcgcag aggatcggag 660
aagtgaaccc gcagccacgc tggcgctacg ccccgccaca acggcggctc gccggcggcc 720
tcgggatccc ccacctaatc agtaatcacg attcacgact cgccggaagc agcacccctg 780
gccctcgtgt tgggcctgtt gtgtccgtgt cgttcgaccc acctcgagcc aaccagatcc 840
ttacacgtgt ccgtgccgtc acatgtttta cttgctcgca gttgcagtgt ggtgccgact 900
cttttgctct cgtctcgtag ccttaggctg acaataagtt ttaaaattta cactatcaaa 960
tttaaagatc gaatcgaatt aaaatcgtcg gactttattt ttattaattt tcaaactaaa 1020
attaatttag aaccctaaca aattgtgaag aaatatttag atcctaatct actaccacgt 1080
cttcgtaccc tccgttagtt tctctctttc ttccatccat ggtggtccat atctactaac 1140
tagtttactt cactgctatt ggcaggttgt ttacctttt cttttcgaaa cgctccctac 1200
attccgaatt ataaaataac ttaatatttt ttaaaaataa attataacag aggctactca 1260
ggcattgcac acgcagtggc cgagcgagct agaacatgtg tttggatgct gcaccgcgct 1320
gttaacagca gccctatcca gtaaaatata tggcatgtca tattcagtac acactagaaa 1380
ataaattcca ccagatagtt acaaagagtc ccttgtacaa aaaaatattc agagccaatg 1440
atccattatc ttctctctta ttagatgtca cgaatcttct catcttgctt cctgcgtaga 1500
cgtagtcagt ataagaacaa gtcttttttt gtttggtctc tccccactta gttttaatat 1560
cgcaacatca tttctctgtt cttcctttaa agtgccagct tcgtatgcca cacgcgaaac 1620
acgtagatct gtttcctctt ttgcgcttct gataggccgt tacgccacat gagccttaag 1680
aaaccagcca atctcaacac gatagaaaat cgcacgaagt atagcactcg agcgtagtac 1740
cacatcggta gctgaagaat gacaagcgac cggacgccct ataaaaaaag ggttgggctc 1800
cttttcaact catatcctta tcagcctttt agctaagata aggtgtaaca tttgttctta 1860
tcaatttaat atttgatagg tgcaccatac attatattaa atttattttt tacgcatatc 1920
agatatgact gtgtgcagtc tgaacacacg atcattgtac tagttactac tttaggactc 1980
tgatcaagtg attaatgccg tggaacaggc tgctggagat atatgaccgt gactttgctc 2040
acgcacacat gcacacattc accgtaccgt acgtcgatct atatatagca gagacacgca 2100
caccacgata cgtgtcataa caactttgaa agtacgccag aagtcctaat agtggactaa 2160
acctgtgcgc cactttttc ctatttttgg agagaacagg tcgatggaga ggaaaaccta 2220
gctagaagaa aaatcacgag tcgatctact acattataca aggttgctta ttgggggcgc 2280
tggttggatc tgtggcgaat ggcgaagcga gaagcgagaa gcgacagaat gggtagtagt 2340
acgtgaagat tccgtggtgg gagatacgac aacaccctcg aaactggtcc ttaattaagc 2400
gctgatgatg gacggcaata atcgtgttgg ctcgctttcc atgtgtgcgt attaattggg 2460
gtgccagtgc agtgccacca ctctcaggct cccgatcgat cgatcgatcc ccaaaggaga 2520
ggagaggaga ggagcagtac gtacgaacta gatttgtcac ttgtgttgcc gcagctcgca 2580
gcagcagcag cagcagcagc tgggtggcct ttcgtgctcc acatcgctcc aaacccaacc 2640
cccccctcc ctccgtctct ctcaccacat ttcctctcct ctctttcctt cctcccactg 2700
aatttccaca aagcccaccg tctctctctc tctctctctc tctctctctc tctctctctc 2760
tctctctctc tctctctctc tctctctctc tctctctctc tgttgtgtgt gtgtgtgttg 2820
tgttctcttt ctctcagctc agcctctcct gatgggtcat cgatccacta cgctccaaaa 2880
cttctcccct atatatacca cgccatgtac ttctctgctt cttacacttc tctcatgcca 2940
ccataccact agtgcaaggt cctagattta cacttggtgc tacaccttgc ttcgcccccct 3000
tccttccttc cttccttcct tccctccttc cttggtctct aggcagctag cagtgtggtg 3060
ctgctgccgg ccgcctattg gccgcctggg actgggatcc attaattact gcgcgcgcgc 3120
ggctaaccaa ccaatcccag cgtgcgtaat ctattgccca catgccgacg ccgtcgcacc 3180
tcaacaagaa cccgcgctac ctggacttcc gggcggcgcg gcgggtgccg gagtcgcacg 3240
cctggccggg cctgcacgac caccccgtcg tggacggcgg cgcgccgggc cccgacgccg 3300
tgccggtggt ggacctgggc gccgcggacc cggcgccggc gccggcggcg gcggtggccc 3360
gcgccgccga gcaatggggc gcgttcctgc tcacgggcca cggcgtcccc gcggacctgc 3420
tggcgcgcgt ggaggaccgg atcgccacca tgttcgcgct gccggccgac gacaagatgc 3480
gcgccgtgcg cgggcccggc gacgcctgcg gctacggctc cccgcccatc tcctccttct 3540
tctccaagtg catgtggtcc gagggctaca ccttctcgcc ggcctccctc cgcgccgacc 3600
tccgcaagct ctggcccaag gccggcgacg actacaccag cttctggtac gttgcgttgc 3660
gtgcttgtgt gcgcgcacac ctgccgaccg cggccacacc gtacgcaacc cacgcgtacg 3720
tacgtgcgct agctacctgc ttcgctcgct tcgctcctct cgcctcgcca tgcatatgca 3780
cgtacggccg tacaggtaca gcagcaggtc acacgcacga acgcacgcac gcaccagcac 3840
cgatatgata catcatcgac gtgtcgtccc cccgtctaag gccatgcatg catgcaagca 3900
cgcctagcta gccctttttgg cttgctagct gacgagggga gctaggacga gcatacttac 3960
tgtgcgcgtc atgctcaatt gctcacacta tactactact tgttactaca gtgatgtgat 4020

```
ggaggagttc cacaagcaca tgcgcgccct cgcggacaag ctgctggagc tgttcctcat  4080
ggcgctgggg ctcaccgacg agcaggccag cgcccgtcgag gccgagcgga ggatcgccga  4140
gacgatgacc gccaccatgc atctcaactg gtgggtatat attattgtct gtcatgttgt  4200
cgtcgtcgta cgcgttgcgg ttgggtgtac atgtatataa cacaaacaac aaaaaactaa  4260
cgccgtgccg acgacgacga cgatcatcag gtacccgagg tgcccggacc cgcggcgcgc  4320
gctggggctg atcgcgcaca ccgactcggg cttcttcacc ttcgtgatgc agagcctcgt  4380
gcccgggctg cagctcttcc gccacgcccc ggaccggtgg gtggcggtgc cggccgtgcc  4440
gggcgccttc gtcgtcaacg tgggcgacct cttccacatc ctcaccaacg gccggttcca  4500
cagcgtgtac caccgcgccg tcgtgaaccg ggacctcgac aggatctcgc tcggctactt  4560
cctcggcccg ccgccgcacg ccaaggtggc gccgctgcgc gaggccgtgc cgcccggccg  4620
ggcccccgcg taccgcgccg tcacgtggcc cgagtacatg ggcgtccgca agaaggcctt  4680
caccaccggc gcctccgcgc tcaagatggt cgccctcgcc gccgccgccg acctcgacga  4740
cgacggcgac gccgccgtcg tccatcagca gcagcagcta gtcgtctcgt cgtagccgag  4800
accgatcgcc ggagactgat gctgatgatg atgcatatat acatgagaga aatcgtcgag  4860
tagactagcc gattgcaaaa gcaaccccag ctgccgaaac ctggcatatc gatcccattc  4920
tctgctgcgc acatgtatgc atgcatgcgc ttcgtccgtt cgactcgtgt gtgcttgctt  4980
gcttgcgcgt gcagcagaac taattccgtt ccgcagctag ctgctctgct ctgctctgct  5040
ggaatgtaat taagtagtag tatatggtag tagagaaaag attagctagg cgatcgatat  5100
agatgacggg ccggggaaga agacgaatta attaagatcg atcgacgacg acgagctgtg  5160
cgtggctggc tgtgttcttc tctagcctag ttacagaggc cggctgctgc tgcttccaat  5220
cgggctgctt gtcgctactg acgatcgtta gtggatccat taactaatct ggaattctgg  5280
attaatgcat gtggtttggc atctggctgg cgtaaagatg ggggaggcca ggccggggtc  5340
ccctagccag tagccaggct ggtcaatgat aggtctataa cctgatcccg tactgttgtt  5400
tctctctcgg tctgcgctgc ggagaaaata ataattgatc gatccgccgc ccggcctggc  5460
gtactctgaa ctgaacgaaa cgatgggtga tgcaagagcg ttatttgcaa taagctgcag  5520
tgagtagcag tggagatgtg taaaaataaa tatatatata tatatatata tatatatata  5580
tatatatata tatatatata tatatcttct agttattcta ggtcatggat gtgcagtgca  5640
gctacggctg ttactgtaga ggacacacct ggctcgtacc gtcgtacacg cgctagccaa  5700
ggaggaagag acacggcccg gctcatgtgt cagcctgcgc tactacctac gtactgcatg  5760
cgtgcttgtt gcctgctctc gcttcgaaca aagctgcatc gtgcatggaa tggaacaaac  5820
cacaccatgc atgctaccac caaggcaaga tatatgcaag ttactgcgag aatctttacg  5880
tgtgctccag taaaatttta accgttggcg tggcaacata gtattaactg ttacagcggt  5940
gcttattagc ttgtctggaa atgaaaagaa gacgccagtg atttcacttc tccaaacggg  6000
acctggggt atttacttgt agtaacgtgt acagtaatta ataatgcgcg cgggcacaac  6060
tcacaagggg ggaagctagt accagtacca gtacctgctg ggggggtttg catctgcatg  6120
cggccaagtg agccccttt gtgtaatggt gccggcacta cttccacgaa ggaaaaaaaa  6180
ggatcggagc caagaactgg gccgggatcc tgaggagatc tgcagtggag ctgagacccg  6240
ggggagggga ggatccgctt ttaccttttg aatcctgcct ggccacaccc cgttctgctg  6300
ctgctggcgt gatgcaaacc aaggagaaga cgccatggcg tgagagaccc acccacccct  6360
tagcccccca actaacattc agatcaggct gcaacttgcg gaacagtgtc agactcggac  6420
agtactcggt gctgtcagta ctaccaacgc agcagcgcca ctgcatctgt gcatcatatt  6480
cttatcctcc tccttcatag gccatgccaa atcagatcat gtctgggcag gatagctcca  6540
cgaactaaaa aaaaattggg atctaacatt cacctacatc tatcgcgtaa aacaacaaca  6600
ccgatacaat aaactgggat ccatcgacat acaaacctga gctttcatat gaaccgaatg  6660
acaggtctga gatttaataa aaagagaggg ttcaagtcat ctccaacctc tagagctagc  6720
ctcttccttc tctctttcat gtctacaaaa aaaaatcatg aggaactcca ttgtcataca  6780
ggtggtagta ggggcttaag ccccactcgc ccccaccact acagtaaact aataaacatc  6840
cgacggcctc cggcggcggc ctacgaggcc gtcggagata agattatgtc cgacggccac  6900
aaagggcgct cggaaatagc gcttatctcc gacggcctcg aaggcagccg tcggagataa  6960
ggttatgtcc gacggctggc agcgtagccg tcggaggtaa gactttttaa tccgcaggaa  7020
ccggcgcgcg gttcatttcc acgcgcgcgc tcttctcttc tcttctctgt ctctgcccac  7080
gcgccgccgc cgtcgactgc gccgccgccg tccgctgccc ggcgccgtcg cccactgcgc  7140
cgccgcgccg ccgccgcccc tcccactgcc ccgccgcccc gcctcccaaa gccccaccgc  7200
cgtcgacgca gccccgccca cacgcctccc cgcccagccg ccgtcgccgc cggccgccgg  7260
ccgccggtcg ccgccccgct cgccccgtcg ctcacgtcaa caggggtgcc ccgtcgctgc  7320
cggctacatc tccgcccgcc atattatcaa agtaagtatt tttagattta ttttgtatat  7380
attaatattg ttttatagtt tctaatgttg ttattaaata attagtatgt taaataatgt  7440
ttatcttatt atatccgatg gcctaaattt gattatttgg cgaaatttga ttatatggcc  7500
taaatttgat tacgtaatta aattaccttg ttttagttta tttagtggtg ctttagataa  7560
tttaaatttt aaatttccga gggtaattat tatgccctcg gaaataaggt cattttatat  7620
gatttgtcat tcataacaat gttatttcgt atgtaatatt gtattgtggt ttattagttt  7680
aattatttaa taatacacga tgattctagt taatcatagt gtatcgtagt gtgaacaaac  7740
gaaacctagg cgtcacccgt ttcggcccaa cacaccttac aagcgacgca tgtgaggtat  7800
gttgggccgg aattgtcctt ttattggaca gcctcggggt gaccgacaga gttcgtgttt  7860
atgacaaaag catgtgctcc tgcttagttt cggcagcata acccctctgt tctccaattg  7920
caccattttt aggcgtgcga ttggagaaca gcggggttat gctgccgaaa tttcgcacga  7980
ccacatgtct tgtcataaac acggcctcgt cggtcactcc tgggtgggtt taggacctat  8040
cctttcctac agatgtaggg gcgtgatttc ttcgtaaaaa cggatggccc gtgcattact  8100
tatctaatta agttaacgtc tcgtagctag tatggaggag aatcgtcgat ggatgtatga  8160
aggttggaag aaaagaggtg ctctatcaag tgagtgggtg gccaagactg atgcttttct  8220
cgaccatgct tttgctcggt cagagactgg aaccgatgtt aggtgccctt gtagcaagtg  8280
tcggaacatt aatttccttg acaggaggac tatgtcgata catatttgca agaacggtta  8340
tatgccaggc tatgaggtgt gggtgcacca cggtgaggac ccacctcctc gtattgtatc  8400
ggaagt                                                            8406
```

```
SEQ ID NO: 169          moltype = DNA  length = 7581
FEATURE                 Location/Qualifiers
source                  1..7581
                        mol_type = genomic DNA
```

organism = Zea mays
SEQUENCE: 169
gctcctattc tgatatttac ttcaattcaa ctcaaaagtg tattttttaa ttcaatatac 60
atgaataaag aactatactt ctaataatct ccaatgtcga agtaaactaa atcataacta 120
ataataatta ataaaataac agatcaagtg aggaagtaca aattaaaatg gtagaaagca 180
aatagtcatt ttactttacc aatattttgg gattaaaaaa atattacaca aatagacatt 240
aaagtacttg cgtatatgac attatagcat tgacaaggat cactagtaca aagaaactct 300
ataaagacgg tttataaact attttcactg acattaagac gatagcttat aaaaataata 360
tagttaccaa tatatattca acaattaaat gtattcatta atattatatt ataaaaatat 420
tcaacataaa aagtataaaa tattcgacat ccataaataa aaaataaaag tatttaaata 480
attcaaaacg ataaatggtt tgaattaaat tacgaaaata ctaaatattt atgtaacatt 540
agttatttgt agatatacta ttaaatggta tcaatgcatc attagtaata ataaaattaa 600
ataattggac attccttata gagagaaaac tttttaaata ggttcatgat acattgcttc 660
ttttgcggat atggatagtc actacaggaa aaactggaaa aaaaacgtca gccagaataa 720
gaacgttggc cccgacgttc ttaaatcgcc taagaacgtc ggttcctaca gaccggcgta 780
cttaagtcta agaacgttga cctttgcttt gccgacgtac cttaagttaa gaacgtcagc 840
cctgtctggc tgacgttctt atatgaatta tataacagca cgcgatcctt ctctttcttg 900
tgttctctcg cgtgcatacc ctatagcgcc gccaccagag cccgccatcg ccccaccgcg 960
tgcccgcccg ccccactacg cggccgctgg agcccgccac cgctagccac catcgaagcc 1020
caccaacgcc ccaccacatg gtcacccaag ccaccgcgcg ctgccaccgg cgcccgccac 1080
cgcaccgctg acctcctcct caccacgccg ctgtccttcg cgccaccgca cctgctcgcc 1140
gctgcacatc gagatcgcgc aggtgattag tttatgcttt tattccatta tgagtatgaa 1200
tgcctaatct gaatttttgg agcgcaagaa ataatgtatg attagtttat gcttttatta 1260
cattattttg cttgaaaatg gtttaatgta tagaaaaacc atgtgttgta ttgtgaaata 1320
gcgctgaatt taatcatatc gtgtttgagt atgattgtgt atcttggcat atgtatgtta 1380
ggttaatgac aaatagtcct cgccccccgac gcttggtggt cgccccttcc ctcgcccgtt 1440
gccagcacgc tcgccggttt gctccgtcta ggccgccctt cgtccaccgt cgaggccgag 1500
tccacgccgg tgcctccact accactcgct tgggggccca cctccagcac cgtccctacg 1560
cttcaaaggt ttaaaatctt ttgtgtttag attcatcttt tgtgttgctg caattgcaat 1620
cgctatttgg atatgattgt aggtactgcc atttacctca agcacttgtg tttaaagtaa 1680
atagtgatac ctaatgtttt tcacacattt attttgtcat tggcacattt acttacacgt 1740
aggacacaca cttagaaaaa catatgcgtc acccgttcgg gaacgacaca tctcacattt 1800
acttgtgagg tgcatagtcc gaattgtcta gcttatgttg gacatcctga gaatggtagc 1860
ggttgtgtgt tatttggtct ctgactcgtg tacctcccgc tcgtgatttc ggtagtccgg 1920
agaacaatgg ggttatgctg ccgaaatcat gagcataagg tacacgagtc agaccaaata 1980
acacgcaacg gctagcattc ttatgtacga tggttccaac agtgacaccc tagggcactc 2040
tgatgcatgg gttagggttg ctgacgaaat ttgtggcacg cgcatttgct ggcgagcctc 2100
gtgtggcgaa atgcccatgt actaggtgtc gaaacctgat ccgactggac aagtttgacc 2160
tctccattca tatttgcaaa tatagcttta agctagacaa tctggtgtgg cgtgagcatg 2220
gaaaggtgga tgctcctccg gagtcgaata tagacgaggt cgtagaccga atagaggaca 2280
tgctagatga catctgacat gagtatccat cactagagac cgactgacac ccgtcggtgg 2340
aagtgcagta gttgctcacg aaggcaccaa agtaactgta cttcatatcg taatacggct 2400
tatggagatg aagtccaagc ataacttctc aaataactgc tacaacgata tcgtgacaac 2460
ggatatttat attacacgtt tatccgataa tgaggttgga taatttggat atccatttct 2520
attttccatc gctagctata agcctataat aagtttaatt caatttgtcc tatttcctgc 2580
ttcttcacct caagtcctca aactacatgt tgtaaagatg aggaagtcga acactccacg 2640
cggtgcccac ctcttttcat gcactcacca actgatcatt tgttcatggt tttcatcacc 2700
acgcgtgcat caaaaaaaac ctagctgata agctcaagcc gcatctcaca gaaggttcaa 2760
gaaattatac tgaaatcact gccagcgccc aaacaagtgt cagccgttct tgccatttgc 2820
atgccacgcg tgctgcaggc ttacgtggca gaaacgttgc acggacatgc tggcacagtt 2880
gtcactcgcc ccatgaattg cttgccttgt gttgcatgca tggtcgctca cacacatgaa 2940
tgatttcatg ttattcgtct tgtatgctat ataactgcag tttgtgttga cctccatttt 3000
gattatctct atcctgtacg tgccgagagt ccttcaaagc cgacgacgag acgacgatgc 3060
agtgcgtcgtc gtcatcagcc tcgacgccgg ctgccgcttc cggcctcgtc ttcgatctcg 3120
ggtctgcggc gggcgtgccg gagacacacg cgtggccggg ggtgaacgag tacccgtcgg 3180
tggagtccgc tggccgcgac gtggtcccgg tggtggacat gggggtggcc tgcccggacg 3240
cgacgcgggc gttggcgcgc gccgcagacg agtggggcgt gtttctgctc gtcggccacg 3300
gcgtgccccg ggaagtggcg gcgcgtgccg aggagcaggt cgcgcgcctg ttcgtgctcc 3360
cggctcctga caaggcccgc gcggggcgcc gccccgggga gcccacggcc accggctacg 3420
gcaggccgcc cctggcactc cgcttctcca agctcatgtg gtccgagggg tacacgttcc 3480
gcgccgccac cgtccgcgaa gagttccgcc gcgtctggcc cgacggcggc gacgactacc 3540
tccgcttctg gtacgtacga gcgccatgtc acgtgcttgt gctttcatgc ctcgtaccgt 3600
cgtcgtgctg tacgtgttat gtttatcggc cggtacgtca cgcgtgctac actggttaac 3660
gacgtgagcg tgcccacgtt gactgcatgc atgtgcatgc gcgcgcccag cgacgtgatg 3720
gaggagtacg acagagagat gagggctctc ggtggcaggc tgctcgacct cttcttcatg 3780
gcgctcggcc tcaccgacgt ccagttcgcc accggcgaga cggagcggag gatccgcgag 3840
acctggacgg cgacgatgca cccaatcctg tacgtacgtc aaaaacgaat atctgaccaa 3900
tgcaaacgtt tttctgcaat gccagtcatc cactcatcct gtacgtacct ctggactctg 3960
cttgtccatc tactgatgac acgtatggta ggtaccccag gtgtccggaa ccggagcgcg 4020
ccatcgggct gacggcgcac acggactcgg gcttcatcac gctcatcatg cagagccccg 4080
tgcccgggct gcagctgctc cgccgcgggc cggaccggtg ggtgacggtg ccggcgccgc 4140
cgggcgcgct catcgtcatg ctcggcgacc tgttccaggt gctcacgaac ggccgcttcc 4200
ggagccctat ccaccgcgcc gtcgtaagcc gagagcgcga gcggatctcc gtgccctact 4260
tcctctgccc gccggaggac atgacggtgg cgccgctcgc gtccgctctg ctgccgggga 4320
ggaaggccgt gttccgggcc gtgacgtggc cagagtacat ggaggtcaag cacaaggtgt 4380
tcggcacgga tgcgccggcc ctggagatgc tgcagctgca ggtggatgag gaagaacaag 4440
gtgaaagggc cgccaccacc taagccctaa ggaactacta gctgaatcca taaactaata 4500
aagaattcgt gaataagggc gttggaagac tggacacaac acaagagagt tgctatatat 4560
cgtatttctg aaatttaagg caaatatctt agttaaaaaa ctggtatatt taaatagaca 4620

```
atatatatct aaaataaaga tagttcacca tttttacggt cgaacaatga taaagttata  4680
tattgtctga atagtaacaa attaaagatt tccaggagat ggatgcgatt gtttcttgtt  4740
catccactcg ttcataccat gttgccagag tattacacac agttatgaga agggcgctgc  4800
tatctcgtat gggatatggt gaggcactca aacatacaac agtggctttt gggtgctcta  4860
gtttcttaca tagttttcgg tgtggttgac tatgagatag aggatacaat tttgaatgga  4920
ctcacggcgc caagtgacgg tgattttgcc ggaaacttga taaagatttt gccaagtgtc  4980
acttggtact cgcaaagaaa agtcgccgtc acggcgcaag tgacggtgac aaagactttg  5040
ccgagtatcc tccaacacac tcgacaaaga ctccctcttt gtcgagtgct tactatccta  5100
gtatcaaaca attcagctcg gggacgagtt gcctctcgag gaggggagag atgtcacgtc  5160
cagacgtaca cgaggcgtcg ggcacaagat gtgcgacgtg cagcggaacg cggcgcgcac  5220
ccaggtgcga gtgaacatga aggcaaggaa agtggctaac taggaaatag agatagcttc  5280
ctattagctc ctaaattagt gggctgattg gttcctatta tttattagat cctaaattag  5340
tgggttgatt ccttcctatt attagctcct agattggggg gttgttcctt ccttttttatt  5400
agttaccaaa gtagtgggtc tttcctatta tgaggcccta aattagtggg ctgcgggcat  5460
atatatcctt gtaaaccaca gggaggaggc aagcaataaa ctatctcttt cactactcct  5520
attaattctc tcaagctcgc ggttgaggtg ctgatcctca ccggagaaga cggatggcag  5580
ctacgagcta cgtagccgtg gtccggctag ttaggggttt gacgctcttg acaaatgtcg  5640
aggaacccac tcactactaa ttcagaattt acaaggtgta tttacataga acttgctagg  5700
ctagaccatc tgtattttca gaatgtcata tgagaaggtc tgttaatcaa gtgtgtaaag  5760
tctagccaga gttcagtttt tagtcctcaa actccatctt tctgcattga gttacaaagt  5820
gaggaggtca attaagtgtc catcaaagaa aaagaccgta gcgtgtagag aaggaatgat  5880
aaaatagatc acaaatgcta tcagctttta ggatagataa atccactact gattcaaaac  5940
ggactataca tccatcttta agtaattcaa aacaaatgat gtttatatta ttttgagagc  6000
aagttaaaaa atacaattta ttacaataag cacatctatt atcatcgaaa acacttaatc  6060
agtaacgaag tggattataa tgaagtgcct taatcagtaa cgaagtggat tatagcgaaa  6120
actatagcag caataatgcc gcagatgatg gcaatgacgc caatcaccgt agccactgtt  6180
aagatagctg ccaaaatagg ggctaagcat agaagaattg aggatctgac gcagcaactg  6240
ttaagtacgg gaactagatc tgttatgatg gctgagaggc tttgcgggag cttggctttg  6300
atacatccga ctattggaga tatgtggttc tggaagaatc cccttgcgaa ttgcaatgca  6360
ttgcgaagtt tgggcgatgc gtgcttttgg aaaagccttc taagaagtgc ctgttcatgg  6420
agtaacagga tgatgaaggg tgtgaggagt tgcggcgaaa ccgcgagaag cgggagcaca  6480
catgccgcag cggcgatgtg cggatcgatt ggagcgaagg caaggtacgc cgccagcacg  6540
aagacagcga ccacagccaa acatgcaatc cggagggaga agcccgcaat gccgaggtgc  6600
acaaggcgcg ttggacgatc catggtggag aacccagcga agatgctgca gaacgcggcc  6660
agtgaagacg aagcgaatgt cagggcgtca gagactatga gtgccctgaa tgcacgtccc  6720
ctcgctcggc tgatgagcgg aggcggcaga acaacagcat cagcagatag attctgtttc  6780
gcaacgttgt agaatgtggc taccgatatg ttcagcatga aaatggcaca gacagccgtg  6840
agccctgcgg acttgctgat agactctgat aacttgtctt gatcgagctc tcctcgtgcc  6900
ttgtcctcac ccttgagcag atcccttcga taggtaccat gatcagatcc agacagtctc  6960
aagtgatact ttatcaatac tcgggagttc tgcacaacaa caacaacaac aacaacaaaa  7020
gagtttggtt ttttatatta acctttgatg aaaattaagg taattaatca atggaaagaa  7080
aagaattaaa gacagaagga aacaagtgat ggtaccagta agaggtgcag tccaggttta  7140
atgcataaga tggagaggtc gagaggtgtg tgcccctcct tgttcgcgaa actgaggccg  7200
acgctgatgt tgctcaccaa actgcagaag atgcgggtat tcccagtctt caccgccaga  7260
tgcagagcgg tattcccatc ccaatcggcc aagttcagta tccccgccaa gctccgttgg  7320
ctgcatacgt ggtccacgac gctctccatc ttcttctcca cagcgaggtg gaggaaagtc  7380
tggcctgaat cgttgcgtga ctgcgtgcag ccagggcaca cctccacaag tttcctgacg  7440
atgtcaagcc ttccatttgc cgcagcgaca tgtatgggaa accagccatt ggagtccttc  7500
ttcagcgcag cagcagtaca agagcccccc tctctcgtgt cgtcgtcgtc ggcggcggcg  7560
gcattcccag ctggtgatgt a                                            7581
```

```
SEQ ID NO: 170          moltype = DNA  length = 7332
FEATURE                 Location/Qualifiers
source                  1..7332
                        mol_type = genomic DNA
                        organism = Zea mays
SEQUENCE: 170
tataattata gatgaatgta agggacatag atgaaatttt acccgggctg catcctgtaa  60
atagatgaag agtaacaccg tactgttcag gttggattgt aatcactctc ttgcatccat  120
accttcgagc aagccgaagg tatcaatgtt atattaattc ttcctatatt catgtgtgtt  180
ttatgaatac taatatgaat gaatcattca atcatatttg ccatttttgc gtgttcctat  240
ttatctatgg aatgatgaag acacgttctt catgaccttc agccgaagat cattatctcc  300
gagaggagat aacgcttcga aggacgaagg tccttaatac ttaacaaatg tgttgcctgg  360
ttcttgactc acaacatttg agaacaagtg accaacaggt tcatagtttg agttggtctt  420
tagctgagat tcccaggtac tcgccttctt gtatgatgta ttcggcccct taggttgaga  480
ggtgtgccgc gaggacaaaa cctggtgagg cgttgtcgcg tgggggtctt tagaattgta  540
agtatgaatg ctgccttatg gggtaggtgg gtcttcggta cgaggatgct tgctgtcgag  600
tgcccctgtt tcattgtttt cggctgcgac atgtagcgtg tcctctgcga gggctgattt  660
gcctttcttg tcgacgaggg tcaccttcgt ggcgtcgtcc aatgaggtgt tggctctggt  720
ggtcactttc ttcggagcca tcgcaggttt tggtttacga agcacgaacg ataggcgcca  780
aatgttggaa ccaactaaca cgtggatagg tgggcccaga cactcaggaa atggcagagc  840
tcaagtgcac aacgaagttg taggtaggga actgtagcgt cttgttatgt gtgtccatag  900
atgtaaagaa tgatgatatt tataggtaac tggacgggta ggtggtccca agtaccatta  960
tacccccggt tacctactgc attcctagaa tattcctcgc aacggggtca ttacaatgcg  1020
gttaggtact gtaacctaaa catacccctaa agtataccccc tcgaaggggc ttacaagtgg  1080
gcccgaaccg tcgtagggtg aagcctggcc ccacgaaaag ctcgcgaggc ctttgcccat  1140
aagtcagacc cttgacttcg tcgggacttg gactccgcta tcgagggagg agttgagcct  1200
tcaggacacg tggcgacggt tgctgcgagt cgctctcttc tcgcgtggcc cttcgcgcag  1260
ccttcttcga cagccatggt cgaggactcc gtcgctgacg cggggtgaag tcctccaccg  1320
```

-continued ttattgatcc tggactcaaa tatggttaat tatagccgga tagggctgat cgaggtcgtg 1380
ttcgaccttc gttctaacag tgtgtagata ccaaaagtaa tcttaatcct catataacgt 1440
cttgatgtaa ttgtctaata ttaataaagc ttgctttatg aaaaaaacac gctgttgcaa 1500
ggagagtcgt atcaaaaagc tattttatgc ttccgtctac agagacaaat gcgtgtccgt 1560
gacatccatt aggccccgtt tgtttccttt catttcgagg aattggaatc ttactaatgg 1620
aatatgctat ttttttagaa tatgacattc caccactttc caaagttatc atataagcct 1680
acctcaaatt catggggtgg gaaatggaaa ttgattctat agatttacat gttatttttc 1740
cgatgtacaa cttatagcac attcttatac ttgcgcctgt ataacataaa tgtagtatat 1800
aactatctct ctcatatgat ttaggataat atacaaatat attatatata taaatatata 1860
aacttaatta gttttgtcta aattataatt attaaaatgg aattcaattc caacgaaaca 1920
aacgggtcct tatattaatt caacactata gtaattcttg attacatgtg gcctaccaca 1980
acaattatgg aaatctttgt caagtcccca gtgtggtcag ttcagcactt tgtcgacctg 2040
gatgcaatgc aactagcaaa acaccatctg atgaaagtct tcaagataag aatcttgcac 2100
tacttttctc ccccctgctt ttactggata tagagtgtcg tgcaccaatt ctaaggctat 2160
gcgcagcgca tcccgccagc cgcctctccc cttggtttag gccctgtttg ggaacaaagt 2220
ttttgaaaac acagtttttg aaatactaca atatacttta gtcataacaa tactgcagtt 2280
tacaatacca caattttgga aactgaggtc cagacctaag tttagaatac cttaaaacaa 2340
ctatagtatt tgcaatactt cagttttgaa aacagagatt ttagccaact tgctaaacac 2400
aattctgtat ataatactgc agtattcttc caaaactgtg aaaaaacttc actcccaaac 2460
accccccttag tgtgtgtaga gcaacattgt atactgcagc actcaccgct tatactgcag 2520
cactcaccgc tataagccta taactgctac agtacaaacg tgatgcacag tgacccacca 2580
tatgcagggt aacgctagcc gcttctctgg cgtggttttg tatacacgtg agtatttatt 2640
agatatagaa aaattaataa tagataaaaa gtaggtatag taaatgatat tttatcggtg 2700
tagtggggta tatagggaga atatagggggg agataaaaaa ataagagatg aaatgttaat 2760
gatgtgacgc gaaaaagtag tatagaggaa aaaaaattag agaaaatcac tgcggatagc 2820
ctaaaatgta ctgaattttt gtttccttgt gctgctattg cactttgcgt tttttcttct 2880
tatgaaaaaa aagagcccat aaacaaaagc aaaaagttct ctgtcttgct cctgccccaa 2940
ggtacgaagg taaacgacga gcacgatttg gtcgcccgag ctagcggcct cagccctcac 3000
atgacgaaga cgaactagcc gcacctgctg cgctgacttc cgcagccact acaccccacg 3060
cgaagcacag caagatttca ctagcagaag ccagatcgag tagaggcggg atccggcgga 3120
ggcgcgaggc atggagatcg cgacggttga cctccgcggg gtggtgccgg ggggcgccgg 3180
gtgggaggcc gcccgcgcgg cggtgaccgc gtccatggtg gcgcacggct gcgtcgtcgt 3240
ggcgcacgac gcggtcggcg cggacctccg gcaggcgctg ttctcccgcg cgctgccgga 3300
gctcttcgcg ctccctctcg aggccaagca gcggacggtg tcgcccaatg ggagttcag 3360
gggctacatc ggccagcgcc ccggcatgga ctgggagagc ctccgcgtcg gaaagcccac 3420
ggacgccgcc agcgtcagcg gcttcgctga gacgctctgg ccggagggaa acccagagtt 3480
ctggtgaccc atccttcctt ccttggccac ctttgaatct aactggctgc catctttagt 3540
tcttctgttc gattgctgat ctaactggcc acgcacgcgc agtgacacga tcgtggcgtt 3600
cgccgagaac atgatggagc tggaggggac ggtggagacg ctggtcctgg aaggcctcgg 3660
cgcccgcggg cagagcatcc gcgcccactt cggctcgctc gaccacgccg tccggctgtc 3720
gcactacggc gtgccgccgg acacggagag cagcatgtcg atgcagccgc actacgacga 3780
cagcgtggtg accgcgatcg tgcagcacga ggtggaaggg ctcgagatgc acgccgggga 3840
cgggcgctgg gtcgccgtcc ctgccgaagt cggcaccctc accttcgtcg ccggcgagca 3900
gttcagggta cgagcacggt ccgatccgat tgactcctct ccctgaatcc tgacggtgac 3960
cagccatata tattgacatt gccgctgcgt acgtgcaggt cgtgacgaac gggcgcgtgc 4020
cggcgtgcct ccaccgcgtg aggacgccca gcaaccgcga gcggttctcg gtgctgttcg 4080
gccgccggca gaaggacggc gtggcggtgc gcgcgatgga ggacctcgtc gacgcggagc 4140
acccgctggc gtacaacccg ctgcgccatg aggagtactc caggtggcgt gtcacacccg 4200
gttttagaag gcaaaccgaa tgcgaaccat gtacgtgcca ggatcagtta ttcacgtaca 4260
cagcagttac ataatatgga catcatcaca cagtgctcaa aatagtatta aaaggggaaa 4320
tagtcgatta catcatacgt ctgagacgtc catatagttc ttacaataaa tcaaagtgcg 4380
gaaaagaaac gtagataaca cggccttcac aggcagccga ctggggggttg ccgctaaccc 4440
acacctagaa ctcgtcgtaa tcttggaact cctggaagtc tccttccaca gcttcatctt 4500
cgcctgagca gtggttgcaa tgctgacaac ctgggggggg tttggtgtgt agagcaaggg 4560
tgagtacaca tcaacatact cagcaagtat cctgtttggc tgtagtggac tagctttatg 4620
tggggataag tcaagcagtt gcttttagtt ggtcagatta ttatttacta gtagaaagcc 4680
aagttttagc attacccaag ttattaaccc aatgtatcct ttccaaacgg aaagaatacc 4740
acttaccaat accataatca taaccggaaa catcaatctc ataaccacct gtaccacaat 4800
gtctctgatc aagtatcact aatctctgga gctcccttgg ccgctcataa ccgcgagcac 4860
ggctgatata tcagtttcat aacactctgc agaggttgtg cactttaccc acaagccgtg 4920
attccctctc tggcccgggc ttgcaagacc cttattcact cccgaggtga atggccaggg 4980
attcactacg aagcctttac aaagattccc cggggctgta gccacccgtt aggtttccta 5040
aatgcactgc actcctcccc aaggggcgaa cccaaacttg gcagagcgag ccgcatacac 5100
cgagccccat tgacggcacg acggctaagt gaactacacc ccggatcctc taattattca 5160
gctaagggca ccccattcca ccctcatggt tgcactgttt tcccgggcgg tcatccatag 5220
aacaggtcct tacggagagg cactcgagaa accgctcgag tccccttgaa aaccacaagt 5280
ataatcataa agaagaacgg gaaaacagcg tatcatagat aatcacatca tgttcattga 5340
ttagagttga gcaatagcat cagactaagt agtaataatc cgacccaaat aggtaaacaa 5400
ggacatggat aacaaaagct agtcaatcct taggtataaa tgtgtaatgc gggaggtgaa 5460
ttaaagaatg aataggacat agataggtca aaagacactt gcctccacca aacgactgct 5520
gctcaggggc ttctcctgcg aattcctcgg gctcttcgac cggatcgttc tctatgcgag 5580
cgcaaacata catacataca tccacatatt taatacaaaa gaacagtaca ccatacaaga 5640
taacaaataa agcgaatatg catcaagtat gacattcgat aacgcatttg ttatggttag 5700
aaagaaacgg gaaaggtctc gcaggggggt taaatcttat gcactaatga cacaattggt 5760
ttttaacaaa ataattctgt tatacatatt tatatatact aatggaaacc taatcacttt 5820
tagttgatca acattgcaca gggtaaacaa ttaactacgt gaatcaatag cataacggaa 5880
ttttaaatta aacttcctat tttcccatag catgaacagt gattagccta cttaaaatac 5940
agtaattatg atcacagaaa gtaaataaaa taaaataaaa aaaaaataaa aaaaacagag 6000
ggggggcgg ttgaaccggc cctagggcgg ttgaaccggc ccgggggcag gcggccgagc 6060

```
tggggcggcc gagcgcgggg ggcggccgag ctgggggggg gggcggctga gccggggcca  6120
agcggctgaa ccggcccggg acaggggggg gggcgcgacc aggggccagg gcgggcggcg  6180
ggcgcggcca gggggccgag cggcgcgggc gcggccaggg ggccgagcgg cgcggggctg  6240
ggggcggccg ggcggccggg cggcgcggcc aagggccagc ggccaagggg agaaggaggg  6300
gagggggaag gagagaggag ggagaagggg gaggggaggg ggctcaccgg cgaggggggt  6360
ggccgacggc gagggcgcgc agccggggtc ggggcagcgg cgacggctag ggcagggagg  6420
tgggtggggg cggcggcttg ggtggggagg gagagaggga gagaatgagg gagagggaga  6480
ggggatttgg ggaaaaagag gggggggggt gggggcggct gggcctgctt tgggcccaag  6540
aggggggcgc aagggggcgg ctgggccggc cggggtcggc ccagggcgcg ggagagagag  6600
agagagggga gagagaaaga gagagagaaa agagaaagaa agatcttctt ctcattttcg  6660
aaatccgatc tttctacatg aatgcatttg cactttcaaa gcaatcaaaa gaaatgcaag  6720
ggcggcatgg tgcatcaaac aacataaagc atttagggtt tttatacgta cgggaattcc  6780
aaaccggatc ccgctagaac tttggaaaag gtcaaggttt agcgagggga aaaagaaaag  6840
gaaaaggtaa cgcccgaatt ttggcgagta aagaaaagaa aaaattcaac tgcaaaattc  6900
ggggcgttac aaacctatcc cccttaaaag aatctcgccc tcgagattca gggctggcta  6960
gcaaagagct ccgggtactt agccatcaga tcatcttcac gctcccaggt tgcttcttcc  7020
tcagagtggt gactccatct gactttgcac attctgacgg tcttccttcg ggtgactcta  7080
tctgcaacct caaggatctg agctggcttc tcaacatagg tcaagtcctc ctggacttcc  7140
agaccttcca ctggcaactg ctcttctggc acacgcaagc acttcttcaa ctgagacaca  7200
tgaaagacat catgcacagc agacaaattc tctggcaaac tgagctgata agccacttct  7260
cctcgtctcg caagaatctg atacggacca atgtagcggg gtgctagctt gcctttgact  7320
ccgaatcttc tg                                                      7332

SEQ ID NO: 171          moltype = DNA  length = 1142
FEATURE                 Location/Qualifiers
source                  1..1142
                        mol_type = other DNA
                        organism = Zea mays
SEQUENCE: 171
atgacgaaga cgaactagcc gcacctgctg cgctgacttc cgcagccact acaccccacg  60
cgaagcacag caagatttca ctagcagaag ccagatcgag tagaggcggg atccggcgga  120
ggcgcgaggc atggagatcg cgacggttga cctccgcggg gtggtgccgg ggggcgccgg  180
gtgggaggcc gcccgcgcgg cggtgaccgc gtccatggtg gcgcacggct gcgtcgtcgt  240
ggcgcacgac gcggtcggcg cggacctccg gcaggcgctg ttctcccgcg cgctgccgga  300
gctcttcgcg ctccctctcg aggccaagca gcggacggtg tcgcccaatg gggagttcag  360
gggctacatc ggccagcgcc ccggcatgga ctgggagagc ctccgcgtcg gaaagcccac  420
ggacgccgcc agcgtcagcg gcttcgctga gacgctctgg ccggagggaa acccagagtt  480
ctgtgacacg atcgtggcgt tcgccgagaa catgatggag ctggagggga cggtggagac  540
gctggtcctg gaaggcctcg gcgcccgcgg gcagagcatc cgcgcccact tcggctcgct  600
cgaccacgcc gtccggctgt cgcactacgg cgtgccgccg gacacggaga gcagcatgtc  660
gatgcagccg cactacgacg acagcgtggt gaccgcgatc gtgcagcacg aggtggaagg  720
gctcgagatg cacgccgggg acgggcgctg ggtcgccgtc cctgccgaag tcggcaccct  780
caccttcgtc gccggcgagc agttcagggt cgtgacgaac gggcgcgtgc cggcgtgcct  840
ccaccgcgtg aggacgccca gcaaccgcga gcggttctcg gtgctgttcg gccgccggca  900
gaaggacggc gtggcggtgc gcgcgatgga ggacctcgtc gacgcggagc acccgctggc  960
gtacaacccg ctgcgccatg aggagtactc caggtggcgt gtcacacccg gttttagaag  1020
gcaaaccgaa tgcgaaccat gtacgtgcca ggatcagtta ttcacgtaca cagcagttac  1080
ataatatgga catcatcaca cagtgctcaa aatagtatta aaaggggaaa tagtcgatta  1140
ca                                                                 1142

SEQ ID NO: 172          moltype = DNA  length = 954
FEATURE                 Location/Qualifiers
source                  1..954
                        mol_type = other DNA
                        organism = Zea mays
SEQUENCE: 172
atggagatcg cgacggttga cctccgcggg gtggtgccgg ggggcgccgg gtgggaggcc  60
gcccgcgcgg cggtgaccgc gtccatggtg gcgcacggct gcgtcgtcgt ggcgcacgac  120
gcggtcggcg cggacctccg gcaggcgctg ttctcccgcg cgctgccgga gctcttcgcg  180
ctccctctcg aggccaagca gcggacggtg tcgcccaatg gggagttcag gggctacatc  240
ggccagcgcc ccggcatgga ctgggagagc ctccgcgtcg gaaagcccac ggacgccgcc  300
agcgtcagcg gcttcgctga gacgctctgg ccggagggaa acccagagtt ctgtgacacg  360
atcgtggcgt tcgccgagaa catgatggag ctggagggga cggtggagac gctggtcctg  420
gaaggcctcg gcgcccgcgg gcagagcatc cgcgcccact tcggctcgct cgaccacgcc  480
gtccggctgt cgcactacgg cgtgccgccg gacacggaga gcagcatgtc gatgcagccg  540
cactacgacg acagcgtggt gaccgcgatc gtgcagcacg aggtggaagg gctcgagatg  600
cacgccgggg acgggcgctg ggtcgccgtc cctgccgaag tcggcaccct caccttcgtc  660
gccggcgagc agttcagggt cgtgacgaac gggcgcgtgc cggcgtgcct ccaccgcgtg  720
aggacgccca gcaaccgcga gcggttctcg gtgctgttcg gccgccggca gaaggacggc  780
gtggcggtgc gcgcgatgga ggacctcgtc gacgcggagc acccgctggc gtacaacccg  840
ctgcgccatg aggagtactc caggtggcgt gtcacacccg gttttagaag gcaaaccgaa  900
tgcgaaccat gtacgtgcca ggatcagtta ttcacgtaca cagcagttac ataa        954

SEQ ID NO: 173          moltype = AA  length = 317
FEATURE                 Location/Qualifiers
source                  1..317
                        mol_type = protein
                        organism = Zea mays
SEQUENCE: 173
```

-continued

```
MEIATVDLRG VVPGGAGWEA ARAAVTASMV AHGCVVVAHD AVGADLRQAL FSRALPELFA  60
LPLEAKQRTV SPNGEFRGYI GQRPGMDWES LRVGKPTDAA SVSGFAETLW PEGNPEFCDT  120
IVAFAENMME LEGTVETLVL EGLGARGQSI RAHFGSLDHA VRLSHYGVPP DTESSMSMQP  180
HYDDSVVTAI VQHEVEGLEM HAGDGRWVAV PAEVGTLTFV AGEQFRVVTN GRVPACLHRV  240
RTPSNRERFS VLFGRRQKDG VAVRAMEDLV DAEHPLAYNP LRHEEYSRWR VTPGFRRQTE  300
CEPCTCQDQL FTYTAVT                                                317
```